US011312955B2

(12) United States Patent
Berry et al.

(10) Patent No.: US 11,312,955 B2
(45) Date of Patent: Apr. 26, 2022

(54) METHODS AND COMPOSITIONS FOR MODULATING GENE EXPRESSION

(71) Applicant: FLAGSHIP PIONEERING INNOVATIONS V, INC., Cambridge, MA (US)

(72) Inventors: David Arthur Berry, Chestnut Hill, MA (US); Rahul Karnik, Cambridge, MA (US); Laura Gabriela Lande, Chestnut Hill, MA (US)

(73) Assignee: FLAGSHIP PIONEERING INNOVATIONS V, INC., Cambridge, MA (US)

( * ) Notice: Subject to any disclaimer, the term of this patent is extended or adjusted under 35 U.S.C. 154(b) by 40 days.

(21) Appl. No.: 15/821,632

(22) Filed: Nov. 22, 2017

(65) Prior Publication Data

US 2018/0179525 A1 Jun. 28, 2018

Related U.S. Application Data

(63) Continuation of application No. PCT/US2017/050553, filed on Sep. 7, 2017.

(60) Provisional application No. 62/542,703, filed on Aug. 8, 2017, provisional application No. 62/439,327, filed on Dec. 27, 2016, provisional application No. 62/416,501, filed on Nov. 2, 2016, provisional application No. 62/384,603, filed on Sep. 7, 2016.

(51) Int. Cl.
| | |
|---|---|
| *C12N 15/113* | (2010.01) |
| *C12N 9/22* | (2006.01) |
| *C12N 15/63* | (2006.01) |
| *C12N 15/85* | (2006.01) |
| *C12N 15/87* | (2006.01) |
| *C12N 15/90* | (2006.01) |
| *C12N 9/00* | (2006.01) |
| *C12N 9/10* | (2006.01) |
| *C12N 9/80* | (2006.01) |
| *A61K 35/12* | (2015.01) |

(52) U.S. Cl.
CPC ............ *C12N 15/113* (2013.01); *A61K 35/12* (2013.01); *C12N 9/00* (2013.01); *C12N 9/1007* (2013.01); *C12N 9/22* (2013.01); *C12N 9/80* (2013.01); *C12N 15/63* (2013.01); *C12N 15/85* (2013.01); *C12N 15/87* (2013.01); *C12N 15/90* (2013.01); *C12N 15/907* (2013.01); *C12Y 201/01037* (2013.01); *C12Y 201/01043* (2013.01); *C12Y 305/01098* (2013.01); *A01K 2217/056* (2013.01); *A01K 2227/706* (2013.01); *A01K 2267/0318* (2013.01); *C07K 2319/00* (2013.01); *C07K 2319/85* (2013.01); *C12N 2310/14* (2013.01); *C12N 2310/20* (2017.05)

(58) Field of Classification Search
CPC ...... C12N 15/113; C12N 15/63; C12N 15/90; C12N 2310/14; A01K 2227/706; A01K 2267/0318; A01K 2217/056
See application file for complete search history.

(56) References Cited

U.S. PATENT DOCUMENTS

| | | | |
|---|---|---|---|
| 8,513,207 | B2 | 8/2013 | Brown |
| 9,801,877 | B2 | 10/2017 | Yao et al. |
| 2012/0115227 | A1 | 5/2012 | Cohen-Haguenauer et al. |
| 2014/0273226 | A1 | 9/2014 | Wu |
| 2014/0322707 | A1 | 10/2014 | He et al. |
| 2015/0071906 | A1 | 3/2015 | Liu et al. |
| 2015/0376612 | A1* | 12/2015 | Lee .................. C12N 15/113 514/44 A |
| 2016/0010076 | A1 | 1/2016 | Joung et al. |
| 2016/0024474 | A1 | 1/2016 | Conway et al. |
| 2016/0186208 | A1 | 6/2016 | Jaenisch et al. |
| 2016/0215280 | A1 | 7/2016 | Fanucchi et al. |
| 2016/0340749 | A1 | 11/2016 | Stelzer et al. |
| 2017/0014449 | A1 | 1/2017 | Bangera et al. |
| 2017/0130247 | A1 | 5/2017 | Dowen et al. |
| 2017/0362649 | A1 | 12/2017 | Lieberman-Aiden et al. |
| 2018/0245079 | A1 | 8/2018 | Lieberman Aiden et al. |
| 2019/0024086 | A1 | 1/2019 | Lande et al. |
| 2019/0241964 | A1 | 8/2019 | Hunter et al. |
| 2019/0309291 | A1 | 10/2019 | Lee et al. |
| 2019/0359959 | A1* | 11/2019 | Jaenisch .................. C12N 9/22 |
| 2020/0224274 | A1 | 7/2020 | Bernstein et al. |
| 2020/0002558 | A1 | 8/2020 | Aiden et al. |

FOREIGN PATENT DOCUMENTS

| | | |
|---|---|---|
| WO | WO-2009/146033 A2 | 12/2009 |
| WO | 2012019168 A2 | 2/2012 |
| WO | 2015038892 A1 | 3/2015 |
| WO | 2015191780 A2 | 12/2015 |
| WO | 2015196128 A2 | 12/2015 |
| WO | 2016022363 A9 | 4/2016 |
| WO | 2016063264 A1 | 4/2016 |
| WO | WO-2016/022363 A9 | 4/2016 |
| WO | 2016/070037 A2 | 5/2016 |
| WO | 2016073990 A2 | 5/2016 |
| WO | 2016081798 A1 | 5/2016 |
| WO | WO-2016/073990 A2 | 5/2016 |
| WO | WO-2016/081798 A1 | 5/2016 |
| WO | 2016103233 A2 | 6/2016 |
| WO | WO-2016/103233 A2 | 6/2016 |
| WO | 2016115326 A1 | 7/2016 |
| WO | WO-2016/115326 A1 | 7/2016 |
| WO | 2016154330 A1 | 9/2016 |

(Continued)

OTHER PUBLICATIONS

Li et al. (Nature Communications (2019) article No. 1535; pp. 1-13) (Year: 2019).*

(Continued)

*Primary Examiner* — J. E. Angell
(74) *Attorney, Agent, or Firm* — K&L Gates LLP

(57) ABSTRACT

The present disclosure provides compositions with a modulating gene expression and methods for modulating transcription.

13 Claims, 20 Drawing Sheets

Specification includes a Sequence Listing.

(56) References Cited

FOREIGN PATENT DOCUMENTS

| WO | 2016164356 A1 | 10/2016 | | |
|---|---|---|---|---|
| WO | WO-2016164356 A1 * | 10/2016 | ............... | C12N 9/22 |
| WO | 2016174250 A1 | 11/2016 | | |
| WO | WO-2016/174250 A1 | 11/2016 | | |
| WO | 2017011710 A2 | 1/2017 | | |
| WO | WO-2017/011710 A2 | 1/2017 | | |
| WO | 2017031370 A1 | 2/2017 | | |
| WO | WO-2017/031370 A1 | 2/2017 | | |
| WO | 2017040793 A1 | 3/2017 | | |
| WO | WO-2017/040793 A1 | 3/2017 | | |
| WO | 2017064546 A1 | 4/2017 | | |
| WO | WO-2017/064546 A1 | 4/2017 | | |
| WO | 2017106290 A1 | 6/2017 | | |
| WO | 2017143042 A2 | 8/2017 | | |
| WO | WO-2017/143042 A2 | 8/2017 | | |
| WO | 2018035495 A1 | 2/2018 | | |
| WO | 2018049073 A1 | 3/2018 | | |
| WO | 2018049075 A1 | 3/2018 | | |
| WO | 2018049077 A1 | 3/2018 | | |
| WO | 2018049079 A1 | 3/2018 | | |
| WO | 2018111944 A1 | 6/2018 | | |
| WO | WO-2018111944 A1 * | 6/2018 | ........... | A61K 38/465 |
| WO | 2018129544 A1 | 7/2018 | | |
| WO | 2018204764 A1 | 11/2018 | | |
| WO | 2019036430 A1 | 2/2019 | | |
| WO | 2019071054 A1 | 4/2019 | | |

OTHER PUBLICATIONS

Deng et al., "Controlling Long-Range Genomic Interactions at a Native Locus by Targeted Tethering of a Looping Factor," Cell (2012) vol. 149, pp. 1233-1244.
Hsu, "Completion of a Programmable DNA-Binding Small Molecule Library," Thesis, California Institute of Technology (2008) retrieved from thesis.library.caltech.edu/4398, 153 pages.
International Search Report and Written Opinion issued in PCT/US2017/050553, dated Jan. 30, 2018.
Kim et al., "Genome-wide target specificities of CRISPR RNA-guided programmable deaminases," Nat Biotechnol (2017) vol. 35, pp. 475-480.
Krylov et al., "A general method to design dominant negatives to B-HLHZip proteins that abolish DNA binding," PNAS (1997) vol. 94, No. 23, pp. 12274-12279.
McDonald et al., "Reprogrammable CRISPR/Cas9-based system for inducing site-specific DNA methylation," Biology Open (2016) vol. 5, pp. 866-874.
Morgan et al., "Manipulation of nuclear architecture through CRISPR-mediated chromosomal looping," Nature Communications (2017) vol. 8, Article 15993, 9 pages.
Torres et al., "Potent and sustained cellular inhibition of miR-122 by lysine-derivatized peptide nucleic acids (PNA) and phosphorothioate locked nucleic acid (LNA)/2'O-methyl (OMe) mixmer antimiRs in the absence of transfection agents," Artif DNA PNA XNA (2011) vol. 2, No. 3, pp. 71-78.
Viscidi et al., "Novel Chemical Method for the Preparation of Nucleic Acids for Nonisotopic Hybridization," J Clin Microbiol (1986) vol. 23, No. 2, pp. 311-317.
Amabile et al. "Inheritable Silencing of Endogenous Genes by Hit-and-Run Targeted Epigenetic Editing" Cell (2016) vol. 167, pp. 219-232.
Banani et al. "Biomolecular condensates: organizers of cellular biochemistry" Nature Reviews Molecular Cell Biology (2017) vol. 18, No. 5, pp. 285-298.
Cho et al., "Antisense Transcription and Short Article Heterochromatin at the DMI CTG Repeats Are Constrained by CTCF" Molecular Cell (2005) vol. 20, pp. 483-489.
Cong et al., "Multiplex Genome Engineering Using CRISPR/Cas Systems" Science (2013) vol. 339, pp. 819-823.

De Groote et al. "Epigenetic Editing: targeted rewriting of epigenetic marks to modulate expression of selected target genes" Nucleic Acids Res. (2012) vol. 40, No. 21, pp. 10596-10613.
Herold et al. "CTCF: insights into insulator function during development" Development (2012) vol. 139, pp. 1045-1057.
Kearns et al., "Functional annotation of native enhancers with a Cas9-histone demethylase fusion" Nature Methods (2015) vol. 12, No. 5, pp. 401-403.
Koferle et al., "Brave new epigenomes: the dawn of epigenetic engineering" Genome Medicine (2015) vol. 7, No. 59, pp. 1-3.
Lin et al., "Formation and Maturation of Phase-Separated Liquid Droplets by RNA-Binding Proteins" Molecular Cell (2015) vol. 60, pp. 208-219.
McDonald et al., "Reprogrammable CRISPR/Cas9-based system for inducing site-specific DNA methylation" Biology Open (2016) doi: 10.1242/bio.019067, pp. 1-9.
Patterson et al., "DNA Methylation: Bisulphite Modification and Analysis" J Vis Exp. (2011) vol. 56, e3170, pp. 1-9.
Ran et al. "Genome engineering using the CRISPR-Cas9 system" Nature Protocols (2013) vol. 8, No. 11, pp. 2281-2308.
Sabari et al., "Coactivator condensation at super-enhancers links phase separation and gene control" Science (2018) doi: 10.1126/science.aar3958, pp. 1-16.
Shin et al., "Spatiotemporal control of intracellular phase transitions using light-activated optoDroplets" Cell (2017) vol. 168, No. 1-2, pp. 159-171.
Wu et al., "MicroRNAs direct rapid deadenylation of mRNA" Proc Natl Acad Sci (2006) vol. 103, pp. 4034-4039.
Xu et al., "A CRISPR-based approach for targeted DNA demethylation" Cell Discovery (2016) vol. 2, No. 16009, pp. 1-12, doi:10.1038/celldisc.2016.9.
Hsu, Carey Frank, Completion of a Programmable DNA-Binding Small Molecule Library, Thesis, California Institute of Technology [retrieved Nov. 22, 2017], from the internet: https://thesis.library.caltech.edu/4398/, 30 pages (Oct. 30, 2008).
International Search Report for PCT/US2017/50553 (Methods and Compositions for Modulating Gene Expression, filed Sep. 7, 2017), issued by ISA/US, 6 pages (Jan. 30, 2018).
International Search Report for PCT/US2017/50556 (Methods and Compositions for Modulating Gene Expression, filed Sep. 7, 2017), issued by ISA/US, 5 pages (Dec. 26, 2017).
International Search Report for PCT/US2017/50558 (Methods and Compositions for Modulating Gene Expression, filed Sep. 7, 2017), issued by ISA/US, 5 pages (Dec. 18, 2017).
International Search Report for PCT/US2017/50561 (Methods and Compositions for Modulating Gene Expression, filed Sep. 7, 2017), issued by ISA/US, 5 pages (Dec. 18, 2017).
Kim, D. et al., Genome-wide target specificities of CRISPR RNA-guided programmable deaminases, Nature Biotechnology, 35:475-480 (2017).
Krylov, D. et al., A general method to design dominant negatives to B-HLHZip proteins that abolish DNA binding, Proc. Natl. Acad. Sci. USA, 94:12274-12279 (1997).
McDonald, J. et al., Reprogrammable CRISPR/Cas9-based system for inducing site-specific DNA methylation, Biology Open, 0:1-9, 26 pages (2016).
Torres, A. et al., Potent and sustained cellular inhibition of miR-122 by lysine-derivatized peptide nucleic acids (PNA) and phosphorothioate locked nucleic acid (LNA)/2'-O-methyl (OMe) mixmer antimiRs in the absence of transfection agents, Artificial DNA: PNA & XNA, 2(3):71-78 (2011).
Viscidi, R. et al., Novel Chemical Method for the Preparation of Nucleic Acids for Nonisotopic Hybridization, Journal of Clinical Microbiology, 23(2):311-317 (1986).
Written Opinion for PCT/US2017/50553 (Methods and Compositions for Modulating Gene Expression, filed Sep. 7, 2017), issued by ISA/US, 12 pages (dated Jan. 30, 2018).
Written Opinion for PCT/US2017/50556 (Methods and Compositions for Modulating Gene Expression, filed Sep. 7, 2017), issued by ISA/US, 8 pages (dated Dec. 26, 2017).
Written Opinion for PCT/US2017/50558 (Methods and Compositions for Modulating Gene Expression, filed Sep. 7, 2017), issued by ISA/US, 6 pages (dated Dec. 18, 2017).

(56) References Cited

OTHER PUBLICATIONS

Written Opinion for PCT/US2017/50561 (Methods and Compositions for Modulating Gene Expression, filed Sep. 7, 2017), issued by ISA/US, 6 pages (dated Dec. 18, 2017).
Amabile, A. et al., Inheritable Silencing of Endogenous Genes by Hit-and-Run Targeted Epigenetic Editing, Cell, 167:219-232 (2016).
Barrera, L. et al., Survey of variation in human transcription factors reveals prevalent DNA binding changes, Science, 351 (6280):1450-1454 (2016).
Dowen, J. et al., Control of Cell Identity Genes Occurs in Insulated Neighborhoods in Mammalian Chromosomes, Cell, 159:374-387 (2014).
Guo, C. et al., CTCF Binding Elements Mediate Control of V(D)J Recombination, Nature, 477(7365):424-430 (2011).
Herold, M. et al., CTCF: insights into insulator function during development, Development, 139:1045-1057 (2012).
Hnisz, D. et al., Activation of proto-oncogenes by disruption of chromosome neighborhoods, Science, 351(6280):1454-1458 (2016).
Hnisz, D. et al., Convergence of Developmental and Oncogenic Signaling Pathways at Transcriptional Super-Enhancers, Molecular Cell, 58:362-370 (2015).
Hnisz, D. et al., Super-Enhancers in the Control of Cell Identity and Disease, Cell, 155:934-947 (2013).
Ji, X. et al., 3D Chromosome Regulatory Landscape of Human Pluripotent Cells, Cell Stem Cell, 18:262-275 (2016).
Ji, X. et al., Chromatin proteomic profiling reveals novel proteins associated with histone-marked genomic regions, PNAS, 112(12):3841-3846 (2015).
Liu, X. et al., Editing DNA Methylation in the Mammalian Genome, Cell, 167:233-247 (2016).
Mansour, M. et al., An oncogenic super-enhancer formed through somatic mutation of a noncoding intergenic element, Science, downloaded from www.sciencemag.org/content/early/recent, 9 pages (Nov. 13, 2014).
Spencer, R. et al., A Boundary Element Between Tsix and Xist Binds the Chromatin Insulator Ctcf and Contributes to Initiation of X-Chromosome Inactivation, Genetics, 189:441-454 (2011).
Szabó, P. et al., Role of CTCF Binding Sites in the Igf2/H19 Imprinting Control Region, Molecular and Cellular Biology, 24(11):4791-4800 (2004).
Tang, Z. et al., CTCF-Mediated Human 3D Genome Architecture Reveals Chromatin Topology for Transcription, Cell, 163:1-17 (2015).
Ma et al."Targeted Gene Suppression by Inducing De Novo DNA Methylation in the Gene Promotor" Epigenetics & Chromatin (2014) vol. 7:20, pp. 1-11.
Guo et al., "YY1 Target DB: an intergral information resource for Yin Yang 1 target loci" Database (2013) vol., pp. 1-10.

Ecker et al. "Genomics: ENCODE explained". Nature (2012) Sep. 6; vol. 489 (7414) pp. 52-55.
Dunham et al. "An Integrated Encyclopedia of DNA Elements in the Human Genome" Nature (2012) vol. 6; 489 (7414):57-74.
Ziebarth et al., "CTCFBSDB 2.0: a database for CTCF-binding sites and genome organization" Nucleic Acid Research (2013) vol. 41; D188-94.
Rada-Iglesias et al."Whole-genome maps of USFI and USF2 binding and histone H3 acetylation reveal new aspects of promoter structure and candidate genes for common human disorders" Genome Research (2008) vol. 18(3), pp. 380-392.
Vojta et al. Repurposing the CRISPR-Cas9 system for Targeted DNA Methylation (Nucleic Acids Res Advance Acess (published online Mar. 2016) 44 (12); 5615-5628.
Woloszynska-Read et al. DNA Methylation-dependent Regulation of BORIS/CTCFL Expression in Ovarian Cancer (Cancer Immunity (2007) vol. 7, 1 pp. 1-10).
Lei et al. "Targeted DNA methylation in vivo using an engineered dCas 9-MQ1 fushion protein." Nature Communications (2017) vol. 16026; pp. 1-10.
Liu et al. "Editing DNA methylation in the mammalian genome." (Cell) 2016; vol. 167 (1); pp. 233-247.
Varun Narenda et al. "CTCF establishes discrete functional chromatin domains at the Hox clusters during differentiation" (Science) 2015, vol. 347, No. 6225, pp. 1017-1021.
Flavahan et al. "Insulator dysfunction and oncogene activation in IDH mutant gliomas" (Nature) 2015, vol. 529, No. 7584, pp. 110-114.
De Wit Elzo et al. "CTCF Binding Polarity Deterrmines Chromatin Looping" (Molecular Cell) vol. 60. No. 4, pp. 676-684.
Ling J Q et al. "Long-range DNA interactions are specifically altered by locked nucleic acid-targeting of a CTFC binding site" (Biochimica et Biophysica Acta. Gene Regulatory Mechanisms) vol. 1809, No. 1. pp. 24-33.
Extended European Search Report for application No. 17849560.2 dated Mar. 31, 2020.
Jinek et al., "A Programmable Dual-RNA-Guided DNA Endonuclease in Adaptive Bacterial Immunity," (Science) 2012, vol. 337, pp. 816-821.
Komor et al., "Programmable editing of a target base in genomic DNA without double-stranded DNA cleavage," (Nature) 2016, vol. 533, pp. 420-424, Supplement.
De Souza et al., "DNA methylation profiling in human Huntington's disease brain," Human Molecular Genetics (2016) vol. 25, No. 10, pp. 2013-2030.
Thakore et al., "Highly Specific Epigenome Editing by CRISPR/Cas9 Repressors for Silencing of Distal Regulatory Elements," Nat Methods (2015) vol. 12, No. 12, pp. 1143-1149.

* cited by examiner

DISRUPTION OF ANCHOR SEQUENCE-MEDIATED CONJUNCTIONS UPSTREAM OF THE *MYC* GENE LEADS TO DOWNREGULATION OF *MYC* EXPRESSION LEVELS

DISRUPTION OF ANCHOR SEQUENCE-MEDIATED CONJUNCTIONS UPSTREAM OF THE MYC GENE LEADS TO DOWNREGULATION OF MYC EXPRESSION LEVELS

DISRUPTION OF AN ANCHOR SEQUENCE-MEDIATED CONJUNCTION ASSOCIATED WITH THE *FOXJ3* GENE LEADS TO DOWNREGULATION OF *FOXJ3* EXPRESSION LEVELS

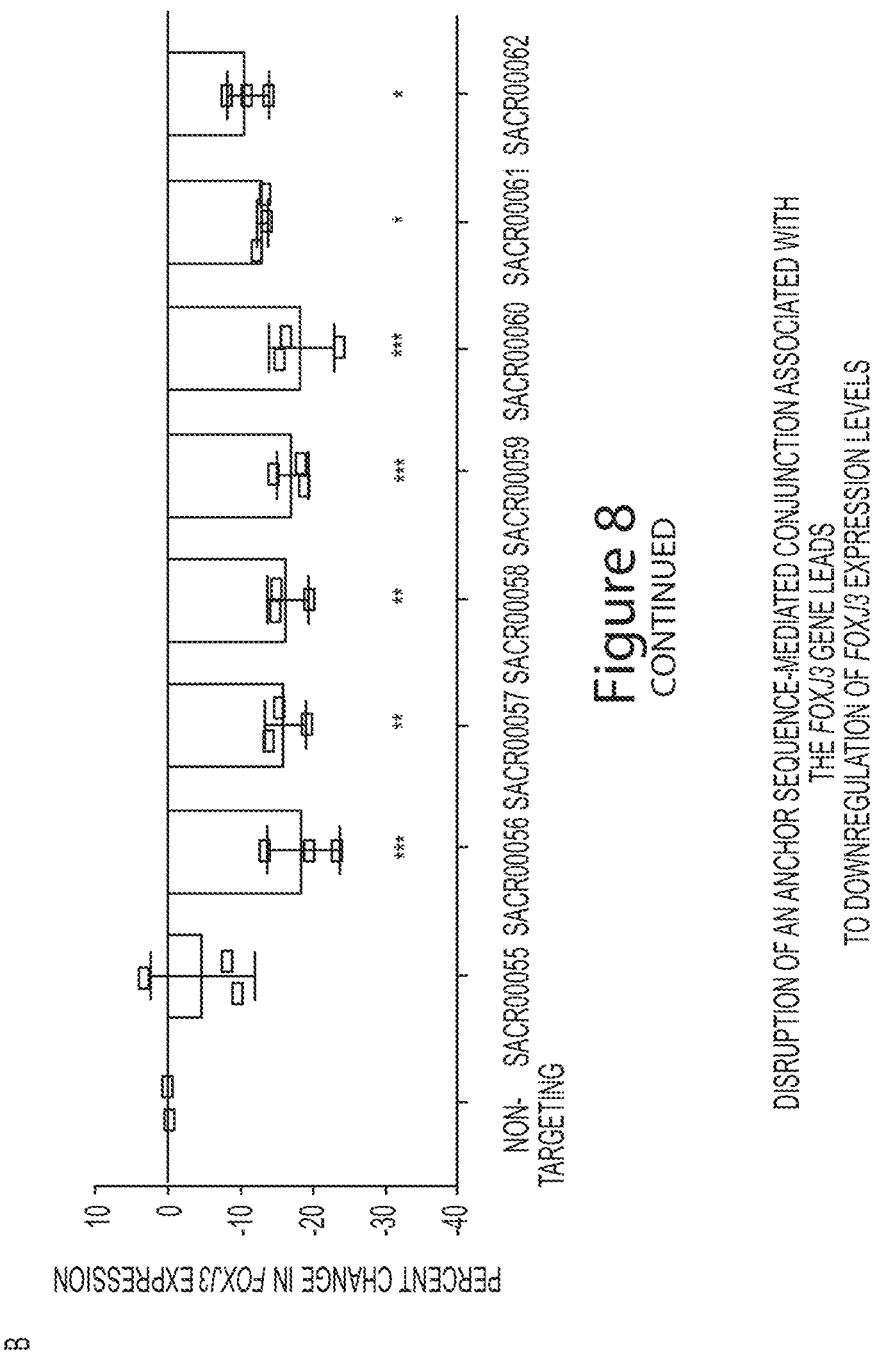

DISRUPTION OF AN ANCHOR SEQUENCE-MEDIATED CONJUNCTION ASSOCIATED WITH THE FOXJ3 GENE LEADS TO DOWNREGULATION OF FOXJ3 EXPRESSION LEVELS

DISRUPTION OF ANCHOR SEQUENCE-MEDIATED CONJUNCTIONS ASSOCIATED WITH THE *TUSC5* GENE LEADS TO UPREGULATION OF *TUSC5* EXPRESSION LEVELS

DISRUPTION OF AN ANCHOR SEQUENCE-MEDIATED CONJUNCTION UPSTREAM OF THE *DAND5* GENE LEADS TO UPREGULATION OF *DAND5* EXPRESSION LEVELS

DISRUPTION OF ANCHOR SEQUENCE-MEDIATED CONJUNCTIONS UPSTREAM OR DOWNSTREAM OF THE SHMT2 GENE LEADS TO DOWNREGULATION OF SHMT2 EXPRESSION LEVELS

DISRUPTION OF AN ANCHOR SEQUENCE-MEDIATED CONJUNCTION UPSTREAM OF THE *TTC21B* GENE LEADS TO UPREGULATION OF *TTC21B* EXPRESSION LEVELS

GENETIC PERTURBATION (Cas9); BOLD INDICATES INCLUSION IN AN EXAMPLE

| LOOP TYPE | TARGET UPREGULATED | TARGET DOWNREGULATED | TARGET UNCHANGED |
|---|---|---|---|
| TYPE 1 | | *FOXJ3* (-19%, p = 0.0001)<br>*CDK6* (-28%, p = 0.0061) | SCN1A, GUCA2B |
| TYPE 2, SUBTYPE 1 | TUSC5 (+12,826%, p = 0.0001)<br>DAND5 (+124%, p = 0.0028)<br>GUCA2A (+3,692%, p = 0.0006) | | |
| TYPE 3 | | SHMT2 (-24%, p = 0.0266) | NXPH4<br>PWP1<br>PRDM4 |
| TYPE 4 | | *MYC* (-63%, p = 0.0001) | HLA-A |
| TYPE 1, EP SUB-TYPE | | | |
| TYPE 2, SUBTYPE 2 | TTC21B (+32%, p = 0.0020) | | |

EPIGENETIC PERTURBATION (dCas9-DNMT3a-3L, dCas9-KRAB)

| LOOP TYPE | TARGET UPREGULATED | TARGET DOWNREGULATED | TARGET UNCHANGED |
|---|---|---|---|
| TYPE 1 | | *FOXJ3* (-21%, p = 0.0035) | |
| TYPE 2, SUBTYPE 1 | | | |
| TYPE 3 | | SHMT2 (-18%, p = 0.0012)<br>PRDM4 (-39%, p = 0.0001) | NXPH4<br>PWP1 |
| TYPE 4 | | *MYC* (-42%, p = 0.0001) | |
| TYPE 1, EP SUB-TYPE | | | |
| TYPE 2, SUBTYPE 2 | | | |

Figure 17

SUMMARY OF CERTAIN TARGETED LOOP DISRUPTION EXPERIMENTAL DATA

METHODS AND COMPOSITIONS FOR MODULATING GENE EXPRESSION

CROSS-REFERENCE TO RELATED APPLICATIONS

The present application is a continuation of International Patent Application No. PCT/US17/50553, filed Sep. 7, 2016, which claims priority to and benefit from U.S. provisional applications U.S. Ser. No. 62/384,603 (filed Sep. 7, 2016), Ser. No. 62/416,501 (filed Nov. 2, 2016), Ser. No. 62/439,327 (filed Dec. 27, 2016), and Ser. No. 62/542,703 (filed Aug. 8, 2017), the contents of each of which are herein incorporated by reference.

SEQUENCE LISTING

The instant application contains a Sequence Listing which has been submitted electronically in ASCII format and is hereby incorporated by reference in its entirety. Said ASCII copy, created on Mar. 16, 2018, is 2012802-0009_ST25.txt and is 25 kilobytes in size.

BACKGROUND

Many diseases are caused by defective regulation of expression of certain genes.

SUMMARY

Among other things, the present disclosure provides various agents, compositions, and methods for modulating gene expression, delivery to a cell (e.g., a mammalian cell such as a mammalian somatic cell; e.g., delivery across a cell membrane), and related methods of treatment. To the inventor's knowledge, the present disclosure provides the first disclosure of site-specific agents that physically disrupt and/or modify anchor-sequence mediated conjunctions. The present disclosure also provides, among other things, site-specific agents that act to disrupt and/or modify anchor sequence-mediated conjunctions by genetic and/or epigenetic methods.

In some embodiments, the present disclosure provides a site-specific disrupting agent, comprising: a DNA-binding moiety that binds specifically to one or more target anchor sequences within a cell and not to non-targeted anchor sequences within the cell with sufficient affinity that it competes with binding of an endogenous nucleating polypeptide within the cell.

In some embodiments, the present disclosure provides a method of modulating expression of a gene within an anchor sequence-mediated conjunction that comprises a first anchor sequence and a second anchor sequence, the method comprising a step of: contacting the first and/or second anchor sequence with a site-specific disrupting agent as disclosed herein In some embodiments, the present disclosure provides a method of modulating expression of a gene within 10 kb of a first anchor sequence within an anchor sequence-mediated conjunction comprising a first anchor sequence and a second anchor sequence, the method comprising a step of: contacting the first and/or second anchor sequence with a site-specific disrupting agent as disclosed herein.

In some embodiments, the present disclosure provides a method of increasing expression of a gene within an anchor sequence-mediated conjunction that comprises a first anchor sequence and a second anchor sequence, wherein the first and/or the second anchor sequence is located within 10 kb of an external enhancing sequence, the method comprising a step of contacting the first and/or second anchor sequence with a site-specific disrupting agent as disclosed herein.

In some embodiments, the present disclosure provides methods comprising a step of delivering a site-specific disrupting agent as disclosed herein to a mammalian cell.

In some embodiments, the present disclosure provides fusion molecules comprising: (i) a site-specific targeting moiety and (ii) a deaminating agent, wherein the site-specific targeting moiety targets the fusion molecule to a target anchor sequence but not to at least one non-target anchor sequence.

In some embodiments, the present disclosure provides compositions comprising: (i) a fusion polypeptide comprising an enzymatically inactive Cas polypeptide and a deaminating agent, or a nucleic acid encoding the fusion polypeptide; and (ii) a guide RNA, wherein the guide RNA targets the fusion polypeptide to a target anchor sequence but not to at least one non-target anchor sequence.

In some embodiments, the present disclosure provides methods of modulating expression of a gene within an anchor sequence-mediated conjunction that comprises a first anchor sequence and a second anchor sequence, the method comprising a step of: contacting the first and/or second anchor sequence with a site-specific disrupting agent as disclosed herein.

In some embodiments, the present disclosure provides methods of modulating expression of a gene within 10 kb of a first anchor sequence within an anchor sequence-mediated conjunction comprising a first anchor sequence and a second anchor sequence, the method comprising a step of: contacting the first and/or second anchor sequence with a site-specific disrupting agent as disclosed herein.

In some embodiments, the present disclosure provides methods of decreasing expression of a gene within an anchor sequence-mediated conjunction that comprises a first anchor sequence, a second anchor sequence, and an internal enhancing sequence, the method comprising a step of: contacting the first and/or second anchor sequence with a site-specific disrupting agent as disclosed herein.

In some embodiments, the present disclosure provides methods comprising a step of: (a) delivering the fusion molecule or composition as described herein to a mammalian cell.

In some embodiments, the present disclosure provides methods comprising a step of: (a) substituting, adding, or deleting one or more nucleotides of an anchor sequence within a mammalian somatic cell.

In some embodiments, the present disclosure provides methods comprising a step of delivering a mammalian somatic cell to a subject having a disease or condition, wherein one or more nucleotides of an anchor sequence within the mammalian somatic cell has been substituted, added, or deleted.

In some embodiments, the present disclosure provides methods comprising a step of:
(a) administering somatic mammalian cells to a subject, wherein the somatic mammalian cells were obtained from the subject, and a fusion molecule or composition as disclosed herein had been delivered ex vivo to the mammalian cells.

In some embodiments, the present disclosure provides fusion molecules comprising: (i) a site-specific targeting moiety and (ii) an epigenetic modifying agent, wherein the site-specific targeting moiety targets the fusion molecule to a target anchor sequence but not to at least one non-target anchor sequence.

In some embodiments, the present disclosure provides site-specific guide RNAs that comprises a targeting domain complementary to a target nucleic acid comprising an anchor sequence.

In some embodiments, the present disclosure provides compositions comprising: (i) a fusion polypeptide comprising an enzymatically inactive Cas polypeptide and an epigenetic modifying agent, or a nucleic acid encoding the fusion polypeptide; and (ii) a guide RNA, wherein the guide RNA targets the fusion polypeptide to a target anchor sequence but not to at least one non-target anchor sequence.

In some embodiments, the present disclosure provides methods of modulating expression of a gene within an anchor sequence-mediated conjunction that comprises a first anchor sequence and a second anchor sequence, the method comprising a step of: contacting the first and/or second anchor sequence with a fusion molecule or composition as disclosed herein.

In some embodiments, the present disclosure provides methods of modulating expression of a gene within 10 kb of a first anchor sequence within an anchor sequence-mediated conjunction comprising a first anchor sequence and a second anchor sequence, the method comprising a step of: contacting the first and/or second anchor sequence with a fusion molecule or composition as disclosed herein.

In some embodiments, the present disclosure provides methods of decreasing expression of a gene within an anchor sequence-mediated conjunction that comprises a first anchor sequence, a second anchor sequence, and an internal enhancing sequence, the method comprising a step of: contacting the first and/or second anchor sequence with a fusion molecule or composition as disclosed herein.

In some embodiments, the present disclosure provides methods of increasing expression of a gene within an anchor sequence-mediated conjunction that comprises a first anchor sequence and a second anchor sequence, wherein the first and/or the second anchor sequence is located within 10 kb of an external enhancing sequence, the method comprising a step of: contacting the first and/or second anchor sequence with a fusion molecule or composition as disclosed herein.

In some embodiments, the present disclosure provides methods comprising a step of:
(a) delivering a fusion molecule or composition as disclosed herein to a mammalian cell.

In some embodiments, the present disclosure provides an engineered site-specific nucleating agent, comprising: an engineered DNA-binding moiety that binds specifically to one or more target sequences within a cell and not to non-targeted sequences within the cell with sufficient affinity that it competes binding of an endogenous nucleating polypeptide within the cell; and a nucleating polypeptide dimerization domain associated with the engineered DNA-binding moiety so that, so that, when the engineered DNA-binding moiety is bound at the at least one target sequences, the nucleating polypeptide dimerization domain is localized thereto, and each at least one targeted sequence is a target anchor sequence wherein the at least one or more target anchor sequences is positioned relative to an anchor sequence to which a nucleating polypeptide binds so that, when the nucleating polypeptide dimerization domain is localized to the target anchor sequence, interaction between the nucleating polypeptide dimerization domain and the nucleating polypeptide generates an anchor-sequence-mediated conjunction.

In one aspect, the disclosure includes a pharmaceutical preparation comprising a composition that binds an anchor sequence of an anchor sequence-mediated conjunction and alters formation of the anchor sequence-mediated conjunction, wherein the composition modulates transcription, in a human cell, of a target gene associated with the anchor sequence-mediated conjunction.

In one aspect, the disclosure includes a composition comprising a targeting moiety that binds an anchor sequence of an anchor sequence-mediated conjunction and alters formation of the anchor sequence-mediated conjunction (e.g., alters affinity of the anchor sequence to a conjunction nucleating molecule, e.g., at least 10%, 15%, 20%, 25%, 30%, 35%, 40%, 45%, 50%, 55%, 60%, 65%, 70%, 75%, 80%, 85%, 90%, 95%, or more.

In one aspect, the disclosure includes a pharmaceutical preparation comprising a composition comprising a targeting moiety that binds an anchor sequence of an anchor sequence-mediated conjunction and alters formation of the anchor sequence-mediated conjunction, wherein the composition modulates transcription, e.g., in a human cell, of a target gene in an expression unit associated with the anchor sequence-mediated conjunction.

In various aspects of the disclosure delineated herein, one or more of the various embodiments described herein may be combined.

In some embodiments, the targeting moiety comprises an effector moiety that: (i) is a chemical, e.g., a chemical that modulates a cytosine (C) or an adenine(A) (e.g., Na bisulfite, ammonium bisulfite); (ii) has enzymatic activity (methyl transferase, demethylase, nuclease (e.g., Cas9), deaminase); or (iii) sterically hinders formation of the anchor sequence-mediated conjunction. [e.g., membrane translocating polypeptide+nanoparticle].

In some embodiments, the anchor sequence-mediated conjunction is associated with one or more transcriptional control sequences. In one embodiment, one or more transcriptional control sequences are inside the anchor sequence-mediated conjunction, e.g., a Type 1 anchor sequence-mediated conjunction. In another embodiment, one or more one or more transcriptional control sequences are outside the anchor sequence-mediated conjunction comprises, e.g., a Type 2 anchor sequence-mediated conjunction. In another embodiment, one or more one or more transcriptional control sequences are inside, e.g., enhancing sequences, and outside, at least partially, e.g., silencing sequences, the anchor sequence-mediated conjunction, e.g., a Type 3 anchor sequence-mediated conjunction. In another embodiment, one or more one or more transcriptional control sequences are inside, e.g., enhancing sequences, and outside, at least partially, e.g., enhancing sequences, the anchor sequence-mediated conjunction, e.g., a Type 4 anchor sequence-mediated conjunction.

In some embodiments, the composition disrupts formation of the anchor sequence-mediated conjunction (e.g., decreases affinity of the anchor sequence to a conjunction nucleating molecule, e.g., at least 10%, 15%, 20%, 25%, 30%, 35%, 40%, 45%, 50%, 55%, 60%, 65%, 70%, 75%, 80%, 85%, 90%, 95%, or more). In some embodiments, the composition promotes formation of the anchor sequence-mediated conjunction (e.g., increases affinity of the anchor sequence to a conjunction nucleating molecule, e.g., at least 10%, 15%, 20%, 25%, 30%, 35%, 40%, 45%, 50%, 55%, 60%, 65%, 70%, 75%, 80%, 85%, 90%, 95%, or more). In some embodiments, the target gene is inside the anchor sequence-mediated conjunction. In some embodiments, the target gene is outside the anchor sequence-mediated conjunction. In some embodiments, the target gene is inside and outside the anchor sequence-mediated conjunction. In some embodiments, the composition physically disrupts formation of the anchor sequence-mediated conjunction, e.g., composition is both targeting and effector, e.g., membrane translocating polypeptide. In some embodiments, the composition comprises a targeting moiety (e.g., gRNA, membrane translocating polypeptide) that binds the anchor sequence, operably linked to an effector moiety that modulates the formation of a conjunction mediated by the anchor sequence. In some embodiments, the effector moiety is a chemical, e.g., a chemical that modulates a cytosine (C) or an adenine(A) (e.g., Na bisulfite, ammonium bisulfite). In some embodiments, the effector moiety has enzymatic activity (methyl transferase, demethylase, nuclease (e.g., Cas9), deaminase). In some embodiments, the effector moiety sterically hinders formation of the anchor sequence-mediated conjunction, e.g., membrane translocating polypeptide and/or nanoparticle.

In some embodiments, the composition or method described herein further comprises at least one polypeptide with each comprising at least one sequence of $ABX^nC$, where A is selected from a hydrophobic amino acid or an amide containing backbone, e.g., aminoethyl-glycine, with a nucleic acid side chain; B and C may be the same or different, and are each independently selected from arginine, asparagine, glutamine, lysine, and analogs thereof; X is each independently a hydrophobic amino acid or X is each independently an amide containing backbone, e.g., aminoethyl-glycine, with a nucleic acid side chain; and n is an integer from 1 to 4, wherein the polypeptide hybridizes a nucleic acid sequence within an anchor sequence-mediated conjunction (e.g., anchor sequence of an anchor sequence-mediated conjunction, e.g., CTCF binding motif, BORIS binding motif, cohesin binding motif, USF1 binding motif, YY1 binding motif, TATA-box, ZNF143 binding motif, etc).

The composition and method as described in various embodiments of the above aspect may be utilized in any other aspect delineated herein.

In one aspect, the disclosure includes a method of modulating expression of a target gene in an anchor sequence-mediated conjunction comprising targeting a sequence outside of or that is not part of the target gene or its associated transcriptional control sequences that influence transcription of the gene, such as targeting an anchor sequence, thereby modulating the gene's expression.

In one aspect, the disclosure includes a method of modulating transcription of a target gene comprising targeting a sequence non-contiguous with the target gene or its associated transcriptional control sequences that influence transcription of the target gene, such as targeting an anchor sequence, to alter formation of the anchor sequence-mediated conjunction.

In some embodiments, the method comprises an anchor sequence-mediated conjunction with one or more associated genes and one or more transcriptional control sequences within the anchor sequence-mediated conjunction. In some embodiments, the anchor sequence-mediated conjunction comprises one or more associated genes and one or more transcriptional control sequences reside outside the anchor sequence-mediated conjunction. In some embodiments, the anchor sequence-mediated conjunction comprises one or more associated genes and one or more transcriptional control sequences reside inside and outside, at least partially, the anchor sequence-mediated conjunction. For example, one or more repressive signals may be outside the anchor sequence-mediated conjunction and one or more enhancing sequences and the target gene are inside the anchor sequence-mediated conjunction. In another example, one or more enhancing sequences reside inside and outside the anchor sequence-mediated conjunction.

In some embodiments, the target gene is non-contiguous with one or more anchor sequences. In some embodiments where the gene is non-contiguous with the anchor sequence, the gene may be separated from the anchor sequence by about 10 0 bp to about 500 Mb, about 500 bp to about 200 Mb, about 1 kb to about 100 Mb, about 25 kb to about 50 Mb, about 50 kb to about 1 Mb, about 100 kb to about 750 kb, about 150 kb to about 500 kb, or about 175 kb to about 500 kb. In some embodiments, the gene is separated from the anchor sequence by about 100 bp, 300 bp, 500 bp, 600 bp, 700 bp, 800 bp, 900 bp, 1 kb, 5 kb, 10 kb, 15 kb, 20 kb, 25 kb, 30 kb, 35 kb, 40 kb, 45 kb, 50 kb, 55 kb, 60 kb, 65 kb, 70 kb, 75 kb, 80 kb, 85 kb, 90 kb, 95 kb, 100 kb, 125 kb, 150 kb, 175 kb, 200 kb, 225 kb, 250 kb, 275 kb, 300 kb, 350 kb, 400 kb, 500 kb, 600 kb, 700 kb, 800 kb, 900 kb, 1 Mb, 2 Mb, 3 Mb, 4 Mb, 5 Mb, 6 Mb, 7 Mb, 8 Mb, 9 Mb, 10 Mb, 15 Mb, 20 Mb, 25 Mb, 50 Mb, 75 Mb, 100 Mb, 200 Mb, 300 Mb, 400 Mb, 500 Mb, or any size therebetween.

In some embodiments, the anchor sequence-mediated conjunction comprises the target gene and is associated with one or more transcriptional control sequences, e.g., silencing/repressive sequences and enhancing sequences. In some embodiments, the anchor sequence-mediated conjunction comprises one or more, e.g., 2, 3, 4, 5, or more, genes. In some embodiments, the anchor sequence-mediated conjunction is associated with one or more, e.g., 2, 3, 4, 5, or more, transcriptional control sequences.

In some embodiments, the target gene is non-contiguous with one or more transcriptional control sequences. In some embodiments where the gene is non-contiguous with the transcriptional control sequence, the gene may be separated from the transcriptional control sequence by about 100 bp to about 500 Mb, about 500 bp to about 200 Mb, about 1 kb to about 100 Mb, about 25 kb to about 50 Mb, about 50 kb to about 1 Mb, about 100 kb to about 750 kb, about 150 kb to about 500 kb, or about 175 kb to about 500 kb. In some embodiments, the gene is separated from the transcriptional control sequence by about 100 bp, 300 bp, 500 bp, 600 bp, 700 bp, 800 bp, 900 bp, 1 kb, 5 kb, 10 kb, 15 kb, 20 kb, 25 kb, 30 kb, 35 kb, 40 kb, 45 kb, 50 kb, 55 kb, 60 kb, 65 kb, 70 kb, 75 kb, 80 kb, 85 kb, 90 kb, 95 kb, 100 kb, 125 kb, 150 kb, 175 kb, 200 kb, 225 kb, 250 kb, 275 kb, 300 kb, 350 kb, 400 kb, 500 kb, 600 kb, 700 kb, 800 kb, 900 kb, 1 Mb, 2 Mb, 3 Mb, 4 Mb, 5 Mb, 6 Mb, 7 Mb, 8 Mb, 9 Mb, 10 Mb, 15 Mb, 20 Mb, 25 Mb, 50 Mb, 75 Mb, 100 Mb, 200 Mb, 300 Mb, 400 Mb, 500 Mb, or any size therebetween.

In one aspect, the disclosure includes a pharmaceutical composition comprising (a) a targeting moiety and (b) a DNA sequence, e.g., comprising an anchor sequence.

In one aspect, the disclosure includes a composition comprising a targeting moiety that binds an anchor sequence of an anchor sequence-mediated conjunction and alters formation of the anchor sequence-mediated conjunction (e.g., alters affinity of the anchor sequence to a conjunction nucleating molecule, e.g., at least 10%, 15%, 20%, 25%, 30%, 35%, 40%, 45%, 50%, 55%, 60%, 65%, 70%, 75%, 80%, 85%, 90%, 95%, or more.

In one aspect, the disclosure includes a protein comprising a domain, e.g., an enzyme domain, that acts on DNA (e.g., a nuclease domain, e.g., a Cas9 domain, e.g., a dCas9 domain; a DNA methyltransferase, a demethylase, a deaminase), in combination with at least one guide RNA (gRNA) or antisense DNA oligonucleotide that targets the protein to an anchor sequence of a target anchor sequence-mediated conjunction, wherein the composition is effective to alter, in a human cell, the target anchor sequence-mediated conjunction.

In some embodiments, the enzyme domain is a Cas9 or a dCas9. In some embodiments, the protein comprises two enzyme domains, e.g., a dCas9 and a methylase or demethylase domain.

The composition as described in various embodiments of the above aspect may be utilized in any other aspect delineated herein.

In one aspect, the disclosure includes a composition for introducing a targeted alteration to an anchor sequence-mediated conjunction to modulate transcription of a nucleic acid sequence, the composition comprising a targeting moiety that binds the anchor sequence.

In some embodiments, the targeting moiety includes a sequence targeting polypeptide, such as an enzyme, e.g., Cas9. In some embodiments, the targeting moiety includes a fusion of a sequence targeting polypeptide and a conjunction nucleating molecule, e.g. a fusion of dCas9 and a conjunction nucleating molecule. In some more embodiments, the targeting moiety further includes a guide RNA or nucleic acid encoding the guide RNA. In some additional embodiments, the targeting moiety targets one or more nucleotides, such as through CRISPR, TALEN, dCas9, recombination, transposon, etc., of an anchor sequence within the anchor sequence-mediated conjunction for substitution, addition or deletion. In some embodiments, the targeting moiety targets one or more DNA methylation sites within the anchor sequence-mediated conjunction. In some more embodiments, the targeting moiety introduces at least one of the following: at least one exogenous anchor sequence; an alteration in at least one conjunction nucleating molecule binding site, such as by altering binding affinity for the conjunction nucleating molecule; a change in an orientation of at least one common nucleotide sequence, such as a CTCF binding motif, YY1 binding motif, ZNF143 binding motif, or other binding motif mentioned herein; and a substitution, addition or deletion in at least one anchor sequence, such as a CTCF binding motif, YY1 binding motif, ZNF143 binding motif, or other binding motif mentioned herein.

In certain embodiments, the composition modifies a chromatin structure.

In some embodiments, the composition comprises a vector comprising the targeting moiety, such as a viral vector, e.g., a lentiviral vector.

In certain embodiments, the targeted alteration alters at least one of a binding site for a conjunction nucleating molecule, such as the binding affinity for an anchor sequence within the anchor sequence-mediated conjunction, an alternative splicing site, and a binding site for a non-translated RNA.

In some embodiments, the disclosure includes a pharmaceutical composition comprising the composition described herein.

The composition as described in various embodiments of the above aspect may be utilized in any other aspect delineated herein.

In one aspect, the disclosure includes a composition comprising a synthetic conjunction nucleating molecule with a selected binding affinity for an anchor sequence within a target anchor sequence-mediated conjunction.

In some embodiments, the binding affinity may be at least 10%, 20%, 25%, 30%, 35%, 40%, 45%, 50%, 55%, 60%, 65%, 70%, 75%, 80%, 85%, 90%, 95%, or higher or lower than the affinity of an endogenous conjunction nucleating molecule that associates with the target anchor sequence. In some embodiments, the synthetic conjunction nucleating molecule has between about 30-90%, about 30-85%, about 30-80%, about 30-70%, about 50-80%, about 50-90% amino acid sequence identity to the endogenous conjunction nucleating molecule.

In some embodiments, the conjunction nucleating molecule disrupts, such as through competitive binding, the binding of an endogenous conjunction nucleating molecule to its binding site. In some more embodiments, the conjunction nucleating molecule is engineered to bind a target sequence.

In some embodiments, the composition further includes a carrier, such as a polymeric carrier or targeting moiety, e.g., a liposome, peptide, aptamer, or combination therein.

In certain embodiments, the disclosure includes a method of preparing the conjunction nucleating molecule with selected binding affinity.

The composition as described in various embodiments of the above aspect may be utilized in any other aspect delineated herein.

In one aspect, the disclosure includes a composition comprising a targeting moiety that binds a specific anchor sequence-mediated conjunction to alter a topology of the anchor sequence-mediated conjunction.

In some embodiments, the targeting moiety is a nucleic acid sequence, a protein, protein fusion, or a membrane translocating polypeptide. In some embodiments, the nucleic acid sequence is selected from the group consisting of a gRNA, and a sequence complementary or a sequence comprising at least 80%, at least 90%, at least 95%, at least 96%, at least 97%, at least 98%, at least 99% complementary sequence to an anchor sequence. In some embodiments, the nucleic acid sequence comprises a sequence complementary or a sequence comprising at least 80%, at least 90%, at least 95%, at least 96%, at least 97%, at least 98%, at least 99% complementary sequence to a binding motif for a conjunction nucleating molecule or consensus sequence. In some embodiments, the protein is a conjunction nucleating molecule, e.g., CTCF, cohesin, USF1, YY1, TAF3, ZNF143, or another polypeptide, a dominant negative conjunction nucleating molecule, a protein with a DNA-binding sequence, e.g., transcription factor, a fusion of a sequence targeting polypeptide and a conjunction nucleating molecule. In some embodiments, the membrane translocating polypeptide comprises at least one sequence of $ABX^nC$, wherein A is selected from a hydrophobic amino acid or an amide containing backbone, e.g., aminoethyl-glycine, with a nucleic acid side chain; B and C may be the same or different, and are independently selected from arginine, asparagine, glutamine, lysine, and analogs thereof; X is each independently a hydrophobic amino acid or X is each independently an amide containing backbone, e.g., aminoethyl-glycine, with a nucleic acid side chain; and n is an integer from 1 to 4. In some embodiments, the protein is selected from the group consisting of epigenetic enzymes (DNA methylases (e.g., DNMT3a, DNMT3b, DNMTL), DNA demethylases (e.g., the TET family), histone methyltransferases, histone deacetylase (e.g., HDAC1, HDAC2, HDAC3), sirtuin 1, 2, 3, 4, 5, 6, or 7, lysine-specific histone demethylase 1 (LSD1), histone-lysine-N-methyltransferase (Setdb1), euchromatic histone-lysine N-methyltransferase 2 (G9a), histone-lysine N-methyltransferase (SUV39H1), enhancer of zeste homolog 2 (EZH2), viral lysine methyltransferase (vSET), histone methyltransferase (SET2), and protein-lysine N-methyltransferase (SMYD2)), a fusion of a sequence targeting polypeptide and a conjunction nucleating molecule.

In some embodiments, the targeting moiety comprises a sequence targeting polypeptide, e.g. Cas9, a fusion of a sequence targeting polypeptide, e.g. a fusion of dCas9 and a conjunction nucleating molecule, or a conjunction nucleating molecule. In some embodiments, the targeting moiety comprises a guide RNA or nucleic acid encoding the guide RNA. In some embodiments, the targeting moiety introduces a targeted alteration into the anchor sequence-mediated conjunction to modulate transcription, in a human cell, of a gene in the anchor sequence-mediated conjunction.

In some embodiments, the targeting moiety binds an anchor sequence of the anchor sequence-mediated conjunction and the targeting moiety introduces a targeted alteration into the anchor sequence to modulate transcription, in a human cell, of a gene in the anchor sequence-mediated conjunction. In some embodiments, the targeted alteration comprises at least one of a substitution, addition or deletion of one or more nucleotides, e.g., in the anchor sequence. In some embodiments, the targeted alteration comprises at least one of a substitution, addition or deletion of one or more nucleotides in a anchor sequence, e.g., a binding motif for a conjunction nucleating molecule, such as one described herein. In some embodiments, the targeted alteration comprises an opposite orientation of at least one common nucleotide sequence, e.g., a binding motif for a conjunction nucleating molecule. In some embodiments, the targeted alteration comprises a non-naturally occurring anchor sequence to form or disrupt the anchor sequence-mediated conjunction.

The composition as described in various embodiments of the above aspect may be utilized in any other aspect delineated herein.

In one aspect, the disclosure includes a composition comprising a protein comprising a first polypeptide comprising a Cas or modified Cas protein domain and a second polypeptide comprising a polypeptide having DNA methyltransferase activity [or associated with demethylation or deaminase activity], in combination with at least one guide RNA (gRNA) or antisense DNA oligonucleotide that targets the protein to an anchor sequence of a target anchor sequence-mediated conjunction, wherein the system is effective to alter, in a human cell, the target anchor sequence-mediated conjunction.

In some embodiments, the composition is effective to alter, in a human cell, the target anchor sequence-mediated conjunction.

The composition as described in various embodiments of the above aspect may be utilized in any other aspect delineated herein.

In one aspect, the disclosure includes a pharmaceutical composition comprising a Cas protein and at least one guide RNA (gRNA) that targets the Cas protein to an anchor sequence of a target anchor sequence-mediated conjunction, wherein the Cas protein is effective to cause a mutation of the target anchor sequence that decreases the formation of an anchor sequence-mediated conjunction associated with the target anchor sequence.

In one aspect, the disclosure includes a synthetic nucleic acid comprising a plurality of anchor sequences, a gene sequence, and a transcriptional control sequence.

In some embodiments, the gene sequence and the transcriptional control sequence are between the plurality of anchor sequences. In some embodiments, the nucleic acid comprises, in order, (a) an anchor sequence, a gene sequence, a transcriptional control sequence, and an anchor sequence or (b) an anchor sequence, a transcriptional control sequence, a gene sequence, and an anchor sequence.

In some embodiments, the sequences are separated by linker sequences. In some embodiments, the anchor sequences are between 7-100 nts, 10-100 nts, 10-80 nts, 10-70 nts, 10-60 nts, 10-50 nts, or 20-80 nts. In some embodiments, the nucleic acid is between 3,000-50,000 bp, 3,000-40,000 bp, 3,000-30,000 bp, 3,000-20,000 bp, 3,000-15,000 bp, 3,000-12,000 bp, 3,000-10,000 bp, 3,000-8,000 bp, 5,000-30,000 bp, 5,000-20,000 bp, 5,000-15,000 bp, 5,000-12,000 bp, 5,000-10,000 bp or any range therebetween.

In some embodiments, a vector comprises the nucleic acid described herein.

In some embodiments, a cell comprises the nucleic acid described herein.

In some embodiments, a pharmaceutical composition comprises the nucleic acid described herein.

In some embodiments, a method of modulating expression of a gene by administering a composition comprises the nucleic acid described herein.

The nucleic acid as described in various embodiments of the above aspect may be utilized in any other aspect delineated herein.

In one aspect, the disclosure includes a kit comprising (a) a nucleic acid encoding a protein comprising a first polypeptide domain that comprises a Cas or modified Cas protein and a second polypeptide domain that comprises a polypeptide having DNA methyltransferase activity [or associated with demethylation or deaminase activity]; and (b) at least one guide RNA (gRNA) for targeting the protein to an anchor sequence of a target anchor sequence-mediated conjunction in a target cell.

In some embodiments, (a) and (b) are provided in the same vector, e.g., a plasmid, an AAV vector, an AAV9 vector. In some embodiments, (a) and (b) are provided in separate vectors.

The kit as described in various embodiments of the above aspect may be utilized in any other aspect delineated herein.

In one aspect, the disclosure includes a method of preparing a conjunction nucleating molecule with selected binding affinity.

In one aspect, the disclosure includes a method of (altering gene expression/altering an anchor sequence-mediated conjunction) in a mammalian subject comprising administering to the subject (separately or in the same pharmaceutical composition) (i) a protein comprising a first polypeptide domain that comprises a Cas or modified Cas protein and a second polypeptide domain that comprises a polypeptide having DNA methyltransferase activity [or associated with demethylation or deaminase activity] or (ii) a nucleic acid encoding a protein comprising a first polypeptide domain that comprises a Cas or modified Cas protein and a second polypeptide domain that comprises a polypeptide has a role in DNA methyltransferase activity [or associated with demethylation or deaminase activity], and at least one guide RNA (gRNA) that targets an anchor sequence of an anchor sequence-mediated conjunction.

In some embodiments, the anchor sequence is or comprises a CTCF binding motif, such as SEQ ID NO:1 or SEQ ID NO:2. In some embodiments, the anchor sequence is or comprises a CTCF binding motif associated with a target disease gene.

In some embodiments, the Cas protein is dCas9; dCas9 is human codon optimized. In some embodiments, the methyltransferase is a DNMT family methyltransferase. In some embodiments, the polypeptide is a TET family enzyme. In some embodiments, the protein has a linker between the first and second polypeptide.

In some embodiments, the gRNAs are selected from gRNAs for different diseases.

The method as described in various embodiments of the above aspect may be utilized in any other aspect delineated herein.

In one aspect, the disclosure includes a method of modifying a chromatin structure, such as a two-dimensional structure, comprising altering a topology of an anchor sequence-mediated conjunction to modulate transcription of a nucleic acid sequence. The altered topology of the anchor sequence-mediated conjunction, such as a loop, modulates transcription of the nucleic acid sequence.

In another aspect, the disclosure includes a method of modifying a chromatin structure, such as a two-dimensional structure, comprising altering a topology of a plurality of anchor sequence-mediated conjunctions to modulate transcription of a nucleic acid sequence. The altered topology of the plurality of anchor sequence-mediated conjunctions, such as multiple loops, modulates transcription of the nucleic acid sequence.

In another aspect, the disclosure includes a method of modulating transcription of a nucleic acid sequence comprising altering an anchor sequence-mediated conjunction, such as a loop, that influences transcription of a nucleic acid sequence. The anchor sequence-mediated conjunction modulates transcription of the nucleic acid sequence.

In certain embodiments, altering the anchor sequence-mediated conjunction modifies a chromatin structure. For example, modifying the chromatin structure by substituting, adding or deleting one or more nucleotides within an anchor sequence of the anchor sequence-mediated conjunction modifies the chromatin structure.

In various embodiments of the above aspects or any other aspect of the disclosure delineated herein, the topology is altered by substituting, adding or deleting one or more nucleotides of an anchor sequence within the anchor sequence-mediated conjunction. For example, the one or more nucleotides substituted, added or deleted may be within at least one anchor sequence, such as a binding motif for a conjunction nucleating molecule.

In some embodiments, the topology is altered by at least one of the following: modulating DNA methylation at one or more sites within the anchor sequence-mediated conjunction; changing an orientation of at least one common nucleotide sequence, such as a binding motif for a conjunction nucleating molecule; altering a spatial separation within the anchor sequence-mediated conjunction; altering a free energy of rotation within the anchor sequence-mediated conjunction; and altering a positional degree of freedom within the anchor sequence-mediated conjunction.

In some additional embodiments, the topology is altered by any one or more of the following:

disrupting the anchor sequence-mediated conjunction, forming a non-naturally occurring anchor sequence-mediated conjunction, forming a plurality of non-naturally occurring anchor sequence-mediated conjunctions, and introducing an exogenous anchor sequence.

In certain embodiments, the topology is altered to result in a modulation, e.g., stable, of transcription, such as a modulation that persists for at least about 1 hr to about 30 days, or at least about 2 hrs, 6 hrs, 12 hrs, 18 hrs, 24 hrs, 2 days, 3, days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, or longer or any time therebetween.

In certain embodiments, the topology is altered to result in a modulation, e.g., transient, of transcription, such as a modulation that persists for no more than about 30 mins to about 7 days, or no more than about 1 hr, 2 hrs, 3 hrs, 4 hrs, 5 hrs, 6 hrs, 7 hrs, 8 hrs, 9 hrs, 10 hrs, 11 hrs, 12 hrs, 13 hrs, 14 hrs, 15 hrs, 16 hrs, 17 hrs, 18 hrs, 19 hrs, 20 hrs, 21 hrs, 22 hrs, 24 hrs, 36 hrs, 48 hrs, 60 hrs, 72 hrs, 4 days, 5 days, 6 days, 7 days, or any time therebetween.

In some embodiments, the method further includes modulating a conjunction nucleating molecule, such as a binding affinity for an anchor sequence within the anchor sequence-mediated conjunction, that interacts with the anchor sequence-mediated conjunction.

In certain embodiments, the anchor sequence-mediated conjunction includes at least a first anchor sequence and a second anchor sequence. In one embodiment, the anchor sequence-mediated conjunction is mediated by a first conjunction nucleating molecule bound to the first anchor sequence, a second conjunction nucleating molecule bound to the second anchor sequence, and an association between the first and second conjunction nucleating molecules. In another embodiment, the first or second conjunction nucleating molecule has a binding affinity for the anchor sequence greater than or less than a reference value, such as a binding affinity for the anchor sequence in the absence of the alteration.

In some embodiments, the second anchor sequence is non-contiguous with the first anchor sequence. In one embodiment, the anchor sequence-mediated conjunction is mediated by a first conjunction nucleating molecule bound to the first anchor sequence, a second conjunction nucleating molecule bound to the non-contiguous second anchor sequence, and an association between the first and second conjunction nucleating molecules. In another embodiment, the first or second conjunction nucleating molecule has a binding affinity for the anchor sequence greater than or less than a reference value, such as the binding affinity for the anchor sequence in the absence of the alteration.

In some embodiments where the anchor sequences are non-contiguous with one another, the first anchor sequence is separated from the second anchor sequence by about 500 bp to about 500 Mb, about 750 bp to about 200 Mb, about 1 kb to about 100 Mb, about 25 kb to about 50 Mb, about 50 kb to about 1 Mb, about 100 kb to about 750 kb, about 150 kb to about 500 kb, or about 175 kb to about 500 kb. In some embodiments, the first anchor sequence is separated from the second anchor sequence by about 500 bp, 600 bp, 700 bp, 800 bp, 900 bp, 1 kb, 5 kb, 10 kb, 15 kb, 20 kb, 25 kb, 30 kb, 35 kb, 40 kb, 45 kb, 50 kb, 55 kb, 60 kb, 65 kb, 70 kb, 75 kb, 80 kb, 85 kb, 90 kb, 95 kb, 100 kb, 125 kb, 150 kb, 175 kb, 200 kb, 225 kb, 250 kb, 275 kb, 300 kb, 350 kb, 400 kb, 500 kb, 600 kb, 700 kb, 800 kb, 900 kb, 1 Mb, 2 Mb, 3 Mb, 4 Mb, 5 Mb, 6 Mb, 7 Mb, 8 Mb, 9 Mb, 10 Mb, 15 Mb, 20 Mb, 25 Mb, 50 Mb, 75 Mb, 100 Mb, 200 Mb, 300 Mb, 400 Mb, 500 Mb, or any size therebetween.

In certain embodiments, the first anchor sequence and second anchor sequence each includes a common nucleotide sequence, such as a binding motif for a conjunction nucleating molecule, such as one described herein. In some embodiments, the first anchor sequence and second anchor sequence include different sequences, such as the first anchor sequence comprises a binding motif for a conjunction nucleating molecule and the second anchor sequence comprises an anchor sequence a binding motif for another molecule, e.g., another conjunction nucleating molecule.

In some embodiments, the anchor sequence-mediated conjunction includes a plurality of anchor sequences. In one embodiment, at least one of anchor sequences includes a CTCF binding motif.

In some more embodiments, the anchor sequence-mediated conjunction comprises a loop, such as an intra-chromosomal loop. In one embodiment, the loop includes a first anchor sequence, a nucleic acid sequence, a transcriptional control sequence, such as an enhancing or silencing sequence, and a second anchor sequence. In another embodiment, the loop includes, in order, a first anchor sequence, a transcriptional control sequence, and a second anchor sequence; or a first anchor sequence, a nucleic acid sequence, and a second anchor sequence. In yet another embodiment, either one or both of the nucleic acid sequence and the transcriptional control sequence is located within or outside the loop.

In certain embodiments, the anchor sequence-mediated conjunction has a plurality of loops. In one embodiment, the anchor sequence-mediated conjunction includes the plurality of loops, and the anchor sequence-mediated conjunction includes at least one of an anchor sequence, a nucleic acid sequence, and a transcriptional control sequence in one or more of the loops.

In some embodiments, transcription of the nucleic acid sequence is modulated, such as transcription of a target nucleic acid sequence, as compared with a reference value, e.g., transcription of the target sequence in the absence of the altered anchor sequence-mediated conjunction.

In some embodiments, transcription is activated by inclusion of an activating loop. In one embodiment, the anchor sequence-mediated conjunction includes a transcriptional control sequence, such as an enhancing sequence, that increases transcription of the nucleic acid sequence. In some more embodiments, transcription is activated by exclusion of a repressive loop. In one embodiment, the anchor sequence-mediated conjunction excludes a transcriptional control sequence, such as a silencing sequence, that decreases transcription of the nucleic acid sequence.

In some embodiments, transcription is repressed by inclusion of a repressive loop. In one embodiment, the anchor sequence-mediated conjunction includes a transcriptional control sequence such as a silencing sequence, that decreases transcription of the nucleic acid sequence. In some more embodiments, transcription is repressed by exclusion of an activating loop. In one embodiment, the anchor sequence-mediated conjunction excludes a transcriptional control sequence, such as an enhancing sequence, that increases transcription of the nucleic acid sequence.

In certain embodiments, the anchor sequence-mediated conjunction is altered in vivo, such as in a subject, e.g., a human subject. In some embodiments, the methods delineated herein further include administering a targeting moiety selected from at least one of an exogenous conjunction nucleating molecule, a nucleic acid encoding the conjunction nucleating molecule, and a fusion of a sequence targeting polypeptide and a conjunction nucleating molecule to the subject. In one embodiment, the conjunction nucleating molecule disrupts, such as through competitive binding, the binding of an endogenous conjunction nucleating molecule to its binding site. In another embodiment, the targeting moiety includes a sequence targeting polypeptide, such as an enzyme, e.g., Cas9. In yet another embodiment, the targeting moiety further includes a conjunction nucleating molecule. In still another embodiment, the targeting moiety further includes a guide RNA or nucleic acid encoding the guide RNA.

In some embodiments, the administration includes administering a vector, such as a viral vector, e.g., lentiviral vector, that comprises the nucleic acid encoding the targeting moiety, e.g., the conjunction nucleating molecule. In some more embodiments, the administration includes administering a formulation, such as formulated in a polymeric carrier, e.g., a liposome.

In one aspect, the disclosure includes an engineered cell comprising a targeted alteration in an anchor sequence-mediated conjunction.

In another aspect, the disclosure includes an engineered nucleic acid sequence comprising an anchor sequence-mediated conjunction with a targeted alteration.

In various embodiments of the above aspects or any other aspect of the disclosure delineated herein, the targeted alteration includes any one or more of the following: a substitution, addition or deletion of one or more nucleotides of an anchor sequence within the anchor sequence-mediated conjunction; a substitution, addition or deletion of one or more nucleotides in at least one anchor sequence, e.g., a CTCF binding motif; an alteration of one or more DNA methylation sites within the anchor sequence-mediated conjunction; and at least one exogenous anchor sequence.

In some embodiments, the targeted alteration alters at least one conjunction nucleating molecule binding site, such as altering its binding affinity for the conjunction nucleating molecule. In some more embodiments, the targeted alteration changes an orientation of at least one common nucleotide sequence, e.g., a CTCF binding motif; disrupts the anchor sequence-mediated conjunction; and forms a non-naturally occurring anchor sequence-mediated conjunction.

In certain embodiments, the anchor sequence-mediated conjunction includes at least a first anchor sequence and a second anchor sequence. In one embodiment, the anchor sequence-mediated conjunction is mediated by a first conjunction nucleating molecule bound to the first anchor sequence, a second conjunction nucleating molecule bound to the second anchor sequence, and an association between the first and second conjunction nucleating molecules. In another embodiment, the first or second conjunction nucleating molecule has a binding affinity for the anchor sequence greater than or less than a reference value, such as a binding affinity for the anchor sequence in the absence of the alteration.

In some embodiments, the second anchor sequence is non-contiguous with the first anchor sequence. In one embodiment, the anchor sequence-mediated conjunction is mediated by a first conjunction nucleating molecule bound to the first anchor sequence, a second conjunction nucleating molecule bound to the non-contiguous second anchor sequence, and an association between the first and second conjunction nucleating molecules. In another embodiment, the first or second conjunction nucleating molecule has a binding affinity for the anchor sequence greater than or less than a reference value, such as the binding affinity for the anchor sequence in the absence of the alteration.

In some embodiments where the anchor sequences are non-contiguous with one another, the first anchor sequence is separated from the second anchor sequence by about 500 bp to about 500 Mb, about 750 bp to about 200 Mb, about 1 kb to about 100 Mb, about 25 kb to about 50 Mb, about 50 kb to about 1 Mb, about 100 kb to about 750 kb, about 150 kb to about 500 kb, or about 175 kb to about 500 kb. In some embodiments, the first anchor sequence is separated from the second anchor sequence by about 500 bp, 600 bp, 700 bp, 800 bp, 900 bp, 1 kb, 5 kb, 10 kb, 15 kb, 20 kb, 25 kb, 30 kb, 35 kb, 40 kb, 45 kb, 50 kb, 55 kb, 60 kb, 65 kb, 70 kb, 75 kb, 80 kb, 85 kb, 90 kb, 95 kb, 100 kb, 125 kb, 150 kb, 175 kb, 200 kb, 225 kb, 250 kb, 275 kb, 300 kb, 350 kb, 400 kb, 500 kb, 600 kb, 700 kb, 800 kb, 900 kb, 1 Mb, 2 Mb, 3 Mb, 4 Mb, 5 Mb, 6 Mb, 7 Mb, 8 Mb, 9 Mb, 10 Mb, 15 Mb, 20 Mb, 25 Mb, 50 Mb, 75 Mb, 100 Mb, 200 Mb, 300 Mb, 400 Mb, 500 Mb, or any size therebetween.

In certain embodiments, the first anchor sequence and second anchor sequence each includes a common nucleotide sequence, such as a CTCF binding motif. In some embodiments, the first anchor sequence and second anchor sequence include different sequences, such as the first anchor sequence comprises a CTCF binding motif and the second anchor sequence comprises an anchor sequence other than a CTCF binding motif.

In some embodiments, the anchor sequence-mediated conjunction includes a plurality of anchor sequences. In one embodiment, at least one of anchor sequences includes a CTCF binding motif.

In some more embodiments, the anchor sequence-mediated conjunction comprises a loop, such as an intra-chromosomal loop. In one embodiment, the loop includes a first anchor sequence, a nucleic acid sequence, a transcriptional control sequence, such as an enhancing or silencing sequence, and a second anchor sequence. In another embodiment, the loop includes, in order, a first anchor sequence, a transcriptional control sequence, and a second anchor sequence; or a first anchor sequence, a nucleic acid sequence, and a second anchor sequence. In yet another embodiment, either one or both of the nucleic acid sequence and the transcriptional control sequence is located within or outside the loop.

In certain embodiments, the anchor sequence-mediated conjunction has a plurality of loops. In one embodiment, the anchor sequence-mediated conjunction includes the plurality of loops, and the anchor sequence-mediated conjunction includes at least one of an anchor sequence, a nucleic acid sequence, and a transcriptional control sequence in one or more of the loops.

In some embodiments, transcription of the nucleic acid sequence is modulated, such as transcription of a target nucleic acid sequence, as compared with a reference value, e.g., transcription of the target sequence in the absence of the altered anchor sequence-mediated conjunction.

In some embodiments, transcription is activated by inclusion of an activating loop. In one embodiment, the anchor sequence-mediated conjunction includes a transcriptional control sequence, such as an enhancing sequence, that increases transcription of the nucleic acid sequence. In some more embodiments, transcription is activated by exclusion of a repressive loop. In one embodiment, the anchor sequence-mediated conjunction excludes a transcriptional control sequence, such as a silencing sequence, that decreases transcription of the nucleic acid sequence.

In some embodiments, transcription is repressed by inclusion of a repressive loop. In one embodiment, the anchor sequence-mediated conjunction includes a transcriptional control sequence such as a silencing sequence, that decreases transcription of the nucleic acid sequence. In some more embodiments, transcription is repressed by exclusion of an activating loop. In one embodiment, the anchor sequence-mediated conjunction excludes a transcriptional control sequence, such as an enhancing sequence, that increases transcription of the nucleic acid sequence.

In some embodiments, the disclosure includes a pharmaceutical composition with the engineered cell described herein, or the engineered nucleic acid sequence described herein. In some more embodiments, the disclosure includes a plurality of cells with the engineered cell described herein. In some additional embodiments, the disclosure includes a vector with the engineered nucleic acid sequence described herein.

In one aspect, the disclosure includes a method of treating a disease or condition comprising administering a targeting moiety selected from at least one of an exogenous conjunction nucleating molecule, a nucleic acid encoding the conjunction nucleating molecule, and a fusion of a sequence targeting polypeptide and a conjunction nucleating molecule to a subject.

In certain embodiments, the conjunction nucleating molecule disrupts, such as through competitive binding, the binding of an endogenous conjunction nucleating molecule to its binding site.

In some embodiments, the targeting moiety includes a sequence targeting polypeptide, such as an enzyme, e.g., Cas9. In some embodiments, the targeting moiety further includes a conjunction nucleating molecule. In some more embodiments, the targeting moiety further includes a guide RNA or nucleic acid encoding the guide RNA. In some additional embodiments, the targeting moiety targets one or more nucleotides, such as through CRISPR, TALEN, dCas9, recombination, transposon, etc., of an anchor sequence within the anchor sequence-mediated conjunction for substitution, addition or deletion. In some embodiments, the targeting moiety targets one or more DNA methylation sites within the anchor sequence-mediated conjunction. In some more embodiments, the targeting moiety introduces at least one of the following: at least one exogenous anchor sequence; an alteration in at least one conjunction nucleating molecule binding site, such as by altering binding affinity for the conjunction nucleating molecule; a change in an orientation of at least one common nucleotide sequence, such as a CTCF binding motif; and a substitution, addition or deletion in at least one anchor sequence, such as a CTCF binding motif.

In certain embodiments, the administration includes administering a vector, e.g., a viral vector, that comprises the nucleic acid encoding the targeting moiety, e.g., the conjunction nucleating molecule. In some more embodiments, the administration includes administering a formulation, e.g., a liposome.

In some embodiments, the disease or condition is selected from the group consisting of cancer, trinucleotide repeats (Huntington's Chorea, Fragile X, all the spinocerebellar ataxias, Friedrich ataxia, myotonic dystrophy and others), an autosomal dominant condition, a disease of an imprinted gene (Prader Willi Syndrome, Angelman Syndrome), a disease of haploinsufficiency, a dominant negative mutation (Severe congenital neutropenia), a viral disease (HIV, HBV, HCV, HPV etc), and an environmentally driven transcriptional-epigenetic alteration (effects from smoking, maternal diet on gene expression).

In one aspect, the disclosure includes a pharmaceutical composition comprising at least one polypeptide, e.g., a membrane translocating polypeptide, with each comprising at least one sequence of $ABX^nC$, where A is selected from a hydrophobic amino acid or an amide containing backbone, e.g., aminoethyl-glycine, with a nucleic acid side chain; B and C may be the same or different, and are each independently selected from arginine, asparagine, glutamine, lysine, and analogs thereof; X is each independently a hydrophobic amino acid or X is each independently an amide containing backbone, e.g., aminoethyl-glycine, with a nucleic acid side chain; and n is an integer from 1 to 4, wherein the polypeptide is capable of hybridizing a nucleic acid sequence within an anchor sequence-mediated conjunction (e.g., anchor sequence of an anchor sequence-mediated conjunction, e.g., CTCF binding motif, BORIS binding motif, cohesin binding motif, USF1 binding motif, YY1 binding motif, TATA-box, ZNF143 binding motif, etc).

The composition as described in various embodiments of the above aspect may be utilized in any other aspect delineated herein. In some embodiments, the targeting moiety of one or more embodiments described herein comprises a membrane translocating polypeptide, e.g., the polypeptide described herein.

In some embodiments, the hydrophobic amino acid is selected from alanine, valine, isoleucine, leucine, methionine, phenylalanine, tyrosine, trytophan, and analogs thereof. In some embodiments, B is selected from arginine or glutamine. In some embodiments, C is arginine. In some embodiments, n is 2.

In some embodiments, the polypeptides have sizes in the range of about 5 to about 50 amino acid units in length.

In some embodiments, the composition comprises two or more polypeptides that are linked to one another. In some embodiments, the polypeptides are linked to one another, e.g., amino acids on one polypeptide are linked with one or more amino acids or a carboxy or amino terminal on another polypeptide, branched polypeptide, or through new peptide bonds, linear polypeptide. In some embodiments, the polypeptides are linked by a linker as described herein.

In some embodiments, the nucleic acid side chain is independently selected from the group consisting of a purine side chain, a pyrimidine side chain, and a nucleic acid analog side chain. In some embodiments, the nucleic acid side chain hybridizes to the heterologous moiety, wherein the heterologous moiety comprises a nucleic acid side chain, e.g., a PNA, or nucleic acid.

In some embodiments, the composition comprises the membrane translocating polypeptide and at least one heterologous moiety. In one embodiment, the heterologous moiety is a conjunction nucleating molecule that interacts with the anchor sequence-mediated conjunction. In another embodiment, the heterologous moiety is a sequence targeting polypeptide, e.g. Cas9. In another embodiment, the heterologous moiety is a guide RNA or nucleic acid encoding the guide RNA.

In some embodiments, the heterologous moiety is selected from the group consisting of a small molecule (e.g., a drug), a peptide (e.g., ligand), and a nucleic acid (e.g., siRNA, DNA, modified RNA, RNA). In another embodiment, the heterologous moiety possesses at least one effector activity selected from the group consisting of modulates a biological activity, binds a regulatory protein, modulates enzymatic activity, modulates substrate binding, modulates receptor activation, modulates protein stability/degradation, and modulates transcript stability/degradation. In another embodiment, the heterologous moiety possesses at least one targeted function selected from the group consisting of modulates a function, modulates a molecule (e.g., enzyme, protein or nucleic acid), and is localized to a specific location. In another embodiment, the heterologous moiety is a tag or label, e.g., cleavable. In another embodiment, the heterologous moiety is selected from the group consisting of an epigenetic modifying agent, epigenetic enzyme, a bicyclic peptide, a transcription factor, a DNA or protein modification enzyme, a DNA-intercalating agent, an efflux pump inhibitor, a nuclear receptor activator or inhibitor, a proteasome inhibitor, a competitive inhibitor for an enzyme, a protein synthesis inhibitor, a nuclease, a protein fragment or domain, a tag or marker, an antigen, an antibody or antibody fragment, a ligand or a receptor, a synthetic or analog peptide from a naturally-bioactive peptide, an anti-microbial peptide, a pore-forming peptide, a targeting or cytotoxic peptide, a degradation or self-destruction peptide, a CRISPR system or component thereof, DNA, RNA, artificial nucleic acids, a nanoparticle, an oligonucleotide aptamer, a peptide aptamer, and an agent with poor pharmacokinetics or pharmacodynamics (PK/PD).

In some embodiments, the composition further comprises two or more heterologous moieties linked, e.g., via a linker or directly, to the polypeptide on amino termini, on carboxy termini, all termini, a combination of some carboxy and some amino termini of the polypeptides, one or more amino acids of the polypeptide, or any combination thereof. In some embodiments, the heterologous moiety is linked, e.g., via a linker or directly, to one of the polypeptides on an amino terminus, a carboxy terminus, both termini, or one or more amino acids of the polypeptide.

In some embodiments, the composition further comprises a linker, e.g., between polypeptides or between the polypeptide and the heterologous moiety. The linker may be a chemical bond, e.g., one or more covalent bonds or non-covalent bonds. In some embodiments, the linker is a peptide linker (e.g., a non $ABX^nC$ polypeptide). Such a linker may be between 2-30 amino acids, or longer. The linker includes flexible, rigid or cleavable linkers described herein.

In some embodiments, the composition modulates DNA methylation at one or more sites within the anchor sequence-mediated conjunction.

In some embodiments, the composition transiently modulates transcription, e.g., a modulation that persists for no more than about 30 mins to about 7 days, or no more than about 1 hr, 2 hrs, 3 hrs, 4 hrs, 5 hrs, 6 hrs, 7 hrs, 8 hrs, 9 hrs, 10 hrs, 11 hrs, 12 hrs, 13 hrs, 14 hrs, 15 hrs, 16 hrs, 17 hrs, 18 hrs, 19 hrs, 20 hrs, 21 hrs, 22 hrs, 24 hrs, 36 hrs, 48 hrs, 60 hrs, 72 hrs, 4 days, 5 days, 6 days, 7 days, or any time therebetween.

In some embodiments, the composition stably modulates transcription, e.g., a modulation that persists for at least about 1 hr to about 30 days, or at least about 2 hrs, 6 hrs, 12 hrs, 18 hrs, 24 hrs, 2 days, 3, days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, or longer or any time therebetween.

In some embodiments, the composition modulates a conjunction nucleating molecule, e.g. a binding affinity for an anchor sequence within the anchor sequence-mediated conjunction, that interacts with the anchor sequence-mediated conjunction.

In some embodiments, the composition disrupts, e.g., by competitive binding, binding of an endogenous conjunction nucleating molecule to its binding site.

In one aspect, the disclosure includes a method of modifying expression of a target gene, comprising altering an anchor sequence-mediated conjunction associated with the target gene, wherein the alteration modulates transcription of the target gene.

In one aspect, the disclosure includes a method of modifying expression of a target gene, comprising administering the composition described herein to a cell, tissue or subject.

In one aspect, the disclosure includes a method of modulating transcription of a nucleic acid sequence comprising administering the composition described herein to alter an anchor sequence-mediated conjunction, e.g., a loop, that modulates transcription of a nucleic acid sequence, wherein the altered anchor sequence-mediated conjunction modulates transcription of the nucleic acid sequence.

The method as described in various embodiments of the above aspect may be utilized in any other aspect delineated herein.

In some embodiments, the composition modulates DNA methylation at one or more sites within the anchor sequence-mediated conjunction.

In some embodiments, altering the anchor sequence-mediated conjunction results in a transient modulation of transcription, e.g., a modulation that persists for no more than about 30 mins to about 7 days, or no more than about 1 hr, 2 hrs, 3 hrs, 4 hrs, 5 hrs, 6 hrs, 7 hrs, 8 hrs, 9 hrs, 10 hrs, 11 hrs, 12 hrs, 13 hrs, 14 hrs, 15 hrs, 16 hrs, 17 hrs, 18 hrs, 19 hrs, 20 hrs, 21 hrs, 22 hrs, 24 hrs, 36 hrs, 48 hrs, 60 hrs, 72 hrs, 4 days, 5 days, 6 days, 7 days, or any time therebetween.

In some embodiments, altering the anchor sequence-mediated conjunction results in a stable modulation of transcription, e.g., a modulation that persists for at least about 1 hr to about 30 days, or at least about 2 hrs, 6 hrs, 12 hrs, 18 hrs, 24 hrs, 2 days, 3, days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, or longer or any time therebetween.

In some embodiments, the composition modulates a conjunction nucleating molecule, e.g. a binding affinity for an anchor sequence within the anchor sequence-mediated conjunction, that interacts with the anchor sequence-mediated conjunction.

In some embodiments, the composition disrupts, e.g., by competitive binding, binding of an endogenous conjunction nucleating molecule to its binding site.

In some embodiments, the heterologous moiety is a sequence targeting polypeptide, e.g. Cas9. In some embodiments, the heterologous moiety is a guide RNA or nucleic acid encoding the guide RNA.

In one aspect, the disclosure includes a method of modulating gene expression comprising providing the composition described herein, e.g., the heterologous moiety inhibits CpG binding, is an endogenous effector, is an exogenous effector, or agonist or antagonist thereof.

In one aspect, the disclosure includes a method of delivering a therapeutic comprising administering the composition described herein to a subject, wherein the heterologous moiety is the therapeutic, and wherein the composition increases intracellular delivery of the therapeutic as compared to the therapeutic alone.

The method as described in various embodiments of the above aspect may be utilized in any other aspect delineated herein.

In some embodiments, the composition is targeted to a specific cell, or a specific tissue. For example, the composition is targeted to an epithelial, connective, muscular, or nervous tissue or cells, or combinations thereof. For example, the composition is targeted to a cell or tissue of a particular organ system, e.g., the cardiovascular system (heart, vasculature); digestive system (esophagus, stomach, liver, gallbladder, pancreas, intestines, colon, rectum and anus); endocrine system (hypothalamus, pituitary gland, pineal body or pineal gland, thyroid, parathyroids, adrenal glands); excretory system (kidneys, ureters, bladder); lymphatic system (lymph, lymph nodes, lymph vessels, tonsils, adenoids, thymus, spleen); integumentary system (skin, hair, nails); muscular system (e.g., skeletal muscle); nervous system (brain, spinal cord, nerves); reproductive system (ovaries, uterus, mammary glands, testes, vas deferens, seminal vesicles, prostate); respiratory system (pharynx, larynx, trachea, bronchi, lungs, diaphragm); skeletal system (bone, cartilage), and combinations thereof. In some embodiments, the composition crosses a blood-brain-barrier, a placental membrane, or a blood-testis barrier.

In some embodiments, the composition is administered systemically. In some embodiments, the administration is non-parenteral and the therapeutic is a parenteral therapeutic.

In some embodiments, the composition has improved PK/PD, e.g., increased pharmacokinetics or pharmacodynamics, such as improved targeting, absorption, or transport (e.g., at least 5%, 10%, 15%, 20%, 30%, 40%, 50%, 60%, 75%, 80%, 90% improved or more) as compared to the therapeutic alone. In some embodiments, the composition has reduced undesirable effects, such as reduced diffusion to non-target location, off-target activity, or toxic metabolism, as compared to the therapeutic alone (e.g., at least 5%, 10%, 15%, 20%, 30%, 40%, 50%, 60%, 75%, 80%, 90% or more reduced, as compared to the therapeutic alone). In some embodiments, the composition increases efficacy and/or decreases toxicity of the therapeutic (e.g., at least 5%, 10%, 15%, 20%, 30%, 40%, 50%, 60%, 75%, 80%, 90% or more) as compared to the therapeutic alone.

In one aspect, the disclosure includes a method of intracellular delivery of a therapeutic comprising contacting a cell with the composition described herein, wherein the heterologous moiety is the therapeutic, and wherein the composition increases intracellular delivery of the therapeutic as compared to the therapeutic alone.

The method as described in various embodiments of the above aspect may be utilized in any other aspect delineated herein.

In some embodiments, the composition has differential PK/PD as compared to the therapeutic alone. For example, the composition exhibits increased or decreased absorption or distribution, metabolism or excretion (e.g., at least 5%, 10%, 15%, 20%, 30%, 40%, 50%, 60%, 75%, 80%, 90% or more increased or decreased), as compared to the therapeutic alone.

In some embodiments, the composition is administered at a dose sufficient to increase intracellular delivery of the therapeutic without significantly increasing endocytosis, e.g., less than about 50%, 40%, 20%, 15%, 10%, 5%, 4%, 3%, 2%, 1%, or any percentage therebetween. In some embodiments, the composition is administered at a dose sufficient to increase intracellular delivery of the therapeutic without significantly increasing calcium influx, e.g., less than about 50%, 40%, 20%, 15%, 10%, 5%, 4%, 3%, 2%, 1%, or any percentage therebetween. In some embodiments, the composition is administered at a dose sufficient to increase intracellular delivery of the therapeutic without significantly increasing endosomal activity, e.g., less than about 50%, 40%, 20%, 15%, 10%, 5%, 4%, 3%, 2%, 1%, or any percentage therebetween.

In one aspect, the disclosure includes a method of modulating transcription of a gene in a cell comprising contacting the cell with the composition described herein, wherein the composition targets the gene and modulates its transcription.

The method as described in various embodiments of the above aspect may be utilized in any other aspect delineated herein.

In some embodiments, the composition is administered in an amount and for a time sufficient to effect intracellular delivery of the therapeutic with decreased off target transcriptional activity compared to the heterologous moiety alone, e.g., without significantly altering off-target transcriptional activity.

In one aspect, the disclosure includes a method of modulating a membrane protein, e.g., such as an ion channel, a cell surface receptor and a synaptic receptor, on a cell comprising contacting the cell with the composition described herein, wherein the composition targets the cell and modulates the membrane protein.

In one aspect, the disclosure includes a method of inducing cell death comprising contacting a cell with the composition described herein, wherein the composition targets the cell and induces apoptosis.

The method as described in various embodiments of the above aspect may be utilized in any other aspect delineated herein.

In some embodiments, the composition targets a cell harboring a viral DNA sequence or a mutation in a gene. In one embodiment, the cell is virally infected. In another embodiment, the cell harbors a genetic mutation. In some embodiments, the composition targets a cell in the early stages of necrosis, e.g., binding the necrotic cell marker.

In one aspect, the disclosure includes a method of increasing bioavailability of a therapeutic comprising administering the composition described herein, wherein the therapeutic is the heterologous moiety.

The method as described in various embodiments of the above aspect may be utilized in any other aspect delineated herein.

In some embodiments, the composition improves (e.g., by at least 5%, 10%, 15%, 20%, 30%, 40%, 50%, 60%, 75%, 80%, 90% or more) at least one PK/PD parameter, such as improved targeting, absorption, or transport, as compared to the therapeutic alone. In some embodiments, the composition reduces (e.g., by at least 5%, 10%, 15%, 20%, 30%, 40%, 50%, 60%, 75%, 80%, 90% or more) at least one unwanted parameter, such as reduced diffusion to non-target location, off-target activity, or toxic metabolism, as compared to the therapeutic alone. In some embodiments, the composition increases efficacy and/or decreases toxicity of the therapeutic as compared to the therapeutic alone.

In one aspect, the disclosure includes a method of treating an acute or chronic infection comprising administering the composition described herein.

The method as described in various embodiments of the above aspect may be utilized in any other aspect delineated herein.

In some embodiments, the composition targets an infected cell harboring a pathogen. In some embodiments, the infection is caused by a pathogen selected from the group consisting of a virus, bacteria, parasite, and a prion. In some embodiments, the composition induces cell death in the infected cell, e.g., the heterologous moiety is an antibacterial, an antiviral, or an antiparasitic therapeutic.

In one aspect, the disclosure includes a method of treating a cancer comprising administering the composition described herein.

The method as described in various embodiments of the above aspect may be utilized in any other aspect delineated herein.

In some embodiments, the heterologous moiety is a therapeutic that modulates gene expression of one or more genes.

In some embodiments, the composition targets a cancer cell harboring a mutation in a gene. In some embodiments, the composition induces cell death in the cancer cell, e.g., the heterologous moiety is a chemotherapeutic agent.

In one aspect, the disclosure includes a method of treating a neurological disease or disorder comprising administering the composition described herein.

The method as described in various embodiments of the above aspect may be utilized in any other aspect delineated herein.

In some embodiments, the composition modulates neuroreceptor activity or activation of a neurotransmitter, neuropeptide, or neuroreceptor.

In some embodiments, the neurological disease or disorder is Dravet's syndrome.

In one aspect, the disclosure includes a method of treating a disease/disorder/condition in a subject comprising administering the composition described herein, wherein the composition modulates transcription to treat the disease/disorder/condition.

The method as described in various embodiments of the above aspect may be utilized in any other aspect delineated herein.

In some embodiments, the disease/disorder/condition is a genetic disease.

In one aspect, the disclosure includes a method of inducing immune tolerance comprising providing the composition described herein, e.g., the heterologous moiety is an antigen.

In one aspect, the disclosure includes a method of altering expression of a target gene in a genome, comprising: administering to the genome a pharmaceutical composition comprising (a) a targeting moiety and (b) a DNA sequence comprising an anchor sequence, wherein the anchor sequence promotes the formation of a conjunction that brings a gene expression factor (an enhancing sequence, a silencing/repressive sequence) into operable linkage with the target gene.

In one aspect, the disclosure includes a system for pharmaceutical use comprising a protein comprising a first polypeptide domain that comprises a Cas or modified Cas protein and a second polypeptide domain that comprises a polypeptide having DNA methyltransferase activity [or associated with demethylation or deaminase activity], in combination with at least one guide RNA (gRNA) or antisense DNA oligonucleotide that targets the protein to an anchor sequence of a target anchor sequence-mediated conjunction, wherein the system is effective to alter, in a human cell, the target anchor sequence-mediated conjunction.

In one aspect, the disclosure includes a system for altering, in a human cell, expression of a target gene, comprising a targeting moiety (e.g., a gRNA, an LDB) that associates with an anchor sequence associated with the target gene, optionally, a heterologous moiety (e.g., an enzyme, e.g., a nuclease or deactivated nuclease (e.g., a Cas9, dCas9), a methylase, a de-methylase, a deaminase) operably linked to the targeting moiety, wherein the system is effective to modulate a conjunction mediated by the anchor sequence and alter expression of the target gene.

The system as described in various embodiments of the above aspect may be utilized in any other aspect delineated herein.

In some embodiments, the targeting moiety and the effector moiety are linked. In some embodiments, the system comprises a synthetic polypeptide comprising the targeting moiety and the heterologous moiety. In some embodiments, the system comprises a nucleic acid vector or vectors encoding at least one of the targeting moiety and the heterologous moiety.

The aspects as described here may be utilized with any one or more of the embodiments delineated herein.

Definitions

The term "anchor sequence" as used herein, refers to a sequence recognized by a conjunction nucleating agent (e.g., a nucleating protein) that binds sufficiently to form an anchor sequence-mediated conjunction, e.g., a loop. In some embodiments, an anchor sequence comprises one or more CTCF binding motifs. In some embodiments, an anchor sequence is not located within a gene coding region. In some embodiments, an anchor sequence is located within an intergenic region. In some embodiments, an anchor sequence is not located within either of an enhancer or a promoter. In some embodiments, an anchor sequence is located at least 400 bp, at least 450 bp, at least 500 bp, at least 550 bp, at least 600 bp, at least 650 bp, at least 700 bp, at least 750 bp, at least 800 bp, at least 850 bp, at least 900 bp, at least 950 bp, or at least 1 kb away from any transcription start site. In some embodiments, an anchor sequence is located within a region that is not associated with genomic imprinting, monoallelic expression, and/or monoallelic epigenetic marks. In some embodiments of the present disclosure, technologies are provided that may specifically target a particular anchor sequence or anchor sequences, without targeting other anchor sequences (e.g., sequences that may contain a conjunction nucleating agent (e.g., CTCF) binding motif in a different context); such targeted anchor sequences may be referred to as the "target anchor sequence". In some embodiments, sequence and/or activity of a target anchor sequence is modulated while sequence and/or activity of one or more other anchor sequences that may be present in the same system (e.g., in the same cell and/or in some embodiments on the same nucleic acid molecule—e.g., the same chromosome) as the targeted anchor sequence is not modulated.

The phrase "anchor sequence-mediated conjunction" as used herein, refers to a DNA structure, in some cases, a loop, that occurs and/or is maintained via the physical interaction or binding of at least two anchor sequences in the DNA by one or more proteins, such as nucleating proteins, or one or more proteins and/or a nucleic acid entity (such as RNA or DNA), that bind the anchor sequences to enable spatial proximity and functional linkage between the anchor sequences (see FIG. 1).

The term "associated with" as used herein, refers to a target gene is associated with an anchor sequence-mediated conjunction if the formation or disruption of the anchor sequence-mediated conjunction causes an alteration in expression (e.g., transcription) of the gene. For example, the formation or disruption of the anchor sequence-mediated conjunction causes an enhancing or silencing/repressive sequence to associate with or become unassociated with the gene.

The phrase "non-naturally occurring anchor sequence-mediated conjunction" as used herein, refers the formation of an anchor sequence-mediated conjunction not existing in nature. The generation of the non-naturally occurring anchor sequence-mediated conjunction may be through, but not limited to, alteration, addition or deletion of one or more anchor sequences, and alteration of one or more conjunction nucleating molecules.

The term "common nucleotide sequence" as used herein, refers to a conjunction nucleating molecule binding site in an anchor sequence. Examples of common nucleotide sequences include, but are not limited to, CTCF binding motifs, USF1 binding motifs, YY1 binding motifs, TAF3 binding motifs, and ZNF143 binding motifs.

By the term "conjunction nucleating agent" as used herein, refers to a protein that associates with an anchor sequence directly or indirectly and may interact with one or more conjunction nucleating agents (that may interact with an anchor sequence or other nucleic acids) to form a dimer (or higher order structure) comprised of two or more such conjunction nucleating agents, which may or may not be identical to one another. When conjunction nucleating agents associated with different anchor sequences associate with each other so that the different anchor sequences are maintained in physical proximity with one another, the structure generated thereby is an anchor-sequence-mediated conjunction. That is, the close physical proximity of a conjunction nucleating molecule-anchor sequence interacting with another conjunction nucleating molecule-anchor sequence generates an anchor sequence-mediated conjunction (e.g., in some cases, a DNA loop), that begins and ends at the anchor sequence (see FIG. 2). As those skilled in the art, reading the present specification will immediately appreciate, terms such as "nucleating polypeptide", "nucleating molecule", "conjunction nucleating protein", may sometimes be used to refer to a conjunction nucleating agent. As will similarly be immediately appreciated by those skilled in the art reading the present specification, an assembles collection of two or more conjunction nucleating agents (which may, in some embodiments, include multiple copies of the same agent and/or in some embodiments one or more of each of a plurality of different agents) may be referred to as a "complex", a "dimer" a "multimer", etc.

The term "loop" refers to a type of chromatin structure that may be created by co-localization of two or more anchor sequences as an anchor sequence-mediated conjunction. Thus, the loop is formed as a consequence of the interaction of at least two anchor sequences in DNA with one or more proteins, such as nucleating proteins, or one or more proteins and/or a nucleic acid entity (such as RNA or DNA), that bind the anchor sequences to enable spatial proximity and functional linkage between the anchor sequences. Those skilled in the art, reading the present specification, will appreciate that a 2D representation of such a structure may be presented as a loop, e.g., as depicted in FIG. 2. An "activating loop" is a structure that is open to active gene transcription, for example, a structure comprising a transcription control sequence (enhancing sequence) that enhances transcription. A "repressive loop" is a structure that is closed off from active gene transcription, for example, a structure comprising a transcription control sequence (silencing sequence) that represses transcription.

The term "sequence targeting polypeptide" as used herein, refers to a protein, such as an enzyme, e.g., Cas9, that recognizes or specifically binds to a target sequence. In some embodiments, the sequence targeting polypeptide is a catalytically inactive protein, such as dCas9, that lacks endonuclease activity.

The term "subject," as used herein refers to an organism, for example, a mammal (e.g., a human, a non-human mammal, a non-human primate, a primate, a laboratory animal, a mouse, a rat, a hamster, a gerbil, a cat, or a a dog). In some embodiments a human subject is an adult, adolescent, or pediatric subject. In some embodiments, a subject had a disease or a condition. In some embodiments, the subject is suffering from a disease, disorder or condition, e.g., a disease, disorder or condition that can be treated as provided herein. In some embodiments, a subject is susceptible to a disease, disorder, or condition; in some embodiments, a susceptible subject is predisposed to and/or shows an increased risk (as compared to the average risk observed in a reference subject or population) of developing the disease, disorder or condition. In some embodiments, a subject displays one or more symptoms of a disease, disorder or condition. In some embodiments, a subject does not display a particular symptom (e.g. clinical manifestation of disease) or characteristic of a disease, disorder, or condition. In some embodiments, a subject does not display any symptom or characteristic of a disease, disorder, or condition. In some embodiments, a subject is a patient. In some embodiments, a subject is an individual to whom diagnosis and/or therapy is and/or has been administered.

The term "targeting moiety" or "targeting element" as used herein, refers to molecule that specifically binds a sequence in or around the anchor sequence-mediated conjunction. Examples of a targeting moiety include, but are not limited to, a sequence targeting polypeptide, such as an enzyme, e.g., Cas9, a fusion of a sequence targeting polypeptide and a conjunction nucleating molecule, e.g. a fusion of dCas9 and a conjunction nucleating molecule, or a guide RNA or nucleic acid, such as RNA, DNA, or modified RNA or DNA.

The term "transcriptional control sequence" as used herein, refers to a nucleic acid sequence that increases or decreases transcription of a gene. An "enhancing sequence" increases the likelihood of gene transcription. A "silencing or repressive sequence" decreases the likelihood of gene transcription. Enhancing and silencing sequences are around 50-3500 bp in length and may influence gene transcription up to 1 Mb away.

BRIEF DESCRIPTION OF THE DRAWINGS

The following detailed description of the embodiments of the disclosure will be better understood when read in conjunction with the appended drawings. For the purpose of illustrating the disclosure, there are shown in the drawings embodiments, which are presently exemplified. It should be understood, however, that the disclosure is not limited to the precise arrangement and instrumentalities of the embodiments shown in the drawings.

FIG. 17 provides a summary of certain experimental data for targeted disruption anchor sequence-mediation conjunctions.

DETAILED DESCRIPTION

Figure 1:
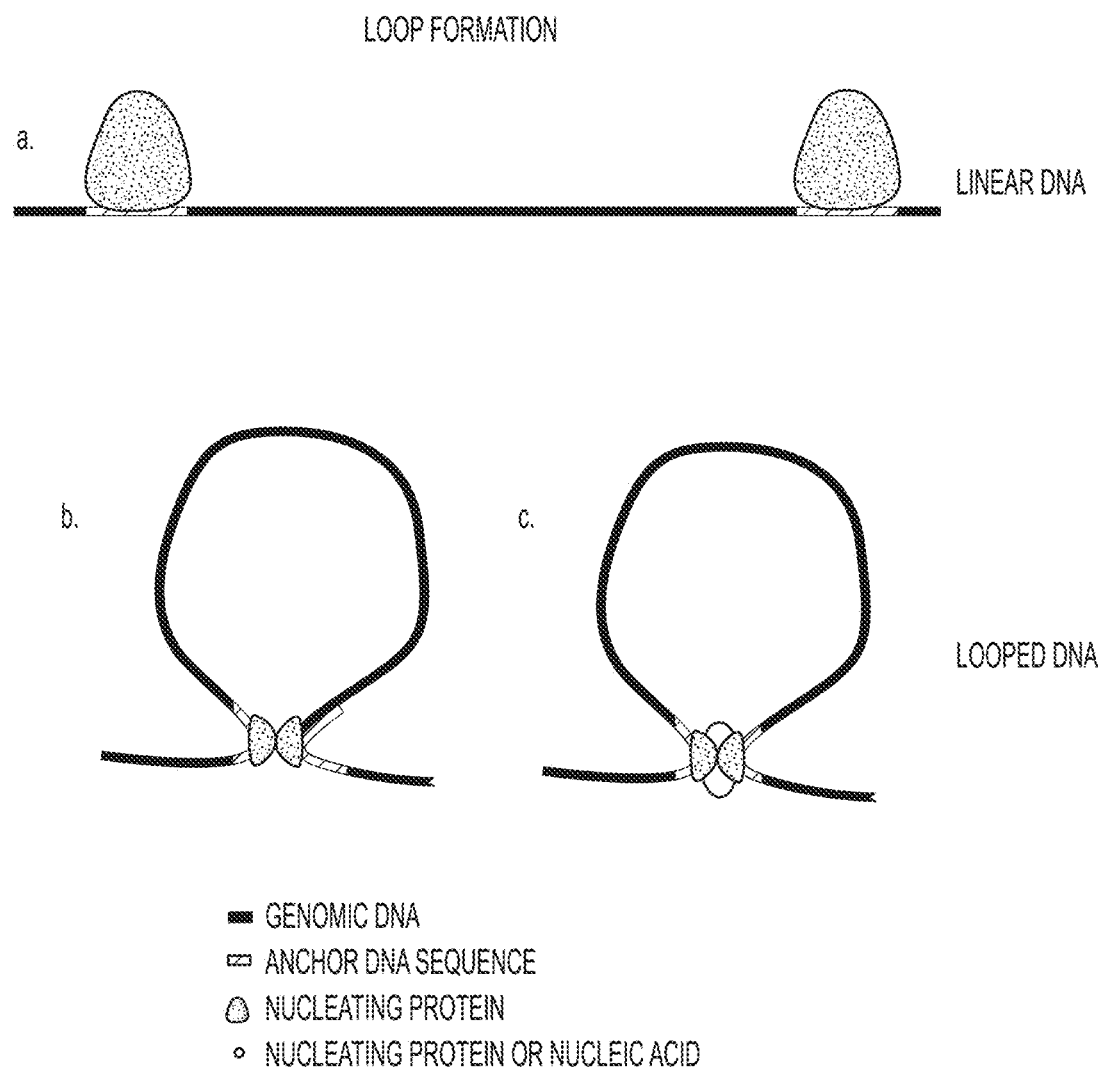
FIG. 1 is an illustration depicting the physical interaction or binding of one conjunction nucleating molecule-anchor sequence with another conjunction nucleating molecule-anchor sequence to generate an anchor sequence-mediated conjunction.
Figure 2:
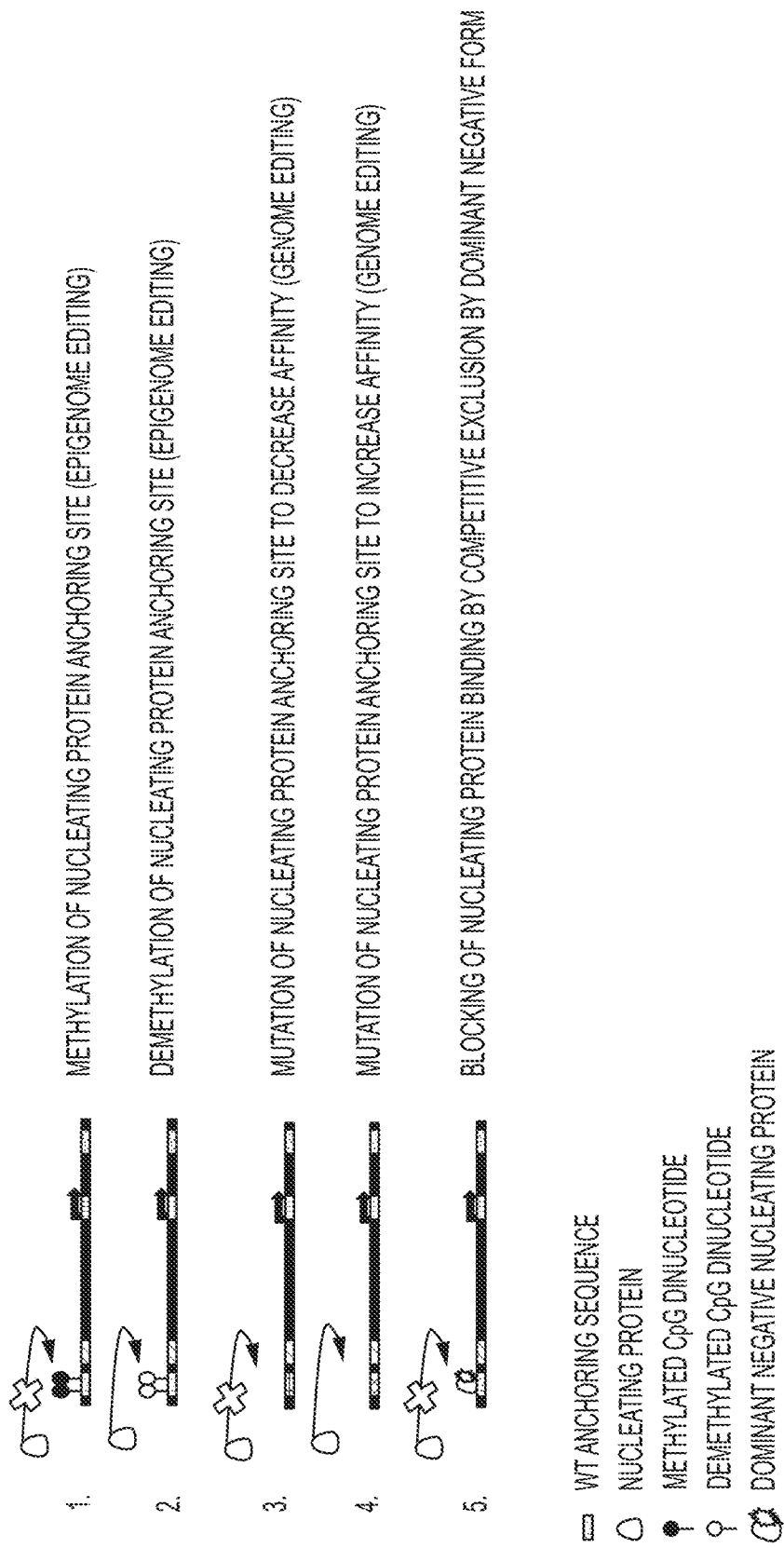
FIG. 2 is an illustration depicting methods of targeted disruption and generation of anchor sequence-mediated conjunctions, e.g., loops.

The compositions described herein alter a two-dimensional chromatin structure (e.g., anchor sequence-mediated conjunctions which, as will be appreciated by those skilled in the art, can be graphically represented in two dimensions as having higher order structure than a straight line) in order to modulate gene expression in a subject, e.g., by modifying anchor sequence-mediated conjunctions in DNA, e.g., genomic DNA.

In one aspect, the disclosure includes a composition comprising a targeting moiety that binds a specific anchor sequence-mediated conjunction to alter a topology of the anchor sequence-mediated conjunction, e.g., an anchor sequence-mediated conjunction having a physical interaction of two or more DNA loci bound by a conjunction nucleating molecule.

The formation of an anchor sequence-mediated conjunction forces gene expression regulators to interact with a target gene or spatially constrains the activity of the regulators. Altering anchor sequence-mediated conjunctions allows for gene therapy, e.g., modulating gene expression, without altering coding sequences of the gene being modulated.

In some embodiments, the composition modulates transcription of a gene associated with an anchor sequence-mediated conjunction by physically interfering between one or more anchor sequences and a conjunction nucleating molecule. For example, a DNA binding small molecule (e.g., minor or major groove binders), peptide (e.g., zinc finger, TALEN, novel or modified peptide), protein (e.g., CTCF, modified CTCF with impaired CTCF binding and/or cohesion binding affinity), or nucleic acids (e.g., ssDNA, modified DNA or RNA, peptide oligonucleotide conjugates, locked nucleic acids, bridged nucleic acids, polyamides, and/or triplex forming oligonucleotides) may physically prevent a conjunction nucleating molecule from interacting with one or more anchor sequences to modulate gene expression.

In some embodiments, the composition modulates transcription of a gene associated with an anchor sequence-mediated conjunction by modification of an anchor sequence, e.g., epigenetic modifications. For example, one or more anchor sequences associated with an anchor sequence-mediated conjunction comprising a target gene may be targeted for methylation modification by a DNA methyltransferase, e.g., dCas9-methyltransferase fusion, e.g., antisense oligonucleotide-enzyme fusion, to modulate expression of the gene.

In some embodiments, the composition modulates transcription of a gene associated with an anchor sequence-mediated conjunction by modification of an anchor sequence, e.g., genomic modifications. For example, one or more anchor sequences associated with an anchor sequence-mediated conjunction comprising a target gene may be targeted by a deaminating enzyme (e.g., deaminating oligonucleotide (e.g. oligo-sodium bisulfite conjugate), dCas-enzyme fusion, antisense oligonucleotide-enzyme fusion, deaminating antisense oligonucleotide-enzyme fusion) to modulate expression of the gene.

In some embodiments, the composition modulates transcription of a gene associated with an anchor sequence-mediated conjunction, e.g., activates or represses transcription, e.g., induces epigenetic changes to chromatin.

Anchor Sequence-Mediated Conjunction

In some embodiments, an anchor sequence-mediated conjunction includes one or more anchor sequences, one or more genes, and one or more transcriptional control sequences, such as an enhancing or silencing sequence. In some embodiments, the transcriptional control sequences is within, partially within, or outside the anchor sequence-mediated conjunction.

In one embodiment, the anchor sequence-mediated conjunction comprises a loop, such as an intra-chromosomal loop. In certain embodiments, the anchor sequence-mediated conjunction has a plurality of loops. One or more loops may include a first anchor sequence, a nucleic acid sequence, a transcriptional control sequence, and a second anchor sequence. In another embodiment, at least one loop includes, in order, a first anchor sequence, a transcriptional control sequence, and a second anchor sequence; or a first anchor sequence, a nucleic acid sequence, and a second anchor sequence. In yet another embodiment, either one or both of the nucleic acid sequences and the transcriptional control sequence is located within or outside the loop. In still another embodiment, one or more of the loops comprises a transcriptional control sequence.

In some embodiments, the anchor sequence-mediated conjunction includes a TATA box, a CAAT box, a GC box, or a CAP site.

In some embodiments, the anchor sequence-mediated conjunction comprises a plurality of loops, and where the anchor sequence-mediated conjunction comprises at least one of an anchor sequence, a nucleic acid sequence, and a transcriptional control sequence in one or more of the loops.

In one aspect, the composition described herein may comprise a composition for introducing a targeted alteration to an anchor sequence-mediated conjunction to modulate transcription of a nucleic acid sequence with a targeting moiety that binds the anchor sequence. In some embodiments, the anchor sequence-mediated conjunction is altered by targeting one or more nucleotides within the anchor sequence-mediated conjunction for substitution, addition or deletion.

In some embodiments, transcription is activated by inclusion of an activating loop or exclusion of a repressive loop. In one such embodiment, the anchor sequence-mediated conjunction comprises a transcriptional control sequence that increases transcription of the nucleic acid sequence. In another such embodiment, the anchor sequence-mediated conjunction excludes a transcriptional control sequence that decreases transcription of the nucleic acid sequence.

In some embodiments, transcription is repressed by inclusion of a repressive loop or exclusion of an activating loop. In one such embodiment, the anchor sequence-mediated conjunction includes a transcriptional control sequence that decreases transcription of the nucleic acid sequence. In another such embodiment, the anchor sequence-mediated conjunction excludes a transcriptional control sequence that increases transcription of the nucleic acid sequence.

Anchor Sequence

Figure 3:
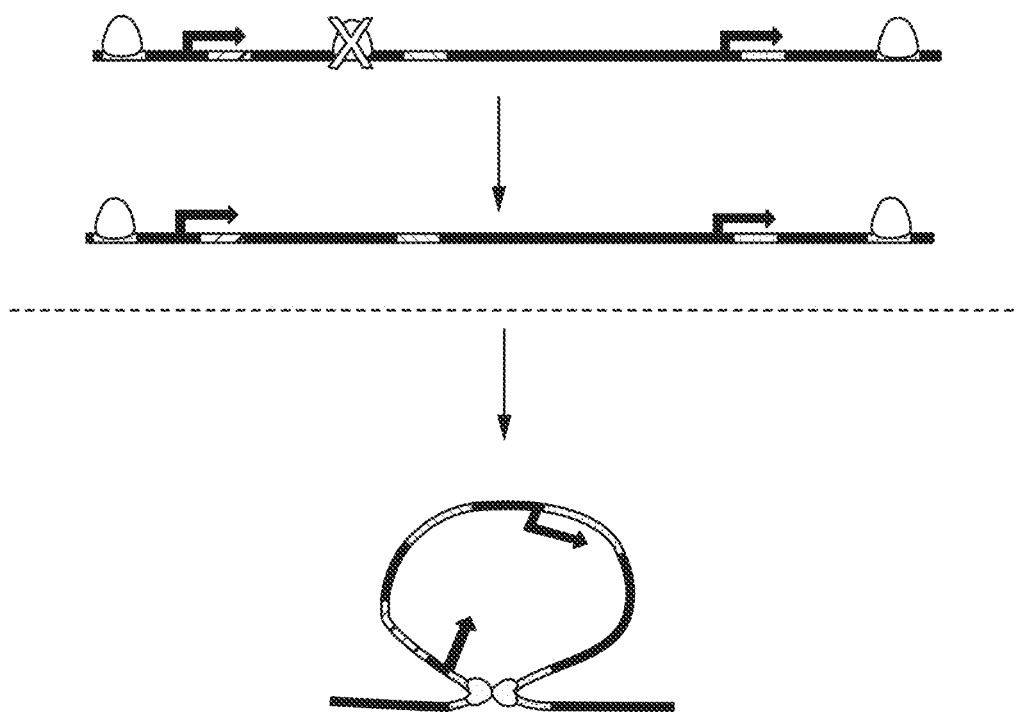
FIG. 3 is an illustration depicting one embodiment of modulating gene expression through the generation of a non-naturally occurring anchor sequence-mediated conjunction (loop inclusion).
Figure 4:
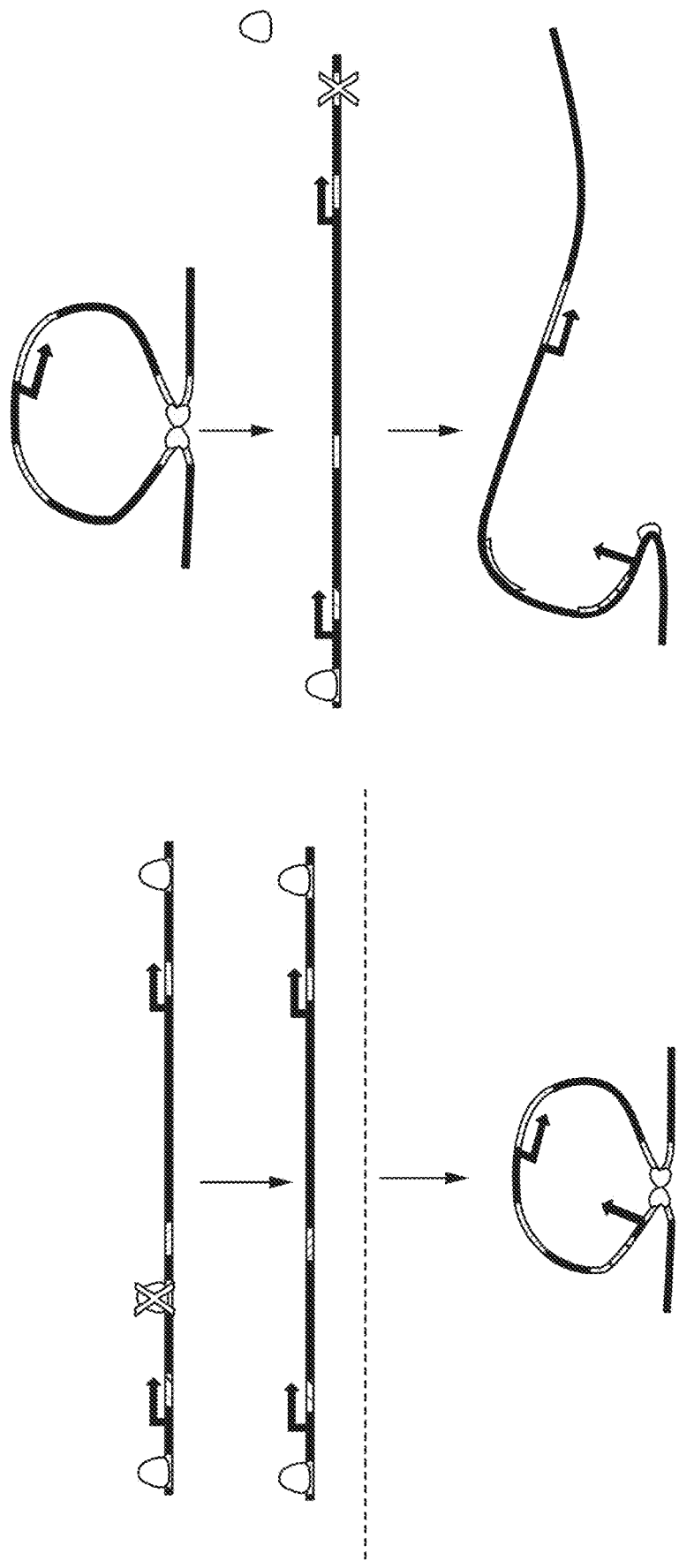
FIG. 4 is an illustration depicting methods of modulating gene expression. The left side of the figure is the same illustration as shown in FIG. 1. The right side of the figure is the disruption of an anchor sequence-mediated conjunction (loop exclusion).
Figure 5:
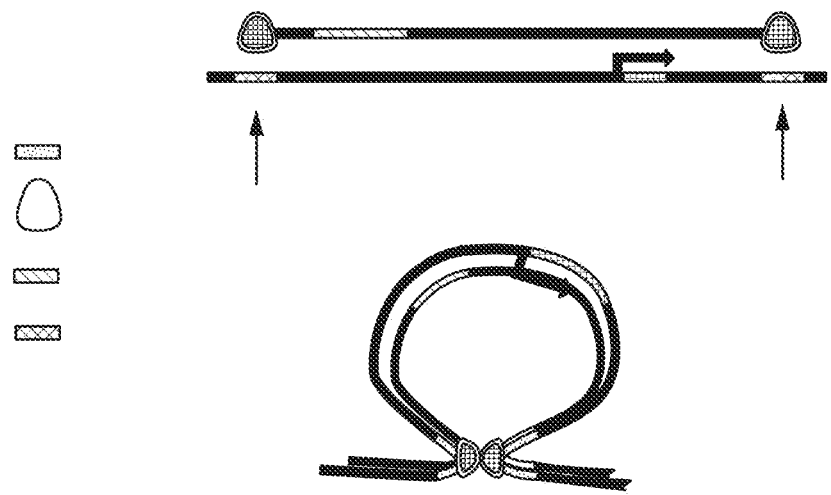
FIG. 5 is an illustration depicting another embodiment of modulating gene expression through the generation of a non-naturally occurring anchor sequence-mediated conjunction by incorporating a new anchor sequence.

Each anchor sequence-mediated conjunction comprises one or more anchor sequences, e.g., a plurality. Anchor sequences can be manipulated or altered to disrupt naturally occurring loops or form new loops (e.g., to form exogenous loops or to form non-naturally occurring loops with exogenous or altered anchor sequences, see FIGS. 3, 4, and 5). Such alterations modulate gene expression by changing the 2-dimensional structure of DNA, e.g., by thereby modulating the ability of a target gene to interact with gene regulation and control factors (e.g., enhancing and silencing/repressive sequences). In some embodiments, the chromatin structure is modified by substituting, adding or deleting one or more nucleotides within an anchor sequence of the anchor sequence-mediated conjunction.

The anchor sequences may be non-contiguous with one another. In embodiments with non-contiguous anchor sequences, the first anchor sequence may be separated from the second anchor sequence by about 500 bp to about 500 Mb, about 750 bp to about 200 Mb, about 1 kb to about 100 Mb, about 25 kb to about 50 Mb, about 50 kb to about 1 Mb, about 100 kb to about 750 kb, about 150 kb to about 500 kb, or about 175 kb to about 500 kb. In some embodiments, the first anchor sequence is separated from the second anchor sequence by about 500 bp, 600 bp, 700 bp, 800 bp, 900 bp, 1 kb, 5 kb, 10 kb, 15 kb, 20 kb, 25 kb, 30 kb, 35 kb, 40 kb, 45 kb, 50 kb, 55 kb, 60 kb, 65 kb, 70 kb, 75 kb, 80 kb, 85 kb, 90 kb, 95 kb, 100 kb, 125 kb, 150 kb, 175 kb, 200 kb, 225 kb, 250 kb, 275 kb, 300 kb, 350 kb, 400 kb, 500 kb, 600 kb, 700 kb, 800 kb, 900 kb, 1 Mb, 2 Mb, 3 Mb, 4 Mb, 5 Mb, 6 Mb, 7 Mb, 8 Mb, 9 Mb, 10 Mb, 15 Mb, 20 Mb, 25 Mb, 50 Mb, 75 Mb, 100 Mb, 200 Mb, 300 Mb, 400 Mb, 500 Mb, or any size therebetween.

In one embodiment, the anchor sequence comprises a common nucleotide sequence, e.g., a CTCF-binding motif: N(T/C/G)N(G/A/T)CC(A/T/G)(C/G)(C/T/A)AG(G/A)(G/T)GG(C/A/T)(G/A)(C/G)(C/T/A)(G/A/C) (SEQ ID NO:1), where N is any nucleotide. A CTCF-binding motif may also be in the opposite orientation, e.g., (G/A/C)(C/T/A)(C/G)(G/A)(C/A/T)GG(G/T)(G/A)GA(C/T/A)(C/G)(A/T/G)CC(G/A/T)N(T/C/G)N (SEQ ID NO:2). In one embodiment, the anchor sequence comprises SEQ ID NO:1 or SEQ ID NO:2 or a sequence at least 75%, at least 80%, at least 90%, at least 95%, at least 96%, at least 97%, at least 98%, at least 99% identical to either SEQ ID NO:1 or SEQ ID NO:2.

In some embodiments, the anchor sequence-mediated conjunction comprises at least a first anchor sequence and a second anchor sequence. The first anchor sequence and second anchor sequence may each comprise a common nucleotide sequence, e.g., each comprises a CTCF binding motif. In some embodiments, the first anchor sequence and second anchor sequence comprise different sequences, e.g., the first anchor sequence comprises a CTCF binding motif and the second anchor sequence comprises an anchor sequence other than a CTCF binding motif. In some embodiments, each anchor sequence comprises a common nucleotide sequence and one or more flanking nucleotides on one or both sides of the common nucleotide sequence.

Two CTCF-binding motifs (e.g., contiguous or non-contiguous CTCF binding motifs) that can form a conjunction may be present in the genome in any orientation, e.g., in the same orientation (tandem) either 5'→3' (left tandem, e.g., the two CTCF-binding motifs that comprise SEQ ID NO:1) or 3'→5' (right tandem, e.g., the two CTCF-binding motifs comprise SEQ ID NO:2), or convergent orientation, where one CTCF-binding motif comprises SEQ ID NO:1 and the other comprises SEQ ID NO:2. *CTCFBSDB 2.0: Database For CTCF binding motifs And Genome Organization* (http://insulatordb.uthsc.edu/) can be used to identify CTCF binding motifs associated with a target gene.

In some embodiments, the anchor sequence comprises a CTCF binding motif associated with a target disease gene.

In some embodiments, chromatin structure is modified by substituting, adding or deleting one or more nucleotides within at least one anchor sequence, e.g., a conjunction nucleating molecule binding site. One or more nucleotides may be specifically targeted, e.g., a targeted alteration, for substitution, addition or deletion within the anchor sequence, e.g., a conjunction nucleating molecule binding site.

In some embodiments, the anchor sequence-mediated conjunction is altered by changing an orientation of at least one common nucleotide sequence, e.g., a conjunction nucleating molecule binding site.

In some embodiments, the anchor sequence comprises a conjunction nucleating molecule binding site, e.g., CTCF binding motif, and the targeting moiety introduces an alteration in at least one conjunction nucleating molecule binding site, e.g. altering binding affinity for the conjunction nucleating molecule.

In some embodiments, the anchor sequence-mediated conjunction is altered by introducing an exogenous anchor sequence. Addition of a non-naturally occurring or exogenous anchor sequence to form or disrupt a naturally occurring anchor sequence-mediated conjunction, e.g., by inducing a non-naturally occurring loop to form that alters transcription of the nucleic acid sequence.

Types of Anchor Sequence-Mediated Conjunctions

In some embodiments, the anchor sequence-mediated conjunction comprises one or more, e.g., 2, 3, 4, 5, or more, genes.

In some embodiments, the disclosure includes a method of modulating expression of a target gene in an anchor sequence-mediated conjunction comprising targeting a sequence outside of or that is not part of the or comprised within the target gene or associated transcriptional control sequences that influence transcription of the gene, such as targeting an anchor sequence, thereby modulating the gene's expression.

In some embodiments, the disclosure includes a method of modulating transcription of a target gene comprising targeting a sequence non-contiguous with the target gene or associated transcriptional control sequences that influence transcription of the target gene, such as targeting an anchor sequence.

In some embodiments, the anchor sequence-mediated conjunction is associated with one or more, e.g., 2, 3, 4, 5, or more, transcriptional control sequences. In some embodiments, the target gene is non-contiguous with one or more of the transcriptional control sequences. In some embodiments where the gene is non-contiguous with the transcriptional control sequence, the gene may be separated from one or more transcriptional control sequences by about 100 bp to about 500 Mb, about 500 bp to about 200 Mb, about 1 kb to about 100 Mb, about 25 kb to about 50 Mb, about 50 kb to about 1 Mb, about 100 kb to about 750 kb, about 150 kb to about 500 kb, or about 175 kb to about 500 kb. In some embodiments, the gene is separated from the transcriptional control sequence by about 100 bp, 300 bp, 500 bp, 600 bp, 700 bp, 800 bp, 900 bp, 1 kb, 5 kb, 10 kb, 15 kb, 20 kb, 25 kb, 30 kb, 35 kb, 40 kb, 45 kb, 50 kb, 55 kb, 60 kb, 65 kb, 70 kb, 75 kb, 80 kb, 85 kb, 90 kb, 95 kb, 100 kb, 125 kb, 150 kb, 175 kb, 200 kb, 225 kb, 250 kb, 275 kb, 300 kb, 350 kb, 400 kb, 500 kb, 600 kb, 700 kb, 800 kb, 900 kb, 1 Mb, 2 Mb, 3 Mb, 4 Mb, 5 Mb, 6 Mb, 7 Mb, 8 Mb, 9 Mb, 10 Mb, 15 Mb, 20 Mb, 25 Mb, 50 Mb, 75 Mb, 100 Mb, 200 Mb, 300 Mb, 400 Mb, 500 Mb, or any size therebetween.

In some embodiments, the type of anchor sequence-mediated conjunction may help to determine how to modulate gene expression, e.g., choice of targeting moiety, by altering the anchor sequence-mediated conjunction. For example, some types of anchor sequence-mediated conjunctions comprise one or more transcription control sequences within the anchor sequence-mediated conjunction. Disruption of such an anchor sequence-mediated conjunction by disrupting the formation of the anchor sequence-mediated conjunction, e.g., altering one or more anchor sequences, is likely to decrease transcription of a target gene within the anchor sequence-mediated conjunction.

Type 1

In some embodiments, expression of the target gene is regulated, modulated, or influenced by one or more transcriptional control sequences associated with the anchor sequence-mediated conjunction. In some embodiments, the anchor sequence-mediated conjunction comprises one or more associated genes and one or more transcriptional control sequences. For example, the target gene and one or more transcriptional control sequences are located within, at least partially, an anchor sequence-mediated conjunction, e.g., a Type 1 anchor sequence-mediated conjunction, see FIG. 6. The anchor sequence-mediated conjunction depicted in FIG. 6 may also be referred to as a "Type 1, EP subtype."

In some embodiments, the target gene has a defined state of expression, e.g., in its native state, e.g., in a diseased state. For example, the target gene may have a high level of expression. By disrupting the anchor sequence-mediated conjunction, expression of the target gene may be decreased, e.g., decreased transcription due to conformational changes of the DNA previously open to transcription within the anchor sequence-mediated conjunction, e.g., decreased transcription due to conformational changes of the DNA creating additional distance between the target gene and the enhancing sequences. In one embodiment, both the gene associated and one or more transcriptional control sequences, e.g., enhancing sequences, reside inside the anchor sequence-mediated conjunction. Disruption of the anchor sequence-mediated conjunction decreases expression of the gene. In one embodiment, the gene associated with the anchor sequence-mediated conjunction is accessible to one or more transcriptional control sequences that reside inside, at least partially, the anchor sequence-mediated conjunction. Disruption of the anchor sequence-mediated conjunction decreases expression of the gene.

For example, a Type 1 anchor sequence-mediated conjunction comprises a gene encoding MYC and disruption of the Type 1 anchor sequence-mediated conjunction decreases expression of the gene and MYC protein levels. In another example, a Type 1 anchor sequence-mediated conjunction comprises a gene encoding Foxj3 and disruption of the Type 1 anchor sequence-mediated conjunction decreases expression of the gene and Foxj3 protein levels.

Type 2

In some embodiments, expression of the target gene is regulated, modulated, or influenced by one or more transcriptional control sequences associated with, but inaccessible due to the anchor sequence-mediated conjunction. For example, the anchor sequence-mediated conjunction associated with a gene disrupts the ability of one or more transcriptional control sequences to regulate, modulate, or influence expression of the gene. The transcriptional control sequences may be separated from the gene, e.g., reside on the opposite side, at least partially, e.g., inside or outside, of the anchor sequence-mediated conjunction as the gene, e.g., the gene is inaccessible to the transcriptional control sequences due to proximity of the anchor sequence-mediated conjunction. In some embodiments, one or more enhancing sequences are separated from the gene by the anchor sequence-mediated conjunction, e.g., a Type 2 anchor sequence-mediated conjunction, see FIG. 6.

In some embodiments, a Type 2 the gene is enclosed within the anchor sequence-mediated conjunction, while the transcriptional control sequence (e.g., enhancing sequence) is not enclosed within the anchor sequence-mediated conjunction. This subtype of Type 2 may be referred to as "Type 2, subtype 1." In some embodiments, a Type 2 the transcriptional control sequence (e.g., enhancing sequence) is enclosed within the anchor sequence-mediated conjunction, while the gene is not enclosed within the anchor sequence-mediated conjunction. This subtype of Type 2 may be referred to as "Type 2, subtype 2."

In some embodiments, the gene is inaccessible to one or more transcriptional control sequences due to the anchor sequence-mediated conjunction, and disruption of the anchor sequence-mediated conjunction allows the transcriptional control sequence to regulate, modulate, or influence expression of the gene. In one embodiment, the gene is inside and outside the anchor sequence-mediated conjunction and inaccessible to the one or more transcriptional control sequences. Disruption of the anchor sequence-mediated conjunction increases access of the transcriptional control sequences to regulate, modulate, or influence expression of the gene, e.g., the transcriptional control sequences increase expression of the gene. In one embodiment, the gene is inside the anchor sequence-mediated conjunction and inaccessible to the one or more transcriptional control sequences residing outside, at least partially, the anchor sequence-mediated conjunction. Disruption of the anchor sequence-mediated conjunction increases expression of the gene. In one embodiment, the gene is outside, at least partially, the anchor sequence-mediated conjunction and inaccessible to the one or more transcriptional control sequences residing inside the anchor sequence-mediated conjunction. Disruption of the anchor sequence-mediated conjunction increases expression of the gene.

In some embodiments, the target gene has a defined state of expression, e.g., in its native state, e.g., in a diseased state. For example, the target gene may have a moderate to low level of expression. By disrupting the anchor sequence-mediated conjunction, expression of the target gene may be modulated, e.g., increased transcription due to conformational changes of the DNA previously closed to transcription within the anchor sequence-mediated conjunction, e.g., increased transcription due to conformational changes of the DNA by bringing the enhancing sequences into closer association with the target gene.

For example, a Type 2 anchor sequence-mediated conjunction comprises a gene encoding SCN1a and disruption of the Type 2 anchor sequence-mediated conjunction increases expression of the gene and SCN1a protein levels. In another example, a Type 2 anchor sequence-mediated conjunction comprises a gene encoding Serpin1a and disruption of the Type 2 anchor sequence-mediated conjunction increases expression of the gene and Serpin1a protein levels. In another example, IL-10 mediated tolerizing responses may be elicited by altering the anchor sequence-mediated conjunction associated with the IL-10 gene, e.g., expression of IL-10 may be increased to improve the autoimmune condition. In another example, IL-6 expression may be increased by altering its associated anchor sequence-mediated conjunction to bring one or more enhancing sequences into closer proximity to the IL-6 gene.

Type 3

In some embodiments, expression of the target gene is regulated, modulated, or influenced by one or more transcriptional control sequences associated with the anchor sequence-mediated conjunction, but not necessarily located on the same side of the anchor sequence-mediated conjunction as each other. For example, the anchor sequence-mediated conjunction is associated with one or more genes and one or more transcriptional control sequences reside inside and outside, at least partially, the anchor sequence-mediated conjunction. In some embodiments, one or more enhancing sequences reside inside the anchor sequence-mediated conjunction and one or more repressive signals, e.g., silencing sequences, reside outside the anchor sequence-mediated conjunction, e.g., a Type 3 anchor sequence-mediated conjunction, see FIG. 6.

In some embodiments, the gene is inaccessible to one or more transcriptional control sequences due to the anchor sequence-mediated conjunction, and disruption of the anchor sequence-mediated conjunction allows the transcriptional control sequence to regulate, modulate, or influence expression of the gene. In one embodiment, the gene is inside the anchor sequence-mediated conjunction and inaccessible to the one or more transcriptional control sequences, e.g., silencing/repressive sequences, residing outside the anchor sequence-mediated conjunction. Disruption of the anchor sequence-mediated conjunction decreases expression of the gene. In one embodiment, the gene is inside and outside the anchor sequence-mediated conjunction and inaccessible to the one or more transcriptional control sequences, e.g., silencing/repressive sequences, anchor sequence-mediated conjunction residing outside the anchor sequence-mediated conjunction. Disruption of the anchor sequence-mediated conjunction decreases expression of the gene. In one embodiment, the gene is outside the anchor sequence-mediated conjunction and inaccessible to the one or more transcriptional control sequences, e.g., silencing/repressive sequences, inside the anchor sequence-mediated conjunction. Disruption of the anchor sequence-mediated conjunction decreases expression of the gene.

In some embodiments, the target gene has a defined state of expression, e.g., in its native state, e.g., in a diseased state. For example, the target gene may have a high level of expression in its native state. By disrupting the anchor sequence-mediated conjunction, expression of the target gene may be modulated, e.g., decreased transcription due to conformational changes of the DNA creating additional distance between the target gene and the enhancing sequences, e.g., decreased transcription due to conformational changes of the DNA previously open to transcription within the anchor sequence-mediated conjunction, e.g., decreased transcription due to conformational changes of the DNA bringing the silencing sequences into closer association with the target gene, e.g., decreased transcription due to conformational changes of the DNA creating additional distance between the target gene and the enhancing sequences.

Type 4

In some embodiments, expression of the target gene is regulated, modulated, or influenced by one or more transcriptional control sequences associated with the anchor sequence-mediated conjunction, but not necessarily located within the anchor sequence-mediated conjunction. For example, the anchor sequence-mediated conjunction is associated with one or more genes and one or more transcriptional control sequences reside inside and outside, at least partially, the anchor sequence-mediated conjunction, e.g., a Type 4 anchor sequence-mediated conjunction, see FIG. 6.

In some embodiments, the gene is inaccessible to one or more transcriptional control sequences due to the anchor sequence-mediated conjunction, and disruption of the anchor sequence-mediated conjunction allows the transcriptional control sequence to regulate, modulate, or influence expression of the gene. In one embodiment, the gene is inside the anchor sequence-mediated conjunction and inaccessible to the one or more transcriptional control sequences residing outside the anchor sequence-mediated conjunction. Disruption of the anchor sequence-mediated conjunction increases expression of the gene. In one embodiment, the gene is inside and outside the anchor sequence-mediated conjunction and inaccessible to the one or more transcriptional control sequences, e.g., enhancing sequences, anchor sequence-mediated conjunction residing outside the anchor sequence-mediated conjunction. Disruption of the anchor sequence-mediated conjunction increases expression of the gene. In one embodiment, the gene is outside the anchor sequence-mediated conjunction and inaccessible to the one or more transcriptional control sequences, e.g., enhancing sequences, inside the anchor sequence-mediated conjunction. Disruption of the anchor sequence-mediated conjunction increases expression of the gene.

In some embodiments, the target gene has a defined state of expression, e.g., in its native state, e.g., in a diseased state. For example, the target gene may have a high level of expression in its native state. By disrupting the anchor sequence-mediated conjunction, expression of the target gene may be modulated, e.g., increased transcription due to conformational changes opening the DNA to transcription within the anchor sequence-mediated conjunction, e.g., increased transcription due to conformational changes of the DNA by bringing one or more enhancing sequences into association with the target gene.

Targeting Moieties

In some embodiments, a composition, agent, fusion molecule, or other molecule as described herein comprises one or more the targeting moieties described herein. The targeting moiety may target an anchor sequence-mediated conjunction for alteration of at least one of the following: at least one exogenous anchor sequence; an alteration in at least one conjunction nucleating molecule binding site, such as by altering binding affinity for the conjunction nucleating molecule; a change in an orientation of at least one common nucleotide sequence, such as a CTCF binding motif; and a substitution, addition or deletion in at least one anchor sequence, such as a CTCF binding motif.

Those skilled in the art reading the below examples of particular kinds of targeting moieties will understand that, in some embodiments, a targeting moiety is site-specific. That is, in some embodiments, a targeting moiety binds specifically to one or more target anchor sequences (e.g., within a cell) and not to non-targeted anchor sequences (e.g., within the same cell).

The targeting moiety may modulate a specific function, modulate a specific molecule (e.g., enzyme, protein or nucleic acid), and specifically bind for localization. The targeting function may act on a specific molecule, e.g. a molecular target. For example, a targeted therapeutic may interact with a specific molecule to increase, decrease or otherwise modulate its function.

In some embodiments, the targeting moiety binds an anchor sequence (e.g., a DNA sequence). In various parts of the present disclosure, the term "DNA binding moiety" may be used to refer to a targeting moiety.

In some embodiments, a composition, agent, fusion molecule, or other molecule as described herein comprises a targeting moiety (e.g., gRNA, antisense, oligonucleotides, peptide oligonucleotide conjugates) that binds the anchor sequence, and is operably linked to an effector moiety that modulates the formation of a conjunction mediated by the anchor sequence. The targeting moiety may bind an anchor sequence of an anchor sequence-mediated conjunction and alter formation of the anchor sequence-mediated conjunction (e.g., alters affinity of the anchor sequence to a conjunction nucleating molecule, e.g., at least 10%, 15%, 20%, 25%, 30%, 35%, 40%, 45%, 50%, 55%, 60%, 65%, 70%, 75%, 80%, 85%, 90%, 95%, or more). The targeting moiety may be any one of the small molecules, peptides, nucleic acids, nanoparticles, aptamers, and pharmacoagents with poor pharmacokinetics described herein.

The targeting moiety may target one or more nucleotides, such as through a gene editing system, of a sequence, e.g., an anchor sequence, e.g., a common nucleotide sequence within an anchor sequence, within the anchor sequence-mediated conjunction for substitution, addition or deletion. In some embodiments, the targeting moiety binds an anchor sequence-mediated conjunction, e.g., the anchor sequence in the anchor sequence-mediated conjunction, and alters a topology of the anchor sequence-mediated conjunction.

In some embodiments, the targeting moiety targets one or more nucleotides, e.g., such as through CRISPR, TALEN, dCas9, oligonucleotide pairing, recombination, transposon, etc., of an anchor sequence within the anchor sequence-mediated conjunction for substitution, addition or deletion. In some embodiments, the targeting moiety targets one or more DNA methylation sites within the anchor sequence-mediated conjunction.

The targeting moiety may alter one or more nucleotides, such as through a gene editing system, of a sequence, e.g., an anchor sequence, e.g., a common nucleotide sequence within an anchor sequence, within the anchor sequence-mediated conjunction by substitution, addition or deletion.

In some embodiments, the targeting moiety introduces a targeted alteration into the anchor sequence-mediated conjunction to modulate transcription, in a human cell, of a gene in the anchor sequence-mediated conjunction. The targeted alteration may include a substitution, addition or deletion of one or more nucleotides, e.g., of an anchor sequence within the anchor sequence-mediated conjunction. The targeting moiety may bind an anchor sequence of the anchor sequence-mediated conjunction and the targeting moiety introduce a targeted alteration into the anchor sequence to modulate transcription, in a human cell, of a gene in the anchor sequence-mediated conjunction. In some embodiments, the targeted alteration alters at least one of a binding site for a conjunction nucleating molecule, e.g. altering binding affinity for an anchor sequence within the anchor sequence-mediated conjunction, an alternative splicing site, and a binding site for a non-translated RNA.

In some embodiments, the targeting moiety edits an anchor sequence-mediated conjunction at least one of the following: at least one exogenous anchor sequence; an alteration in at least one conjunction nucleating molecule binding site, such as by altering binding affinity for the conjunction nucleating molecule; a change in an orientation of at least one common nucleotide sequence, such as a CTCF binding motif; and a substitution, addition or deletion in at least one anchor sequence, such as a CTCF binding motif.

In some embodiments, the targeting moiety is a nucleic acid sequence, a protein, protein fusion, or a membrane translocating polypeptide. In some embodiments, the targeting moiety is selected from an exogenous conjunction nucleating molecule, a nucleic acid encoding the conjunction nucleating molecule, or a fusion of a sequence targeting polypeptide and a conjunction nucleating molecule.

As described in greater detail herein, in some embodiments, a targeting moiety as described herein can be or comprise a polymer or polymeric moiety, e.g., a polymer of nucleotides (such as an oligonucleotide), a peptide nucleic acid, a peptide-nucleic acid mixmer, a peptide or polypeptide, a polyamide, a carbohydrate, etc.

Nucleic Acid Sequences

In some embodiments, the targeting moiety comprises a nucleic acid sequence. In some embodiments, the nucleic acid sequence encodes a gene or an expression product.

As will be readily understand by those skilled in the art reading the present specification, a targeting moiety can comprise a nucleic acid sequence that does not encode a gene or an expression product. For example, in some embodiments, a targeting moiety comprises an oligonucleotide that hybridizes to a target anchor sequence. For example, in some embodiments, the sequence of the oligonucleotide comprises a complement of the target anchor sequence, or has a sequence that is at least 80%, at least 85%, at least 90%, at least 95%, at least 97%, at least 98%, at least 99% identical to the complement of the target anchor sequence.

The nucleic acid sequence may include, but is not limited to, DNA, RNA, modified oligonucleotides (e.g., chemical modifications, such as modifications that alter the backbone linkages, sugar molecules, and/or nucleic acid bases), and artificial nucleic acids. In some embodiments, the nucleic acid sequence includes, but is not limited to, genomic DNA, cDNA, peptide nucleic acids (PNA) or peptide oligonucleotide conjugates, locked nucleic acids (LNA), bridged nucleic acids (BNA), polyamides, triplex forming oligonucleotides, modified DNA, antisense DNA oligonucleotides, tRNA, mRNA, rRNA, modified RNA, miRNA, gRNA, and siRNA or other RNA or DNA molecules.

In some embodiments, the nucleic acid sequence has a length from about 2 to about 5000 nts, about 10 to about 100 nts, about 50 to about 150 nts, about 100 to about 200 nts, about 150 to about 250 nts, about 200 to about 300 nts, about 250 to about 350 nts, about 300 to about 500 nts, about 10 to about 1000 nts, about 50 to about 1000 nts, about 100 to about 1000 nts, about 1000 to about 2000 nts, about 2000 to about 3000 nts, about 3000 to about 4000 nts, about 4000 to about 5000 nts, or any range therebetween.

In one aspect, the disclosure includes a synthetic nucleic acid comprising a plurality of anchor sequences, a gene sequence, and a transcriptional control sequence. In some embodiments, the gene sequence and the transcriptional control sequence are between the plurality of anchor sequences. In some embodiments, the synthetic nucleic acid comprises, in order, (a) an anchor sequence, a gene sequence, a transcriptional control sequence, and an anchor sequence or (b) an anchor sequence, a transcriptional control sequence, a gene sequence, and an anchor sequence. In some embodiments, the sequences are separated by linker sequences. In some embodiments, the anchor sequences are between 7-100 nts, 10-100 nts, 10-80 nts, 10-70 nts, 10-60 nts, 10-50 nts, 20-80 nts, or any range therebetween. In some embodiments, the nucleic acid is between 3,000-50,000 bp, 3,000-40,000 bp, 3,000-30,000 bp, 3,000-20,000 bp, 3,000-15,000 bp, 3,000-12,000 bp, 3,000-10,000 bp, 3,000-8,000 bp, 5,000-30,000 bp, 5,000-20,000 bp, 5,000-15,000 bp, 5,000-12,000 bp, 5,000-10,000 bp or any range therebetween.

In another aspect, the disclosure includes a vector comprising the nucleic acid described herein.

In another aspect, the disclosure includes a cell or tissue comprising the nucleic acid described herein.

In another aspect, the disclosure includes a pharmaceutical composition comprising the nucleic acid described herein.

In another aspect, the disclosure includes a method of modulating expression of a gene by administering the composition comprising the nucleic acid described herein.

Analogs

The nucleic acid sequence may include nucleosides, e.g., purines or pyrimidines, e.g., adenine, cytosine, guanine, thymine and uracil. In some embodiments, the nucleic acid sequence includes one or more nucleoside analogs. The nucleoside analog includes, but is not limited to, a nucleoside analog, such as 5-fluorouracil; 5-bromouracil, 5-chlorouracil, 5-iodouracil, hypoxanthine, xanthine, 4-acetylcytosine, 4-methylbenzimidazole, 5-(carboxyhydroxylmethyl) uracil, 5-carboxymethylaminomethyl-2-thiouridine, 5-carboxymethylaminomethyluracil, dihydrouracil, dihydrouridine, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, 2,6-diaminopurine, 3-nitropyrrole, inosine, thiouridine, queuosine, wyosine, diaminopurine, isoguanine, isocytosine, diaminopyrimidine, 2,4-difluorotoluene, isoquinoline, pyrrolo[2,3-β]pyridine, and any others that can base pair with a purine or a pyrimidine side chain.

gRNA

In some embodiments, the targeting moiety comprises a nucleic acid sequence, e.g., a guide RNA (gRNA). In some embodiments, the targeting moiety comprises a guide RNA or nucleic acid encoding the guide RNA. A gRNA short synthetic RNA composed of a "scaffold" sequence necessary for Cas9-binding and a user-defined ~20 nucleotide targeting sequence for a genomic target. In practice, guide RNA sequences are generally designed to have a length of between 17-24 nucleotides (e.g., 19, 20, or 21 nucleotides) and complementary to the targeted nucleic acid sequence. Custom gRNA generators and algorithms are available commercially for use in the design of effective guide RNAs. Gene editing has also been achieved using a chimeric "single guide RNA" ("sgRNA"), an engineered (synthetic) single RNA molecule that mimics a naturally occurring crRNA-tracrRNA complex and contains both a tracrRNA (for binding the nuclease) and at least one crRNA (to guide the nuclease to the sequence targeted for editing). Chemically modified sgRNAs have also been demonstrated to be effective in genome editing; see, for example, Hendel et al. (2015) Nature Biotechnol., 985-991.

In some embodiments, the nucleic acid sequence comprises a sequence complementary to an anchor sequence. In one embodiment, the anchor sequence comprises a CTCF-binding motif or consensus sequence:
N(T/C/G)N(G/A/T)CC(A/T/G)(C/G)(C/T/A)AG(G/A)(G/T)GG(C/A/T)(G/A)(C/G)(C/T/A)(G/A/C) (SEQ ID NO:1), where N is any nucleotide. A CTCF-binding motif or consensus sequence may also be in the opposite orientation, e.g.,
(G/A/C)(C/T/A)(C/G)(G/A)(C/A/T)GG(G/T)(G/A)GA(C/T/A)(C/G)(A/T/G)CC(G/A/T)N(T/C/G)N (SEQ ID NO:2). In some embodiments, the nucleic acid sequence comprises a sequence complementary to a CTCF-binding motif or consensus sequence.

In some embodiments, the nucleic acid sequence comprises a sequence at least 80%, at least 90%, at least 95%, at least 96%, at least 97%, at least 98%, at least 99% complementary to an anchor sequence. In some embodiments, the nucleic acid sequence comprises a sequence at least 80%, at least 90%, at least 95%, at least 96%, at least 97%, at least 98%, at least 99% complementary to a CTCF-binding motif or consensus sequence. In some embodiments, the nucleic acid sequence is selected from the group consisting of a gRNA, and a sequence complementary or a sequence comprising at least 80%, at least 90%, at least 95%, at least 96%, at least 97%, at least 98%, at least 99% complementary sequence to an anchor sequence.

In some embodiments, the epigenetic modifying agent is a gRNA, antisense DNA, or triplex forming oligonucleotide used as a DNA target and steric presence in the vicinity of the anchoring sequence. The gRNA recognizes specific DNA sequences (e.g., an anchor sequence, a CTCF anchor sequence, flanked by sequences that confer sequence specificity). The gRNA may include additional sequences that interfere with conjunction nucleating molecule sequence to act as a steric blocker. In some embodiments, the gRNA is combined with one or more peptides, e.g., S-adenosyl methionine (SAM), that acts as a steric presence to interfere with a conjunction nucleating molecule.

Protein Encoding Nucleic Acids

In some embodiments, a vector, e.g., a viral vector, comprises a nucleic acid encoding a targeting moiety, e.g., a conjunction nucleating molecule.

The nucleic acids described herein or the nucleic acids encoding a protein described herein, e.g., conjunction nucleating molecule or epigenetic modifying agent, may be incorporated into a vector. Vectors, including those derived from retroviruses such as lentivirus, are suitable tools to achieve long-term gene transfer since they allow long-term, stable integration of a transgene and its propagation in daughter cells. Examples of vectors include expression vectors, replication vectors, probe generation vectors, and sequencing vectors. The expression vector may be provided to a cell in the form of a viral vector. Viral vector technology is well known in the art, and described in a variety of virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers.

Expression of natural or synthetic nucleic acids is typically achieved by operably linking a nucleic acid encoding the gene of interest to a promoter, and incorporating the construct into an expression vector. The vectors can be suitable for replication and integration in eukaryotes. Typical cloning vectors contain transcription and translation terminators, initiation sequences, and promoters useful for expression of the desired nucleic acid sequence.

Additional promoter elements, e.g., enhancing sequences, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is Elongation Growth Factor-1α (EF-1α). However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter.

Further, the disclosure should not be limited to the use of constitutive promoters. Inducible promoters are also contemplated as part of the disclosure. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

The expression vector to be introduced can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate transcriptional control sequences to enable expression in the host cells. Useful selectable markers include, for example, antibiotic-resistance genes, such as neo and the like.

Reporter genes may be used for identifying potentially transfected cells and for evaluating the functionality of transcriptional control sequences. In general, a reporter gene is a gene that is not present in or expressed by the recipient source and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

RNAi

Certain RNA agents can inhibit gene expression through the biological process of RNA interference (RNAi). RNAi molecules comprise RNA or RNA-like structures typically containing 15-50 base pairs (such as about 18-25 base pairs) and having a nucleobase sequence identical (complementary) or nearly identical (substantially complementary) to a coding sequence in an expressed target gene within the cell. RNAi molecules include, but are not limited to: short interfering RNAs (siRNAs), double-strand RNAs (dsRNA), micro RNAs (miRNAs), short hairpin RNAs (shRNA), meroduplexes, and dicer substrates (U.S. Pat. Nos. 8,084,599, 8,349,809 and 8,513,207). In one embodiment, the disclosure includes a composition to inhibit expression of a gene encoding a polypeptide described herein, e.g., a conjunction nucleating molecule or epigenetic modifying agent.

RNAi molecules comprise a sequence substantially complementary, or fully complementary, to all or a fragment of a target gene. RNAi molecules may complement sequences at the boundary between introns and exons to prevent the maturation of newly-generated nuclear RNA transcripts of specific genes into mRNA for transcription. RNAi molecules complementary to specific genes can hybridize with the mRNA for that gene and prevent its translation. The antisense molecule can be DNA, RNA, or a derivative or hybrid thereof. Examples of such derivative molecules include, but are not limited to, peptide nucleic acid (PNA) and phosphorothioate-based molecules such as deoxyribonucleic guanidine (DNG) or ribonucleic guanidine (RNG).

RNAi molecules can be provided to the cell as "ready-to-use" RNA synthesized in vitro or as an antisense gene transfected into cells which will yield RNAi molecules upon transcription. Hybridization with mRNA results in degradation of the hybridized molecule by RNAse H and/or inhibition of the formation of translation complexes. Both result in a failure to produce the product of the original gene.

The length of the RNAi molecule that hybridizes to the transcript of interest should be around 10 nucleotides, between about 15 or 30 nucleotides, or about 15, 16, 17, 18, 19, 20, 21, 22, 23, 24, 25, 26, 27, 28, 29, 30 or more nucleotides. The degree of identity of the antisense sequence to the targeted transcript should be at least 75%, at least 80%, at least 85%, at least 90%, or at least 95.

RNAi molecules may also comprise overhangs, i.e. typically unpaired, overhanging nucleotides which are not directly involved in the double helical structure normally formed by the core sequences of the herein defined pair of sense strand and antisense strand. RNAi molecules may contain 3' and/or 5' overhangs of about 1-5 bases independently on each of the sense strands and antisense strands. In one embodiment, both the sense strand and the antisense strand contain 3' and 5' overhangs. In one embodiment, one or more of the 3' overhang nucleotides of one strand base pairs with one or more 5' overhang nucleotides of the other strand. In another embodiment, the one or more of the 3' overhang nucleotides of one strand base do not pair with the one or more 5' overhang nucleotides of the other strand. The sense and antisense strands of an RNAi molecule may or may not contain the same number of nucleotide bases. The antisense and sense strands may form a duplex wherein the 5' end only has a blunt end, the 3' end only has a blunt end, both the 5' and 3' ends are blunt ended, or neither the 5' end nor the 3' end are blunt ended. In another embodiment, one or more of the nucleotides in the overhang contains a thiophosphate, phosphorothioate, deoxynucleotide inverted (3' to 3' linked) nucleotide or is a modified ribonucleotide or deoxynucleotide.

Small interfering RNA (siRNA) molecules comprise a nucleotide sequence that is identical to about 15 to about 25 contiguous nucleotides of the target mRNA. In some embodiments, the siRNA sequence commences with the dinucleotide AA, comprises a GC-content of about 30-70% (about 30-60%, about 40-60%, or about 45%-55%), and does not have a high percentage identity to any nucleotide sequence other than the target in the genome of the mammal in which it is to be introduced, for example as determined by standard BLAST search.

siRNAs and shRNAs resemble intermediates in the processing pathway of the endogenous microRNA (miRNA) genes (Bartel, Cell 116:281-297, 2004). In some embodiments, siRNAs can function as miRNAs and vice versa (Zeng et al., Mol Cell 9:1327-1333, 2002; Doench et al., Genes Dev 17:438-442, 2003). MicroRNAs, like siRNAs, use RISC to downregulate target genes, but unlike siRNAs, most animal miRNAs do not cleave the mRNA. Instead, miRNAs reduce protein output through translational suppression or polyA removal and mRNA degradation (Wu et al., Proc Natl Acad Sci USA 103:4034-4039, 2006). Known miRNA binding sites are within mRNA 3' UTRs; miRNAs seem to target sites with near-perfect complementarity to nucleotides 2-8 from the miRNA's 5' end (Rajewsky, Nat Genet 38 Suppl:58-13, 2006; Lim et al., Nature 433:769-773, 2005). This region is known as the seed region. Because siRNAs and miRNAs are interchangeable, exogenous siR-NAs downregulate mRNAs with seed complementarity to the siRNA (Birmingham et al., Nat Methods 3:199-204, 2006. Multiple target sites within a 3' UTR give stronger downregulation (Doench et al., Genes Dev 17:438-442, 2003).

Lists of known miRNA sequences can be found in databases maintained by research organizations, such as Wellcome Trust Sanger Institute, Penn Center for Bioinformatics, Memorial Sloan Kettering Cancer Center, and European Molecule Biology Laboratory, among others. Known effective siRNA sequences and cognate binding sites are also well represented in the relevant literature. RNAi molecules are readily designed and produced by technologies known in the art. In addition, there are computational tools that increase the chance of finding effective and specific sequence motifs (Pei et al. 2006, Reynolds et al. 2004, Khvorova et al. 2003, Schwarz et al. 2003, Ui-Tei et al. 2004, Heale et al. 2005, Chalk et al. 2004, Amarzguioui et al. 2004).

The RNAi molecule modulates expression of RNA encoded by a gene. Because multiple genes can share some degree of sequence homology with each other, in some embodiments, the RNAi molecule can be designed to target a class of genes with sufficient sequence homology. In some embodiments, the RNAi molecule can contain a sequence that has complementarity to sequences that are shared amongst different gene targets or are unique for a specific gene target. In some embodiments, the RNAi molecule can be designed to target conserved regions of an RNA sequence having homology between several genes thereby targeting several genes in a gene family (e.g., different gene isoforms, splice variants, mutant genes, etc.). In some embodiments, the RNAi molecule can be designed to target a sequence that is unique to a specific RNA sequence of a single gene.

In some embodiments, the RNAi molecule targets a sequence in a conjunction nucleating molecule, e.g., CTCF, cohesin, USF1, YY1, TATA-box binding protein associated factor 3 (TAF3), ZNF143, or another polypeptide that promotes the formation of an anchor sequence-mediated conjunction, or an epigenetic modifying agent, e.g., an enzyme involved in post-translational modifications including, but are not limited to, DNA methylases (e.g., DNMT3a, DNMT3b, DNMTL), DNA demethylation (e.g., the TET family enzymes catalyze oxidation of 5-methylcytosine to 5-hydroxymethylcytosine and higher oxidative derivatives), histone methyltransferases, histone deacetylase (e.g., HDAC1, HDAC2, HDAC3), sirtuin 1, 2, 3, 4, 5, 6, or 7, lysine-specific histone demethylase 1 (LSD1), histone-lysine-N-methyltransferase (Setdb1), euchromatic histone-lysine N-methyltransferase 2 (G9a), histone-lysine N-methyltransferase (SUV39H1), enhancer of zeste homolog 2 (EZH2), viral lysine methyltransferase (vSET), histone methyltransferase (SET2), protein-lysine N-methyltransferase (SMYD2), and others. In one embodiment, the RNAi molecule targets a protein deacetylase, e.g., sirtuin 1, 2, 3, 4, 5, 6, or 7. In one embodiment, the disclosure includes a composition comprising an RNAi that targets a conjunction nucleating molecule, e.g., CTCF.

Peptide or Protein Moiety

In some embodiments, the targeting moiety comprises a peptide or protein moiety, e.g., a DNA-binding protein, a CRISPR component protein, conjunction nucleating molecule, a dominant negative conjunction nucleating molecule, an epigenetic modifying agent, or any combination thereof.

The peptide or protein moieties may include, but is not limited to, a peptide ligand, antibody fragment, or targeting aptamer that binds a receptor such as an extracellular receptor, neuropeptide, hormone peptide, peptide drug, toxic peptide, viral or microbial peptide, synthetic peptide, and agonist or antagonist peptide.

Peptide or protein moiety may be linear or branched. The peptide or protein moiety may have a length from about 5 to about 200 amino acids, about 15 to about 150 amino acids, about 20 to about 125 amino acids, about 25 to about 100 amino acids, or any range therebetween.

Exemplary peptide or protein moiety used in the methods and compositions described herein include, but are not limited to, ubiquitin, bicyclic peptides as ubiquitin ligase inhibitors, transcription factors, DNA and protein modification enzymes such as topoisomerases, topoisomerase inhibitors such as topotecan, DNA methyltransferases such as the DNMT family (e.g., DNMT3a, DNMT3b, DNMTL), protein methyltransferases (e.g., viral lysine methyltransferase (vSET), protein-lysine N-methyltransferase (SMYD2), deaminases (e.g., APOBEC, UG1), histone methyltransferases such as enhancer of zeste homolog 2 (EZH2), PRMT1, histone-lysine-N-methyltransferase (Setdb1), histone methyltransferase (SET2), euchromatic histone-lysine N-methyltransferase 2 (G9a), histone-lysine N-methyltransferase (SUV39H1), and G9a), histone deacetylase (e.g., HDAC1, HDAC2, HDAC3), enzymes with a role in DNA demethylation (e.g., the TET family enzymes catalyze oxidation of 5-methylcytosine to 5-hydroxymethylcytosine and higher oxidative derivatives), protein demethylases such as KDM1A and lysine-specific histone demethylase 1 (LSD1), helicases such as DHX9, acetyltransferases, deacetylases (e.g., sirtuin 1, 2, 3, 4, 5, 6, or 7), kinases, phosphatases, DNA-intercalating agents such as ethidium bromide, sybr green, and proflavine, efflux pump inhibitors such as peptidomimetics like phenylalanine arginyl β-naphthylamide or quinoline derivatives, nuclear receptor activators and inhibitors, proteasome inhibitors, competitive inhibitors for enzymes such as those involved in lysosomal storage diseases, protein synthesis inhibitors, nucleases (e.g., Cpf1, Cas9, zinc finger nuclease), fusions of one or more thereof (e.g., dCas9-DNMT, dCas9-APOBEC, dCas9-UG1), and specific domains from proteins, such as KRAB domain.

Some examples of peptides include, but are not limited to, fluorescent tags or markers, antigens, antibodies, antibody fragments such as single domain antibodies, ligands and receptors such as glucagon-like peptide-1 (GLP-1), GLP-2 receptor 2, cholecystokinin B (CCKB) and somatostatin receptor, peptide therapeutics such as those that bind to specific cell surface receptors such as G protein-coupled receptors (GPCRs) or ion channels, synthetic or analog peptides from naturally-bioactive peptides, anti-microbial peptides, pore-forming peptides, tumor targeting or cytotoxic peptides, and degradation or self-destruction peptides such as an apoptosis-inducing peptide signal or photosensitizer peptide.

Peptides described herein may also include small antigen-binding peptides, e.g., antigen binding antibody or antibody-like fragments, such as single chain antibodies, nanobodies (see, e.g., Steeland et al. 2016. Nanobodies as therapeutics: big opportunities for small antibodies. Drug Discov Today:

21(7):1076-113). Such small antigen binding peptides may bind a cytosolic antigen, a nuclear antigen, an intra-organellar antigen.

In one aspect, the disclosure includes a cell or tissue comprising any one of the proteins described herein.

In another aspect, the disclosure includes a pharmaceutical composition comprising the protein described herein.

In another aspect, the disclosure includes a method of modulating expression of a gene by administering the composition comprising the protein described herein.

DNA-Binding Domains

In some embodiments, the targeting moiety comprises a DNA-binding domain of a protein. DNA-binding proteins have distinct structural motifs that play a key role in binding DNA.

The helix-turn-helix motif is a common DNA recognition motif in repressor proteins. The motif comprises two helices, one of which recognizes the DNA (aka recognition helix) and the side chains give the specificity of binding. They are common in proteins that regulate developmental processes. Sometimes more than one protein competes for the same sequence or recognizes the same DNA fragment. They may differ in their affinity for the same sequence, or DNA conformation, respectively through H-bonds, salt bridges and Van der Waals interactions.

DNA-binding proteins with an HhH structural motif may be involved in non-sequence-specific DNA binding that occurs via the formation of hydrogen bonds between protein backbone nitrogens and DNA phosphate groups.

DNA-binding proteins with the HLH structural motif are transcriptional regulatory proteins and are principally related to a wide array of developmental processes. The motif is longer, in terms of residues, than the other two motifs. Many of these proteins interact to form homo- and hetero-dimers. The structural motif is composed of two long helix regions, with the N-terminal helix binding to the DNA, while the loop region allows the protein to dimerize.

In some transcription factors, the dimer binding site with DNA forms a leucine zipper. This motif includes two amphipathic helices, one from each subunit, interacting with each other resulting in a left handed coiled-coil super secondary structure. The leucine zipper is an interdigitation of regularly spaced leucine residues in one helix with leucines from an adjacent helix. Mostly, the helices involved in leucine zippers exhibit a heptad sequence (abcdefg) with residues a and d being hydrophobic and all others hydrophilic. Leucine zipper motifs can mediate either homo- or heterodimer formation.

Some eukaryotic transcription factors show a unique motif called a Zn-finger, where a $Zn^{++}$ ion is coordinated by 2 Cys and 2 His residues. The transcription factor includes a trimer with the stoichiometry $\beta\beta'\alpha$. The apparent effect of the $Zn^{++}$ coordination is the stabilization of a small loop structure instead of hydrophobic core residues. Each Zn-finger interacts in a conformationally identical manner with successive triple base pair segments in the major groove of the double helix. The protein-DNA interaction is determined by two factors: (i) H-bonding interaction between $\alpha$-helix and DNA segment, mostly between Arg residues and Guanine bases. (ii) H-bonding interaction with the DNA phosphate backbone, mostly with Arg and His. An alternative Zn-finger motif chelates the $Zn^{++}$ with 6 Cys.

DNA-binding proteins also include TATA box binding proteins, first identified as a component of the class II initiation factor TFIID. They participate in transcription by all three nuclear RNA polymerases acting as subunit in each of them. The structure of TBP shows two $\alpha/\beta$ structural domains of 89-90 amino acids. The C-terminal or core region binds with high affinity to a TATA consensus sequence (TATAa/tAa/t, SEQ ID NO: xx) recognizing minor groove determinants and promoting DNA bending. TBP resemble a molecular saddle. The binding side is lined with the central 8 strands of the 10-stranded anti-parallel $\beta$-sheet. The upper surface contains four $\alpha$-helices and binds to various components of the transcription machinery.

DNA provides base specificity in the form of nitrogen bases. The R-groups of amino acids, with basic residues such as Lysine, Arginine, Histidine, Aspargine and Glutamine can easily interact with adenine of the A: T base pair, and guanine of the G: C base pair, where NH2 and X=O groups of the base pairs can preferably form hydrogen bonds with amino acid residues of Glutamine, Aspargine, Arginine and Lysine.

In some embodiments, the DNA-binding protein is a transcription factor. Transcription factors (TFs) may be modular proteins containing a DNA-binding domain that is responsible for the specific recognition of base sequences and one or more effector domains that can activate or repress transcription. TFs interact with chromatin and recruit protein complexes that serve as coactivators or corepressors.

Gene Editing Systems

In some embodiments, the targeting moiety (e.g., a site-specific targeting moiety) comprises one or more components of a gene editing system. As can be appreciated by those skilled in the art reading the present specification, and as explained further herein, components of gene editing systems may be used in a variety of contexts including but not limited to gene editing. For example, such components may be used to target agents that physically modify, genetically modify, and/or epigenetically modify target anchor sequences, In some embodiments, the targeting moiety targets one or more nucleotides of the anchor sequence-mediated conjunction for substitution, addition and/or deletion. Exemplary gene editing systems include the clustered regulatory interspaced short palindromic repeat (CRISPR) system, zinc finger nucleases (ZFNs), and Transcription Activator-Like Effector-based Nucleases (TALEN). ZFNs, TALENs, and CRISPR-based methods are described, e.g., in Gaj et al. Trends Biotechnol. 31.7 (2013):397-405; CRISPR methods of gene editing are described, e.g., in Guan et al., Application of CRISPR-Cas system in gene therapy: Pre-clinical progress in animal model. DNA Repair 2016 Jul. 30 [Epub ahead of print]; Zheng et al., Precise gene deletion and replacement using the CRISPR/Cas9 system in human cells. BioTechniques, Vol. 57, No. 3, September 2014, pp. 115-124.

For example, in some embodiments the site-specific targeting moiety comprises a Cas nuclease (e.g., Cas9) and a site-specific guide RNA, as described further herein. In some embodiments, the Cas nuclease is enzymatically inactive, e.g., a dCas9, as described further herein.

In one embodiment, the methods and compositions described herein can be used with a CRISPR-based gene editing, whereby guide RNA (gRNA) are used in a clustered regulatory interspaced short palindromic repeat (CRISPR) system for gene editing. CRISPR systems are adaptive defense systems originally discovered in bacteria and archaea. CRISPR systems use RNA-guided nucleases termed CRISPR-associated or "Cas" endonucleases (e. g., Cas9 or Cpf1) to cleave foreign DNA. In a typical CRISPR/Cas system, an endonuclease is directed to a target nucleotide sequence (e. g., a site in the genome that is to be sequence-edited) by sequence-specific, non-coding "guide RNAs" that target single- or double-stranded DNA sequences. Three classes (I-III) of CRISPR systems have been identified. The class II CRISPR systems use a single Cas endonuclease (rather than multiple Cas proteins). One class II CRISPR system includes a type II Cas endonuclease such as Cas9, a CRISPR RNA ("crRNA"), and a trans-activating crRNA ("tracrRNA"). The crRNA contains a "guide RNA", typically about 20-nucleotide RNA sequence that corresponds to a target DNA sequence. The crRNA also contains a region that binds to the tracrRNA to form a partially double-stranded structure which is cleaved by RNase III, resulting in a crRNA/tracrRNA hybrid. The crRNA/tracrRNA hybrid then directs the Cas9 endonuclease to recognize and cleave the target DNA sequence. The target DNA sequence must generally be adjacent to a "protospacer adjacent motif" ("PAM") that is specific for a given Cas endonuclease; however, PAM sequences appear throughout a given genome. CRISPR endonucleases identified from various prokaryotic species have unique PAM sequence requirements; examples of PAM sequences include 5'-NGG (Streptococcus pyogenes), 5'-NNAGAA (Streptococcus thermophilus CRISPR1), 5'-NGGNG (Streptococcus thermophilus CRISPR3), and 5'-NNNGATT (Neisseria meningitidis). Some endonucleases, e. g., Cas9 endonucleases, are associated with G-rich PAM sites, e. g., 5'-NGG, and perform blunt-end cleaving of the target DNA at a location 3 nucleotides upstream from (5' from) the PAM site. Another class II CRISPR system includes the type V endonuclease Cpf1, which is smaller than Cas9; examples include AsCpf1 (from Acidaminococcus sp.) and LbCpf1 (from Lachnospiraceae sp.). Cpf1-associated CRISPR arrays are processed into mature crRNAs without the requirement of a tracrRNA; in other words a Cpf1 system requires only the Cpf1 nuclease and a crRNA to cleave the target DNA sequence. Cpf1 endonucleases, are associated with T-rich PAM sites, e. g., 5'-TTN. Cpf1 can also recognize a 5'-CTA PAM motif. Cpf1 cleaves the target DNA by introducing an offset or staggered double-strand break with a 4- or 5-nucleotide 5' overhang, for example, cleaving a target DNA with a 5-nucleotide offset or staggered cut located 18 nucleotides downstream from (3' from) from the PAM site on the coding strand and 23 nucleotides downstream from the PAM site on the complimentary strand; the 5-nucleotide overhang that results from such offset cleavage allows more precise genome editing by DNA insertion by homologous recombination than by insertion at blunt-end cleaved DNA. See, e. g., Zetsche et al. (2015) Cell, 163:759-771.

A variety of CRISPR associated (Cas) genes or proteins can be used in the methods of the disclosure and the choice of Cas protein will depend upon the particular conditions of the method. Specific examples of Cas proteins include class II systems including Cas1, Cas2, Cas3, Cas4, Cas5, Cas6, Cas7, Cas8, Cas9, Cas10, Cpf1, C2C1, or C2C3. In some embodiments, a Cas protein, e.g., a Cas9 protein, may be from any of a variety of prokaryotic species. In some embodiments a particular Cas protein, e.g., a particular Cas9 protein, is selected to recognize a particular protospacer-adjacent motif (PAM) sequence. In some embodiments, the targeting moiety includes a sequence targeting polypeptide, such as an enzyme, e.g., Cas9. In certain embodiments a Cas protein, e.g., a Cas9 protein, may be obtained from a bacteria or archaea or synthesized using known methods. In certain embodiments, a Cas protein may be from a gram positive bacteria or a gram negative bacteria. In certain embodiments, a Cas protein may be from a Streptococcus, (e.g., a S. pyogenes, a S. thermophilus) a Cryptococcus, a Corynebacterium, a Haemophilus, a Eubacterium, a Pasteurella, a Prevotella, a Veillonella, or a Marinobacter. In some embodiments nucleic acids encoding two or more different Cas proteins, or two or more Cas proteins, may be introduced into a cell, zygote, embryo, or animal, e.g., to allow for recognition and modification of sites comprising the same, similar or different PAM motifs. In some embodiments, the Cas protein is modified to deactivate the nuclease, e.g., nuclease-deficient Cas9, and to recruit transcription activators or repressors, e.g., the w-subunit of the E. coli Pol, VP64, the activation domain of p65, KRAB, or SID4X, to induce epigenetic modifications, e.g., histone acetyltransferase, histone methyltransferase and demethylase, DNA methyltransferase and enzyme with a role in DNA demethylation (e.g., the TET family enzymes catalyze oxidation of 5-methylcytosine to 5-hydroxymethylcytosine and higher oxidative derivatives).

For the purposes of gene editing, CRISPR arrays can be designed to contain one or multiple guide RNA sequences corresponding to a desired target DNA sequence; see, for example, Cong et al. (2013) Science, 339:819-823; Ran et al. (2013) Nature Protocols, 8:2281-2308. At least about 16 or 17 nucleotides of gRNA sequence are required by Cas9 for DNA cleavage to occur; for Cpf1 at least about 16 nucleotides of gRNA sequence is needed to achieve detectable DNA cleavage.

Whereas wild-type Cas9 generates double-strand breaks (DSBs) at specific DNA sequences targeted by a gRNA, a number of CRISPR endonucleases having modified functionalities are available, for example: a "nickase" version of Cas9 generates only a single-strand break; a catalytically inactive Cas9 ("dCas9") does not cut the target DNA but interferes with transcription by steric hindrance. dCas9 can further be fused with a heterologous effector to repress (CRISPRi) or activate (CRISPRa) expression of a target gene. For example, Cas9 can be fused to a transcriptional silencer (e.g., a KRAB domain) or a transcriptional activator (e.g., a dCas9-VP64 fusion). A catalytically inactive Cas9 (dCas9) fused to FokI nuclease ("dCas9-FokI") can be used to generate DSBs at target sequences homologous to two gRNAs. See, e. g., the numerous CRISPR/Cas9 plasmids disclosed in and publicly available from the Addgene repository (Addgene, 75 Sidney St., Suite 550A, Cambridge, Mass. 02139; addgene.org/crispr/). A "double nickase" Cas9 that introduces two separate double-strand breaks, each directed by a separate guide RNA, is described as achieving more accurate genome editing by Ran et al. (2013) Cell, 154:1380-1389.

CRISPR technology for editing the genes of eukaryotes is disclosed in US Patent Application Publications 2016/0138008A1 and US2015/0344912A1, and in U.S. Pat. Nos. 8,697,359, 8,771,945, 8,945,839, 8,999,641, 8,993,233, 8,895,308, 8,865,406, 8,889,418, 8,871,445, 8,889,356, 8,932,814, 8,795,965, and 8,906,616. Cpf1 endonuclease and corresponding guide RNAs and PAM sites are disclosed in US Patent Application Publication 2016/0208243 A1.

In some embodiments, the desired genome modification involves homologous recombination, wherein one or more double-stranded DNA breaks in the target nucleotide sequence is generated by the RNA-guided nuclease and guide RNA(s), followed by repair of the break(s) using a homologous recombination mechanism ("homology-directed repair"). In such embodiments, a donor template that encodes the desired nucleotide sequence to be inserted or knocked-in at the double-stranded break is provided to the cell or subject; examples of suitable templates include single-stranded DNA templates and double-stranded DNA templates (e. g., linked to the polypeptide described herein).

In general, a donor template encoding a nucleotide change over a region of less than about 50 nucleotides is provided in the form of single-stranded DNA; larger donor templates (e. g., more than 100 nucleotides) are often provided as double-stranded DNA plasmids. In some embodiments, the donor template is provided to the cell or subject in a quantity that is sufficient to achieve the desired homology-directed repair but that does not persist in the cell or subject after a given period of time (e. g., after one or more cell division cycles). In some embodiments, a donor template has a core nucleotide sequence that differs from the target nucleotide sequence (e. g., a homologous endogenous genomic region) by at least 1, at least 5, at least 10, at least 20, at least 30, at least 40, at least 50, or more nucleotides. This core sequence is flanked by "homology arms" or regions of high sequence identity with the targeted nucleotide sequence; in embodiments, the regions of high identity include at least 10, at least 50, at least 100, at least 150, at least 200, at least 300, at least 400, at least 500, at least 600, at least 750, or at least 1000 nucleotides on each side of the core sequence. In some embodiments where the donor template is in the form of a single-stranded DNA, the core sequence is flanked by homology arms including at least 10, at least 20, at least 30, at least 40, at least 50, at least 60, at least 70, at least 80, or at least 100 nucleotides on each side of the core sequence. In embodiments where the donor template is in the form of a double-stranded DNA, the core sequence is flanked by homology arms including at least 500, at least 600, at least 700, at least 800, at least 900, or at least 1000 nucleotides on each side of the core sequence. In one embodiment, two separate double-strand breaks are introduced into the cell or subject's target nucleotide sequence with a "double nickase" Cas9 (see Ran et al. (2013) Cell, 154:1380-1389), followed by delivery of the donor template.

In some embodiments, the composition comprises a polypeptide described herein linked to a gRNA and a targeted nuclease, e.g., a Cas9, e.g., a wild type Cas9, a nickase Cas9 (e.g., Cas9 D10A), a dead Cas9 (dCas9), eSpCas9, Cpf1, C2C1, or C2C3, or a nucleic acid encoding such a nuclease. The choice of nuclease and gRNA(s) is determined by whether the targeted mutation is a deletion, substitution, or addition of nucleotides, e.g., a deletion, substitution, or addition of nucleotides to a targeted sequence. Fusions of a catalytically inactive endonuclease e.g., a dead Cas9 (dCas9, e.g., D10A; H840A) tethered with all or a portion of (e.g., biologically active portion of) an (one or more) effector domain (e.g., epigenome editors including but not restricted to: DNMT3a, DNMT3L, DNMT3b, KRAB domain, Tet 1, p300, VP64 and fusions of the aforementioned) create chimeric proteins that can be linked to the polypeptide to guide the composition to specific DNA sites by one or more RNA sequences (e.g., DNA recognition elements including, but not restricted to zinc finger arrays, sgRNA, TAL arrays, peptide nucleic acids described herein) to modulate activity and/or expression of one or more target nucleic acids sequences (e.g., to methylate or demethylate a DNA sequence).

As used herein, a "biologically active portion of an effector domain" is a portion that maintains the function (e.g. completely, partially, minimally) of an effector domain (e.g., a "minimal" or "core" domain) In some embodiments, fusion of a dCas9 with all or a portion of one or more effector domains of an epigenetic modifying agent (such as a DNA methylase or enzyme with a role in DNA demethylation, e.g., DNMT3a, DNMT3b, DNMT3L, a DNMT inhibitor, combinations thereof, TET family enzymes, protein acetyl transferase or deacetylase, dCas9-DNMT3a/3L, dCas9-DNMT3a/3L/KRAB, dCas9/VP64) creates a chimeric protein that is linked to the polypeptide and useful in the methods described herein. Accordingly, in some embodiments, a nucleic acid encoding a dCas9-methylase fusion is linked to the polypeptide and administered to a subject in need thereof in combination with a site-specific gRNA or antisense DNA oligonucleotide that targets the fusion to an anchor sequence (such as a CTCF binding motif), thereby decreasing the affinity or ability of the anchor sequence to bind a nucleating protein. In other some embodiments, a nucleic acid encoding a dCas9-enzyme fusion is linked to the polypeptide in combination with a site-specific gRNA or antisense DNA oligonucleotide that targets the fusion to a conjunction anchor sequence (such as a CTCF binding motif) and all are administered to a subject in need thereof, thereby increasing the affinity or ability of the anchor sequence to bind a nucleating protein. In some embodiments, all or a portion of one or more methyltransferase, or enzyme associated with demethylation, effector domains are fused with an inactive nuclease, e.g., dCas9, and linked to the polypeptide. Exemplary dCAs9 fusion methods and compositions that are adaptable to the methods and compositions described herein are known and are described, e.g., in Kearns et al., Functional annotation of native enhancers with a Cas9-histone demethylase fusion. Nature Methods 12, 401-403 (2015); and McDonald et al., Reprogrammable CRISPR/Cas9-based system for inducing site-specific DNA methylation. Biology Open 2016: doi: 10.1242/bio.019067.

In other aspects, 1, 2, 3, 4, 5, 6, 7, 8, 9, 10, 11, 12, 13, 14, 15, 16, 17, 18, 19, 20, or more methyltransferase, or enzyme with a role in DNA demethylation, effector domains (all or a biologically active portion) are fused with dCas9 and linked to the polypeptide. The chimeric proteins described herein may also comprise a linker as described herein, e.g., an amino acid linker. In some aspects, a linker comprises 2 or more amino acids, e.g., one or more GS sequences. In some aspects, fusion of Cas9 (e.g., dCas9) with two or more effector domains (e.g., of a DNA methylase or enzyme with a role in DNA demethylation) comprises one or more interspersed linkers (e.g., GS linkers) between the domains and is linked to the polypeptide. In some aspects, dCas9 is fused with a plurality (e.g., 2-5, e.g., 2, 3, 4, 5) effector domains with interspersed linkers and is linked to the polypeptide.

In some embodiments, a targeting moiety comprises one or more components of a CRISPR system described hereinabove.

For example, in some embodiments, a targeting moiety comprises a gRNA that comprises a targeting domain that hybridizes to a nucleic acid comprising a target anchor sequence and/or has a sequence that is at least 80%, at least 85%, at least 90%, at least 95%, at least 97%, at least 98%, at least 99% identical to the complement of the nucleic acid comprising the target anchor sequence. In some embodiments, the gRNA is a site-specific gRNA in that its targeting domain does not hybridize to at least one nucleic acid comprising a non-target anchor sequence.

In some embodiments, the site-specific gRNA comprises a sequence of structure I:
(I) X-Y-Z,
where X and Z are 5' and 3' site specific targeting sequences for a target CTCF binding motif, respectively, and Y is selected from:
(a) an RNA sequence complementary to the sequence of SEQ ID NO:1;

(b) an RNA sequence at least 75%, 80%, 85%, 90%, 95% identical to an RNA sequence complementary to the sequence of SEQ ID NO:1;
(c) an RNA sequence complementary to the sequence of SEQ ID NO:1 having at least 1, 2, 3, 4, 5, but less than 15, 12 or 10 nucleotide additions, substitutions or deletions.
(d) an RNA sequence complementary to the sequence of SEQ ID NO:2;
(e) an RNA sequence at least 75%, 80%, 85%, 90%, 95% identical to an RNA sequence complementary to the sequence of SEQ ID NO:2;
(f) an RNA sequence complementary to the sequence of SEQ ID NO:2 having at least 1, 2, 3, 4, 5, but less than 15, 12 or 10 nucleotide additions, substitutions or deletions.

In some embodiments, X and Z are each between 2-50 nucleotides in length, e.g., between 2-20, between 2-10, between 2-5 nucleotides in length.

In some embodiments, a composition or method is described comprising a gRNA that specifically targets a CTCF binding motif associated with an oncogene, a tumor suppressor, or a disease associated with a nucleotide repeat, e.g., *CTCFBSDB 2.0: Database For CTCF Binding Motifs And Genome Organization.*

In some embodiments, provided are pharmaceutical compositions comprising guide RNAs as described herein.

In some embodiments, the methods described herein include a method of delivering one or more CRISPR system component described hereinabove to a subject, e.g., to the nucleus of a cell or tissue of a subject, by linking such component to a polypeptide described herein.

Conjunction Nucleating Molecules

In some embodiments, the targeting moiety comprises a conjunction nucleating molecule, a nucleic acid encoding a conjunction nucleating molecule, or a combination thereof. In some embodiments, an anchor sequence-mediated conjunction is mediated by a first conjunction nucleating molecule bound to the first anchor sequence, a second conjunction nucleating molecule bound to the non-contiguous second anchor sequence, and an association between the first and second conjunction nucleating molecules. In some embodiments, a conjunction nucleating molecule may disrupt, e.g., by competitive binding, the binding of an endogenous conjunction nucleating molecule to its binding site.

The conjunction nucleating molecule may be, e.g., CTCF, cohesin, USF1, YY1, TATA-box binding protein associated factor 3 (TAF3), ZNF143 binding motif, or another polypeptide that promotes the formation of an anchor sequence-mediated conjunction. The conjunction nucleating molecule may be an endogenous polypeptide or other protein, such as a transcription factor, e.g., autoimmune regulator (AIRE), another factor, e.g., X-inactivation specific transcript (XIST), or an engineered polypeptide that is engineered to recognize a specific DNA sequence of interest, e.g., having a zinc finger, leucine zipper or bHLH domain for sequence recognition. The conjunction nucleating molecule may modulate DNA interactions within or around the anchor sequence-mediated conjunction. For example, the conjunction nucleating molecule can recruit other factors to the anchor sequence that alters an anchor sequence-mediated conjunction formation or disruption.

The conjunction nucleating molecule may also have a dimerization domain for homo- or heterodimerization. One or more conjunction nucleating molecules, e.g., endogenous and engineered, may interact to form the anchor sequence-mediated conjunction. In some embodiments, the conjunction nucleating molecule is engineered to further include a stabilization domain, e.g., cohesion interaction domain, to stabilize the anchor sequence-mediated conjunction. In some embodiments, the conjunction nucleating molecule is engineered to bind a target sequence, e.g., target sequence binding affinity is modulated. In some embodiments, the conjunction nucleating molecule is selected or engineered with a selected binding affinity for an anchor sequence within the anchor sequence-mediated conjunction.

Conjunction nucleating molecules and their corresponding anchor sequences may be identified through the use of cells that harbor inactivating mutations in CTCF and Chromosome Conformation Capture or 3C-based methods, e.g., Hi-C or high-throughput sequencing, to examine topologically associated domains, e.g., topological interactions between distal DNA regions or loci, in the absence of CTCF. Long-range DNA interactions may also be identified. Additional analyses may include ChIA-PET analysis using a bait, such as Cohesin, YY1 or USF1, ZNF143 binding motif, and MS to identify complexes that are associated with the bait.

In some embodiments, one or more conjunction nucleating molecules have a binding affinity for an anchor sequence greater than or less than a reference value, e.g., binding affinity for the anchor sequence in the absence of the alteration.

In some embodiments, the conjunction nucleating molecule is modulated, e.g. a binding affinity for an anchor sequence within the anchor sequence-mediated conjunction, to alter its interaction with the anchor sequence-mediated conjunction.

Heterologous Moiety

In some embodiments, the composition, agent, and/or fusion molecule described herein may include one or more heterologous moiety. A heterologous moiety may be an effector (e.g., a drug, small molecule), a tag (e.g., fluorophore, light sensitive agent such as KillerRed), or any of the editing moieties or targeting moieties described herein.

In some embodiments, the heterologous moiety may be linked to a membrane translocating polypeptide as described herein. In some embodiments, a membrane translocating polypeptide described herein is linked to one or more heterologous moieties.

In one aspect, the disclosure includes a cell or tissue comprising any one of the heterologous moieties described herein.

In another aspect, the disclosure includes a pharmaceutical composition comprising the heterologous moiety described herein.

In another aspect, the disclosure includes a method of modulating expression of a gene by administering the composition comprising the heterologous moiety described herein.

In one aspect, the heterologous moiety is any of the targeting moieties that modulate the two-dimensional structure of chromatin (i.e., that modulate the structure of chromatin in a way that would alter its two-dimensional representation).

In one embodiment, the heterologous moiety is a small molecule (e.g., a peptidomimetic or a small organic molecule with a molecular weight of less than 2000 daltons), a peptide or polypeptide (e.g., a non $ABX''C$ polypeptide, e.g., an antibody or antigen-binding fragment thereof), a nucleic acid (e.g., siRNA, mRNA, RNA, DNA, modified DNA or RNA, antisense DNA oligonucleotides, an antisense RNA, a ribozyme, a therapeutic mRNA encoding a protein), a nanoparticle, an aptamer, or pharmacoagent with poor PK/PD.

In some embodiments, the heterologous moiety may cleaved from the polypeptide (e.g., after administration) by specific proteolysis or enzymatic cleavage (e.g. by TEV protease, Thrombin, Factor Xa or Enteropeptidase).

Effector Moiety

A heterologous moiety may be an effector moiety that possesses effector activity. The effector moiety may modulate a biological activity, for example increasing or decreasing enzymatic activity, gene expression, cell signaling, and cellular or organ function. Effector activities may also include binding regulatory proteins to modulate activity of the regulator, such as transcription or translation. Effector activities also may include activator or inhibitor (or "negative effector") functions as described herein. For example, the heterologous moiety may induce enzymatic activity by triggering increased substrate affinity in an enzyme, e.g., fructose 2,6-bisphosphate activates phosphofructokinase 1 and increases the rate of glycolysis in response to the insulin. In another example, the heterologous moiety may inhibit substrate binding to a receptor and inhibit its activation, e.g., naltrexone and naloxone bind opioid receptors without activating them and block the receptors' ability to bind opioids. Effector activities may also include modulating protein stability/degradation and/or transcript stability/degradation. For example, proteins may be targeted for degradation by the polypeptide co-factor, ubiquitin, onto proteins to mark them for degradation. In another example, the heterologous moiety inhibits enzymatic activity by blocking the enzyme's active site, e.g., methotrexate is a structural analog of tetrahydrofolate, a coenzyme for the enzyme dihydrofolate reductase that binds to dihydrofolate reductase 1000-fold more tightly than the natural substrate and inhibits nucleotide base synthesis.

In some embodiments, the composition comprises a targeting moiety (e.g., gRNA, membrane translocating polypeptide) that binds the anchor sequence, and is operably linked to an effector moiety that modulates the formation of a conjunction mediated by the anchor sequence.

In some embodiments, the effector moiety is a chemical, e.g., a chemical that modulates a cytosine (C) or an adenine (A) (e.g., Na bisulfite, ammonium bisulfite). In some embodiments, the effector moiety has enzymatic activity (methyl transferase, demethylase, nuclease (e.g., Cas9), a deaminase). In some embodiments, the effector moiety sterically hinders formation of the anchor sequence-mediated conjunction. [e.g., membrane translocating polypeptide+nanoparticle (def: 1-100 nm)].

The effector moiety with effector activity may be any one of the small molecules, peptides, nucleic acids, nanoparticles, aptamers, and pharmacoagents with poor PK/PD described herein.

Negative Effector Moieties

In some embodiments, the effector is an inhibitor or "negative effector". In the context of a negative effector moiety that modulates formation of an anchor sequence-mediated conjunction, in some embodiments, the negative effector moiety is characterized in that dimerization of an endogenous nucleating polypeptide is reduced when the negative effector moiety is present as compared with when it is absent. For example, in some embodiments, the negative effector moiety is or comprises a variant of the endogenous nucleating polypeptide's dimerization domain, or a dimerizing portion thereof.

Dominant Negative Conjunction Nucleating Molecules

For example, in certain embodiments, an anchor sequence-mediated conjunction is altered (e.g., disrupted) by use of a dominant negative effector, e.g., a protein that recognizes and binds an anchor sequence, (e.g., a CTCF binding motif), but with an inactive (e.g., mutated) dimerization domain, e.g., a dimerization domain that is unable to form a functional anchor sequence-mediated conjunction. For example, the Zinc Finger domain of CTCF can be altered so that it binds a specific anchor sequence (by adding zinc fingers that recognize flanking nucleic acids), while the homo-dimerization domain is altered to prevent the interaction between the engineered CTCF and endogenous forms of CTCF. DNA encoding the protein can be administered to a subject in need thereof.

In some embodiments, the composition comprises a synthetic conjunction nucleating molecule with a selected binding affinity for an anchor sequence within a target anchor sequence-mediated conjunction. (the binding affinity may be at least 10%, 15%, 20%, 25%, 30%, 35%, 40%, 45%, 50%, 55%, 60%, 65%, 70%, 75%, 80%, 85%, 90%, 95%, or higher or lower than the affinity of an endogenous conjunction nucleating molecule that associates with the target anchor sequence. The synthetic conjunction nucleating molecule may have between 30-90%, 30-85%, 30-80%, 30-70%, 50-80%, 50-90% amino acid sequence identity to the endogenous conjunction nucleating molecule). The conjunction nucleating molecule may disrupt, such as through competitive binding, the binding of an endogenous conjunction nucleating molecule to its anchor sequence. In some more embodiments, the conjunction nucleating molecule is engineered to bind a novel anchor sequence within the anchor sequence-mediated conjunction.

In some embodiments, the dominant negative effector has a domain that recognizes specific DNA sequences (e.g., an anchor sequence, a CTCF anchor sequence, flanked by sequences that confer sequence specificity), and a second domain that provides a steric presence in the vicinity of the anchoring sequence.

The second domain may include a dominant negative conjunction nucleating molecule or fragment thereof, a polypeptide that interferes with conjunction nucleating molecule sequence recognition (e.g., the amino acid backbone of a peptide/nucleic acid or PNA), a nucleic acid sequence ligated to a small molecule that imparts steric interference, or any other combination of DNA recognition element and a steric blocker.

Epigenetic Modifying Agents

In some embodiments, the heterologous moiety is an epigenetic modifying agent. Epigenetic modifying agents useful in the methods and compositions described herein include agents that affect, e.g., DNA methylation, histone acetylation, and RNA-associated silencing. In some embodiments, the methods described herein involve sequence-specific targeting of an epigenetic enzyme (e.g., an enzyme that generates or removes epigenetic marks, e.g., acetylation and/or methylation). Exemplary epigenetic enzymes that can be targeted to an anchor sequence using the CRISPR methods described herein include DNA methylases (e.g., DNMT3a, DNMT3b, DNMTL), DNA demethylation (e.g., the TET family), histone methyltransferases, histone deacetylase (e.g., HDAC1, HDAC2, HDAC3), sirtuin 1, 2, 3, 4, 5, 6, or 7, lysine-specific histone demethylase 1 (LSD1), histone-lysine-N-methyltransferase (Setdb1), euchromatic histone-lysine N-methyltransferase 2 (G9a), histone-lysine N-methyltransferase (SUV39H1), enhancer of zeste homolog 2 (EZH2), viral lysine methyltransferase (vSET), histone methyltransferase (SET2), and protein-lysine N-methyltransferase (SMYD2). Examples of such epigenetic modifying agents are described, e.g., in de Groote et al. Nuc. Acids Res. (2012):1-18.

In some embodiments, an epigenetic modifying agent useful herein comprises a construct described in Koferle et al. Genome Medicine 7.59 (2015): 1-3 (e.g., at Table 1), incorporated herein by reference.

Tagging or Monitoring Moiety

A heterologous moiety may be a tag to label or monitor the polypeptide described herein or another heterologous moiety linked to the polypeptide. The tagging or monitoring moiety may be removable by chemical agents or enzymatic cleavage, such as proteolysis or intein splicing. An affinity tag may be useful to purify the tagged polypeptide using an affinity technique. Some examples include, chitin binding protein (CBP), maltose binding protein (MBP), glutathione-S-transferase (GST), and poly(His) tag. A solubilization tag may be useful to aid recombinant proteins expressed in chaperone-deficient species such as *E. coli* to assist in the proper folding in proteins and keep them from precipitating. Some examples include thioredoxin (TRX) and poly (NANP). The tagging or monitoring moiety may include a light sensitive tag, e.g., fluorescence. Fluorescent tags are useful for visualization. GFP and its variants are some examples commonly used as fluorescent tags. Protein tags may allow specific enzymatic modifications (such as biotinylation by biotin ligase) or chemical modifications (such as reaction with FlAsH-EDT2 for fluorescence imaging) to occur. Often tagging or monitoring moiety are combined, in order to connect proteins to multiple other components. The tagging or monitoring moiety may also be removed by specific proteolysis or enzymatic cleavage (e.g. by TEV protease, Thrombin, Factor Xa or Enteropeptidase).

The tagging or monitoring moiety may be a small molecule, peptide, nucleic acid, nanoparticle, aptamer, or other agent.

Nucleic Acids

A heterologous moiety may be a nucleic acid. A nucleic acid heterologous moiety may include, but is not limited to, DNA, RNA, and artificial nucleic acids. The nucleic acid may include, but is not limited to, genomic DNA, cDNA, modified DNA, antisense DNA oligonucleotides, tRNA, mRNA, rRNA, modified RNA, miRNA, gRNA, and siRNA or other RNAi molecule. In one embodiment, the nucleic acid is an siRNA to target a gene expression product. In another embodiment, the nucleic acid includes one or more nucleoside analogs as described herein.

Nucleic acids have a length from about 2 to about 5000 nts, about 10 to about 100 nts, about 50 to about 150 nts, about 100 to about 200 nts, about 150 to about 250 nts, about 200 to about 300 nts, about 250 to about 350 nts, about 300 to about 500 nts, about 10 to about 1000 nts, about 50 to about 1000 nts, about 100 to about 1000 nts, about 1000 to about 2000 nts, about 2000 to about 3000 nts, about 3000 to about 4000 nts, about 4000 to about 5000 nts, or any range therebetween.

Some examples of nucleic acids include, but are not limited to, a nucleic acid that hybridizes to an endogenous gene (e.g., gRNA or antisense ssDNA as described herein elsewhere), nucleic acid that hybridizes to an exogenous nucleic acid such as a viral DNA or RNA, nucleic acid that hybridizes to an RNA, nucleic acid that interferes with gene transcription, nucleic acid that interferes with RNA translation, nucleic acid that stabilizes RNA or destabilizes RNA such as through targeting for degradation, nucleic acid that interferes with a DNA or RNA binding factor through interference of its expression or its function, nucleic acid that is linked to a intracellular protein and modulates its function, and nucleic acid that is linked to an intracellular protein complex and modulates its function.

The disclosure contemplates the use of RNA therapeutics (e.g., modified RNAs) as heterologous moieties useful in the compositions described herein. For example, a modified mRNA encoding a protein of interest may be linked to a polypeptide described herein and expressed in vivo in a subject.

In some embodiments, the modified RNA or DNA oligonucleotide linked to a polypeptide described herein, has modified nucleosides or nucleotides. Such modifications are known and are described, e.g., in WO 2012/019168. Additional modifications are described, e.g., in WO2015038892; WO2015038892; WO2015089511; WO2015196130; WO2015196118 and WO2015196128A2.

In some embodiments, the modified RNA or DNA oligonucleotide linked to the polypeptide described herein has one or more terminal modifications, e.g., a 5'Cap structure and/or a poly-A tail (e.g., of between 100-200 nucleotides in length). The 5' cap structure may be selected from the group consisting of CapO, Capl, ARCA, inosine, N1-methyl-guanosine, 2'fluoro-guanosine, 7-deaza-guanosine, 8-oxo-guanosine, 2-amino-guanosine, LNA-guanosine, and 2-azido-guanosine. In some cases, the modified RNAs also contains a 5' UTR comprising at least one Kozak sequence, and a 3' UTR. Such modifications are known and are described, e.g., in WO2012135805 and WO2013052523. Additional terminal modifications are described, e.g., in WO2014164253 and WO2016011306. WO2012045075 and WO2014093924.

Chimeric enzymes for synthesizing capped RNA molecules (e.g., modified mRNA) which may include at least one chemical modification are described in WO2014028429.

In some embodiments, a modified mRNA may be cyclized, or concatemerized, to generate a translation competent molecule to assist interactions between poly-A binding proteins and 5'-end binding proteins. The mechanism of cyclization or concatemerization may occur through at least 3 different routes: 1) chemical, 2) enzymatic, and 3) ribozyme catalyzed. The newly formed 5'-/3'-linkage may be intramolecular or intermolecular. Such modifications are described, e.g., in WO2013151736.

Methods of making and purifying modified RNAs are known and disclosed in the art. For example, modified RNAs are made using only in vitro transcription (IVT) enzymatic synthesis. Methods of making IVT polynucleotides are known in the art and are described in WO2013151666, WO2013151668, WO2013151663, WO2013151669, WO2013151670, WO2013151664, WO2013151665, WO2013151671, WO2013151672, WO2013151667 and WO2013151736.S Methods of purification include purifying an RNA transcript comprising a polyA tail by contacting the sample with a surface linked to a plurality of thymidines or derivatives thereof and/or a plurality of uracils or derivatives thereof (polyT/U) under conditions such that the RNA transcript binds to the surface and eluting the purified RNA transcript from the surface (WO2014152031); using ion (e.g., anion) exchange chromatography that allows for separation of longer RNAs up to 10,000 nucleotides in length via a scalable method (WO2014144767); and subjecting a modified RMNA sample to DNAse treatment (WO2014152030).

Modified RNAs encoding proteins in the fields of human disease, antibodies, viruses, and a variety of in vivo settings are known and are disclosed in for example, Table 6 of International Publication Nos. WO2013151666, WO2013151668, WO2013151663, WO2013151669, WO2013151670, WO2013151664, WO2013151665, WO2013151736; Tables 6 and 7 International Publication No. WO2013151672; Tables 6, 178 and 179 of International Publication No. WO2013151671; Tables 6, 185 and 186 of International Publication No WO2013151667. Any of the foregoing may be synthesized as an IVT polynucleotide, chimeric polynucleotide or a circular polynucleotide and linked to the polypeptide described herein, and each may comprise one or more modified nucleotides or terminal modifications.

Peptide Oligonucleotide Conjugates

A heterologous moiety may be a peptide oligonucleotide conjugate. Peptide oligonucleotide conjugates include chimeric molecules comprising a nucleic acid moiety linked to a peptide moiety (such as a peptide/nucleic acid mixmer). In some embodiments, the peptide moiety may include any peptide or protein moiety described herein. In some embodiments, the nucleic acid moiety may include any nucleic acid or oligonucleotide, e.g., DNA or RNA or modified DNA or RNA, described herein.

In some embodiments, the peptide oligonucleotide conjugate comprises a peptide antisense oligonucleotide conjugate. In some embodiments, the peptide oligonucleotide conjugate is a synthetic oligonucleotide with a chemically modified backbone. The peptide oligonucleotide conjugate can bind to both DNA and RNA targets in a sequence-specific manner to form a duplex structure. When bound to double-stranded DNA (dsDNA) target, the peptide oligonucleotide conjugate replaces one DNA strand in the duplex by strand invasion to form a triplex structure and the displaced DNA strand may exist as a single-stranded D-loop.

In some embodiments, peptide oligonucleotide conjugate may be cell- and/or tissue-specific targeting (which can be conjugated directly to oligos, peptides, and/or proteins, etc.).

In some embodiments, the peptide oligonucleotide conjugate comprises a membrane translocating polypeptide, for example the membrane translocating polypeptides as described elsewhere herein.

Solid-phase synthesis of several peptide-oligonucleotide conjugates has been described in, for example, Williams, et al., 2010, Curr. Protoc. Nucleic Acid Chem., Chapter Unit 4.41, doi: 10.1002/0471142700.nc0441s42. Synthesis and characterization of very short peptide-oligonucleotide conjugates and stepwise solid-phase synthesis of peptide-oligonucleotide conjugates on new solid supports have been described in, for example, Bongardt, et al., Innovation Perspect. Solid Phase Synth. Comb. Libr., Collect. Pap., Int. Symp., 5th, 1999, 267-270; Antopolsky, et al., Helv. Chim. Acta, 1999, 82, 2130-2140.

Nanoparticles

A heterologous moiety may be a nanoparticle. Nanoparticles include inorganic materials with a size between about 1 and about 1000 nanometers, between about 1 and about 500 nanometers in size, between about 1 and about 100 nm, between about 30 nm and about 200 nm, between about 50 nm and about 300 nm, between about 75 nm and about 200 nm, between about 100 nm and about 200 nm, and any range therebetween. Nanoparticle has a composite structure of nanoscale dimensions. In some embodiments, nanoparticles are typically spherical although different morphologies are possible depending on the nanoparticle composition. The portion of the nanoparticle contacting an environment external to the nanoparticle is generally identified as the surface of the nanoparticle. In nanoparticles described herein, the size limitation can be restricted to two dimensions and so that nanoparticles include composite structure having a diameter from about 1 to about 1000 nm, where the specific diameter depends on the nanoparticle composition and on the intended use of the nanoparticle according to the experimental design. For example, nanoparticles used in therapeutic applications typically have a size of about 200 nm or below.

Additional desirable properties of the nanoparticle, such as surface charges and steric stabilization, can also vary in view of the specific application of interest. Exemplary properties that can be desirable in clinical applications such as cancer treatment are described in Davis et al, Nature 2008 vol. 7, pages 771-782; Duncan, Nature 2006 vol. 6, pages 688-701; and Allen, Nature 2002 vol. 2 pages 750-763, each incorporated herein by reference in its entirety. Additional properties are identifiable by a skilled person upon reading of the present disclosure. Nanoparticle dimensions and properties can be detected by techniques known in the art. Exemplary techniques to detect particles dimensions include but are not limited to dynamic light scattering (DLS) and a variety of microscopies such at transmission electron microscopy (TEM) and atomic force microscopy (AFM). Exemplary techniques to detect particle morphology include but are not limited to TEM and AFM. Exemplary techniques to detect surface charges of the nanoparticle include but are not limited to zeta potential method. Additional techniques suitable to detect other chemical properties comprise by $^{1}$H, $^{11}$B, and $^{13}$C and $^{19}$F NMR, UV/Vis and infrared/Raman spectroscopies and fluorescence spectroscopy (when nanoparticle is used in combination with fluorescent labels) and additional techniques identifiable by a skilled person.

Small Molecules

In one embodiment, the targeting moiety is a small molecule that alters one or more DNA methylation sites, e.g., mutates methylated cysteine to thymine, within the anchor sequence-mediated conjunction. For example, bisulfite compounds, e.g., sodium bisulfite, ammonium bisulfite, or other bisulfite salts, may be used to alter one or more DNA methylation sites, e.g., altering the nucleotide sequence from a cysteine to a thymine.

A heterologous moiety may be a small molecule. Small molecule moieties include, but are not limited to, small peptides, peptidomimetics (e.g., peptoids), amino acids, amino acid analogs, synthetic polynucleotides, polynucleotide analogs, nucleotides, nucleotide analogs, organic and inorganic compounds (including heterorganic and organomettallic compounds) generally having a molecular weight less than about 5,000 grams per mole, e.g., organic or inorganic compounds having a molecular weight less than about 2,000 grams per mole, e.g., organic or inorganic compounds having a molecular weight less than about 1,000 grams per mole, e.g., organic or inorganic compounds having a molecular weight less than about 500 grams per mole, and salts, esters, and other pharmaceutically acceptable forms of such compounds. Small molecules may include, but are not limited to, a neurotransmitter, a hormone, a drug, a toxin, a viral or microbial particle, a synthetic molecule, and agonists or antagonists.

Examples of suitable small molecules include those described in, "The Pharmacological Basis of Therapeutics," Goodman and Gilman, McGraw-Hill, New York, N.Y., (1996), Ninth edition, under the sections: Drugs Acting at Synaptic and Neuroeffector Junctional Sites; Drugs Acting on the Central Nervous System; Autacoids: Drug Therapy of Inflammation; Water, Salts and Ions; Drugs Affecting Renal Function and Electrolyte Metabolism; Cardiovascular Drugs; Drugs Affecting Gastrointestinal Function; Drugs Affecting Uterine Motility; Chemotherapy of Parasitic Infections; Chemotherapy of Microbial Diseases; Chemotherapy of Neoplastic Diseases; Drugs Used for Immunosuppression; Drugs Acting on Blood-Forming organs; Hormones and Hormone Antagonists; Vitamins, Dermatology; and Toxicology, all incorporated herein by reference. Some examples of small molecules include, but are not limited to, prion drugs such as tacrolimus, ubiquitin ligase or HECT ligase inhibitors such as heclin, histone modifying drugs such as sodium butyrate, enzymatic inhibitors such as 5-azacytidine, anthracyclines such as doxorubicin, beta-lactams such as penicillin, anti-bacterials, chemotherapy agents, anti-virals, modulators from other organisms such as VP64, and drugs with insufficient bioavailability such as chemotherapeutics with deficient pharmacokinetics.

In some embodiments, the small molecule is an epigenetic modifying agent, for example such as those described in de Groote et al. Nuc. Acids Res. (2012):1-18. Exemplary small molecule epigenetic modifying agents are described, e.g., in Lu et al. J. Biomolecular Screening 17.5 (2012):555-71, e.g., at Table 1 or 2, incorporated herein by reference. In some embodiments, an epigenetic modifying agent comprises vorinostat, romidepsin. In some embodiments, an epigenetic modifying agent comprises an inhibitor of class I, II, III, and/or IV histone deacetylase (HDAC). In some embodiments, an epigenetic modifying agent comprises an activator of SirTI. In some embodiments, an epigenetic modifying agent comprises Garcinol, Lys-CoA, C646, (+)-JQI, I-BET, BICI, MS120, DZNep, UNC0321, EPZ004777, AZ505, AMI-I, pyrazole amide 7b, benzo[d]imidazole 17b, acylated dapsone derivative (e.e.g, PRMTI), methylstat, 4,4'-dicarboxy-2,2'-bipyridine, SID 85736331, hydroxamate analog 8, tanylcypromie, bisguanidine and biguanide polyamine analogs, UNC669, Vidaza, decitabine, sodium phenyl butyrate (SDB), lipoic acid (LA), quercetin, valproic acid, hydralazine, bactrim, green tea extract (e.g., epigallocatechin gallate (EGCG)), curcumin, sulforphane and/or allicin/diallyl disulfide. In some embodiments, an epigenetic modifying agent inhibits DNA methylation, e.g., is an inhibitor of DNA methyltransferase (e.g., is 5-azacitidine and/or decitabine). In some embodiments, an epigenetic modifying agent modifies histone modification, e.g., histone acetylation, histone methylation, histone sumoylation, and/or histone phosphorylation. In some embodiments, the epigenetic modifying agent is an inhibitor of a histone deacetylase (e.g., is vorinostat and/or trichostatin A).

In some embodiments, the small molecule is a pharmaceutically active agent. In one embodiment, the small molecule is an inhibitor of a metabolic activity or component. Useful classes of pharmaceutically active agents include, but are not limited to, antibiotics, anti-inflammatory drugs, angiogenic or vasoactive agents, growth factors and chemotherapeutic (anti-neoplastic) agents (e.g., tumour suppressers). One or a combination of molecules from the categories and examples described herein or from (Orme-Johnson 2007, Methods Cell Biol. 2007; 80:813-26) can be used. In one embodiment, the disclosure includes a composition comprising an antibiotic, anti-inflammatory drug, angiogenic or vasoactive agent, growth factor or chemotherapeutic agent.

Oligonucleotide Aptamers

A heterologous moiety may be an oligonucleotide aptamer. Aptamer moieties are oligonucleotide or peptide aptamers. Oligonucleotide aptamers are single-stranded DNA or RNA (ssDNA or ssRNA) molecules that can bind to pre-selected targets including proteins and peptides with high affinity and specificity.

Oligonucleotide aptamers are nucleic acid species that may be engineered through repeated rounds of in vitro selection or equivalently, SELEX (systematic evolution of ligands by exponential enrichment) to bind to various molecular targets such as small molecules, proteins, nucleic acids, and even cells, tissues and organisms. Aptamers provide discriminate molecular recognition, and can be produced by chemical synthesis. In addition, aptamers possess desirable storage properties, and elicit little or no immunogenicity in therapeutic applications.

Both DNA and RNA aptamers show robust binding affinities for various targets. For example, DNA and RNA aptamers have been selected for t lysozyme, thrombin, human immunodeficiency virus trans-acting responsive element (HIV TAR), https://en.wikipedia.org/wiki/Aptamer-cite_note-10 hemin, interferon γ, vascular endothelial growth factor (VEGF), prostate specific antigen (PSA), dopamine, and the non-classical oncogene, heat shock factor 1 (HSF1).

Diagnostic techniques for aptamer based plasma protein profiling includes aptamer plasma proteomics. This technology will enable future multi-biomarker protein measurements that can aid diagnostic distinction of disease versus healthy states.

Peptide Aptamers

A heterologous moiety may be a peptide aptamer. Peptide aptamers have one (or more) short variable peptide domains, including peptides having low molecular weight, 12-14 kDa. Peptide aptamers may be designed to specifically bind to and interfere with protein-protein interactions inside cells.

Peptide aptamers are artificial proteins selected or engineered to bind specific target molecules. These proteins include of one or more peptide loops of variable sequence. They are typically isolated from combinatorial libraries and often subsequently improved by directed mutation or rounds of variable region mutagenesis and selection. In vivo, peptide aptamers can bind cellular protein targets and exert biological effects, including interference with the normal protein interactions of their targeted molecules with other proteins. In particular, a variable peptide aptamer loop attached to a transcription factor binding domain is screened against the target protein attached to a transcription factor activating domain In vivo binding of the peptide aptamer to its target via this selection strategy is detected as expression of a downstream yeast marker gene. Such experiments identify particular proteins bound by the aptamers, and protein interactions that the aptamers disrupt, to cause the phenotype. In addition, peptide aptamers derivatized with appropriate functional moieties can cause specific post-translational modification of their target proteins, or change the subcellular localization of the targets Peptide aptamers can also recognize targets in vitro. They have found use in lieu of antibodies in biosensors and used to detect active isoforms of proteins from populations containing both inactive and active protein forms. Derivatives known as tadpoles, in which peptide aptamer "heads" are covalently linked to unique sequence double-stranded DNA "tails", allow quantification of scarce target molecules in mixtures by PCR (using, for example, the quantitative real-time polymerase chain reaction) of their DNA tails.

Peptide aptamer selection can be made using different systems, but the most used is currently the yeast two-hybrid system. Peptide aptamers can also be selected from combinatorial peptide libraries constructed by phage display and other surface display technologies such as mRNA display, ribosome display, bacterial display and yeast display. These experimental procedures are also known as biopannings Among peptides obtained from biopannings, mimotopes can be considered as a kind of peptide aptamers. All the peptides panned from combinatorial peptide libraries have been stored in a special database with the name MimoDB.

Pharmacoagents

In one embodiment, the heterologous moiety is an agent with an undesirable pharmacokinetic or pharmacodynamics (PK/PD) parameter Linking the heterologous moiety to the polypeptide may improve at least one PK/PD parameter, such as targeting, absorption, and transport of the heterologous moiety, or reduce at least one undesirable PK/PD parameter, such as diffusion to off-target sites, and toxic metabolism. For example, linking a polypeptide as described herein to an agent with poor targeting/transport, e.g., doxorubicin, beta-lactams such as penicillin, improves its specificity. In another example, linking a polypeptide as described herein to an agent with poor absorption properties, e.g., insulin, human growth hormone, improves its minimum dosage. In another example, linking a polypeptide as described herein to an agent that has toxic metabolic properties, e.g., acetaminophen at higher doses, improves its maximum dosage.

Membrane Translocating Polypeptide

In one aspect, the composition comprises a polypeptide described herein with properties that allow translocation across a membrane, for example, independent of endosomes, such that the composition is delivered to a target location within a cell, e.g., within a subject. In some embodiments, the targeting moiety comprises a membrane translocating polypeptide.

In one aspect, the disclosure includes a cell or tissue comprising any one of the membrane translocating polypeptides described herein.

In another aspect, the disclosure includes a pharmaceutical composition comprising the membrane translocating polypeptide described herein.

In another aspect, the disclosure includes a method of modulating expression of a gene by administering the composition comprising the membrane translocating polypeptide described herein.

In one aspect, the disclosure includes a method altering gene expression or altering an anchor sequence-mediated conjunction with a membrane translocating polypeptide. In some embodiments, the membrane translocating polypeptide is a targeting moiety. In some embodiments, the membrane translocating polypeptide is a delivery agent that aids delivery of the targeting moiety described herein. The target location may be intracellular, e.g., cytosolic or intra-organellar (e.g., intranuclear, such as a target DNA sequence or chromatin structure). The therapeutic compositions described herein may have further advantageous properties, such as improved targeting, absorption, or transport, or reduced off-target activity, toxic metabolism, or toxic excretion.

In one embodiment, the composition includes at least one membrane translocating polypeptide with each comprising at least one sequence of $ABX''C$, where A is selected from a hydrophobic amino acid or an amide containing backbone, e.g., aminoethyl-glycine, with a nucleic acid side chain; B and C may be the same or different, and are independently selected from arginine, asparagine, glutamine, lysine, and analogs thereof; X is each independently a hydrophobic amino acid or X is each independently an amide containing backbone, e.g., aminoethyl-glycine, with a nucleic acid side chain; and n is an integer from 1 to 4.

Hydrophobic amino acids include amino acids having hydrophobic side chains and include, but are not limited to, alanine (ala, A), valine (val, V), isoleucine (iso, I), leucine (leu, L), methionine (met, M), phenylalanine (phe, F), tyrosine (tyr, Y), tryptophan (trp, W), and analogs thereof.

Amino acid analogs include, but are not limited to, D-amino acids, amino acids lacking a hydrogen on the α-carbon such as dehydroalanine, metabolic intermediates such as ornithine and citrulline, non-alpha amino acids such as β-alanine, γ-aminobutyric acid, and 4-aminobenzoic acid, twin α-carbon amino acids such as cystathionine, lanthionine, djenkolic acid and diaminopimelic acid, and any others known in the art.

Nucleic Acid Side Chains

In one embodiment, the membrane translocating polypeptide includes one or more nucleic acid side chains linked to the amide backbone. An individual amino acid unit in a polypeptide includes the amide bond and its corresponding side chain. One or more amino acid units in the membrane translocating polypeptide have an amide containing backbone, e.g., aminoethyl-glycine, similar to a peptide backbone, with a nucleic acid side chain in place of the amino acid side chain. Peptide nucleic acids (PNA) are known to hybridize complementary DNA and RNA with higher affinity than their oligonucleotide counterparts. This character of PNA not only makes the polypeptide of the disclosure a stable hybrid with the nucleic acid side chains, but at the same time, the neutral backbone and hydrophobic side chains result in a hydrophobic unit within the polypeptide.

The nucleic acid side chain includes, but is not limited to, a purine or a pyrimidine side chain such as adenine, cytosine, guanine, thymine and uracil. In one embodiment, the nucleic acid side chain includes a nucleoside analog as described herein.

Size

In some embodiments, the membrane translocating polypeptide has a size in the range of about 5 to about 500, e.g., 5-400, 5-300, 5-250, 5-200, 5-150, 5-100 amino acid units in length. The polypeptide may have a length in the range of about 5 to about 50 amino acids, about 5 to about 40 amino acids, about 5 to about 30 amino acids, about 5 to about 25 amino acids, or any other range. In one embodiment, the polypeptide has a length of about 10 amino acids. In another embodiment, the polypeptide has a length of about 15 amino acids. In another embodiment, the polypeptide has a length of about 20 amino acids. In another embodiment, the polypeptide has a length of about 25 amino acids. In another embodiment, the polypeptide has a length of about 30 amino acids.

The membrane translocating polypeptide may have more than one sequence of $ABX''C$ within its length. Each $ABX''C$ sequence may be separated from another $ABX''C$ sequence by one or more amino acids. In one embodiment, the polypeptide repeats the $ABX''C$ sequence and separates the sequences by one or more amino acid units. In another embodiment, the polypeptide includes at least two (e.g., 2, 3, 4, 5, 6, 7, 8, 9, 10, 11, 12, 13, 14, 15 or more, e.g., between 2-20, between 2-10, between 2-5) $ABX''C$ sequences and separates the sequences by one or more amino acid units. In another embodiment, the $ABX''C$ sequences are separated by one (or more) hydrophobic amino acid, such as isoleucine or leucine.

The composition may include a plurality of $ABX''C$ sequences that are the same or different. In one embodiment, at least two of the plurality are identical in sequence and/or length. In one embodiment, at least two of the plurality are different in sequence and/or length. In one embodiment, the composition includes a plurality of $ABX''C$ sequences wherein at least two of the plurality are the same and at least 2 of the plurality are different. In one embodiment, the ABX"C sequences in the membrane translocating polypeptide are not identical in sequence or length or a combination thereof.

Production of Proteins or Polypeptides

Methods of making the therapeutic protein or polypeptide described herein are routine in the art. See, in general, Smales & James (Eds.), *Therapeutic Proteins: Methods and Protocols* (*Methods in Molecular Biology*), Humana Press (2005); and Crommelin, Sindelar & Meibohm (Eds.), *Pharmaceutical Biotechnology: Fundamentals and Applications*, Springer (2013).

The protein or polypeptide of the composition can be biochemically synthesized by employing standard solid phase techniques. Such methods include exclusive solid phase synthesis, partial solid phase synthesis methods, fragment condensation, classical solution synthesis. These methods can be used when the peptide is relatively short (i.e., 10 kDa) and/or when it cannot be produced by recombinant techniques (i.e., not encoded by a nucleic acid sequence) and therefore involves different chemistry.

Solid phase synthesis procedures are well known in the art and further described by John Morrow Stewart and Janis Dillaha Young, *Solid Phase Peptide Syntheses,* 2nd Ed., Pierce Chemical Company, 1984; and Coin, I., et al., Nature Protocols, 2:3247-3256, 2007.

For longer peptides, recombinant methods may be used. Methods of making a recombinant therapeutic polypeptide are routine in the art. See, in general, Smales & James (Eds.), *Therapeutic Proteins: Methods and Protocols* (*Methods in Molecular Biology*), Humana Press (2005); and Crommelin, Sindelar & Meibohm (Eds.), *Pharmaceutical Biotechnology: Fundamentals and Applications*, Springer (2013).

Exemplary methods for producing a therapeutic pharmaceutical protein or polypeptide involve expression in mammalian cells, although recombinant proteins can also be produced using insect cells, yeast, bacteria, or other cells under the control of appropriate promoters. Mammalian expression vectors may comprise nontranscribed elements such as an origin of replication, a suitable promoter, and other 5' or 3' flanking nontranscribed sequences, and 5' or 3' nontranslated sequences such as necessary ribosome binding sites, a polyadenylation site, splice donor and acceptor sites, and termination sequences. DNA sequences derived from the SV40 viral genome, for example, SV40 origin, early promoter, splice, and polyadenylation sites may be used to provide the other genetic elements required for expression of a heterologous DNA sequence. Appropriate cloning and expression vectors for use with bacterial, fungal, yeast, and mammalian cellular hosts are described in Green & Sambrook, *Molecular Cloning: A Laboratory Manual* (*Fourth Edition*), Cold Spring Harbor Laboratory Press (2012).

In cases where large amounts of the protein or polypeptide are desired, it can be generated using techniques such as described by Brian Bray, Nature Reviews Drug Discovery, 2:587-593, 2003; and Weissbach & Weissbach, 1988, *Methods for Plant Molecular Biology*, Academic Press, NY, Section VIII, pp 421-463.

Various mammalian cell culture systems can be employed to express and manufacture recombinant protein. Examples of mammalian expression systems include CHO cells, COS cells, HeLA and BHK cell lines. Processes of host cell culture for production of protein therapeutics are described in Zhou and Kantardjieff (Eds.), *Mammalian Cell Cultures for Biologics Manufacturing* (*Advances in Biochemical Engineering/Biotechnology*), Springer (2014). The compositions described herein may include a vector, such as a viral vector, e.g., a lentiviral vector, encoding the recombinant protein. The vector, e.g., a viral vector, that comprises the nucleic acid encoding the recombinant protein.

Purification of protein therapeutics is described in Franks, *Protein Biotechnology: Isolation, Characterization, and Stabilization*, Humana Press (2013); and in Cutler, Protein Purification Protocols (Methods in Molecular Biology), Humana Press (2010).

Formulation of protein therapeutics is described in Meyer (Ed.), *Therapeutic Protein Drug Products: Practical Approaches to formulation in the Laboratory, Manufacturing, and the Clinic*, Woodhead Publishing Series (2012).

Linkers

The proteins or polypeptides describe herein may also include a linker. In some embodiments, the protein described herein, e.g., comprising a first polypeptide domain that comprises a Cas or modified Cas protein and a second polypeptide domain that comprises a polypeptide having DNA methyltransferase activity [or associated with demethylation or deaminase activity], has a linker between the first and second polypeptide. In one embodiment, one or more polypeptides described herein are linked with a linker. A linker may be a chemical bond, e.g., one or more covalent bonds or non-covalent bonds. In some embodiments, the linker is a peptide linker (e.g., a non ABX"C peptide). Such a linker may be between 2-30 amino acids, or longer. The linker includes flexible, rigid or cleavable linkers described herein.

The most commonly used flexible linkers have sequences consisting primarily of stretches of Gly and Ser residues ("GS" linker). Flexible linkers may be useful for joining domains that require a certain degree of movement or interaction and may include small, non-polar (e.g. Gly) or polar (e.g. Ser or Thr) amino acids. Incorporation of Ser or Thr can also maintain the stability of the linker in aqueous solutions by forming hydrogen bonds with the water molecules, and therefore reduce unfavorable interactions between the linker and the protein moieties.

Rigid linkers are useful to keep a fixed distance between domains and to maintain their independent functions. Rigid linkers may also be useful when a spatial separation of the domains is critical to preserve the stability or bioactivity of one or more components in the fusion. Rigid linkers may have an alpha helix-structure or Pro-rich sequence, $(XP)_.$, with X designating any amino acid, preferably Ala, Lys, or Glu.

Cleavable linkers may release free functional domains in vivo. In some embodiments, linkers may be cleaved under specific conditions, such as the presence of reducing reagents or proteases. In vivo cleavable linkers may utilize the reversible nature of a disulfide bond. One example includes a thrombin-sensitive sequence (e.g., PRS) between the two Cys residues. In vitro thrombin treatment of CPRSC results in the cleavage of the thrombin-sensitive sequence, while the reversible disulfide linkage remains intact. Such linkers are known and described, e.g., in Chen et al. 2013. Fusion Protein Linkers: Property, Design and Functionality. Adv Drug Deliv Rev. 65(10): 1357-1369. In vivo cleavage of linkers in fusions may also be carried out by proteases that are expressed in vivo under pathological conditions (e.g. cancer or inflammation), in specific cells or tissues, or constrained within certain cellular compartments. The specificity of many proteases offers slower cleavage of the linker in constrained compartments.

Examples of linking molecules include a hydrophobic linker, such as a negatively charged sulfonate group; lipids, such as a poly ($—CH_2—$) hydrocarbon chains, such as polyethylene glycol (PEG) group, unsaturated variants thereof, hydroxylated variants thereof, amidated or otherwise N-containing variants thereof, noncarbon linkers; carbohydrate linkers; phosphodiester linkers, or other molecule capable of covalently linking two or more polypeptides. Non-covalent linkers are also included, such as hydrophobic lipid globules to which the polypeptide is linked, for example through a hydrophobic region of the polypeptide or a hydrophobic extension of the polypeptide, such as a series of residues rich in leucine, isoleucine, valine, or perhaps also alanine, phenylalanine, or even tyrosine, methionine, glycine or other hydrophobic residue. The polypeptide may be linked using charge-based chemistry, such that a positively charged moiety of the polypeptide is linked to a negative charge of another polypeptide or nucleic acid.

Multimerization of Polypeptides

The composition may include a plurality (two or more) of membrane translocating polypeptides linked together, e.g., through a linker described herein.

The composition may include a plurality of membrane translocating polypeptides that are the same or different. In one embodiment, at least two of the plurality are identical in sequence and/or length. In one embodiment, at least two of the plurality are different in sequence and/or length. In one embodiment, the composition includes a plurality of polypeptides wherein at least two of the plurality are the same and at least 2 of the plurality are different. In one embodiment, the polypeptides in the composition are not identical in sequence or length or a combination thereof.

The composition includes a membrane translocating polypeptide that is linked to another membrane translocating polypeptide, e.g., by a linker. In some embodiments, the composition includes two or more polypeptides linked by a linker. In some embodiments, the composition includes three or more polypeptides linked by linkers. In some embodiments, the composition includes four or more polypeptides linked by linkers. In some embodiments, the composition includes five or more polypeptides linked by linkers. The linker may be a chemical bond, e.g., one or more covalent bonds or non-covalent bonds, e.g., a flexible, rigid or cleavable peptide linker. Such a linker may be between 2-30 amino acids, or longer. Additional linkers are described in more detail elsewhere herein and are also applicable.

In one embodiment, two or more membrane translocating polypeptides are linked through a peptide bond, for example the carboxyl terminal of one polypeptide is bonded to the amino terminal of another polypeptide. In another embodiment, one or more amino acids on one polypeptide are linked with one or more amino acids on another polypeptide, such as through disulfide bonds between cysteine side chains. In another embodiment, one or more amino acids on one polypeptide are linked with a carboxyl or amino terminal on another polypeptide, such as to create a branched polypeptide.

In another embodiment, one or more nucleic acid side chains on one membrane translocating polypeptide interact with one or more amino acid side chains on another membrane translocating polypeptide, such as through arginine forming a pseudo-pairing with guanosine. In another embodiment, one or more nucleic acid side chains on one membrane translocating polypeptide interact with one or more nucleic acid side chains on another membrane translocating polypeptide, such as through hydrogen bonding. In another embodiment, multiple membrane translocating polypeptides interact to create a specific sequence in the arrangement of the nucleic acid side chains. For example, the carboxy terminal nucleic acid side chain from one polypeptide interacts with the amino terminal nucleic acid side chain from another polypeptide to create a pseudo-5' to pseudo-3' nucleotide sequence. In another example, a polypeptide is linked with one or more polypeptides, such as through amino acids and/or terminus on each polypeptide, and their respective nucleic acid side chains align to create a pseudo-5' to pseudo-3' nucleotide sequence. The pseudo-sequence may bind a selected target sequence, such as an anchor sequence of an anchor sequence-mediated conjunction, e.g., a CTCF binding motif, cohesin binding motif, USF1 binding motif, YY1 binding motif, TATA-box, ZNF143 binding motif, etc, or a transcriptional control sequence, e.g., an enhancing or silencing sequence. The pseudo-sequence may bind a selected target sequence, such as a transcriptional control sequence, e.g., an enhancing or silencing sequence. The pseudo-sequence may interfere with factor binding and transcription by binding to a target sequence. The pseudo-sequence may hybridize with a nucleic acid sequence, such as an mRNA to interfere with gene expression.

In one embodiment, the membrane translocating polypeptides are linked to one another and the linked polypeptides create a pseudo-5' to pseudo-3' nucleotide sequence that binds to an anchor sequence that is recognized by a nucleating protein that binds with sufficient avidity to form an anchor sequence-mediated conjunction, e.g., a loop, or a two-dimensional DNA structure generated by the physical interaction or binding of one conjunction nucleating molecule-anchor sequence with another conjunction nucleating molecule-anchor sequence. An example of an anchor sequence includes, but is not limited to, a CTCF binding motif, e.g., CTCF-binding motif or consensus sequence: N(T/C/G)N(G/A/T)CC(A/T/G)(C/G)(C/T/A)AG(G/A)(G/T)GG(C/A/T)(G/A)(C/G)(C/T/A)(G/A/C) (SEQ ID NO:1), where N is any nucleotide. The linked polypeptides may create a pseudo-5' to pseudo-3' nucleotide sequence that binds to a CTCF-binding motif or consensus sequence in the opposite orientation, e.g., (G/A/C)(C/T/A)(C/G)(G/A)(C/A/T)GG(G/T)(G/A)GA(C/T/A)(C/G)(A/T/G)CC(G/A/T)N(T/C/G)N (SEQ ID NO:2).

The membrane translocating polypeptides described herein can be multimerized, e.g., linking two or more polypeptides, by employing standard ligation techniques. Such methods include, general native chemical ligation strategies (Siman, P. and Brik, A. Org. Biomol. Chem. 2012, 10:5684-5697; Kent, S. B. H. Chem. Soc. Rev. 2009, 38:338-351; and Hackenberger, C. P. R. and Schwarzer, D. Angew. Chem., Int. Ed. 2008, 47:10030-10074), click modification protocols (Tasdelen, M. A.; Yagci, Y. Angew. Chem., Int. Ed. 2013, 52:5930-5938; Palomo, J. M. Org. Biomol. Chem. 2012, 10:9309-9318; Eldijk, M. B.; van Hest, J. C. M. Angew. Chem., Int. Ed. 2011, 50:8806-8827; and Lallana, E.; Riguera, R.; Fernandez-Megia, E. Angew. Chem., Int. Ed. 2011, 50:8794-8804), and bioorthogonal reactions (King, M.; Wagner, A. Bioconjugate Chem. 2014, 25:825-839; Lang, K.; Chin, J. W. Chem. Rev. 2014, 114:4764-4806; Patterson, D. M.; Nazarova, L. A.; Prescher, J. A. ACS Chem. Biol. 2014, 9:592-605; Lang, K.; Chin, J. W. ACS Chem. Biol. 2014, 9:16-20; akaoka, Y.; Ojida, A.; Hamachi, I. Angew. Chem., Int. Ed. 2013, 52:4088-4106; Debets, M. F.; van Hest, J. C. M.; Rutjes, F. P. J. T. Org. Biomol. Chem. 2013, 11:6439-6455; and Ramil, C. P.; Lin, Q. Chem. Commun. 2013, 49:11007-11022).

In some embodiments, the ordering of the membrane translocating polypeptides in the multimer is specific or it may be random, e.g., when the polypeptides are not identical. For example, the polypeptides described herein are multimerized by template driven synthesis or multimerization is ordered by physical constraints or hybridization to a template, e.g., DNA, protein, hybrid DNA-protein. In one embodiment, a template, e.g., a DNA sequence, specifically hybridizes to a polypeptide described herein. The polypeptide is linked to another polypeptide via one of the methods described herein, e.g., general chemical ligation, and the choice of which polypeptide is linked may be constrained by the ability to hybridize to the template. Thus, a specific polypeptide multimer may be generated by its ability to specifically hybridize to the template.

In some embodiments, the order of the membrane translocating polypeptides in the multimer is determined by the chemical ligation strategy used. In one embodiment, chemical ligation techniques, such as click chemistry and bioorthogonal reactions, direct which polypeptides are linked because the chemical ligation strategy requires specific entities to react for the ligation technique to proceed. For example, one polypeptide may be labeled with a phenyl azide and another polypeptide is labeled with cyclooctyne. The cyclooctyne and phenyl azide react to link the two polypeptides.

Hybridization

In embodiments where the membrane translocating polypeptide includes nucleic acid side chains, it is capable of interacting with nucleic acids. In one embodiment, one or more nucleic acid side chains on the polypeptide hybridize with a nucleic acid sequence, e.g., a DNA such as genomic DNA, RNA such as siRNA or mRNA molecule. One or more of the nucleic acid side chains on the polypeptide specifically hybridizes with one or more nucleic acid residues in a target nucleic acid sequence. In one embodiment, the polypeptides are linked to one another and the nucleic acid side chains hybridize a nucleic acid sequence (e.g., gene locus, mRNA, anchor sequence of an anchor sequence-mediated conjunction, e.g., CTCF binding motif, cohesin binding motif, USF1 binding motif, YY1 binding motif, TATA-box, ZNF143 binding motif, etc.).

The nucleic acid side chains or pseudo-sequence of nucleic acid side chains may hybridize a target nucleic acid sequence that is substantially matched to hybridize or 100%, 95%, 90%, 85%, 80%, 75%, or 70% complementary to the nucleic acid side chains or pseudo-sequence of nucleic acid side chains. Hybridization of the nucleic acid side chains or pseudo-sequence of nucleic acid side chains with a target nucleic acid sequence may be carried out under suitable hybridization conditions routinely determined by optimization procedures. Conditions such as temperature, concentration of components, hybridization and washing times, buffer components, and their pH and ionic strength may be varied depending on various factors, including the length and GC content of nucleic acid side chains or pseudo-sequence of nucleic acid side chains and the complementary target nucleic acid sequence. For example, when a relatively short length of nucleic acid side chains or pseudo-sequence of nucleic acid side chains is used, lower stringent conditions may be adopted. The detailed conditions for hybridization can be found in *Molecular Cloning, A laboratory manual*, fourth edition (Cold Spring Harbor Laboratory Press, 2012) or the like.

Polypeptide Linked Heterologous Moiety

The composition may include a heterologous moiety described herein linked to the membrane translocating polypeptide of the targeting moiety, such as through covalent bonds or non-covalent bonds or a linker as described herein. In one embodiment, the composition comprises a heterologous moiety linked to the polypeptide through a peptide bond. For example, the amino terminal of the polypeptide is linked to the heterologous moiety, such as through a peptide bond with an optional linker. In another embodiment, the carboxyl terminal of the polypeptide is linked to the heterologous moiety.

In one embodiment, the composition comprises a membrane translocating polypeptide linked to two heterologous moieties. For example, the amino terminal and carboxyl terminal of the polypeptide are linked to heterologous moieties, which may be the same or different heterologous moieties.

In another embodiment, one or more amino acids of the membrane translocating polypeptide are linked with the heterologous moiety, such as through disulfide bonds between cysteine side chains, hydrogen bonding, or any other known chemistry. One heterologous moiety may be an effector with biological activity and the other heterologous moiety may be a ligand or antibody to target the composition to a specific cell expressing the receptor. For example, a chemotherapeutic agent, such as topotecan a topoisomerase inhibitor, is linked to one end of the polypeptide and a ligand or antibody is linked to the other end of the polypeptide to target the composition to a specific cell or tissue. In another example, the heterologous moieties are both effectors with biological activity.

In another embodiment, a plurality of membrane translocating polypeptides, either the same or different membrane translocating polypeptides, are linked to a single heterologous moiety. The polypeptides may act as a coating that surrounds a large heterologous moiety and aids in its membrane penetration. The heterologous moiety may have a molecular weight greater than about 500 grams per mole or daltons, e.g., organic or inorganic compound has a molecular weight greater than about 1,000 grams per mole, e.g., organic or inorganic compound has a molecular weight greater than about 2,000 grams per mole, e.g., organic or inorganic compound has a molecular weight greater than about 3,000 grams per mole, e.g., organic or inorganic compound has a molecular weight greater than about 4,000 grams per mole, e.g., organic or inorganic compound has a molecular weight greater than about 5,000 grams per mole, and salts, esters, and other pharmaceutically acceptable forms of such compounds are included.

In one embodiment, the composition comprises a membrane translocating polypeptide linked to a heterologous moiety on one or both ends and another heterologous moiety linked to another site on the polypeptide. One or both the amino terminal and the carboxyl terminal of the polypeptide is linked to the heterologous moiety and one or more amino acid units in the polypeptide, either amino acids or nucleic acids, is linked to one or more heterologous moieties, such as through disulfide bonds or hydrogen bonding. For example, a DNA modification enzyme is linked to the polypeptide, and a nucleic acid having an unmethylated CTCF binding motif that is complementary to a target methylated gene is hybridized to the nucleic acid side chains of the polypeptide. Upon administration, the composition targets the CTCF genomic binding motif to modulate transcription of the gene. In another example, a double stranded nucleic acid having an unmethylated CTCF binding motif with gene specific flanking sequences is linked to the polypeptide. Upon administration, the unmethylated CTCF binding motif serves as an alternate anchor sequence for CTCF protein to bind. In another example, ubiquitin and another heterologous moiety, such as an effector, are linked to the polypeptide. Upon administration, the composition penetrates the cell membrane and the effector performs a function. Then, ubiquitin targets the composition for degradation.

In one embodiment, the composition comprises a membrane translocating polypeptide linked to one or more heterologous moieties through covalent bonds and another heterologous moiety linked to the nucleic acids in the polypeptide. For example, a protein synthesis inhibitor is covalently linked to the polypeptide, and an siRNA or other target specific nucleic acid is hybridized to the nucleic acids in the polypeptide. Upon administration, the siRNA targets the composition to an mRNA transcript and the protein synthesis inhibitor and siRNA act to inhibit expression of the mRNA.

In some embodiments, the pharmaceutical composition comprises a membrane translocating polypeptide linked to a gRNA that comprises a sequence of structure I:

(II) X-Y-Z, where X and Z are 5' and 3' site specific targeting sequences for a target CTCF binding motif, respectively, and Y is selected from:
(a) an RNA sequence complementary to the sequence of SEQ ID NO:1;
(b) an RNA sequence at least 75%, 80%, 85%, 90%, 95% identical to an RNA sequence complementary to the sequence of SEQ ID NO:1;
(c) an RNA sequence complementary to the sequence of SEQ ID NO:1 having at least 1, 2, 3, 4, 5, but less than 15, 12 or 10 nucleotide additions, substitutions or deletions.
(d) an RNA sequence complementary to the sequence of SEQ ID NO:2;
(e) an RNA sequence at least 75%, 80%, 85%, 90%, 95% identical to an RNA sequence complementary to the sequence of SEQ ID NO:2;
(f) an RNA sequence complementary to the sequence of SEQ ID NO:2 having at least 1, 2, 3, 4, 5, but less than 15, 12 or 10 nucleotide additions, substitutions or deletions.

In some embodiments, X and Z are each between 2-50 nucleotides in length, e.g., between 2-20, between 2-10, between 2-5 nucleotides in length.

In some embodiments, a gRNA comprises a specific targeting sequence for a CTCF binding motif associated with an oncogene, a tumor suppressor, or a disease associated with a nucleotide repeat. The membrane translocating polypeptides described herein can be linked to a heterologous moiety by employing standard ligation techniques, such as those described herein to link polypeptides.

For introducing small mutations or a single-point mutation, a homologous recombination (HR) template can be linked to the membrane translocating polypeptide. In one embodiment, the HR template is a single stranded DNA (ssDNA) oligo or a plasmid. For ssDNA oligo design, one may use around 100-150 bp total homology with the mutation introduced roughly in the middle, giving 50-75 bp homology arms.

In some embodiments, a gRNA or antisense DNA oligonucleotide for targeting a target anchor sequence, e.g., a CTCF binding motif, is linked to the membrane translocating polypeptide in combination with an HR template selected from:
(a) a nucleotide sequence comprising SEQ ID NO:1;
(b) a nucleotide sequence at least 75%, 80%, 85%, 90%, 95% identical to SEQ ID NO:1;
(c) a nucleotide sequence comprising SEQ ID NO:1 having at least 1, 2, 3, 4, 5, but less than 15, 12 or 10 nucleotide additions, substitutions or deletions.
(d) a nucleotide sequence comprising SEQ ID NO:2;
(e) a nucleotide sequence at least 75%, 80%, 85%, 90%, 95% identical to SEQ ID NO:2;
a nucleotide sequence comprising SEQ ID NO:2 having at least 1, 2, 3, 4, 5, but less than 15, 12 or 10 nucleotide additions, substitutions or deletions.

Any of the linkers described herein may be included to covalently or noncovalently link the membrane translocating polypeptide and a heterologous moiety. The linker can be used, e.g., to space the polypeptide from the heterologous moiety. For example, the linker can be positioned between the polypeptide and the heterologous moiety, e.g., to provide molecular flexibility of secondary and tertiary structures. In one embodiment, the linker includes at least one glycine, alanine, and serine amino acids to provide for flexibility. In another embodiment, the linker is a hydrophobic linker, such as including a negatively charged sulfonate group, polyethylene glycol (PEG) group, or pyrophosphate diester group. In another embodiment, the linker is cleavable to selectively release the heterologous moiety from the polypeptide, but sufficiently stable to prevent premature cleavage.

Linkage after Administration

In some embodiments, the membrane translocating polypeptide described herein has the capacity to form linkages, e.g., after administration, to other polypeptides, to a heterologous moiety as described herein, e.g., an effector molecule, e.g., a nucleic acid, protein, peptide or other molecule, or other agents, e.g., intracellular molecules, such as through covalent bonds or non-covalent bonds. In one embodiment, one or more amino acids on the polypeptide are capable of linking with a nucleic acid, such as through arginine forming a pseudo-pairing with guanosine or an internucleotide phosphate linkage or an interpolymeric linkage. In some embodiments, the nucleic acid is a DNA such as genomic DNA, RNA such as tRNA or mRNA molecule. In another embodiment, one or more amino acids on the polypeptide are capable of linking with a protein or peptide.

Fusion Molecules

In some embodiments, the composition comprises a fusion molecule, such as a fusion molecule that comprises a peptide or polypeptide. Those skilled in the art reading the specification would appreciate that the term "protein fusion" may refer to a fusion molecule that comprises a "protein" (or peptide or polypeptide) component. In some embodiments, the protein fusion comprises one or more of the moieties described herein, e.g., a nucleic acid sequence, a peptide or protein moiety, a membrane translocating polypeptide, a targeting peptide/aptamer, or other heterologous moiety described herein.

In one aspect, the disclosure includes a cell or tissue comprising any one of the protein fusions described herein.

In another aspect, the disclosure includes a pharmaceutical composition comprising the protein fusion described herein.

In another aspect, the disclosure includes a method of modulating expression of a gene by administering the composition comprising the protein fusion described herein. For example, the protein fusion may be dCas9-DNMT, dCas9-DNMT-3a-3L, dCas9-DNMT-3a-3a, dCas9-DNMT-3a-3L-3a, dCas9-DNMT-3a-3L-KRAB, dCas9-KRAB, dCas9-APOBEC, APOBEC-dCas9, dCas9-APOBEC-UGI, dCas9-UGI, UGI-dCas9-APOBEC, UGI-APOBEC-dCas9, any variation of the protein fusions described herein, or other fusions of proteins or protein domains described herein.

Exemplary dCas9 fusion methods and compositions that are adaptable to the methods and compositions described herein are known and are described, e.g., in Kearns et al., Functional annotation of native enhancers with a Cas9-histone demethylase fusion. Nature Methods 12, 401-403 (2015); and McDonald et al., Reprogrammable CRISPR/Cas9-based system for inducing site-specific DNA methylation. Biology Open 2016: doi: 10.1242/bio.019067. Using methods known in the art, dCas9 can be fused to any of a variety of agents and/or molecules as described herein; such resulting fusion molecules can be useful in various disclosed methods.

In one aspect, the disclosure includes a composition comprising a protein comprising a domain, e.g., an enzyme domain, that acts on DNA (e.g., a nuclease domain, e.g., a Cas9 domain, e.g., a dCas9 domain; a DNA methyltransferase, a demethylase, a deaminase), in combination with at least one guide RNA (gRNA) or antisense DNA oligonucleotide that targets the protein to an anchor sequence of a target anchor sequence-mediated conjunction, wherein the composition is effective to alter, in a human cell, the target anchor sequence-mediated conjunction. In some embodiments, the enzyme domain is a Cas9 or a dCas9. In some embodiments, the protein comprises two enzyme domains, e.g., a dCas9 and a methylase or demethylase domain.

In some embodiments, the targeting moiety includes a fusion of a sequence targeting polypeptide and a conjunction nucleating molecule, e.g. a fusion of dCas9 and a conjunction nucleating molecule, e.g., one gRNA or antisense DNA oligonucleotides fused with a nuclease, or a nucleic acid encoding the fusion. Fusions of a catalytically inactive endonuclease e.g., a dead Cas9 (dCas9, e.g., D10A; H840A) tethered with all or a portion of (e.g., biologically active portion of) an (one or more) effector domain and/or other agent create chimeric proteins or fusion molecules that can be guided to specific DNA sites by one or more RNA sequences (sgRNA) or antisense DNA oligonucleotides to modulate activity and/or expression of one or more target nucleic acids sequences (e.g., to methylate or demethylate a DNA sequence).

As used herein, a "biologically active portion of an effector domain" is a portion that maintains the function (e.g. completely, partially, minimally) of an effector domain (e.g., a "minimal" or "core" domain) In some embodiments, fusion of a dCas9 with all or a portion of one or more effector domains of an epigenetic modifying agent (such as a DNA methylase or enzyme with a role in DNA demethylation, e.g., DNMT3a, DNMT3b, DNMT3L, a DNMT inhibitor, TET family enzymes, and combinations thereof, or protein acetyl transferase or deacetylase) creates a chimeric protein that is useful in the methods described herein. Accordingly, in some embodiments, the targeting moiety includes a dCas9-methylase fusion in combination with a site-specific gRNA or antisense DNA oligonucleotide that targets the fusion to a conjunction anchor sequence (such as a CTCF binding motif), thereby decreasing the affinity or ability of the anchor sequence to bind a conjunction nucleating protein. In other some embodiments, the targeting moiety includes a dCas9-enzyme fusion in combination with a site-specific gRNA or antisense DNA oligonucleotide that targets the fusion to a conjunction anchor sequence (such as a CTCF binding motif), thereby increasing the affinity or ability of the anchor sequence to bind a conjunction nucleating molecule. In some embodiments, all or a portion of one or more epigenetic modifying agent effector domains (e.g., DNA methylase or enzyme with a role in DNA demethylation, or protein acetyl transferase or deacetylase, or deaminase) are fused with the inactive nuclease, e.g., dCas9. In other aspects, 1, 2, 3, 4, 5, 6, 7, 8, 9, 10, 11, 12, 13, 14, 15, 16, 17, 18, 19, 20, or more effector domains (all or a biologically active portion) are fused with dCas9.

The chimeric proteins described herein may also comprise a linker, e.g., an amino acid linker. In some aspects, a linker comprises 2 or more amino acids, e.g., one or more GS sequences. In some aspects, fusion of Cas9 (e.g., dCas9) with two or more effector domains (e.g., of a DNA methylase or enzyme with a role in DNA demethylation or protein acetyl transferase or deacetylase) comprises one or more interspersed linkers (e.g., GS linkers) between the domains. In some aspects, dCas9 is fused with 2-5 effector domains with interspersed linkers.

Modifying Chromatin Structure

The methods described herein modulate chromatin structure (e.g., anchor sequence-mediated conjunctions) in order to modulate gene expression in a subject, e.g., by modifying anchor sequence-mediated conjunctions in DNA. Those skilled in the art reading the present specification will appreciate that modulations described herein may modulate chromatin structure in a way that would alter its two-dimensional representation (e.g., would add, alter, or delete a loop or other anchor sequence-mediated conjunction); such modulations are referred to herein, in accordance with common parlance, as modulations or modification of a two-dimensional structure.

In one aspect, the methods described herein may comprise modifying a two-dimensional structure by altering a topology of an anchor sequence-mediated conjunction, e.g., a loop, to modulate transcription of a nucleic acid sequence, wherein the altered topology of the anchor sequence-mediated conjunction modulates transcription of the nucleic acid sequence.

In another aspect, the methods described herein may comprise modifying a two-dimensional structure chromatin structure by altering a topology of a plurality of anchor sequence-mediated conjunctions, e.g., multiple loops, to modulate transcription of a nucleic acid sequence, wherein the altered topology modulates transcription of the nucleic acid sequence.

In another aspect, the methods described herein may comprise modulating transcription of a nucleic acid sequence by altering an anchor sequence-mediated conjunction, e.g., a loop, that influences transcription of a nucleic acid sequence, wherein altering the anchor sequence-mediated conjunction modulates transcription of the nucleic acid sequence.

In some embodiments, altering the anchor sequence-mediated conjunction comprises modifying a chromatin structure, e.g., disrupting [reversible or irreversible] a topology of the anchor sequence-mediated conjunction, altering one or more nucleotides in the anchor sequence-mediated conjunction [genetically modifying the sequence], epigenetically modifying [modulating DNA methylation at one or more sites] the anchor sequence-mediated conjunction, or forming a non-naturally occurring anchor sequence-mediated conjunction. In some embodiments, altering the anchor sequence-mediated conjunction comprises modifying a chromatin structure.

As appreciated by those of skill in the art, a given pair of anchor sequences may "breathe" in and out of an anchor sequence-mediated conjunction, though a given pair of anchor sequences may tend to be more or less often in a particular state (either in or out of a conjunction) depending on factors, such as, for example, cell type.

By "disruption" it is meant that formation and/or stability of an anchor sequence-mediated conjunction is negatively affected.

Reversible Disruption

In some embodiments, compositions and methods are described herein for reversibly disrupting an anchor sequence-mediated conjunction. For example, the disruption may transiently modulate transcription, e.g., a modulation that persists for no more than about 30 mins to about 7 days, or no more than about 1 hr, 2 hrs, 3 hrs, 4 hrs, 5 hrs, 6 hrs, 7 hrs, 8 hrs, 9 hrs, 10 hrs, 11 hrs, 12 hrs, 13 hrs, 14 hrs, 15 hrs, 16 hrs, 17 hrs, 18 hrs, 19 hrs, 20 hrs, 21 hrs, 22 hrs, 24 hrs, 36 hrs, 48 hrs, 60 hrs, 72 hrs, 4 days, 5 days, 6 days, 7 days, or any time therebetween.

In some embodiments, a targeting moiety described herein interferes with loop formation by, e.g., CTCF and CTCF-binding motif by blocking the interaction between CTCF and the CTCF-binding motif. In one embodiment, a composition or method is described for disrupting an anchor sequence-mediated conjunction with an epigenetic modifying agent, such as a gRNA, that targets DNA and acts as a steric presence in the vicinity of the anchoring sequence. The gRNA recognizes specific DNA sequences (e.g., an anchor sequence, a CTCF anchor sequence, flanked by sequences that confer sequence specificity). The gRNA may include additional sequences that interfere with a conjunction nucleating molecule sequence to act as a steric blocker. In some embodiments, the gRNA is combined with one or more peptides, e.g., S-adenosyl methionine (SAM), to act as a steric presence to interfere with a conjunction nucleating molecule. Degradation of the gRNA removes the steric presence, thereby allowing the conjunction nucleating molecule to gain access to the conjunction nucleating molecule sequence.

In some embodiments, a targeted alteration described herein reversibly disrupts the anchor sequence-mediated conjunction. In one embodiment, a composition or method is described for modifying an anchor sequence-mediated conjunction with an epigenetic modifying agent, such as a gene editing system, to target DNA in the vicinity of the anchoring sequence. gRNA recognizes specific DNA sequences (e.g., an anchor sequence, a CTCF anchor sequence, flanked by sequences that confer sequence specificity) and nuclease-deficient Cas9 recruits transcription repressors, e.g., to induce epigenetic modifications in the vicinity of the anchoring sequence. Transcription activators, e.g., may be selectively recruited to reverse the epigenetic modification made by the transcription repressors.

In another embodiment, a composition or method is described for introducing an exogenous anchor sequence to alter an anchor sequence-mediated conjunction. A non-naturally occurring or exogenous anchor sequence is introduced that forms a non-naturally occurring loop or disrupts a naturally occurring anchor sequence-mediated conjunction to form that alters transcription of the nucleic acid sequence. Removal of the exogenous anchor sequence prevents formation of the non-naturally occurring loop or the reformation of the naturally occurring anchor sequence-mediated conjunction.

In some embodiments, the binding affinity of a conjunction nucleating molecule is altered, e.g., for an anchor sequence within the anchor sequence-mediated conjunction, an alternative splicing site, or a binding site for a non-translated RNA. In one embodiment, a composition or method is described for disrupting an anchor sequence-mediated conjunction with an engineered conjunction nucleating molecule with altered binding affinity, e.g. conjunction nucleating molecule disrupts, e.g., by competitive binding, the binding of an endogenous conjunction nucleating molecule to its binding site. Replacement of the engineered conjunction nucleating molecule with the endogenous conjunction nucleating molecule reforms the naturally occurring anchor sequence-mediated conjunction.

In some embodiments, a composition or method is described comprising a membrane translocating polypeptide is a targeting moiety. In some embodiments, the membrane translocating polypeptide is a delivery agent that aids delivery of the targeting moiety described herein.

Irreversible Disruption

In some embodiments, compositions or methods are described herein for irreversibly disrupting an anchor sequence-mediated conjunction. For example, the disruption stably modulates transcription forming a non-naturally occurring anchor sequence-mediated conjunction, e.g., a modulation that persists for at least about 1 hr to about 30 days, or at least about 2 hrs, 6 hrs, 12 hrs, 18 hrs, 24 hrs, 2 days, 3, days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, or longer or any time therebetween.

In some embodiments, the interaction between a conjunction nucleating molecule and the anchor sequence is blocked with a targeting moiety. In one embodiment, a composition or method is described for disrupting an anchor sequence-mediated conjunction with an epigenetic modifying agent, such as a gene editing system, to target DNA in the vicinity of the anchoring sequence for editing. gRNA recognizes specific DNA sequences (e.g., an anchor sequence, a CTCF anchor sequence, flanked by sequences that confer sequence specificity) and RNA-guided nuclease introduces breaks in the DNA strands, e.g., addition, deletion, homologous recombination.

In some embodiments, a targeted alteration described herein irreversibly disrupts the anchor sequence-mediated conjunction. In one embodiment, a composition or method is described for altering an anchor sequence-mediated conjunction, e.g., by substituting, adding or deleting one or more nucleotides or changing an orientation of at least one common nucleotide sequence, with a targeting moiety, e.g., a gene editing system. In one embodiment, a composition or method is described for altering one or more DNA methylation sites, e.g., mutating methylated cysteine to thymine, with a targeting moiety, e.g., a small molecule, e.g., bisulfite compound, within the anchor sequence-mediated conjunction.

In some embodiments, a targeted alteration described herein irreversibly disrupts a naturally occurring anchor sequence-mediated conjunction and forms a non-naturally occurring anchor sequence-mediated conjunction. In some embodiment, a composition or method is described for disrupting an anchor sequence-mediated conjunction with an epigenetic modifying agent, such as a gene editing system, by adding an exogenous anchor sequence to form a non-naturally occurring anchor sequence-mediated conjunction.

In some embodiments, a targeted alteration described herein irreversibly disrupts an anchor sequence-mediated conjunction. In some embodiment, a composition or method is described for disrupting an anchor sequence-mediated conjunction with an epigenetic modifying agent, such as a gene editing system, that elminates a gene for a conjunction nucleating molecule.

In some embodiments, a targeting moiety that permanently interferes with loop formation by, e.g., CTCF and CTCF-binding motif by blocking the interaction between CTCF and the CTCF-binding motif. In one embodiment, a composition or method is described for disrupting an anchor sequence-mediated conjunction with an epigenetic modifying agent, an epigenetic modifying agent that covalently binds a conjunction nucleating molecule sequence to act as a steric blocker. In some embodiments, the epigenetic modifying agent is combined with one or more peptides, e.g., S-adenosyl methionine (SAM), to act as a steric presence to interfere with a conjunction nucleating molecule.

Physical Modification

In some embodiments, compositions, agents, fusion molecules, and/or methods are described for altering an anchor sequence-mediated conjunction by site-specific disruption at a target anchor sequence. In some embodiments, such a disruption is achieved using an agent that physically interferes with formation and/or maintenance of an anchor-mediated sequence conjunction, e.g., interferes with binding between an anchor sequence and a nucleating agent. In some embodiments, the agent disrupts binding between an anchor sequence and a nucleating agent via steric inhibition.

In some embodiments, the present disclosure provides a site-specific disrupting agent, comprising: a DNA-binding moiety (such as a DNA-binding moiety or targeting moiety as described herein) that binds specifically to one or more target anchor sequences within a cell and not to non-targeted anchor sequences within the cell with sufficient affinity that it competes with binding of an endogenous nucleating polypeptide within the cell.

Any of a variety of or combination of the DNA-binding moieties or targeting moieties as described herein can be used. For example, possible DNA-binding moieties include, but are not limited to, Synthetic Nucleic Acids (SNAs), Peptide Nucleic Acids (PNAs), Locked Nucleic Acids (LNAs), Bridged Nucleic Acids (BNAs), polyamide-SNA/LNA/BNA/PNA conjugates, DNA intercalating agents (e.g., SNA/LNA/BNA/PNA conjugates), and DNA sequence-specific binding peptide- or protein-SNA/LNA/PNA/BNA conjugates.

In some embodiments, the site-specific disrupting agent further comprises a negative effector moiety (such as any one of or any combination of negative effector moieties described herein) associated with the DNA-binding moiety so that, when the DNA-binding moiety is bound at the one or more target anchor sequences, the negative effector moiety is localized thereto, the negative effector moiety being characterized in that dimerization of the endogenous nucleating polypeptide is reduced when the negative effector moiety is present as compared with when it is absent.

Genetic Modification

In some embodiments, compositions, agents, fusion molecules, and/or methods are described for altering an anchor sequence-mediated conjunction by site specific editing or mutating of an anchor sequence associated with a targeted conjunction. An endogenous or naturally occurring anchor sequence may be altered to inactivate or delete the anchor sequence (e.g., thereby disrupting an anchor sequence-mediated conjunction), or may be altered to mutate or replace the anchor sequence (e.g., to mutate or replace an anchor sequence with an altered anchor sequence that has an altered affinity, e.g., decreased affinity or increased affinity, to a nucleating protein) to modulate the strength of a targeted conjunction. For example, one or a plurality of exogenous anchor sequences can be incorporated into the genome of a subject to create a non-naturally occurring anchor sequence-mediated conjunction that incorporates a target gene, e.g., in order to silence the target gene. In another example, an exogenous anchor sequence can form an anchor sequence-mediated conjunction with an endogenous anchor sequence. The nucleating protein may be, e.g., CTCF, cohesin, USF1, YY1, TAF3, ZNF143 binding motif, or another polypeptide that promotes the formation of an anchor sequence-mediated conjunction.

In one embodiment, a composition or method is described for altering an anchor sequence which is a CTCF-binding motif:
N(T/C/G)N(G/A/T)CC(A/T/G)(C/G)(C/T/A)AG(G/A)(G/T)GG(C/A/T)(G/A)(C/G)(C/T/A)(G/A/C) (SEQ ID NO:1), where N is any nucleotide. A CTCF-binding motif may also be altered to be in the opposite orientation, e.g., (G/A/C)(C/T/A)(C/G)(G/A)(C/A/T)GG(G/T)(G/A)GA(C/T/A)(C/G)(A/T/G)CC(G/A/T)N(T/C/G)N (SEQ ID NO:2).

The alteration can be introduced in the gene of a cell, e.g., in vitro, ex vivo, or in vivo.

In some cases, a composition or method is described for altering the chromatin structure, e.g., such that a two-dimensional representation of the chromatin structure may change from that of a loop to a non-loop (or favor a non-loop over a loop) or vice versa, to inactivate the targeted CTCF-binding motif, e.g., the alteration abolishes CTCF binding thereby abolishing the formation of a targeted conjunction. In other examples, the alteration attenuates (e.g., decreases the level of) CTCF binding, thereby decreasing the formation of a targeted conjunction (e.g., by altering the CTCF sequence to bind with less affinity to a nucleating protein). In some embodiments, a targeted alteration increases CTCF binding by a nucleating protein (e.g., by altering the CTCF sequence to bind with more affinity to a nucleating protein), thereby promoting the formation of a targeted conjunction. The nucleating protein may be, e.g., CTCF, cohesin, USF1, YY1, TAF3, ZNF143 binding motif, or another polypeptide that promotes the formation of an anchor sequence-mediated conjunction.

As can be appreciated by those of skill in the art, a variety of the compositions, agents, and/or fusion molecules described herein may be suitable for genetically modifying an anchor sequence, e.g., a targeted anchor sequence.

For example, in some embodiments, provided are fusion molecules comprising a site-specific targeting moiety (such as any one of the targeting moieties as described herein) and a deaminating agent, wherein the site-specific targeting moiety targets the fusion molecule to a target anchor sequence but not to at least one non-target anchor sequence. A variety of deaminating agents can be used, such as deaminating agents that do not have enzymatic activity (e.g., chemical agents such as sodium bisulfite), and/or deaminating agents that have enzymatic activity (e.g., a deaminase or functional portion thereof).

In some embodiments, provided are pharmaceutical compositions comprising fusion molecules as described herein.

In some embodiments, provided are compositions (e.g., pharmaceutical compositions) comprising (i) a fusion molecule comprising an enzymatically inactive Cas polypeptide and a deaminating agent, or a nucleic acid encoding the fusion molecule; and (ii) a guide RNA, wherein the guide RNA targets the fusion molecule to a target anchor sequence but not to at least one non-target anchor sequence (a "site-specific guide RNA", such as described further herein).

For introducing small mutations or a single-point mutation, a homologous recombination (HR) template can also be used. In one embodiment, the HR template is a single stranded DNA (ssDNA) oligo or a plasmid. For ssDNA oligo design, one may use around 100-150 bp total homology with the mutation introduced roughly in the middle, giving 50-75 bp homology arms. In embodiments, a gRNA for targeting a target anchor sequence, e.g., a CTCF binding motif, is administered in combination with an HR template selected from:
  (a) a nucleotide sequence comprising SEQ ID NO:1;
  (b) a nucleotide sequence at least 75%, 80%, 85%, 90%, 95% identical to SEQ ID NO:1;
  (c) a nucleotide sequence comprising SEQ ID NO:1 having at least 1, 2, 3, 4, 5, but less than 15, 12 or 10 nucleotide additions, substitutions or deletions.
  (d) a nucleotide sequence comprising SEQ ID NO:2;
  (e) a nucleotide sequence at least 75%, 80%, 85%, 90%, 95% identical to SEQ ID NO:2;
  (f) a nucleotide sequence comprising SEQ ID NO:2 having at least 1, 2, 3, 4, 5, but less than 15, 12 or 10 nucleotide additions, substitutions or deletions.

Epigenetic Modification

In some embodiments, compositions and methods are described herein for altering an anchor sequence-mediated conjunction by site specific epigenetic modification (e.g., methylation or demethylation). An endogenous or naturally occurring anchor sequence may be altered to increase its methylation (e.g., thereby decreasing binding of a nucleating protein to the anchor sequence and disrupting or preventing an anchor sequence-mediated conjunction), or may be altered to decrease its methylation (e.g., thereby increasing binding of a nucleating protein to the anchor sequence and promoting or increasing the strength of an anchor sequence-mediated conjunction). The nucleating protein may be, e.g., CTCF, cohesin, USF1, YY1, TAF3, ZNF143 binding motif, or another polypeptide that promotes the formation of an anchor sequence-mediated conjunction.

As can be appreciated by those of skill in the art, a variety of the compositions, agents, and/or fusion molecules described herein may be suitable for epigenetically modifying an anchor sequence, e.g., a targeted anchor sequence.

For example, in some embodiments, provided are fusion molecules comprising a site-specific targeting moiety (such as any one of the targeting moieties as described herein) and an epigenetic modifying agent, wherein the site-specific targeting moiety targets the fusion molecule to a target anchor sequence but not to at least one non-target anchor sequence. The epigenetic modifying agent can be any one of or any combination of epigenetic modifying agents as disclosed herein.

For example, fusions of a catalytically inactive endonuclease e.g., a dead Cas9 (dCas9, e.g., D10A; H840A) tethered with all or a portion of (e.g., biologically active portion of) an (one or more) effector domain create chimeric proteins that can be guided to specific DNA sites by one or more RNA sequences (sgRNA) to modulate activity and/or expression of one or more target nucleic acids sequences (e.g., to methylate or demethylate a DNA sequence).

In some embodiments, fusion of a dCas9 with all or a portion of one or more effector domains of an epigenetic modifying agent (such as a DNA methylase or enzyme with a role in DNA demethylation) creates a chimeric protein that is useful in the methods described herein. Accordingly, in some embodiments, a nucleic acid encoding a dCas9-methylase fusion is administered to a subject in need thereof in combination with a site-specific gRNA or antisense DNA oligonucleotide that targets the fusion to a conjunction anchor sequence (such as a CTCF binding motif), thereby decreasing the affinity or ability of the anchor sequence to bind a conjunction nucleating protein. In other some embodiments, a nucleic acid encoding a dCas9-enzyme fusion is administered to a subject in need thereof in combination with a site-specific gRNA or antisense DNA oligonucleotide that targets the fusion to a conjunction anchor sequence (such as a CTCF binding motif), thereby increasing the affinity or ability of the anchor sequence to bind a conjunction nucleating protein.

In some embodiments, all or a portion of one or more methylase, or enzyme with a role in DNA demethylation, effector domains are fused with the inactive nuclease, e.g., dCas9. In other aspects, 1, 2, 3, 4, 5, 6, 7, 8, 9, 10, 11, 12, 13, 14, 15, 16, 17, 18, 19, 20, or more methylase, or enzyme with a role in DNA demethylation, effector domains (all or a biologically active portion) are fused with dCas9. The chimeric proteins described herein may also comprise a linker, e.g., an amino acid linker. In some aspects, a linker comprises 2 or more amino acids, e.g., one or more GS sequences. In some aspects, fusion of Cas9 (e.g., dCas9) with two or more effector domains (e.g., of a DNA methylase or enzyme with a role in DNA demethylation) comprises one or more interspersed linkers (e.g., GS linkers) between the domains. In some aspects, dCas9 is fused with 2-5 effector domains with interspersed linkers.

In embodiments, a composition or method is described comprising a gRNA that specifically targets a CTCF binding motif associated with an oncogene, a tumor suppressor, or a disease associated with a nucleotide repeat.

Epigenetic modifying agents useful in the methods and compositions described herein include agents that affect, e.g., DNA methylation, histone acetylation, and RNA-associated silencing. In embodiments, the methods described herein involve sequence-specific targeting of an epigenetic enzyme (e.g., an enzyme that generates or removes epigenetic marks, e.g., acetylation and/or methylation). Exemplary epigenetic enzymes that can be targeted to an anchor sequence using the CRISPR methods described herein include DNA methylases (e.g., DNMT3a, DNMT3b, DNMTL), enzymes with a role in DNA demethylation (e.g., the TET family enzymes catalyze oxidation of 5-methylcytosine to 5-hydroxymethylcytosine and higher oxidative derivatives), histone methyltransferases, histone deacetylase (e.g., HDAC1, HDAC2, HDAC3), sirtuin 1, 2, 3, 4, 5, 6, or 7, lysine-specific histone demethylase 1 (LSD1), histone-lysine-N-methyltransferase (Setdb1), euchromatic histone-lysine N-methyltransferase 2 (G9a), histone-lysine N-methyltransferase (SUV39H1), enhancer of zeste homolog 2 (EZH2), viral lysine methyltransferase (vSET), histone methyltransferase (SET2), and protein-lysine N-methyltransferase (SMYD2). Examples of such epigenetic modifying agents are described, e.g., in de Groote et al. Nuc. Acids Res. (2012):1-18.

In embodiments, an epigenetic modifying agent useful herein comprises a construct described in Koferle et al. Genome Medicine 7.59 (2015):1-3 (e.g., at Table 1), incorporated herein by reference.

Exemplary dCAs9 fusion methods and compositions that are adaptable to the methods and compositions described herein are known and are described, e.g., in Kearns et al., Functional annotation of native enhancers with a Cas9-histone demethylase fusion. Nature Methods 12, 401-403 (2015); and McDonald et al., Reprogrammable CRISPR/Cas9-based system for inducing site-specific DNA methylation. Biology Open 2016: doi: 10.1242/bio.019067.

In some embodiments, provided are compositions (e.g., pharmaceutical compositions) comprising (i) a fusion polypeptide comprising an enzymatically inactive Cas polypeptide and an epigenetic modifying agent, or a nucleic acid encoding the fusion polypeptide; and (ii) a guide RNA, wherein the guide RNA targets the fusion molecule to a target anchor sequence but not to at least one non-target anchor sequence (e.g., a "site-specific guide RNA", such as those described further herein).

New Anchor Sequence-Mediated Conjunction

In some embodiments, compositions, agents, fusion molecules, and/or methods are described for altering an anchor sequence-mediated conjunction by generating a new anchor sequence associated with a targeted conjunction.

In some embodiments, provided are engineered site-specific nucleating agents, comprising: an engineered DNA-binding moiety that binds specifically to one or more target sequences within a cell and not to non-targeted sequences within the cell with sufficient affinity that it competes binding of an endogenous nucleating polypeptide within the cell; and a nucleating polypeptide dimerization domain associated with the engineered DNA-binding moiety so that, so that, when the engineered DNA-binding moiety is bound at the at least one target sequences, the nucleating polypeptide dimerization domain is localized thereto, and each at least one targeted sequence is a target anchor sequence. wherein the at least one or more target anchor sequences is positioned relative to an anchor sequence to which a nucleating polypeptide binds so that, when the nucleating polypeptide dimerization domain is localized to the target anchor sequence, interaction between the nucleating polypeptide dimerization domain and the nucleating polypeptide generates an anchor-sequence-mediated conjunction.

In some embodiments, the target anchor sequence does not comprise a CTCF binding motif.

Genetic Engineering

In one aspect, the disclosure includes compositions and methods comprising an engineered cell with a targeted alteration in an anchor sequence-mediated conjunction. In another aspect, the disclosure includes an engineered nucleic acid sequence comprising an anchor sequence-mediated conjunction with a targeted alteration.

In some embodiments, the targeted alteration comprises a substitution, addition or deletion of one or more nucleotides in at least one anchor sequence, e.g., a conjunction nucleating molecule binding sequence, e.g., a CTCF binding motif. In some embodiments, the targeted alteration comprises an alteration of one or more DNA methylation sites within the anchor sequence-mediated conjunction.

In some embodiments, the targeted alteration comprises at least one exogenous anchor sequence. In some embodiments, the targeted alteration alters at least one conjunction nucleating molecule binding site, e.g. altering binding affinity for the conjunction nucleating molecule. In some embodiments, the targeted alteration changes an orientation of at least one common nucleotide sequence.

In some embodiments, the targeted alteration forms a non-naturally occurring anchor sequence-mediated conjunction, such as an intra-chromosomal loop. In some embodiments, the anchor sequence-mediated conjunction is mediated by a first conjunction nucleating molecule bound to the first anchor sequence, a second conjunction nucleating molecule bound to the second anchor sequence, and an association between the first and second conjunction nucleating molecules. In one such embodiment, the first or second conjunction nucleating molecule has a binding affinity for the anchor sequence greater than or less than a reference value, e.g., binding affinity for the anchor sequence in the absence of the alteration.

In one aspect, the disclosure includes a pharmaceutical composition comprising the engineered cell, e.g., plurality of cells, or the engineered nucleic acid sequence, e.g., a vector, described herein.

In some embodiments, the engineered cell or the engineered nucleic acid sequence described herein comprises a targeted alteration that disrupts the anchor sequence-mediated conjunction, e.g., reversible or irreversible disruption.

Methods of Use

The methods described herein enable breadth over controlling gene activity, delivery, and penetrance, e.g., in a cell. In some embodiments, the cell is a mammalian cell. In some embodiments, the cell is a somatic cell. In some embodiments, the cell is a primary cell. For example, in some embodiments, the cell is a mammalian somatic cell. In some embodiments, the mammalian somatic cell is a primary cell. In some embodiments, the mammalian somatic cell is a non-embryonic cell.

In some embodiments, provided are methods comprising a step of: delivering a composition, agent, or fusion molecule to a cell.

In some embodiments, the step of delivering is performed ex vivo. In some embodiments, methods further comprise, prior to the step of delivering, a step of removing the cell (e.g., a mammalian cell) from a subject. In some embodiments, methods further comprise, after the step of delivering, a step of (b) administering the cells (e.g., mammalian cells) to a subject.

In some embodiments, the step of delivering comprises administering a composition comprising the composition, agent, or fusion molecule to a subject. In some embodiments, the subject is has a disease or condition.

In some embodiments, the step of delivering comprises delivery across a cell membrane.

In some embodiments, provided are methods comprising a step of (a) substituting, adding, or deleting one or more nucleotides of an anchor sequence within a cell, e.g., a mammalian somatic cell. In some embodiments, the step of substituting, adding, or deleting is performed in vivo. In some embodiments, the step of substituting, adding, or deleting is performed ex vivo.

In some embodiments, the anchor sequence is a genomic anchor sequence in that the anchor sequence is located in a genome of the cell.

In some embodiments, provided are methods comprising a step of delivering a mammalian somatic cell to a subject having a disease or condition, wherein one or more nucleotides of an anchor sequence within the mammalian somatic cell has been substituted, added, or deleted.

In some embodiments, provided are methods comprising a step of: (a) administering somatic mammalian cells to a subject, wherein the somatic mammalian cells were obtained from the subject, and a composition, agent, or fusion molecule as described herein had been delivered ex vivo to the somatic mammalian cells.

In some embodiments, indications that affect any one of the blood, liver, immune system, neuronal system, etc. or combinations thereof may be treated by modulating gene expression through altering an anchor sequence-mediated conjunction in a mammalian subject. For example, multiple autoimmune conditions improve when IL-10 mediated tolerizing responses are elicited. However, recombinant IL-10 therapies have yet to be efficacious. By altering the anchor sequence-mediated conjunction associated with the IL-10 gene, expression of IL-10 may be increased to improve the autoimmune condition. In another example, IL-6 expression may be increased by altering its associated anchor sequence-mediated conjunction to bring its enhancing sequences in closer proximity to the IL-6 gene.

In one aspect, a method is described for altering gene expression or altering an anchor sequence-mediated conjunction in a mammalian subject. The method includes administering to the subject (separately or in the same pharmaceutical composition): a protein comprising a first polypeptide domain that comprises a Cas or modified Cas protein and a second polypeptide domain that comprises a polypeptide having DNA methyltransferase activity [or associated with demethylation or deaminase activity], or a nucleic acid encoding a protein comprising a first polypeptide domain that comprises a Cas or modified Cas protein and a second polypeptide domain that comprises a polypeptide having DNA methyltransferase activity [or associated with demethylation or deaminase activity], and at least one guide RNA (gRNA) that targets an anchor sequence of an anchor sequence-mediated conjunction.

The methods and compositions described herein treat disease by stably or transiently altering an anchor sequence-mediated conjunction or modulating transcription of a nucleic acid sequence. In some embodiments, chromatin structure or topology of an anchor sequence-mediated conjunction is altered to result in a stable modulation of transcription, such as a modulation that persists for at least about 1 hr to about 30 days, or at least about 2 hrs, 6 hrs, 12 hrs, 18 hrs, 24 hrs, 2 days, 3, days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, or longer or any time therebetween. In some other embodiments, chromatin structure or topology of an anchor sequence-mediated conjunction is altered to result in a transient modulation of transcription, such as a modulation that persists for no more than about 30 mins to about 7 days, or no more than about 1 hr, 2 hrs, 3 hrs, 4 hrs, 5 hrs, 6 hrs, 7 hrs, 8 hrs, 9 hrs, 10 hrs, 11 hrs, 12 hrs, 13 hrs, 14 hrs, 15 hrs, 16 hrs, 17 hrs, 18 hrs, 19 hrs, 20 hrs, 21 hrs, 22 hrs, 24 hrs, 36 hrs, 48 hrs, 60 hrs, 72 hrs, 4 days, 5 days, 6 days, 7 days, or any time therebetween.

In one aspect, provided are methods of modifying expression of a target gene, comprising administering to a cell, tissue or subject a composition, agent, and/or fusion molecule described herein.

In one aspect, the disclosure includes a method of modifying expression of a target gene, comprising altering an anchor sequence-mediated conjunction associated with the target gene, wherein the alteration modulates transcription of the target gene.

In another embodiment, the methods and compositions described herein to alter an anchor sequence-mediated conjunction may be inducible. The use of an inducible alteration to the anchor sequence-mediated conjunction provides a molecular switch capable of turning on the alteration, or turning off the alteration when it is not desired. Examples of systems used for inducing alterations include, but are not limited to an inducible targeting moiety based on a prokaryotic operon, e.g., the lac operon, transposon Tn10, tetracycline operon, and the like, and an inducible targeting moiety based on a eukaryotic signaling pathway, e.g. steroid receptor-based expression systems, e.g. the estrogen receptor or progesterone-based expression system, the metallothionein-based expression system, the ecdysone-based expression system. In another embodiment, the methods and compositions described herein include an inducible conjunction nucleating molecule or other protein that interacts with the anchor sequence-mediated conjunction.

In some embodiments, cells or tissue may be excised from a subject and gene expression, e.g., endogenous or exogenous gene expression, may be altered ex vivo prior to transplantation of the cells or tissues back into a subject. Any cell or tissue may be excised and used for retransplantation. Some examples of cells and tissues include, but are not limited to, stem cells, adipocytes, immune cells, myocytes, bone marrow derived cells, cells from the kidney capsule, fibroblasts, endothelial cells, and hepatocytes. For example, adipose tissue from a patient may be altered ex vivo to increase energy production and lipid utilization. After the adipose tissue is excised, it may be treated with one or more compositions described herein to upregulate UCP-1 or any other protein that increases the entropy of energy production pathways, or increases lipolysis, such as prolyl-4-hydroxylase domain 2 (PHD2), lipoprotein lipase (LPL), hormone-sensitive lipase (HSL), and perilipin. The modified adipose cells are returned to the patient and act as "furnaces," e.g., they uptake lipids from the circulation and use them for energy production. In another example, an effector can be injected intramuscularly into a subject to manipulate the GLUT-4 loop and increase its expression to increase glucose uptake from the circulation into muscle tissue.

In another embodiment, cells or tissues may be altered with one or more compositions described herein to produce one or more secreted factors. The cells or tissues are modified to express the desired secreted protein and transplanted back into the subject. For example, adipose tissue can be modified to express energy utilization or lipolysis proteins to increase energy production. In another example, homing or location specific cells may be modified to secrete one or more factors at a target site once introduced into a subject.

In another embodiment, cells or tissues may be altered with one or more compositions described herein to produce one or more exogenous Current delivery technologies may also have inadvertent effects, e.g., genome wide removal of transcription factors from DNA. In some embodiments, the method described herein modulates transcription of a gene by delivering the composition described herein across a membrane without off-target, e.g., widespread or genome-wide, effects, e.g., removal of transcription factors. In one embodiment, delivering the composition described herein at doses sufficient to increase penetration of the heterologous moiety across a membrane does not significantly alter off-target transcriptional activity, e.g., an increase of less than 50%, 40%, 20%, 15%, 10%, 5%, 4%, 3%, 2%, 1%, or any percentage therebetween of transcriptional activity of one or more off-targets as compared to activity after delivery of the heterologous moiety alone.

The disclosure also includes a method of delivering the composition described herein to a subject. In embodiments, the composition is delivered across a cellular membrane, e.g., a plasma membrane, a nuclear membrane, an organellar membrane. Current polymeric delivery technologies increase endocytic rates in certain cell types, usually cells that preferentially utilize endocytosis, such as macrophages and cancer cells that rely on calcium influx to trigger endocytosis. Although not bound by any particular theory, the polypeptide described herein is believed to aid movement of the composition across membranes typically inaccessible by most agents.

In some embodiments, the method described herein comprises delivering a composition at doses sufficient to increase penetration of the heterologous moiety across a membrane described herein into cells with low endocytic rates. In some embodiments, the method described herein does not significantly increase endocytosis in a target cell. In one embodiment, delivering the composition described herein at doses sufficient to increase penetration of the heterologous moiety across a membrane does not significantly increase endocytosis, e.g., exhibits an increase of less than about 50%, 40%, 20%, 15%, 10%, 5%, 4%, 3%, 2%, 1%, or any percentage therebetween of endocytosis as compared to delivery of the heterologous moiety alone.

In some embodiments, the method of administering a membrane translocating polypeptide described herein does not significantly increase calcium influx. In one embodiment, the method comprises delivering the composition described herein at doses sufficient to increase penetration of the heterologous moiety across a membrane does not significantly increase calcium influx, e.g., an increase of no more than about 50%, 40%, 20%, 15%, 10%, 5%, 4%, 3%, 2%, 1%, or any percentage therebetween of calcium influx as compared to delivery of the heterologous moiety alone. In another embodiment, the method comprises delivering the composition described herein at doses sufficient to increase penetration of the heterologous moiety across a membrane with less compartmentalized calcium movement, e.g., less than about 50%, 40%, 20%, 15%, 10%, 5%, 4%, 3%, 2%, 1%, or any percentage therebetween of compartmentalized calcium movement as compared to delivery of the heterologous moiety alone.

In some embodiments, the method of administering a membrane translocating polypeptide described herein delivers the composition described herein across a membrane independent of endosomes. In one embodiment, delivering the composition described herein at doses sufficient to increase penetration of the heterologous moiety across a membrane does not significantly increase endosomal activity, e.g., an increase of less than 50%, 40%, 20%, 15%, 10%, 5%, 4%, 3%, 2%, 1%, or any percentage therebetween of endosomal activity as compared to delivery of the heterologous moiety alone.

In one aspect, the disclosure includes a method of delivering the composition, where the composition includes a therapeutic heterologous moiety, e.g., a drug, and the composition increases intracellular delivery of the therapeutic as compared to the therapeutic alone. For example, the composition comprising a membrane translocating polypeptide described herein described herein can penetrate at least the blood-brain barrier, the placental membrane separating maternal and fetal blood, and the blood-testis barrier between the Sertoli cells in the seminiferous tubule and the blood. When the composition of the disclosure includes a polypeptide linked to a therapeutic agent that has poor penetrance or bioavailability, the composition increases penetrance or bioavailability of the therapeutic. In another example, the composition includes a polypeptide linked to a heterologous moiety that is an inhibitor of a blood-brain barrier efflux pump, e.g., phenylalanine-arginine β-naphthylamide (PAβN), verapamil, tricyclic chemosensitizers such as phenothiazines. Administration of the composition aids in blood-brain barrier penetration by selectively inhibiting blood-brain barrier efflux pumps, such as P-glycoprotein and Oat3.

In one aspect, the disclosure includes a method of delivering the composition to a target tissue or cell (e.g., CD34+ cells, liver, caudate and putamen nuclei of the telencephalon), where the composition includes a targeting heterologous moiety, e.g., a receptor ligand, that targets the specific tissue or cell and a therapeutic heterologous moiety. Upon administration, the composition increases targeted delivery of the therapeutic as compared to the therapeutic alone. When the composition of the disclosure is used in combination with an existing therapeutic that suffers from diffusion or off-target effects, the specificity of the therapeutic is increased. For example, the composition described herein includes a polypeptide linked to a chemotherapeutic agent and a ligand moiety that specifically binds a receptor on cancer cells. Administration of the composition increases specificity of the chemotherapeutic agent to the cancer cells through the ligand-receptor interaction.

In one aspect, the disclosure includes a method of intracellular delivery of a therapeutic comprising contacting a cell or tissue with the composition described herein. In one embodiment, the therapeutic is the heterologous moiety linked to the polypeptide described herein, and the composition increases intracellular delivery of the therapeutic as compared to the therapeutic alone.

In one aspect, the disclosure includes a method of inducing cell death comprising contacting a cell with the composition described herein. In one embodiment, the composition comprises a polypeptide linked to topoisomerase inhibitor such as topotecan as described herein and a nucleic acid sequence specific for a target cell, such as a viral DNA sequence or a mutation in a gene, etc. The polypeptide translocates into the nucleus of the cell and specifically binds the viral DNA sequence or the gene mutation. The topoisomerase inhibitor prevents the DNA replication machinery from repairing double strand breaks in the genome and the cell ultimately induces apoptosis. In one embodiment, the composition comprises a polypeptide linked to topoisomerase inhibitor such as topotecan as described herein and a heterologous moiety that specifically binds a necrotic cell marker, such as cyclophilin A (CypA), a cytosolic peptidyl-prolyl cis-trans isomerase released early in necrosis, etc. The polypeptide targets cells in the early stages of necrosis by binding the necrotic cell marker and the topoisomerase inhibitor ultimately induces apoptosis to clear the necrotic cells more efficiently.

In one aspect, the disclosure includes a method of modulating a membrane protein by contacting a cell with the composition described herein. In one embodiment, a membrane protein modulator is the heterologous moiety linked to the polypeptide described herein, and contacting the composition with the cell results in membrane protein modulation.

In one aspect, the disclosure includes a method of administering the composition described herein to a subject to modulate a membrane protein, such as an ion channel, a cell surface receptor and a synaptic receptor. In one embodiment, a membrane protein modulator is the heterologous moiety linked to the polypeptide described herein, and administration of the composition results in membrane protein modulation.

In one aspect, the disclosure includes a method of non-parenteral administration of the composition described herein to a subject to increase efficacy and decrease toxicity of a parenteral therapeutic. In one embodiment, a parenteral therapeutic is the heterologous moiety linked to the polypeptide described herein, and administration of the composition results in increased efficacy and decreased toxicity of the parenteral therapeutic. In one embodiment, the method includes oral delivery of the composition. In another embodiment, the parenteral therapeutic treats a mucosal indication.

In one aspect, the disclosure includes a method of contacting the composition described herein with a bacteria or pathogen to decrease infectious capacity, toxicity or viability of a bacteria or pathogen.

In one aspect, the disclosure includes a method of inducing apoptosis in a cell harboring a mutation comprising providing the composition described herein. In one embodiment, the polypeptide described herein is linked to one heterologous moiety that is a nucleic acid that specifically binds a mutation sequence in the cell and another heterologous moiety that induces apoptosis, such as Fas, Fas ligand, neurotrophin receptor, FADD, BID, TPEN, BAM7, cisplatin, cladribine, puromycin, monensin, sulindac sulfone, triptolide, betulinic acid, bufalin, gambogic acid, apicidin, and other known agents.

In another aspect, a kit is described that includes: (a) a nucleic acid encoding a protein comprising a first polypeptide domain that comprises a Cas or modified Cas protein and a second polypeptide domain, e.g., a polypeptide having DNA methyltransferase activity or associated with demethylation or deaminase activity, and (b) at least one guide RNA (gRNA) for targeting the protein to an anchor sequence of a target anchor sequence-mediated conjunction in a target cell. In some embodiments, the nucleic acid encoding a protein and the gRNA are in the same vector, e.g., a plasmid, an AAV vector, an AAV9 vector. In another embodiment, the nucleic acid encoding a protein and the gRNA are in separate vectors.

Formulation, Delivery, and Administration

In various embodiments, the pharmaceutical compositions described herein may be formulated for delivery to a cell and/or to a subject via any route of administration. Modes of administration to a subject may include injection, infusion, inhalation, intranasal, intraocular, topical delivery, intercannular delivery, or ingestion. Injection includes, without limitation, intravenous, intramuscular, intra-arterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. In some embodiments, administration includes aerosol inhalation, e.g., with nebulization. In some embodiments, administration is systemic (e.g., oral, rectal, nasal, sublingual, buccal, or parenteral), enteral (e.g., system-wide effect, but delivered through the gastrointestinal tract), or local (e.g., local application on the skin, intravitreal injection). In one embodiment, the composition is administered systemically. In another embodiment, the administration is non-parenteral and the therapeutic is a parenteral therapeutic.

The compositions may be administered once to the subject or, alternatively, multiple administrations may be performed over a period of time. For example, two, three, four, five, or more administrations may be given to the subject during one treatment or over a period of time. In some embodiments, six, eight, ten, 12, 15 or 20 or more administrations may be given to the subject during one treatment or over a period of time as a treatment regimen.

In some embodiments, administrations may be given as needed, e.g., for as long as symptoms associated with the disease, disorder or condition persist. In some embodiments, repeated administrations may be indicated for the remainder of the subject's life. Treatment periods may vary and could be, e.g., one day, two days, three days, one week, two weeks, one month, two months, three months, six months, a year, or longer.

In various embodiments, the present disclosure includes pharmaceutical compositions described herein with a pharmaceutically acceptable excipient. Pharmaceutically acceptable excipient includes an excipient that is useful in preparing a pharmaceutical composition that is generally safe, non-toxic, and desirable, and includes excipients that are acceptable for veterinary use as well as for human pharmaceutical use. Such excipients may be solid, liquid, semisolid, or, in the case of an aerosol composition, gaseous.

The pharmaceutical compositions described herein can also be tableted or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols and water. Solid carriers include starch, lactose, calcium sulfate, dihydrate, terra alba, magnesium stearate or stearic acid, talc, pectin, acacia, agar or gelatin. The carrier may also include a sustained release material such as glyceryl monostearate or glyceryl distearate, alone or with a wax.

The pharmaceutical preparations are made following the conventional techniques of pharmacy involving milling, mixing, granulation, and compressing, when necessary, for tablet forms; or milling, mixing and filling for hard gelatin capsule forms. When a liquid carrier is used, the preparation will be in the form of a syrup, elixir, emulsion or an aqueous or non-aqueous solution or suspension. Such a liquid formulation may be administered directly per os.

The pharmaceutical compositions according to the disclosure may be delivered in a therapeutically effective amount. The precise therapeutically effective amount is that amount of the composition that will yield the most effective results in terms of efficacy of treatment in a given subject. This amount will vary depending upon a variety of factors, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration.

Pharmaceutical compositions described herein may be formulates for example including a carrier, such as a pharmaceutical carrier and/or a polymeric carrier, e.g., a liposome, and delivered by known methods to a subject in need thereof (e.g., a human or non-human agricultural or domestic animal, e.g., cattle, dog, cat, horse, poultry). Such methods include transfection (e.g., lipid-mediated, cationic polymers, calcium phosphate); electroporation or other methods of membrane disruption (e.g., nucleofection) and viral delivery (e.g., lentivirus, retrovirus, adenovirus, AAV). Methods of delivery are also described, e.g., in Gori et al., Delivery and Specificity of CRISPR/Cas9 Genome Editing Technologies for Human Gene Therapy. Human Gene Therapy. July 2015, 26(7): 443-451. doi:10.1089/hum.2015.074; and Zuris et al. Cationic lipid-mediated delivery of proteins enables efficient protein-based genome editing in vitro and in vivo. Nat Biotechnol. 2014 Oct. 30; 33(1):73-80.

Liposomes are spherical vesicle structures composed of a uni- or multilamellar lipid bilayer surrounding internal aqueous compartments and a relatively impermeable outer lipophilic phospholipid bilayer. Liposomes may be anionic, neutral or cationic. Liposomes are biocompatible, nontoxic, can deliver both hydrophilic and lipophilic drug molecules, protect their cargo from degradation by plasma enzymes, and transport their load across biological membranes and the blood brain barrier (BBB) (see, e.g., Spuch and Navarro, Journal of Drug Delivery, vol. 2011, Article ID 469679, 12 pages, 2011. doi:10.1155/2011/469679 for review).

Vesicles can be made from several different types of lipids; however, phospholipids are most commonly used to generate liposomes as drug carriers. Vesicles may comprise without limitation DOTMA, DOTAP, DOTIM, DDAB, alone or together with cholesterol to yield DOTMA and cholesterol, DOTAP and cholesterol, DOTIM and cholesterol, and DDAB and cholesterol. Methods for preparation of multilamellar vesicle lipids are known in the art (see for example U.S. Pat. No. 6,693,086, the teachings of which relating to multilamellar vesicle lipid preparation are incorporated herein by reference). Although vesicle formation can be spontaneous when a lipid film is mixed with an aqueous solution, it can also be expedited by applying force in the form of shaking by using a homogenizer, sonicator, or an extrusion apparatus (see, e.g., Spuch and Navarro, Journal of Drug Delivery, vol. 2011, Article ID 469679, 12 pages, 2011. doi:10.1155/2011/469679 for review). Extruded lipids can be prepared by extruding through filters of decreasing size, as described in Templeton et al., Nature Biotech, 15:647-652, 1997, the teachings of which relating to extruded lipid preparation are incorporated herein by reference.

As described herein, additives may be added to vesicles to modify their structure and/or properties. For example, either cholesterol or sphingomyelin may be added to the mixture in order to help stabilize the structure and to prevent the leakage of the inner cargo. Further, vesicles can be prepared from hydrogenated egg phosphatidylcholine or egg phosphatidylcholine, cholesterol, and dicetyl phosphate. (see, e.g., Spuch and Navarro, Journal of Drug Delivery, vol. 2011, Article ID 469679, 12 pages, 2011. doi:10.1155/2011/469679 for review). Also vesicles may be surface modified during or after synthesis to include reactive groups complementary to the reactive groups on the carrier cells. Such reactive groups include without limitation maleimide groups. As an example, vesicles may be synthesized to include maleimide conjugated phospholipids such as without limitation DSPE-MaL-PEG2000.

A vesicle formulation may be mainly comprised of natural phospholipids and lipids such as 1,2-distearoryl-sn-glycero-3-phosphatidyl choline (DSPC), sphingomyelin, egg phosphatidylcholines and monosialoganglioside. Formulations made up of phospholipids only are less stable in plasma. However, manipulation of the lipid membrane with cholesterol reduces rapid release of the encapsulated bioactive compound into the plasma or 1,2-dioleoyl-sn-glycero-3-phosphoethanolamine (DOPE) increases stability (see, e.g., Spuch and Navarro, Journal of Drug Delivery, vol. 2011, Article ID 469679, 12 pages, 2011. doi:10.1155/2011/469679 for review).

In another embodiment, lipids may be used to form lipid microparticles. Lipids include, but are not limited to, DLin-KC2-DMA4, C12-200 and colipids disteroylphosphatidyl choline, cholesterol, and PEG-DMG may be formulated (see, e.g., Novobrantseva, Molecular Therapy-Nucleic Acids (2012) 1, e4; doi:10.1038/mtna.2011.3) using a spontaneous vesicle formation procedure. The component molar ratio may be about 50/10/38.5/1.5 (DLin-KC2-DMA or C12-200/disteroylphosphatidyl choline/cholesterol/PEG-DMG). Tekmira has a portfolio of approximately 95 patent families, in the U.S. and abroad, that are directed to various aspects of lipid microparticles and lipid microparticles formulations (see, e.g., U.S. Pat. Nos. 7,982,027; 7,799,565; 8,058,069; 8,283,333; 7,901,708; 7,745,651; 7,803,397; 8,101,741; 8,188,263; 7,915,399; 8,236,943 and 7,838,658 and European Pat. Nos. 1766035; 1519714; 1781593 and 1664316), all of which may be used and/or adapted to the present disclosure.

Some vesicles and lipid-coated polymer particles are able to spontaneously adsorb to cell surfaces.

The methods and compositions described herein may comprise a pharmaceutical composition administered by a regimen sufficient to alleviate a symptom of the disease, disorder or condition. In one aspect, the disclosure includes a method of delivering a therapeutic by administering the composition described herein.

Pharmaceutical compositions are also described that include any of the compositions described herein. In one aspect, a system for pharmaceutical use comprises: a protein comprising a first polypeptide domain, e.g., a Cas or modified Cas protein, and a second polypeptide domain, e.g., a polypeptide having DNA methyltransferase activity or associated with demethylation or deaminase activity, in combination with at least one guide RNA (gRNA) or antisense DNA oligonucleotide that targets the protein to an anchor sequence of a target anchor sequence-mediated conjunction. The system is effective to alter, in at least a human cell, the target anchor sequence-mediated conjunction.

In one aspect, a system for pharmaceutical use comprising a composition that binds an anchor sequence of an anchor sequence-mediated conjunction and alters formation of the anchor sequence-mediated conjunction, wherein the composition modulates transcription, in a human cell, of a target gene associated with the anchor sequence-mediated conjunction.

In one aspect, a system for altering, in a human cell, expression of a target gene, comprises a targeting moiety (e.g., a gRNA, a membrane translocating polypeptide) that associates with an anchor sequence associated with the target gene, and, optionally, a heterologous moiety (e.g., an enzyme, e.g., a nuclease or deactivated nuclease (e.g., a Cas9, dCas9), a methylase, a de-methylase, a deaminase) operably linked to the targeting moiety, wherein the system is effective to modulate a conjunction mediated by the anchor sequence and alter expression of the target gene. The targeting moiety and the heterologous moiety may be linked. In some embodiments, the system comprises a synthetic polypeptide comprising the targeting moiety and the heterologous moiety. In some embodiments, the system comprises a nucleic acid vector or vectors encoding at least one of the targeting moiety and the heterologous moiety.

In one aspect, a pharmaceutical composition includes a composition that binds an anchor sequence of an anchor sequence-mediated conjunction and alters formation of the anchor sequence-mediated conjunction, wherein the composition modulates transcription, in a human cell, of a target gene associated with the anchor sequence-mediated conjunction. In some embodiments, the composition disrupts formation of the anchor sequence-mediated conjunction (e.g., decreases affinity of the anchor sequence to a conjunction nucleating molecule, e.g., at least 10%, 15%, 20%, 25%, 30%, 35%, 40%, 45%, 50%, 55%, 60%, 65%, 70%, 75%, 80%, 85%, 90%, 95%, or more). In some embodiments, the composition promotes formation of the anchor sequence-mediated conjunction (e.g., increases affinity of the anchor sequence to a conjunction nucleating molecule, e.g., at least 10%, 15%, 20%, 25%, 30%, 35%, 40%, 45%, 50%, 55%, 60%, 65%, 70%, 75%, 80%, 85%, 90%, 95%, or more). "Disrupting formation" or "promoting" formation" refers to an alteration in the affinity of the anchor sequence to a conjunction nucleating molecule, e.g., disrupted or promoted, at least 10%, 15%, 20%, 25%, 30%, 35%, 40%, 45%, 50%, 55%, 60%, 65%, 70%, 75%, 80%, 85%, 90%, 95%, or more.

In some embodiments, the target gene is inside the anchor sequence-mediated conjunction. In some embodiments, the target gene is outside the anchor sequence-mediated conjunction. In some embodiments, the target gene is inside and outside the anchor sequence-mediated conjunction. In some embodiments, the composition physically disrupts formation of the anchor sequence-mediated conjunction. For example, the composition comprising both targeting and effector activity, e.g., membrane translocating polypeptide. In some embodiments, the composition comprises a targeting moiety (e.g., gRNA, membrane translocating polypeptide) that binds the anchor sequence, and is operably linked to an effector moiety that modulates the formation of a conjunction mediated by the anchor sequence. In some embodiments, the effector moiety is a chemical, e.g., a chemical that modulates a cytosine (C) or an adenine(A) (e.g., Na bisulfite, ammonium bisulfite). In some embodiments, the effector moiety has enzymatic activity (methyl transferase, demethylase, nuclease (e.g., Cas9), deaminase). In some embodiments, the effector moiety sterically hinders formation of the anchor sequence-mediated conjunction. [e.g., membrane translocating polypeptide+nanoparticle].

In another aspect, the disclosure includes a pharmaceutical composition comprising (a) a targeting moiety and (b) a DNA sequence comprising an anchor sequence.

In another aspect, the disclosure includes a composition comprising a targeting moiety that binds an anchor sequence of an anchor sequence-mediated conjunction and alters formation of the anchor sequence-mediated conjunction (e.g., alters affinity of the anchor sequence to a conjunction nucleating molecule, e.g., at least 10%, 15%, 20%, 25%, 30%, 35%, 40%, 45%, 50%, 55%, 60%, 65%, 70%, 75%, 80%, 85%, 90%, 95%, or more).

In another aspect, a pharmaceutical composition includes a Cas protein and at least one guide RNA (gRNA) that targets the Cas protein to an anchor sequence of a target anchor sequence-mediated conjunction. The Cas protein should be effective to cause a mutation of the target anchor sequence that decreases the formation of an anchor sequence-mediated conjunction associated with the target anchor sequence.

In some embodiments, a gRNA is administered in combination with a targeted nuclease, e.g., a Cas9, e.g., a wild type Cas9, a nickase Cas9 (e.g., Cas9 D10A), a dead Cas9 (dCas9), eSpCas9, Cpf1, C2C1, or C2C3, or a nucleic acid encoding such a nuclease. The choice of nuclease and gRNA(s) is determined by whether the targeted mutation is a deletion, substitution, or addition of nucleotides, e.g., a deletion, substitution, or addition of nucleotides to a targeted anchor sequence, e.g., a CTCF binding motif. For example, in some embodiments, one gRNA is administered, e.g., to produce an inactivating indel mutation in an anchor sequence, e.g., a CTCF site, e.g., one gRNA is administered in combination with a nuclease, e.g., wtCas9. As another example, two gRNAs are administered, e.g., in combination with an insertion cassette and a nucleic acid encoding a nuclease to produce a replacement sequence at the targeted anchor sequence. The replacement sequence may have greater or lesser affinity to a nucleating protein, e.g., the replacement sequence may have greater identity to SEQ ID NO:1 or SEQ ID NO:2 than the target sequence, e.g., to produce a stronger loop, or lesser identity to SEQ ID NO:1 or SEQ ID NO:2 than the target sequence, e.g., to produce a weaker loop. In some embodiments, the replacement sequence has at least 75%, 80%, 85%, 90%, 95% identity to SEQ ID NO:1 or SEQ ID NO:2. In other embodiments, the replacement sequence has less than 75%, 80%, 85%, 90%, 95% identity to SEQ ID NO:1 or SEQ ID NO:2. The nucleating protein may be, e.g., CTCF, cohesin, USF1, YY1, TAF3, ZNF143 binding motif, or another polypeptide that promotes the formation of an anchor sequence-mediated conjunction.

In some embodiments, nucleic acids comprising: a gRNA, a nucleic acid sequence encoding a nuclease, and an insertion cassette are administered to change the orientation of an anchor sequence, e.g., from being in tandem with a partner sequence to being convergent with a partner sequence, e.g., to create a stronger loop, e.g., a gRNA, a nuclease and an insertion cassette are administered to replace an anchor sequence having the consensus SEQ ID NO:1 with a sequence having the consensus sequence SEQ ID NO:2. In other embodiments, a gRNA, a nucleic acid sequence encoding a nuclease, and an insertion cassette are administered to change the orientation of an anchor sequence, e.g., from being convergent with a partner sequence to being in tandem with a partner sequence, e.g., to create a weaker loop, e.g., a gRNA, a nuclease and an insertion cassette are administered to replace an anchor sequence having the consensus SEQ ID NO:2 with a sequence having the consensus sequence SEQ ID NO:1.

In one aspect, the disclosure includes a composition comprising a nucleic acid or combination of nucleic acids that when administered to a subject in need thereof introduce a site specific alteration (e.g., insertion, deletion (e.g., knockout), translocation, inversion, single point mutation) in an anchor sequence of an anchor sequence-mediated conjunction, e.g., a CTCF-binding motif, thereby modulating gene expression in the subject.

In one aspect, the disclosure includes a pharmaceutical composition comprising a guide RNA (gRNA) for use in a clustered regulatory interspaced short palindromic repeat (CRISPR) system for gene editing. For example, a gRNA can be administered in combination with a nuclease (e.g., Cpf1 or Cas9) or a nucleic acid encoding the nuclease, to specifically cleave double-stranded DNA. In the absence of a homologous repair template, wtCas9 causes non-homologous end joining and results in disrupting the target sequence, e.g., a CTCF binding motif. Alternatively, precise mutations and knock-ins to the target CTCF binding motif can be made by providing a homologous repair template and exploiting the homology directed repair pathway. Alternatively, double nicking with paired Cas9 nickases can be used to introduce a staggered double-stranded break which can then undergo homology directed repair to introduce one more nucleotides into the target CTCF binding motif in a site specific manner Custom gRNA generators and algorithms are available commercially for use in developing the methods and compositions described herein.

In some embodiments, the pharmaceutical composition comprises a zinc finger nuclease (ZFN), or a mRNA encoding a ZFN, that targets (e.g., cleaves) a CTCF-binding motif.

Methods of Treatment

The compositions and methods described herein can be used to treat disease in human and non-human animals. In one aspect, the disclosure includes a method of altering expression of a target gene in a genome, comprising: administering to the genome a pharmaceutical composition comprising (a) a targeting moiety and (b) a DNA sequence comprising an anchor sequence, wherein the anchor sequence promotes the formation of a conjunction that brings a gene expression factor (an enhancing sequence, a silencing/repressive sequence) into operable linkage with the target gene. In one aspect, a method of treating a disease or condition comprises administering a targeting moiety selected from at least one of an exogenous conjunction nucleating molecule, a nucleic acid encoding the conjunction nucleating molecule, and a fusion of a sequence targeting polypeptide and a conjunction nucleating molecule to a subject. The table below describes examples of inherited types of diseases that can be targeted with the disclosure.

| Inheritance | Disease Type | # of mutated alleles |
|---|---|---|
| Monoallelic | Imprinted | 1 |
| | Hemizygous | 1 |
| Autosomal | Haploinsufficient | 1 |
| Dominant | Dominant Negative | 1 |
| Co-Dominant | Biallelic | 2 |
| Autosomal Recessive | Regulatory sequence mutation | 2 |
| | ORF mutation | 2 |
| Exogenous | Viral infection | N/A |

In some embodiments, the disclosure described herein may also be useful for targeting other diseases, e.g., cancer and neurodegeneration. For example, oncology indications can be targeted by use of the disclosure to repress oncogenes and/or activate tumor suppressors. Diseases characterized by nucleotide repeats, e.g., trinucleotide repeats in which silencing of the gene through methylation drives symptoms, can be can be targeted by use of the disclosure to tether the affected gene to an enhancing sequence within an anchor sequence-mediated conjunction. Examples if such diseases include: DRPLA (Dentatorubropallidoluysian atrophy), HD (Huntington's disease), SBMA (Spinal and bulbar muscular atrophy), SCA1 (Spinocerebellar ataxia Type 1), SCA2 (Spinocerebellar ataxia Type 2), SCA3 (Spinocerebellar ataxia Type 3 or Machado-Joseph disease), SCA6 (Spinocerebellar ataxia Type 6), SCAT (Spinocerebellar ataxia Type 7), SCA17 (Spinocerebellar ataxia Type 17), FRAXA (Fragile X syndrome), FXTAS (Fragile X-associated tremor/ataxia syndrome), FRAXE (Fragile XE mental retardation), FRDA (Friedreich's ataxia) FXN or X25, DM (Myotonic dystrophy), SCA8 (Spinocerebellar ataxia Type 8) and SCA12 (Spinocerebellar ataxia Type 12). In addition, the genomic loci listed in Table 1 of Herold, et al (Development, 2012) were found to be associated with CTCF, and diseases related to the genes in the loci may be targeted by this disclosure as well.

Therapies

The compositions and methods described herein can be used to treat disease in human and non-human animals. In one aspect, a method of treating a disease or condition comprises administering the composition described herein to a subject.

In some embodiments, the subject is a mammal, e.g., a human. In some embodiments, the subject has a disease or condition.

Modulating Gene Expression

In some embodiments, transcription of a nucleic acid sequence is modulated, e.g., transcription of a target nucleic acid sequence, as compared with a reference value, e.g., transcription of the target sequence in the absence of the altered anchor sequence-mediated conjunction.

In some embodiments, provided are methods of modulating expression of a gene associated with an anchor sequence-mediated conjunction, which conjunction comprises a first anchor sequence and a second anchor sequence. A gene that is associated with an anchor sequence-mediated conjunction may be at least partially within the conjunction (that is, situated sequence-wise between the first and second anchor sequences), or it may be external to the conjunction in that it is not situated sequence-wise between the first and second anchor sequences, but is located on the same chromosome and in sufficient proximity to at least the first or the second anchor sequence such that its expression can be modulated by controlling the topology of the anchor sequence-mediated conjunction. Those of ordinary skill in the art will understand that the distance in three-dimensional space between two elements (e.g., between the gene and the anchor sequence-mediated conjunction) may, in some embodiments, be more relevant than the distance in terms of basepairs. In some embodiments, an external but associated gene is located within 2 Mb, within 1.9 Mb, within 1.8 Mb, within 1.7 Mb, within 1.6 Mb, within 1.5 Mb, within 1.4 Mb, with 1.3 Mb, within 1.3 Mb, within 1.2 Mb, within 1.1 Mb, within 1 Mb, within 900 kb, within 800 kb, within 700 kb, within 500 kb, within 400 kb, within 300 kb, within 200 kb, within 100 kb, within 50 kb, within 20 kb, within 10 kb, or within 5 kb of the first or second anchor sequence.

In some embodiments, modulating expression of the gene comprises altering the accessibility of a transcriptional control sequence to the gene. A transcriptional control sequence, whether internal or external to the anchor sequence-mediated conjunction, can be an enhancing sequence or a silencing (or repressive) sequence.

Figure 6:
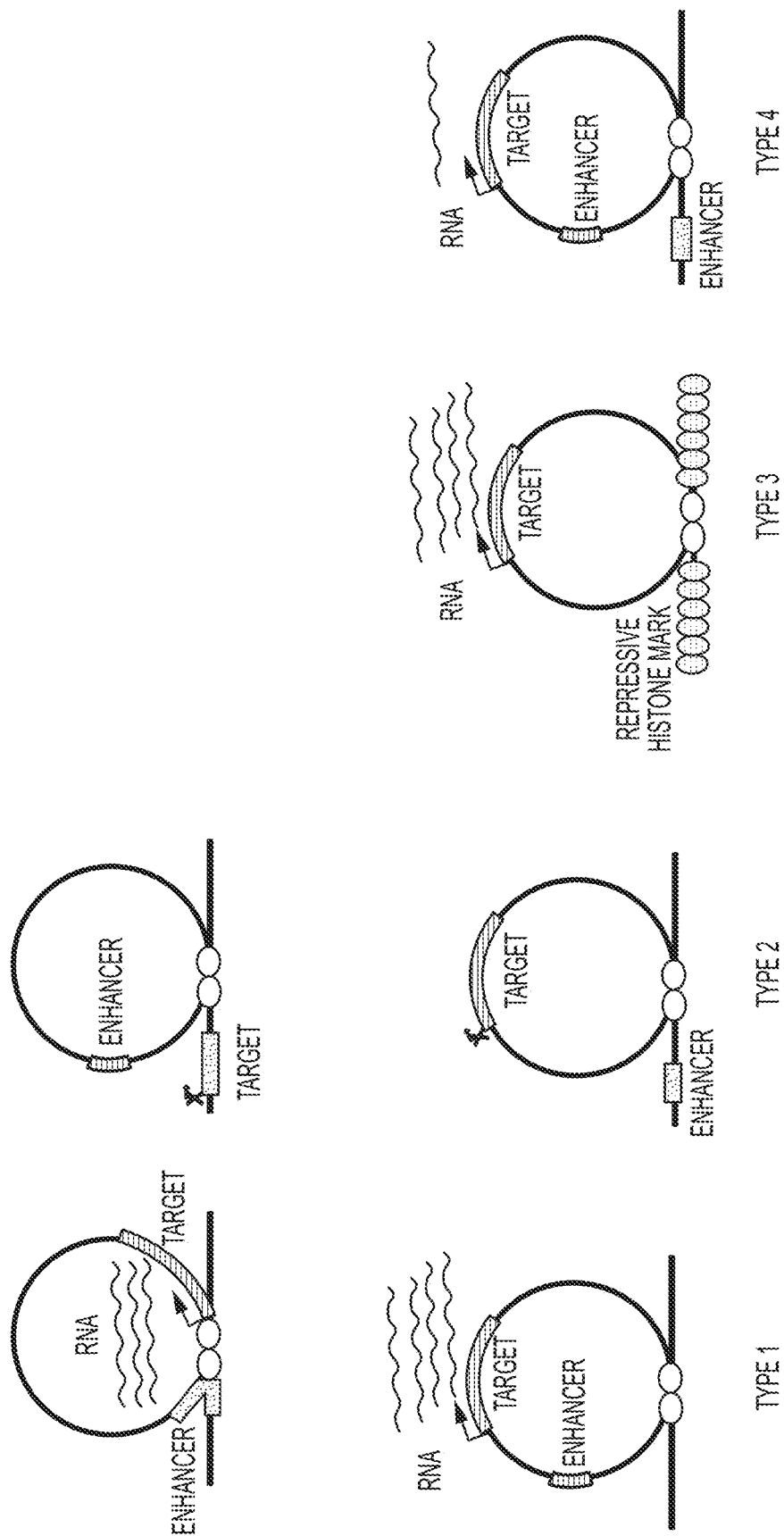
FIG. 6 is an illustration depicting some of the types of anchor sequence-mediated conjunctions.

For example, in some embodiments, provided are methods of modulating expression of a gene within an anchor sequence-mediated conjunction comprising a step of: contacting the first and/or second anchor sequence with a composition, agent, and/or fusion molecule as described herein. In some embodiments, the anchor sequence-mediated conjunction comprises at least one transcriptional control sequence that is "internal" to the conjunction in that it is at least partially located sequence-wise between the first and second anchor sequences. Thus, in some embodiments, both the gene whose expression is to be modulated (the "target gene") and a transcriptional control sequence are within the anchor sequenc-mediated conjunction. See, e.g., a Type 1 anchor sequence-mediated conjunction as depicted in FIG. 6.

In some embodiments, the gene is separated from the internal transcriptional control sequence by at least 300, at least 400, at least 500, at least 600, at least 700, at least 800, or at least 900 base pairs. In some embodiments, the gene is separated from the internal transcriptional control sequence by at least 1.0, at least 1.2, at least 1.4, at least 1.6, or at least 1.8 kb. In some embodiments, the gene is separated from the internal transcriptional control sequence by at least 2 kb, at least 3 kb, at least 4 kb, at least 5 kb, at least 6 kb, at least 7 kb, at least 8 kb, at least 9 kb, or at least 10 kb. In some embodiments, the gene is separated from the internal transcriptional control sequence by at least 20 kb, at least 30 kb, at least 40 kb, at least 50 kb, at least 60 kb, at least 70 kb, at least 80 kb, at least 90 kb, or at least 100 kb. In some embodiments, the gene is separated from the internal transcriptional control sequence by at least 150 kb, at least 200 kb, at least 250 kb, at least 300 kb, at least 350 kb, at least 400 kb, at least 450 kb, or at least 500 kb. In some embodiments, the gene is separated from the internal transcriptional control sequence by at least 600 kb, at least 700 kb, at least 800 kb, at least 900 kb, or at least 1 Mb.

In some embodiments, the anchor sequence-mediated conjunction comprises at least one transcriptional control sequence that is "external" to the conjunction in that it is not located sequence-wise between the first and second anchor sequences. (See, e.g., Types 2, 3, and 4 anchor sequence-mediated conjunctions depicted in FIG. 6.) In some embodiments, the first and/or the second anchor sequence is located within 1 Mb, within 900 kb, within 800 kb, within 700 kb, within 600 kb, within 500 kb, within 450 kb, within 400 kb, within 350 kb, within 300 kb, within 250 kb, within 200 kb, within 180 kb, within 160 kb, within 140 kb, within 120 kb, within 100 kb, within 90 kb, within 80 kb, within 70 kb, within 60 kb, within 50 kb, within 40 kb, within 30 kb, within 20 kb, or within 10 kb of an external transcriptional control sequence. In some embodiments, the first and/or the second anchor sequence is located within 9 kb, within 8 kb, within 7 kb, within 6 kb, within 5 kb, within 4 kb, within 3 kb, within 2 kb, or within 1 kb of an external transcriptional control sequence.

For example, in some embodiments, provided are methods of modulating expression of a gene external to an anchor sequence-mediated conjunction comprising a step of: contacting the first and/or second anchor sequence with a composition, agent, and/or fusion molecule as described herein. In some embodiments, the anchor sequence-mediated conjunction comprises at least one internal transcriptional control sequence.

In some embodiments, the anchor sequence-mediated conjunction comprises at least one external transcriptional control sequence.

For example, compositions and methods described herein may be used to treat severe congenital neutropenia (SCN). In some embodiments, expression of the Elane gene, which causes the disease, is inhibited. A targeting moiety is administered to target one or more anchor sequences adjacent to the Elane gene for alteration and create a repressive loop comprising the Elane gene.

In one aspect, the disclosure includes a method of treating SCN with a pharmaceutical composition described herein. In one embodiment, administration of a composition described herein modulates gene expression of one or more genes, such as inhibiting gene expression of the Elane gene, to treat SCN.

Compositions and methods described herein may be used to treat sickle cell anemia and beta thalassemia. In some embodiments, expression of the HbF from the HBG genes, shown to restore normal hemoglobin levels, is activated. A targeting moiety is administered to target one or more anchor sequences adjacent in the HBB gene cluster or the HBG genes. In one embodiment, an inhibitory loop comprising the HBB gene cluster is created. In another embodiment, an activation loop comprising the HBG genes is created. Downregulating BCL11A has also been shown to downregulate HBB and upregulate HBG expression. In one embodiment, an inhibitory anchor sequence mediated conjunction associated with the BCL11A gene cluster is created.

In one aspect, the disclosure includes a method of treating sickle cell anemia and beta thalassemia with a pharmaceutical composition described herein. In one embodiment, administration of a composition described herein modulates gene expression of one or more genes, such as modulating gene expression from the HBB gene cluster or the HBG genes, to treat SCN.

Compositions and methods described herein may be used to treat MYC-related tumors, e.g., MYC-addicted cancers. In some embodiments, expression of MYC, shown to cause tumors, is inhibited. A targeting moiety is administered to target one or more anchor sequences adjacent in the MYC gene. In one embodiment, an inhibitory loop comprising the MYC gene is created. In another embodiment, MYC expression is decreased by disrupting the MYC-associated anchor sequence-mediated conjunction, e.g., decreased transcription due to conformational changes of the DNA previously open to transcription within the anchor sequence-mediated conjunction, e.g., decreased transcription due to conformational changes of the DNA creating additional distance between the MYC gene and the enhancing sequence.

In one aspect, the disclosure includes a method of treating MYC-related tumors with a pharmaceutical composition described herein. In one embodiment, administration of a composition described herein modulates gene expression of one or more genes, such as modulating gene expression from the MYC gene, to treat MYC-related tumors.

The compositions and methods described herein may be used to treat myoclonic epilepsy of infancy (SMEI or Dravet's syndrome). In some embodiments, loss-of-function mutations in $Na_v1.1$, also known as the sodium channel, voltage-gated, type I, alpha subunit (SCN1A), from the SCN1A gene, cause severe Dravet's syndrome. In one embodiment, a targeting moiety is administered to target one or more anchor sequences adjacent in the SCN1A gene. In another embodiment, a targeting moiety is administered to target one or more anchor sequences adjacent in the SCN3A gene to increase expression of $Na_v1.3$, also known as the sodium channel, voltage-gated, type III, alpha subunit (SCN3A). In another embodiment, a targeting moiety is administered to target one or more anchor sequences adjacent in the SCN5A gene to increase expression of $Na_v1.5$, also known as the sodium channel, voltage-gated, type V, alpha subunit (SCN5A). In another embodiment, a targeting moiety is administered to target one or more anchor sequences adjacent in the SCN8A gene to increase expression of $Na_v1.6$, also known as the sodium channel, voltage-gated, type VIII, alpha subunit (SCN8A). In one embodiment an activation loop comprising any one of SCN1A, SCN3A, SCN5A, and SCN8A genes is created to increase expression of $Na_v1.1$, $Na_v1.3$, $Na_v1.5$, and $Na_v1.6$, respectively.

In one aspect, the disclosure includes a method of treating Dravet's syndrome with a pharmaceutical composition described herein. In one embodiment, administration of a composition described herein modulates gene expression of one or more genes, such as modulating gene expression from the SCN1A, SCN3A, SCN5A, and SCN8A genes, to treat Dravet's syndrome. In another embodiment, administration of a composition comprising a membrane translocating polypeptide linked to a GABA agonist to increase GABA activity.

The compositions and methods described herein may be used to treat familial erythromelalgia. In some embodiments, loss-of-function mutations in $Na_v1.7$, also known as the sodium channel, voltage-gated, type IX, alpha subunit (SCN9A), from the SCN9A gene, cause severe familial erythromelalgia. In one embodiment, a targeting moiety is administered to target one or more anchor sequences adjacent in the SCN9A gene. In one embodiment an activation loop comprising the SCN9A gene is created to increase expression of $Na_v1.7$.

In one aspect, the disclosure includes a method of treating familial erythromelalgia with a pharmaceutical composition described herein. In one embodiment, administration of a composition described herein modulates gene expression of one or more genes, such as modulating gene expression from the SCN9A gene, to treat familial erythromelalgia.

The methods described herein may also improve existing therapeutics to increase bioavailability and/or reduce toxicokinetics.

Bioavailability

In one embodiment, administration of the composition described herein improves at least one pharmacokinetic or pharmacodynamic parameter of the heterologous moiety, such as targeting, absorption, and transport, as compared to the heterologous moiety alone, or reduces at least one toxicokinetic parameter, such as diffusion to non-target location, off-target activity, and toxic metabolism, as compared to the heterologous moiety alone (e.g., by at least 5%, 10%, 20%, 25%, 30%, 40%, 50%, 60%, 70%, 80% or more). In another embodiment, administration of the composition described herein increases the therapeutic range of the heterologous moiety (e.g., by at least 5%, 10%, 20%, 25%, 30%, 40%, 50%, 60%, 70%, 80% or more). In another embodiment, administration of the composition described herein reduces the minimum effective dose, as compared to the heterologous moiety alone (e.g., by at least 5%, 10%, 20%, 25%, 30%, 40%, 50%, 60%, 70%, 80% or more). In another embodiment, administration of the composition described herein increases the maximum tolerated dose, as compared to the heterologous moiety alone (e.g., by at least 5%, 10%, 20%, 25%, 30%, 40%, 50%, 60%, 70%, 80% or more). In another embodiment, administration of the composition increases efficacy or decreases toxicity of the therapeutic, such as non-parenteral administration of a parenteral therapeutic. In another embodiment, administration of the composition described herein increases the therapeutic range of the heterologous moiety while decreasing toxicity, as compared to the heterologous moiety alone (e.g., by at least 5%, 10%, 20%, 25%, 30%, 40%, 50%, 60%, 70%, 80% or more).

Cancer Therapies

The compositions and methods described herein may be used to treat cancer. The methods described herein may also improve existing cancer therapeutics to increase bioavailability and/or reduce toxicokinetics. Cancer or neoplasm includes solid or liquid cancer and includes benign or malignant tumors, and hyperplasias, including gastrointestinal cancer (such as non-metastatic or metastatic colorectal cancer, pancreatic cancer, gastric cancer, esophageal cancer, hepatocellular cancer, cholangiocellular cancer, oral cancer, lip cancer); urogenital cancer (such as hormone sensitive or hormone refractory prostate cancer, renal cell cancer, bladder cancer, penile cancer); gynecological cancer (such as ovarian cancer, cervical cancer, endometrial cancer); lung cancer (such as small-cell lung cancer and non-small-cell lung cancer); head and neck cancer (e.g. head and neck squamous cell cancer); CNS cancer including malignant glioma, astrocytomas, retinoblastomas and brain metastases; malignant mesothelioma; non-metastatic or metastatic breast cancer (e.g. hormone refractory metastatic breast cancer); skin cancer (such as malignant melanoma, basal and squamous cell skin cancers, Merkel Cell Carcinoma, lymphoma of the skin, Kaposi Sarcoma); thyroid cancer; bone and soft tissue sarcoma; and hematologic neoplasias (such as multiple myeloma, acute myelogenous leukemia, chronic myelogenous leukemia, myelodysplastic syndrome, acute lymphoblastic leukemia, Hodgkin's lymphoma).

In one aspect, the disclosure includes a method of treating a cancer with a pharmaceutical composition described herein. For example, a heterologous moiety of a composition described herein may be an anti-neoplastic agent, chemotherapeutic agent or other anti-cancer therapeutic agent. In one embodiment, administration of a composition described herein modulates gene expression of one or more genes, such as inhibiting gene expression of an oncogene, to treat the cancer.

For example, oncology indications can be targeted by use of the disclosure to repress oncogenes (e.g., MYC, RAS, HER1, HER2, JUN, FOS, SRC, RAF, etc.) and/or activate tumor suppressors (e.g., P16, P53, P73, PTEN, RB1, BRCA1, BRCA2, etc.).

In another example, administration of the composition described herein targets a cancer cell for cell death. The polypeptide is linked to a topoisomerase inhibitor such as topotecan and linked to a nucleic acid, such as through hybridization to the nucleic acid side chains in the polypeptide. The nucleic acid sequence includes complementary sequences that specifically bind the cancer mutation. Upon administration, the polypeptide translocates into the nucleus to specifically bind the cancer mutation and the topotecan prevents the DNA replication machinery from repairing double strand breaks in the genome. The cell ultimately induces apoptosis.

Neurological Diseases or Disorders

The methods described herein may also treat a neurological disease. A "neurological disease" or "neurological disorder" as used herein, is a disease or disorder that affects the nervous system of a subject including a disease that affects the brain, spinal cord, or peripheral nerves. A neurological disease or disorder may affect the nerve cells or the supporting ells of the nervous system, such as the glial cells. The causes of neurological disease or disorder include infection, inflammation, ischemia, injury, tumor, or inherited illness. Neurological diseases or disorders also includes neurodegenerative diseases and myodegenerative diseases. Some examples of neurodegenerative diseases include, but are not limited to, amyotrophic lateral sclerosis, Alzheimer's disease, frontotemporal dementia, frontotemporal dementia with TDP-43, frontotemporal dementia linked to chromosome-17, Pick's disease, Parkinson's disease, Huntington's disease, Huntington's chorea, mild cognitive impairment, Lewy Body disease, multiple system atrophy, progressive supranuclear palsy, an α-synucleinopathy, a tauopathy, a pathology associated with intracellular accumulation of TDP-43, and cortico-basal degeneration in a subject. Some other examples of neurological diseases or disorders include, but are not limited to, tinnitus, epilepsy, depression, stroke, multiple sclerosis, migraines, and anxiety.

Many bacterial (i.e. Mycobacterial tuberculosis, *Neisseria meningitides*), viral (i.e. Human Immunodeficiency Virus (HIV), Enteroviruses, West Nile Virus, Zika), fungal (i.e. *Cryptococcus, Aspergillus*), and parasitic (i.e. malaria, Chagas) infections can affect the nervous system. Neurological symptoms may occur due to the infection itself, or due to an immune response.

In one aspect, the disclosure includes a method of treating a neurological disease or disorder with a pharmaceutical composition described herein. For example, a heterologous moiety of a composition described herein may be a corticosteroid, an anti-inflammatory, a dopamine-affecting drug, or an acetylcholine inhibitor. In one embodiment, administration of a composition described herein modulates activation of a neurotransmitter, neuropeptide, or neuroreceptor.

For example, compositions of the disclosure can be used to modulate neuroreceptor activity (e.g., adrenergic receptor, GABA receptor, acetylcholine receptor, dopamine receptor, serotonin receptor, cannabinoid receptor, cholecystokinin receptor, oxytocin receptor, vasopressin receptor, corticotropin receptor, secretin receptor, somatostatin receptor, etc.) with a neurotransmitter, neuropeptide, agonist or antagonist thereof (e.g., acetylcholine, dopamine, norepinephrine, epinephrine, serotonin, melatonin, cirodhamine, oxytocin, vasopressin, cholecystokinin, neurophysins, neuropeptide Y, enkephalin, orexins, somatostatin, etc.).

Treatments for Acute and Chronic Infections

The methods described herein may also improve existing acute and chronic infection therapeutics to increase bioavailability and reduce toxicokinetics. As used herein, "acute infection" refers to an infection that is characterized by a rapid onset of disease or symptoms. As used herein, by "persistent infection" or "chronic infection" is meant an infection in which the infectious agent (e.g., virus, bacterium, parasite, mycoplasm, or fungus) is not cleared or eliminated from the infected host, even after the induction of an immune response. Persistent infections may be chronic infections, latent infections, or slow infections. While acute infections are relatively brief (lasting a few days to a few weeks) and resolved from the body by the immune system, persistent infections may last for months, years, or even a lifetime. These infections may also recur frequently over a long period of time, involving stages of silent and productive infection without cell killing or even producing excessive damage to the host cells. Mammals are diagnosed as having a persistent infection according to any standard method known in the art and described, for example, in U.S. Pat. Nos. 6,368,832, 6,579,854, and 6,808,710.

In some embodiments, the infection is caused by a pathogen from one of the following major categories:

i) viruses, including the members of the Retroviridae family such as the lentiviruses (e.g. Human immunodeficiency virus (HIV) and deltaretroviruses (e.g., human T cell leukemia virus I (HTLV-I), human T cell leukemia virus II (HTLV-II)); Hepadnaviridae family (e.g. hepatitis B virus (HBV)), Flaviviridae family (e.g. hepatitis C virus (HCV)), Adenoviridae family (e.g. Human Adenovirus), Herpesviridae family (e.g. Human cytomegalovirus (HCMV), Epstein-Barr virus, herpes simplex virus 1 (HSV-1), herpes simplex virus 2 (HSV-2), human herpesvirus 6 (HHV-6), varicella-zoster virus), Papillomaviridae family (e.g. Human Papillomavirus (HPV)), Parvoviridae family (e.g. Parvovirus B19), Polyomaviridae family (e.g. JC virus and BK virus), Paramyxoviridae family (e.g. Measles virus), Togaviridae family (e.g. Rubella virus) as well as other viruses such as hepatitis D virus;

ii) bacteria, such as those from the following families: *Salmonella* (e.g. *S. enterica Typhi*), *Mycobacterium* (e.g. *M. tuberculosis* and *M. leprae*), *Yersinia* (*Y. pestis*), *Neisseria* (e.g. *N. meningitides*, N. gonorrhea), *Burkholderia* (e.g. *B. pseudomallei*), *Brucella*, *Chlamydia*, *Helicobacter*, *Treponema*, *Borrelia*, *Rickettsia*, and *Pseudomonas*;

iii) parasites, such as *Leishmania*, *Toxoplasma*, *Trypanosoma*, *Plasmodium*, *Schistosoma*, or *Encephalitozoon*; and iv) prions, such as prion protein.

In one embodiment, administration of the composition described herein suppresses transcription or activates transcription of one or more genes to treat an infection such as a viral infection. For example, a polypeptide linked to an inhibitor of viral DNA transcription, e.g., nucleoside analogs such as acyclovir, valaciclovir, penciclovir, denavir, famciclovir, bromovinyldeoxiuridine, ganciclovir; product analogs such as hydroxycarbamide or pyrophosphate analogs like foscarnet, allosteric inhibitors or inhibitors that intercalate or directly interact with nucleic acids, is administered to treat the viral infection. The polypeptide may further include a cell targeting ligand for targeted delivery of the anti-viral therapeutic.

In another example, administration of the composition described herein targets a virally infected cell for cell death. The polypeptide is linked to a topoisomerase inhibitor such as topotecan and linked to a nucleic acid that specifically binds a viral sequence, such as through hybridization to the nucleic acid side chains in the polypeptide. The nucleic acid sequence includes complementary sequences that specifically bind viral DNA integrated into the genome. Upon administration, the polypeptide translocates into the nucleus to specifically bind the integrated viral DNA and the topotecan prevents the DNA replication machinery from repairing double strand breaks in the genome. The cell ultimately induces apoptosis.

Treatments of Other Diseases/Disorders/Conditions

Some additional diseases that may be treated by the composition described herein include, but are not limited to, imprinted or hemizygous mono-allelic diseases, bi-allelic diseases, autosomal recessive disorders, autosomal dominant disorders, and diseases characterized by nucleotide repeats, e.g., trinucleotide repeats in which silencing of the gene through methylation drives symptoms, can be targeted by use of the disclosure to modulate expression of the affected gene. Examples of such diseases include: Jacobsen syndrome, cystic fibrosis, sickle cell anemia, and Tay Sachs disease, tuberous sclerosis, marfan syndrome, neurofibromatosis, retinoblastoma, Waardenburg syndrome, familial hypercholesterolemia, DRPLA (Dentatorubropallidoluysian atrophy), HD (Huntington's disease), Beckwith-Wiedemann syndrome, Silver-Russell syndrome, SBMA (Spinal and bulbar muscular atrophy), SCA1 (Spinocerebellar ataxia Type 1), SCA2 (Spinocerebellar ataxia Type 2), SCA3 (Spinocerebellar ataxia Type 3 or Machado-Joseph disease), SCA6 (Spinocerebellar ataxia Type 6), SCAT (Spinocerebellar ataxia Type 7), SCA17 (Spinocerebellar ataxia Type 17), FRAXA (Fragile X syndrome), FXTAS (Fragile X-associated tremor/ataxia syndrome), FRAXE (Fragile XE mental retardation), FRDA (Friedreich's ataxia) FXN or X25, DM (Myotonic dystrophy), SCA8 (Spinocerebellar ataxia Type 8), and SCA12 (Spinocerebellar ataxia Type 12).

In one aspect, the disclosure includes a method of treating a genetic disease/disorder/condition with the pharmaceutical composition described herein. In one embodiment, administration of the composition described herein modulates gene expression of one or more genes that are indicated in the genetic disease/disorder/condition, such as activating, suppressing, or modulating expression of the gene.

In one aspect, the disclosure includes a method of treating a disease/disorder/condition with the pharmaceutical composition described herein. In one embodiment, administration of the composition described herein modulates gene expression of one or more genes to treat the disease/disorder/condition, such as activating, suppressing, or modulating expression of the gene.

All references and publications cited herein are hereby incorporated by reference.

The following examples are provided to further illustrate some embodiments of the present disclosure, but are not intended to limit the scope of the disclosure; it will be understood by their exemplary nature that other procedures, methodologies, or techniques known to those skilled in the art may alternatively be used.

EXAMPLES

The below Examples demonstrate use of methods, reagents, and compositions of the present disclosure to modulate expression of a gene associated with an anchor sequence-mediated conjunction. Unless described in the past tense, descriptions of experiments are not intended to convey that the experiments have actually been performed.

The present Examples describe, among other things, experiments in cells such as cultured cells. However, those of ordinary skill in the art reading the present specification will understand that the present specification also teaches application of the disclosed methods, agents, and compositions in a therapeutic context, for example, in mammalian cells that are somatic, non-embryonic, and/or non-cultured (e.g., primary) (as described further herein).

Example 1: Disruption of a CTCF Anchor Sequence-Mediated Conjunction by Genetic Modification, Epigenetic Modification and Physical Perturbation to Decrease Expression of the MYC Gene The present Example demonstrates various strategies to decrease expression of a gene (in this case, MYC) within a Type 1 anchor sequence-mediated conjunction. Among other things, the present Example demonstrates the successful reduction of gene expression by disruption of the anchor sequence-mediated conjunction via, e.g., modification of and/or perturbation at a CTCF anchor sequence.

Using methods of the present disclosure that involve using an RNA-guided nuclease domain as part of a targeting moiety, the present Example also provides evidence of synergistic effects when using a combination of guide RNAs.

MYC (c-Myc) is a regulator gene that encodes a transcription factor that plays a role in cell cycle progression, apoptosis and cellular transformation through activation and repression of gene transcription. About 70% of human cancers have been shown to have dysregulation of MYC expression. MYC inhibition has been explored as a cancer therapeutic and demonstrated some tumor regression. However, MYC remains difficult to target intracellularly using conventional pharmacological modalities.

Production of agents: All plasmids and guide RNAs (gRNA) have been chemically synthesized from commercially available vendors. All agents were reconstituted in sterile water. All sequences are provided in the Materials and Methods section.

A1) Genetic Modification by CRISPR/Cas9

This example demonstrates disruption of MYC gene associated CTCF anchor sequence-mediated conjunction by genetic modifications.

A CTCF anchor sequence is located upstream of the MYC gene, allowing enhancers within the loop to influence the MYC promoter. The MYC gene is associated with an activating enhancer-promoter (E-P) anchor sequence-mediated conjunction.

TABLE 1

Sequences of guide RNAs (gRNAs) targeting putative CTCF anchor sequences associated with the MYC gene E-P anchor sequence-mediated conjunction.

| ID | Guide RNA Sequence (5'-3') |
|---|---|
| IHSP-00018 | AAAGTAAGTGTGCCCTCTAC (SEQ ID NO: 7) |

HEK293T cells were transfected with plasmid encoding Cas9 and either co- or serially transfected with a non-targeting gRNA ("Non-targeting," where the gRNA sequence has no homology to the human genome) or a gRNA, as listed in Table 1, targeted to the CTCF anchor sequence. HEK293T cells were transfected serially first with a plasmid encoding Cas9, and then 8 hr later with either a chemically synthesized gRNA targeting the anchor sequence or a non-targeting gRNA ("Non-targeting," where the guide RNA sequence has no homology to the human genome).

At 72 hr post-transfection, cells were harvested for RNA extraction and cDNA synthesis using commercially available reagents and protocols (Qiagen; Thermo Fisher Scientific) and genomic DNA was extracted (Qiagen). The resulting cDNA was used for quantitative real-time PCR (Thermo Fisher Scientific).

Figure 7:
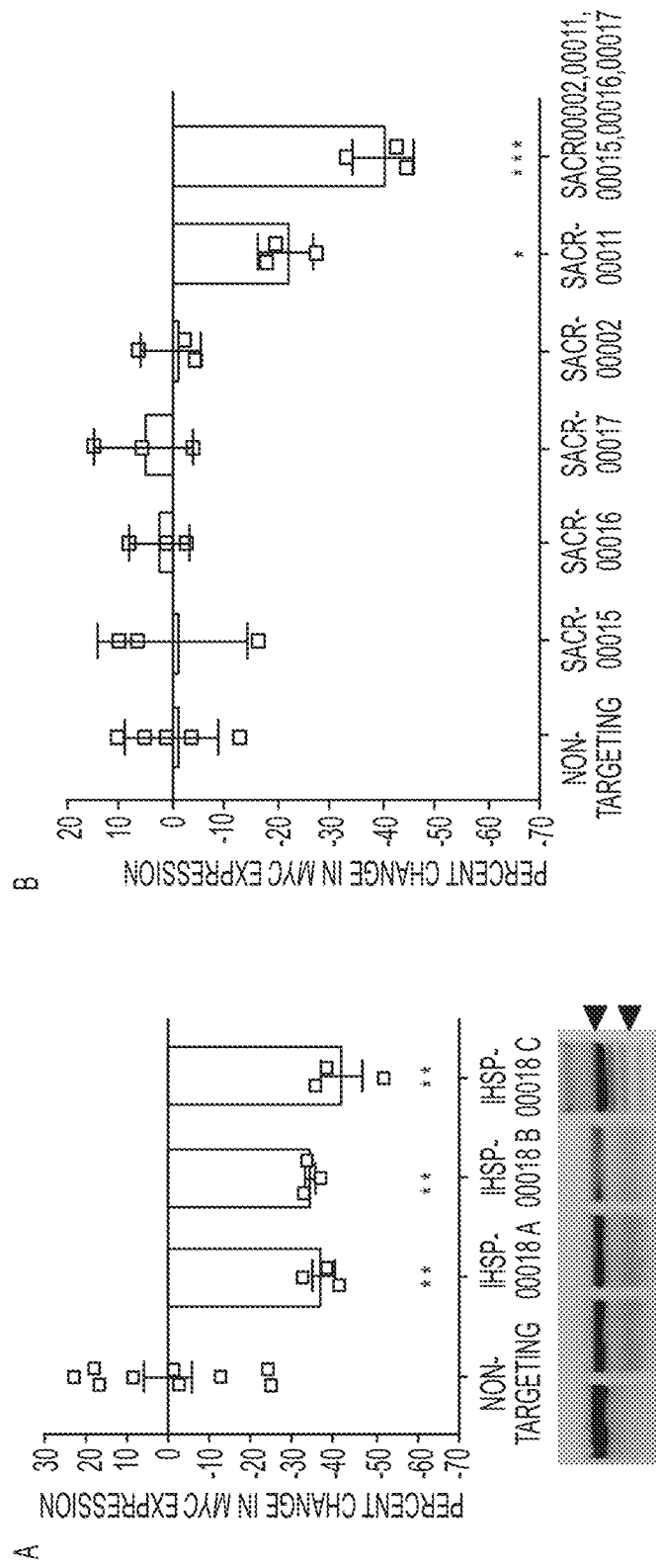
FIG. 7 illustrates disruption of anchor sequence-mediated conjunctions upstream of the MYC gene, leading to downregulation of MYC expression levels. As further described in Examples 1 and 2, panels A, B, C, and D illustrates reduction in MYC expression, and panel E depicts a map of gRNA sequences.
Figure 7:
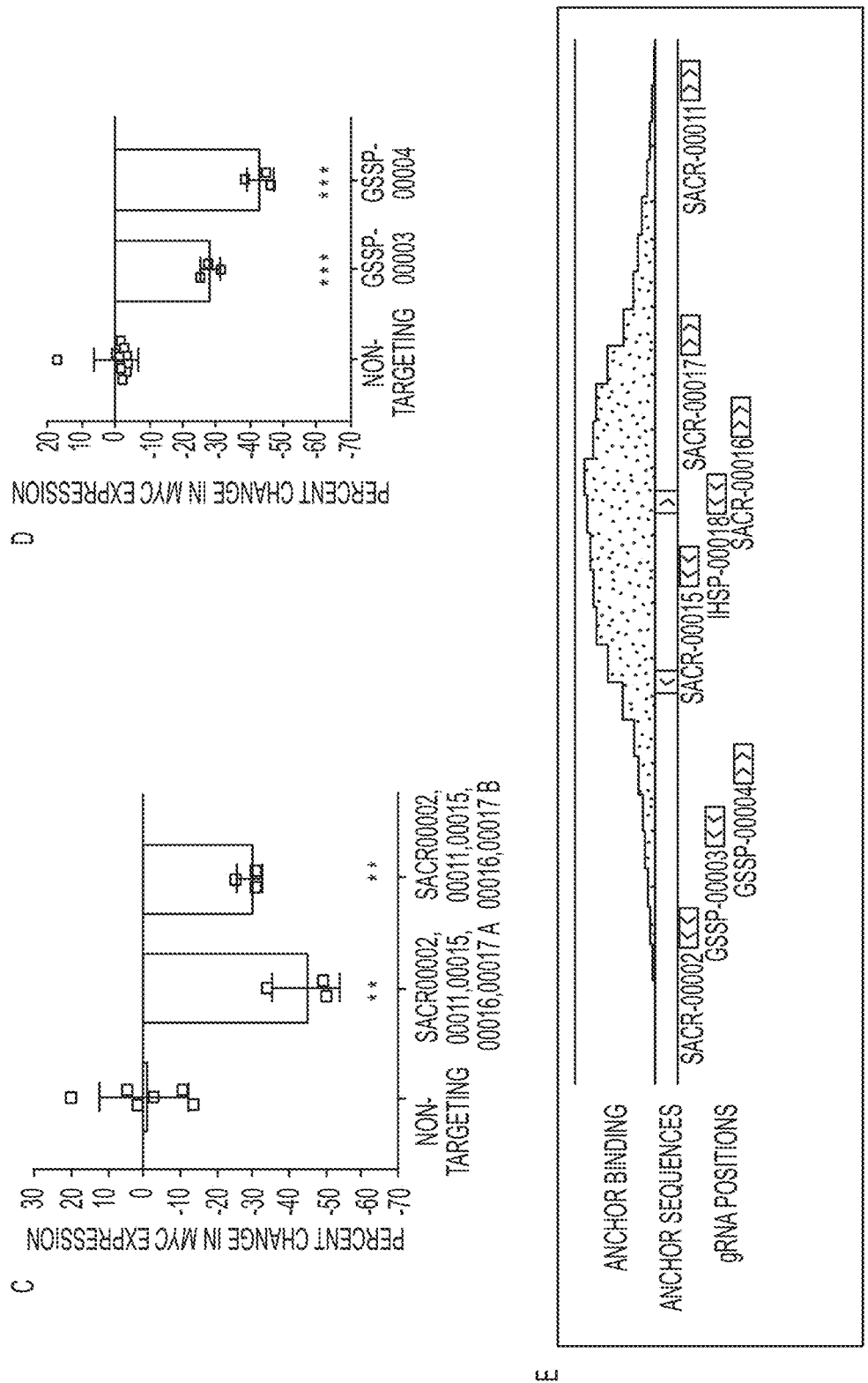

The locations of potential CTCF binding (black) associated with the MYC gene alongside the locations of the anchor sequences and gRNAs are shown in FIG. 7E.

MYC-specific quantitative PCR probes/primers (Assay ID Hs00153408_m1, Thermo Fisher Scientific) were multiplexed with internal control quantitative PCR probes/primers, which were either PPIB (Assay ID Hs00168719_m1, Thermo Fisher Scientific) or GAPDH (Assay ID Hs02786624_g1, Thermo Fisher Scientific) using the FAM-MGB and VIC-MGB dyes, respectively, and gene expression was subsequently analyzed by a real time PCR kit (Applied Biosystems, Thermo Fisher Scientific). Cells transfected with guide RNAs proximal to the CTCF anchor sequence showed reduction in MYC expression at 72 hr (FIG. 7A, upper panel). Each technical replicate is represented by empty box symbol.

To detect Cas9-generated genetic modifications (indels), extracted genomic DNA was used as a template to amplify the anchor sequence DNA region by PCR (Promega). The resulting PCR products were then subjected to a nuclease assay (Integrated DNA Technologies) according to the manufacturer's instructions. Cas9-generated indels were detected by subjecting the resultant PCR products to gel electrophoresis (FIG. 7A, lower panel). Gel electrophoresis images show PCR products of the anchor sequences subjected to the nuclease assay, which cleaves mismatched DNA products. The top arrow in the lower panel of FIG. 7A shows the uncleaved PCR products (no Cas9-generated indel) and the bottom arrow shows the cleaved PCR products caused by Cas9-generated indels. Nuclease cleavage products are present in each of the MYC indel Cas9 samples. The letters A, B and C denote independent biological replicates of each experiment. Empty box symbols show technical replicates.

As shown in the FIG. 7A, upper panel, an approximately 40% reduction in MYC gene expression was observed. As shown in the FIG. 7A, upper panel, an approximately 40% reduction in MYC gene expression was observed.

To determine differential CTCF binding at anchor sequences targeted by gRNAs versus non-targeting control gRNAs, a CTCF chromatin immunoprecipitation-quantitative PCR assay (ChIP-qPCR) is performed. At 72 hr post-transfection, HEK293T cells are trypsinized and fixed with 1% formaldehyde in 10% fetal bovine serum and 90% phosphate buffered saline (PBS). Following glycine quenching of fixation, cells are pelleted by centrifugation, washed and then sonicated using a E220 evolution instrument (Covaris) to shear the chromatin. Following another centrifugation step, the sheared chromatin supernatant is collected and added to pre-cleared magnetic beads (Thermo Fisher Scientific) complexed with a CTCF-specific antibody (Abcam). Following overnight incubation at 4° C., the CTCF-chromatin complexes bound to the beads are washed and resuspended in the elution buffer. Subsequently, CTCF-chromatin complexes are eluted from the beads at 65° C. for 15 min. The crosslinks are then reversed overnight at 65° C., and DNA is purified by phenol:chloroform extraction. The resulting DNA serves as a template for SYBR Green (Thermo Scientific) qPCR using sequence-specific primers (IDT) flanking the CTCF-binding region. The primer sequences used for the amplification reaction are as follows: 5'-GCTGGAAACCTTGCACCTC-3' and 5'-CGTTCAGGTTTGCGAAAGTA-3'. Diminished input-normalized amplification, by 5% to 100%, indicates reduced CTCF binding due to the targeted genetic modifications.

A2) Genetic Modification by Cytidine Deaminase-CRISPR/dCas9

This example demonstrates disruption of the MYC gene associated CTCF anchor sequence-mediated conjunction by genome base editing with targeted cytidine deaminases at and in proximity to the CTCF anchor sequences.

Targeted base editing such as that achieved by a targeted cytidine deaminase allows genomic editing without creating indels. Without wishing to be bound by any particular theory, the inventors propose that, base editing can provide certain advantages over methods that involve creating indels. For example, base editing may allow more precise control over which mutations are induced. Without wishing to be bound by any particular theory, the inventors recognize that particularly in therapeutic contexts, increased precision may be particularly valuable from safety and/or regulatory standpoints.

TABLE 2

Sequences of gRNAs targeting putative CTCF anchor sequences associated with the MYC gene E-P anchor sequence-mediated conjunction.

| ID | Guide RNA Sequence (5'-3') |
|---|---|
| SACR-00002 | CTATTCAACCGCATAAGAGA (SEQ ID NO: 10) |
| SACR-00011 | CGCTGAGCTGCAAACTCAAC (SEQ ID NO: 11) |
| SACR-00015 | GCCTGGATGTCAACGAGGGC (SEQ ID NO: 12) |
| SACR-00016 | GCGGGTGCTGCCCAGAGAGG (SEQ ID NO: 13) |
| SACR-00017 | GCAAAATCCAGCATAGCGAT (SEQ ID NO: 14) |

HEK293T cells are transfected with plasmids encoding fusion proteins consisting of APOBEC1, a cytidine deaminase that converts cytosine (C) to the RNA base (U), fused to dCas9 and UGI, a uracil glycosylase inhibitor protein (APOBEC1-dCas9-UGI). Then, 8 hr later, cells are transfected with chemically synthesized gRNAs tiled at or around the anchor sequence (listed in Table 2), or a non-targeting gRNA ("non-targeting," where the guide RNA sequence has no homology to the human genome).

At 72 hr post-transfection, cells are harvested for RNA extraction and cDNA synthesis using commercially available reagents and protocols (Qiagen; Thermo Fisher Scientific) and genomic DNA was extracted (Qiagen). The resulting cDNA is used for quantitative real-time PCR (Thermo Fisher Scientific).

For analyzing the conversion of cytosine (C) to uracil (U), gDNA extracted at 72 hr post-transfection (Qiagen) is used as template to amplify the CTCF-binding DNA region by a PCR kit (Promega). APOBEC1-dCas9-UGI-mediated base editing (C→U) is determined by sequencing of the resultant PCR products. By aligning the sequence of the resultant PCR products to the original reference sequence of the amplified DNA region, C-to-U editing by APOBEC1-dCas9-UGI is identified where thymidine (T) is sequenced in place of cytosine (C). Any number of non-zero C-to-T sequencing calls on a chromatogram indicate genetic modification by APOBEC1-dCas9-UGI.

MYC-specific quantitative PCR probes/primers, as described in Example 1A.1, are multiplexed with internal control quantitative PCR probes/primers and gene expression is subsequently analyzed by a real-time PCR kit (Applied Biosystems, Thermo Fisher Scientific). Guide RNAs at or around the CTCF anchor sequence show reduction in MYC expression after DNA editing by cytidine deamination.

Enzymatic effectors that modify DNA at or near the CTCF anchor sequence associated with the MYC gene demonstrate disruption of the MYC gene anchor-mediated conjunction to decrease MYC mRNA levels as compared to the non-targeting controls.

B) Epigenetic Modification

This example demonstrates disruption of the MYC gene associated CTCF anchor sequence-mediated conjunction by epigenetic modifications.

TABLE 3

Sequences of gRNAs targeting putative CTCF anchor sequences associated with the MYC gene E-P anchor sequence-mediated conjunction.

| ID | Guide RNA Sequence (5'-3') |
|---|---|
| SACR-00015 | GCCTGGATGTCAACGAGGGC (SEQ ID NO: 12) |
| SACR-00016 | GCGGGTGCTGCCCAGAGAGG (SEQ ID NO: 13) |
| SACR-00017 | GCAAAATCCAGCATAGCGAT (SEQ ID NO: 14) |
| SACR-00002 | CTATTCAACCGCATAAGAGA (SEQ ID NO: 10) |
| SACR-00011 | CGCTGAGCTGCAAACTCAAC (SEQ ID NO: 11) |
| SACR-00002 | CTATTCAACCGCATAAGAGA (SEQ ID NO: 10) |
| SACR-00011 | CGCTGAGCTGCAAACTCAAC (SEQ ID NO: 11) |
| SACR-00017 | GCAAAATCCAGCATAGCGAT (SEQ ID NO: 14) |

HEK293T cells were serially transfected, first with plasmid encoding either dCas9-DNMT3A-3L (a fusion protein including the active domains from a DNA methyltransferase) or dCas9-KRAB (a transcriptional repressor fusion protein), then 8 hr later with one of five gRNAs tiled around the anchor sequence (listed in Table 3) or a mixture of all five gRNAs tiled around the anchor sequence (FIG. 7B for dCas9-DNMT3A-3L; FIG. 7C for dCas9-KRAB).

At 72 hr post-transfection, cells were harvested for RNA extraction and cDNA synthesis using commercially available reagents and protocols (Qiagen; Thermo Fisher Scientific) and genomic DNA was extracted (Qiagen). The resulting cDNA was used for quantitative real-time PCR (Thermo Fisher Scientific).

MYC-specific quantitative PCR probes/primers were multiplexed with internal control quantitative PCR probes/primers as described in the previous examples and gene expression was subsequently analyzed by a real time PCR kit (Applied Biosystems, Thermo Fisher Scientific). Guide RNAs proximal to the CTCF anchor sequence showed reduction in MYC expression at 72 hr after methylation with either dCas9-DNMT3A-3L (FIG. 7B) or dCas9-KRAB (FIG. 7C). In FIG. 7B empty boxes are representing different biological replicates. In FIG. 7C, A and B represent biological replicates while empty boxes denote the value of each technical replicate.

As shown in FIGS. 7A and 7B, transcriptional repression was achieved using single guides. An approximately 40% or more reduction in transcriptional repression was observed when combinations of gRNAs were used. As can be seen in FIG. 7B, a synergistic effect was observed with a combination of guide RNAs in that the extent of reduction observed with the "SACR-00002, 00011, 00015, 00016, 00017" combination was greater than the sum of the reductions of observed with each of the gRNAs in the combination.

For analyzing DNA methylation, extracted genomic DNA is bisulfite converted using commercially available reagents and protocols (Qiagen), and purified, bisulfite-converted genomic DNA is used as template to amplify the CTCF-binding DNA region by a PCR kit (New England Biolabs). dCas9-DNMT3A-3L-mediated CpG methylation is determined by sequencing the resultant PCR products (bisulfite sequencing). By aligning the sequence of the resultant PCR products to the unconverted reference DNA sequence, unmethylated CpGs are identified by thymidine (T) base calls where T is sequenced in place of C. Thus, CpG methylation is represented by any number of non-zero C base calls followed by guanosine (G). The degree of dCas9-DNMT3A-3L-mediated CpG methylation is subsequently ascertained by comparing the number and position of C base calls in the MYC-targeted samples compared to the non-targeting control, where an integer increase in C base calls indicates dCas9-DNMT3A-3L targeted CpG methylation.

Effectors that target epigenetic modifications at or near the CTCF anchor sequence associated with the MYC gene demonstrated disruption of the MYC gene anchor-mediated conjunction to decrease MYC mRNA levels as compared to the non-targeting controls.

Without wishing to be bound by any particular theory, the inventors propose that, in some embodiments, combinations of gRNAs may be more effective that single gRNAs in that such combinations contribute to increased unwinding of a target nucleic acid, allow improved access to proteins, and/or allow physical displacement of nucleosomes. The inventors propose that such effects on the target nucleic acid may reduce steric hindrances and thereby result in enhanced activity of proteins targeted to the nucleic acid. The inventors propose that reduction of steric hindrances may be particularly relevant for effectors such as DNMT3A/3L that act as multimers (e.g., dimers, tetramers, etc.) or are otherwise bulky. The inventors propose that some effectors such as DNMT3A/3L may act as helicases.

Without wishing to be bound by any particular theory, the inventors propose that combinations of guide RNAs may, in some embodiments, allow reduction in off-target (non-target) activity (i.e., activity at off-target sites). The inventors propose that methods in which a robust synergistic effect can be achieved with multiple guide RNAs (such as methods involving epigenetic modification, as disclosed herein) are particularly amenable to fine tuning and/or reduction of off-target activity. Such a reduction of off-target activity may improve safety, e.g., in a therapeutic context.

C1) Physical Perturbation with Synthetic Nucleic Acids

This example demonstrates disruption of MYC gene associated CTCF anchor sequence-mediated conjunction by physically preventing CTCF binding at the anchor sequence.

TABLE 4

Sequences of Synthetic Nucleic Acids (SNAs) targeting putative CTCF anchor sequences associated with the MYC gene E-P anchor sequence-mediated conjunction.

| ID | SNA Sequence (5'-3') (* = phosphothiolate linkage) |
|---|---|
| 5024 | T*C*C*A*G*GCGCGATGATCTCTGCTGCCAGTAGAGGGCACAC TTACTTTACTTTCG*C*A*A*A*C (SEQ ID NO: 15) |
| 5025 | A*G*G*C*G*CGATGATCTCTGCTGCCAGTAGAGGGCACA*C*T *T*A*C (SEQ ID NO: 16) |
| 5026 | T*G*A*T*C*TCTGCTGCCAGTAGAGGGCACA*C*T*T*A*C (SEQ ID NO: 17) |
| 5027 | G*T*T*T*G*CGAAAGTAAAGTAAGTGTGCCCTCTACTGGCAGC AGAGATCATCGCGC*C*T*G*G*A (SEQ ID NO: 18) |
| 5028 | G*T*A*A*G*TGTGCCCTCTACTGGCAGCAGA*G*A*T*C*A (SEQ ID NO: 19) |

HEK293T cells are transfected using lipid based transfection reagent (Invitrogen), according to manufacturer's instructions, with Synthetic Nucleic Acids (SNAs) located proximally around the CTCF anchor sequences upstream or downstream of the MYC gene, listed in Table 4, or a non-targeting SNA. At 72 hr post-transfection, cells are harvested for RNA extraction and cDNA is synthesized (Thermo Fisher Scientific) according to the manufacturer's protocols. cDNA is used as a template for quantitative real-time PCR.

MYC-specific quantitative PCR probes/primers are multiplexed with internal control quantitative PCR probes/primers as described in the previous examples and gene expression is subsequently analyzed by a real time PCR kit (Applied Biosystems, Thermo Fisher Scientific). Cells transfected with SNAs proximal to the CTCF anchor sequence are expected to show reduction in MYC expression.

For determination of differential CTCF binding at anchor sequences targeted by SNAs versus non-targeting SNAs, a CTCF ChIP-qPCR is performed on HEK293T cells transfected with various concentrations of SNAs. The CTCF ChIP protocol is performed as described in Example 1A.1. Phenol:chloroform purified DNA serves as template for SYBR Green (Thermo Scientific) qPCR using sequence-specific primers (IDT) flanking the CTCF-binding sequence region. As the SNA dosage increases, a corresponding decrease in the input-normalized amplification of the target region demonstrates the displacement of CTCF from anchor sequences due to SNA-targeted physical perturbation.

C2) Physical Perturbation with Targeted Protein Binding

This example demonstrates disruption of MYC gene associated CTCF anchor sequence-mediated conjunction by physically preventing CTCF binding at the anchor sequence using bulky effector molecules (in this case, fusion proteins).

HEK293T cells were serially transfected, first with plasmid encoding two different dCas9 fusion proteins, then 8 hr later with the gRNA targeted to the CTCF anchor sequence (listed in Table 1).

At 72 hr post-transfection, cells were harvested for RNA extraction and cDNA synthesis using commercially available reagents and protocols (Qiagen; Thermo Fisher Scientific; Thermo Fisher Scientific) and genomic DNA was extracted (Qiagen). The resulting cDNA was used for quantitative real-time PCR (Thermo Fisher Scientific).

MYC-specific quantitative PCR probes/primers were multiplexed with internal control quantitative PCR probes/primers as described in the previous examples and gene expression was subsequently analyzed by a real time PCR kit (Applied Biosystems, Thermo Fisher Scientific). Guide RNAs proximal to the CTCF anchor sequence showed reduction in MYC expression at 72 hr after methylation with either dCas9-DNMT3A-3L (FIG. 7B) or dCas9-KRAB (FIG. 7C). The letters A and B denote independent biological replicates of each experiment. Empty box symbols show technical replicates.

To determine differential CTCF binding at anchor sequences by targeted gRNAs and protein fusions versus non-targeting control gRNAs and protein fusions, a CTCF chromatin immunoprecipitation-quantitative PCR assay (ChIP-qPCR) is performed. The CTCF ChIP protocol is performed as described in Example 1A.1. Phenol:chloroform purified DNA serves as template for SYBR Green (Thermo Scientific) qPCR using sequence-specific primers (IDT) flanking the CTCF-binding sequence region Diminished input-normalized amplification indicates reduced CTCF binding due to the targeted physical disruptions.

Bulky effectors that physically disrupt CTCF binding at CTCF anchor sequences associated with the MYC gene demonstrate disruption of the MYC gene anchor-mediated conjunction and decrease MYC mRNA levels as compared to the non-targeting controls.

Without wishing to be bound by any particular theory, the inventors propose that, in some embodiments, bulkiness of effectors may contribute to one or more aspects of disruption. Results shown in FIG. 7B, for example, were obtained using a bulky fusion protein (dCas9-DNMT3A-3L) that may act as a multimer.

Thus, the present Example demonstrates that methods and agents of the present disclosure can be used to substantially reduce expression of a gene within a Type 1 loop.

Example 2: Disruption of a YY1 Anchor Sequence-Mediated Conjunction by Genetic Modification, Epigenetic Modification and Physical Perturbation to Decrease Expression of the MYC Gene The present Example demonstrates various strategies to decrease expression of a gene (in this case, MYC) within a Type 1 anchor sequence-mediated conjunction. Among other things, the present Example demonstrates the successful reduction of gene expression by disruption of the anchor sequence-mediated conjunction via, e.g., modification of and/or perturbation at a YY1 anchor sequence.

The present Example confirms, among other things, that methods and agents of the present disclosure can be applied to modify more than one type of anchor sequence to modulate expression of a gene associated with an anchor sequence-mediated conjunction.

Additionally, the present Example demonstrates that in the context of methods RNA-guided nucleases, substantial changes in gene expression can be achieved using an individual guide RNA.

Production of agents: All plasmids and guide RNAs have been chemically synthesized from commercially available vendors. All agents were reconstituted in sterile water. All sequences are provided in the Materials and Methods section.

A) Genetic Modification

A YY1 anchor sequence is located upstream of the MYC gene, close to where distal super-enhancers influence the MYC promoter.

This example demonstrates disruption of MYC gene associated YY1 anchor sequence-mediated conjunction by genetic modifications.

TABLE 5

Sequences of gRNAs targeting putative YY1 anchor sequences associated with the MYC gene E-P anchor sequence-mediated conjunction.

| ID | Guide RNA Sequence (5'-3') |
|---|---|
| GSSP-00003 | TGCAGAAGGTCCGAAGAAAG (SEQ ID NO: 20) |
| GSSP-00004 | AAGAATAACAAGGAGGTGGC (SEQ ID NO: 21) |

HEK293T cells were serially transfected, first with plasmid encoding Cas9 and then 8 hr later with a non-targeting gRNA ("Non-targeting," where the guide RNA sequence has no homology to the human genome) or a gRNA, as listed in Table 5, targeted to the YY1 anchor sequence.

At 72 hr post-transfection, cells were harvested for RNA extraction and cDNA synthesis using commercially available reagents and protocols (Qiagen; Thermo Fisher Scientific) and genomic DNA was extracted (Qiagen). The resulting cDNA was used for quantitative real-time PCR (Thermo Fisher Scientific).

MYC-specific quantitative PCR probes/primers (Assay ID Hs00153408_m1, Thermo Fisher Scientific) were multiplexed with internal control quantitative PCR probes/primers, which were PPIB (Assay ID Hs00168719_m1, Thermo Fisher Scientific) as described in Example 1 and gene expression was subsequently analyzed by a real time PCR kit (Applied Biosystems, Thermo Fisher Scientific). Guide RNAs proximal to the YY1 anchor sequence showed reduction in MYC expression at 72 hr (FIG. 7D). Empty box symbols denote the value of each biological replicate.

As shown in the FIG. 7D, substantial reductions of approximately 40% and greater in MYC gene expression was obtained with individual guides.

To determine differential YY1 binding at anchor sequences by targeted gRNAs versus non-targeting gRNAs, a YY1 chromatin immunoprecipitation-quantitative PCR assay (ChIP-qPCR) is performed. The YY1 ChIP protocol is performed as described in Example 1, A1. Phenol:chloroform purified DNA serves as template for SYBR Green (Thermo Scientific) qPCR using sequence-specific primers (IDT) flanking the YY1-binding sequence region. Diminished input-normalized amplification indicates reduced YY1 binding due to the targeted epigenetic modifications.

Effectors that target epigenetic modifications at or near the YY1 anchor sequence associated with the MYC gene demonstrate disruption of the MYC gene anchor-mediated conjunction to decrease MYC mRNA levels as compared to the non-targeting controls.

Enzymatic effectors that modify DNA at or near the YY1 anchor sequence associated with the MYC gene demonstrated disruption of the MYC gene anchor-mediated conjunction to decrease MYC mRNA levels as compared to the non-targeting controls.

B) Epigenetic Modification

This example demonstrates disruption of MYC gene associated YY1 anchor sequence-mediated conjunction by epigenetic modifications.

HEK293T cells are serially transfected, first with plasmid encoding either dCas9-DNMT3A-3L (a fusion protein including the active domains from a DNA methyltransferase) or dCas9-KRAB (a transcriptional repressor fusion protein), then 8 hr later with one of five gRNAs tiled around the anchor sequence (listed in Table 3) or a mixture of all five gRNAs tiled around the anchor sequence.

At 72 hr post-transfection, cells are harvested for RNA extraction and cDNA synthesis using commercially available reagents and protocols (Qiagen; Thermo Fisher Scientific; Thermo Fisher Scientific) and genomic DNA is extracted (Qiagen). The resulting cDNA is used for quantitative real-time PCR (Thermo Fisher Scientific).

MYC-specific quantitative PCR probes/primers are multiplexed with internal control quantitative PCR probes/primers as described in the previous examples and gene expression is subsequently analyzed by a real time PCR kit (Applied Biosystems, Thermo Fisher Scientific). Cells transfected with guide RNAs proximal to the YY1 anchor sequence are expected to show reduction in MYC expression after methylation of the YY1 anchor sequences.

To determine differential YY1 binding at anchor sequences by targeted methyltransferase or transcriptional repressor proteins versus non-targeted protein fusions, a YY1 chromatin immunoprecipitation-quantitative PCR assay (ChIP-qPCR) is performed. The YY1 ChIP protocol is performed as described in Example 1A.1. Phenol:chloroform purified DNA serves as template for SYBR Green (Thermo Scientific) qPCR using sequence-specific primers (IDT) flanking the YY1-binding sequence region Diminished input-normalized amplification indicates reduced YY1 binding due to the targeted epigenetic modifications.

Effectors that target epigenetic modifications at or near the YY1 anchor sequence associated with the MYC gene demonstrate disruption of the MYC gene anchor-mediated conjunction and decrease MYC mRNA levels as compared to the non-targeting controls.

C) Physical Perturbation

This example demonstrates disruption of MYC gene associated YY1 anchor sequence-mediated conjunction by physically preventing YY1 binding at the anchor sequence.

HEK293T cells are transfected using lipid based transfection reagent (Invitrogen), according to manufacturer's instructions, with Synthetic Nucleic Acids (SNAs) listed in Table 4 or a non-targeting SNA. At 72 hr post-transfection, cells are harvested for RNA extraction and cDNA is synthesized (Thermo Fisher Scientific) according to the manufacturer's protocols. cDNA is used as template for quantitative real-time PCR.

MYC-specific quantitative PCR probes/primers are multiplexed with internal control quantitative PCR probes/primers as described in the previous examples and gene expression is subsequently analyzed by a real time PCR kit (Applied Biosystems, Thermo Fisher Scientific). SNAs proximal to the YY1 anchor sequence show reduction in MYC expression.

For determination of differential YY1 binding at anchor sequences targeted by SNAs versus non-targeting SNAs, a YY1 ChIP-qPCR is performed on HEK293T cells transfected with various concentrations of SNAs. The YY1 ChIP protocol is performed as described in Example 1A.1. Phenol:chloroform purified DNA serves as template for SYBR Green (Thermo Scientific) qPCR using sequence-specific primers (IDT) flanking the YY1-binding sequence region. As the SNA dosage increases, a corresponding decrease in the input-normalized amplification of the target region demonstrates the displacement of CTCF from anchor sequences due to SNA-targeted physical perturbation.

Effectors that physically disrupt YY1 binding at YY1 anchor sequences associated with the MYC gene demonstrate disruption of the MYC gene anchor-mediated conjunction to decrease MYC mRNA levels as compared to the non-targeting controls.

Example 3: Disruption of a CTCF Anchor Sequence-Mediated Conjunction by Genetic, Epigenetic, and Physical Perturbation to Decrease Expression of the FOXJ3 Gene The present Example demonstrates various strategies to decrease expression of a gene (in this case, FOXJ3) within a Type 1 anchor sequence-mediated conjunction. Among other things, the present Example demonstrates the successful site-specific modulation (in this case, repression) of gene expression by disruption of the anchor sequence-mediated conjunction via, e.g., modification of and/or perturbation at a CTCF anchor sequence.

Ovarian cancer is one of the most common cancers and causes of death among women in the United States. Forkhead box J3 (FOXJ3) belongs to a family of transcription factors that plays an important role in regulating the expression of genes involved in cell growth, proliferation, differentiation, and longevity. FOXJ3 has been shown to be amplified in up to 10% of ovarian cancers, suggesting that disruption of the FOXJ3 gene anchor-mediated conjunction and decrease in FOXJ3 gene expression may be therapeutic in ovarian cancer.

The FOXJ3 gene is in a Type 1 anchor sequence-mediated conjunction. The anchor sequence-mediated conjunction includes the gene encoding FOXJ3 and an associated transcription control sequence, e.g., an enhancer.

Production of agents: All plasmids and guide RNAs (gRNA) have been chemically synthesized from commercially available vendors. All agents were reconstituted in sterile water. All sequences are provided in the Materials and Methods section.

A) Genetic Perturbation

This example demonstrates disruption of the FOXJ3 gene Type 1 anchor sequence-mediated conjunction through genetic mutation of the putative CTCF anchor sequences using CRISPR Cas9.

TABLE 6

Sequences of gRNAs targeting putative CTCF anchor sequences associated with the FOXJ3 gene Type 1 anchor sequence-mediated conjunction.

| ID | Guide RNA Sequence (5'-3') |
|---|---|
| SACR-00055 | AGATTCTAAAGGCTGGCTAG (SEQ ID NO: 22) |
| SACR-00056 | GGGAGCACAGCCCTAAGTAA (SEQ ID NO: 23) |
| SACR-00057 | GAAACCCTCCAAAAGAGGAA (SEQ ID NO: 24) |
| SACR-00058 | GAGTGCCTGTGGCCACTAGG (SEQ ID NO: 25) |
| SACR-00059 | GCCTAATTGCAAAGTAGCTT (SEQ ID NO: 26) |

TABLE 6-continued

Sequences of gRNAs targeting putative CTCF anchor sequences associated with the FOXJ3 gene Type 1 anchor sequence-mediated conjunction.

| ID | Guide RNA Sequence (5'-3') |
|---|---|
| SACR-00060 | AGCGACCAGGCGGAGAATGA (SEQ ID NO: 27) |
| SACR-00061 | GGGCCTGAAACAGCACAATG (SEQ ID NO: 28) |
| SACR-00062 | ACATTGGAGCTGAATGGCCT (SEQ ID NO: 29) |

HEK293T cells were serially transfected using transfection reagent (Promega), according to the manufacturer's instructions, first with plasmid encoding Cas9, then 8 hr later with chemically synthesized gRNAs (Table 6) that target at or near putative CTCF anchor sequences or a non-targeting gRNA ("Non-targeting," where the guide RNA sequence has no homology to the human genome). At 72 hr post-transfection, cells were harvested for RNA extraction and cDNA was synthesized (Thermo Fisher Scientific) according to the manufacturer's protocol. The resulting cDNA was then used for quantitative real-time PCR (Thermo Fisher Scientific).

FOXJ3-specific quantitative PCR probes/primers (Assay ID: Hs00961536, Thermo Fisher Scientific) were multiplexed with internal control PPIB probes/primers (Assay ID: Hs00168719, Thermo Fisher Scientific) using the FAM-MGB and VIC-MGB dyes, respectively, and gene expression was subsequently analyzed by a real time PCR kit (Applied Biosystems, Thermo Fisher Scientific).

Figure 8:
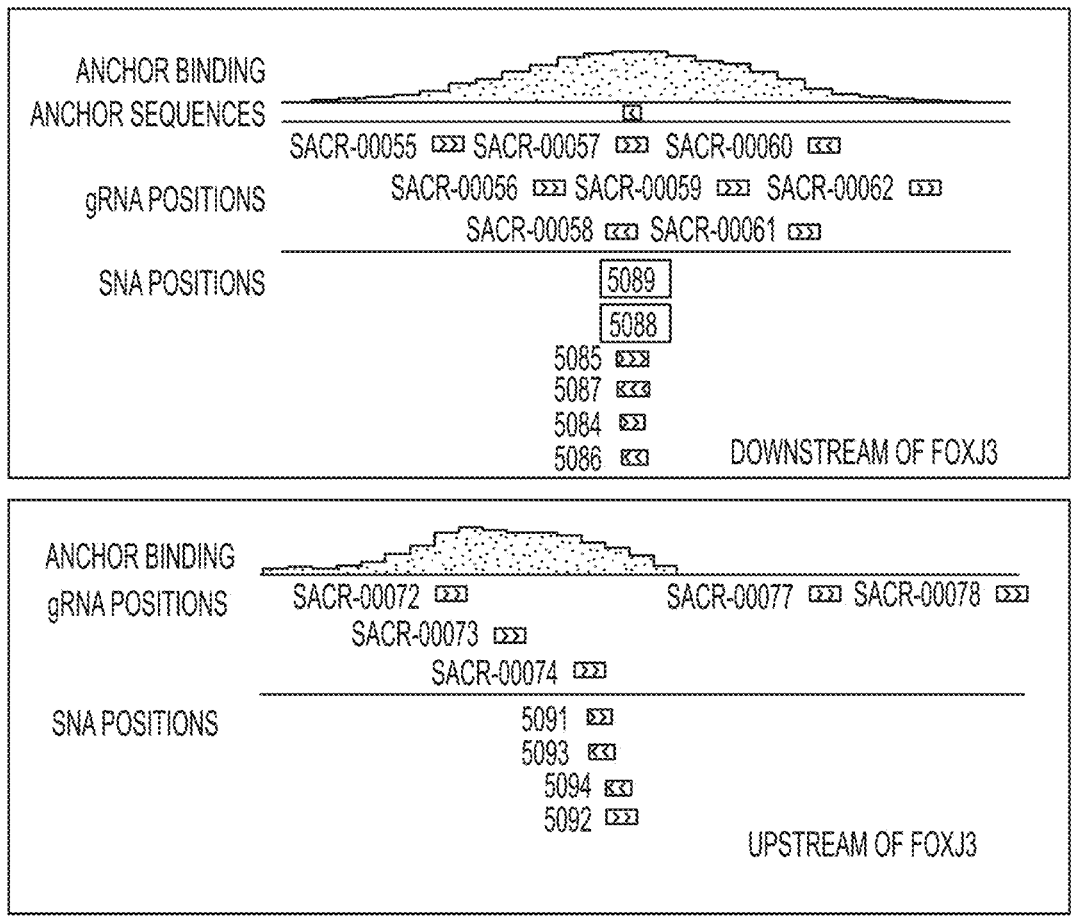
FIG. 8 illustrates disruption of an anchor sequence-mediated conjunction associated with the FOXJ3 gene, leading to downregulation of FOXJ3 expression levels. As further described in Example 3, panel A depicts a map of gRNA and SNA sequences, and panels B, C, D, and E illustrate reduction in FOXJ3 levels.
Figure 8:
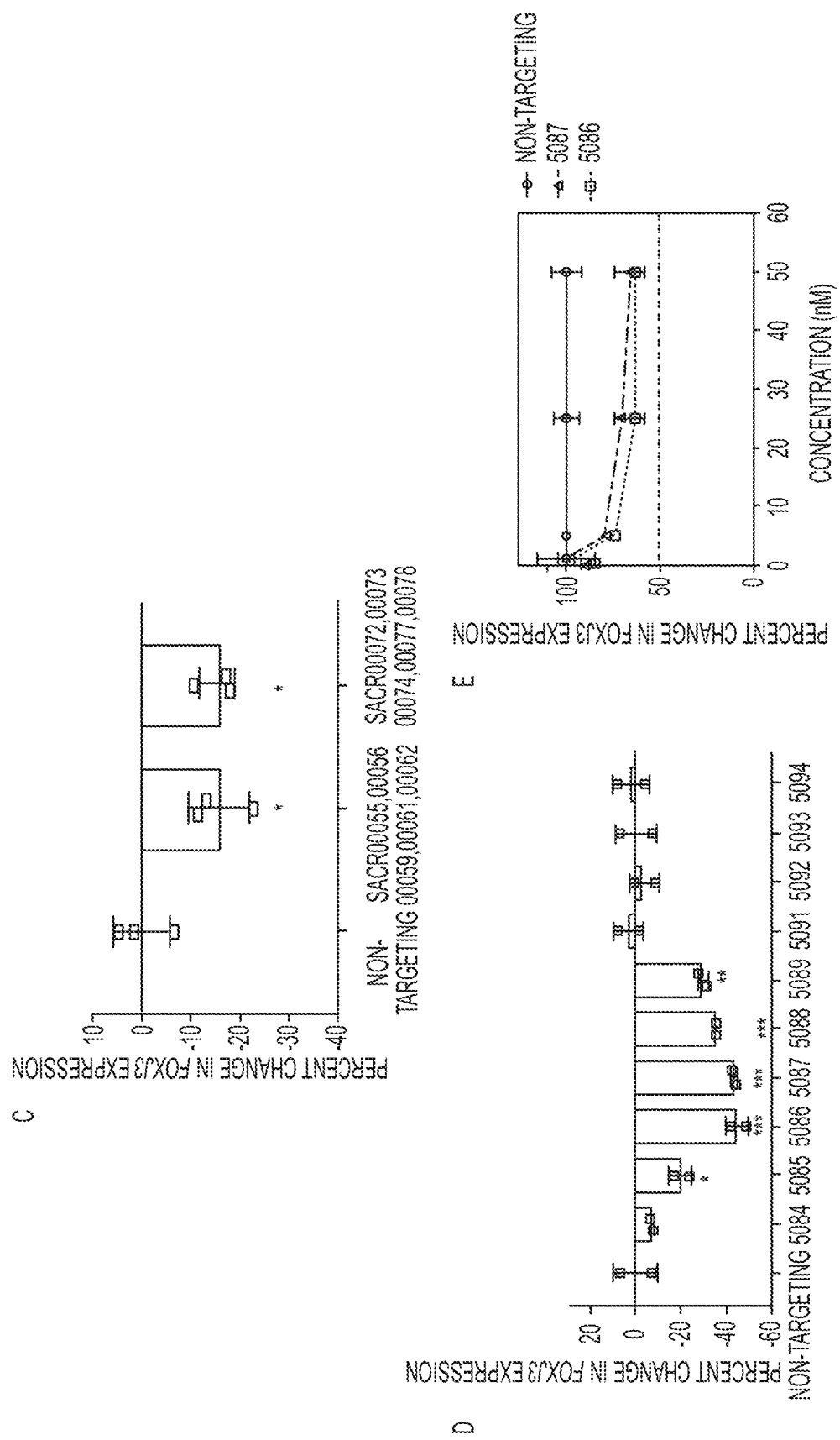

The locations of potential CTCF binding (black) associated with the FOXJ3 gene alongside the locations of the anchor sequences (top right arrows, bottom left arrows) gRNA, and SNAs are shown in FIG. 8A.

The average change of FOXJ3 gene expression in HEK293T cells 72 hr post-transfection with the indicated gRNAs is shown in FIG. 8B. Each biological replicate is depicted by empty box symbols. Guide RNAs proximal to the anchor sequence showed reduction in FOXJ3 mRNA levels. * $p<0.001$,  $p<0.01$, * $p<0.05$, n.s. not significant.

As shown in FIG. 8B, a greater decrease in expression was observed with guide RNAs that targeted regions closer to the CTCF binding site.

To determine whether targeting the FOXJ3 anchor sequence-mediated conjunction does not affect another gene in another anchor sequence-mediated conjunction, HLA-A-specific quantitative PCR probes/primers (Assay ID: Hs01058806_g1, Thermo Fisher Scientific) were multiplexed with internal control PPIB probes/primers (Assay ID: Hs00168719, Thermo Fisher Scientific) using the FAM-MGB and VIC-MGB dyes, respectively, and gene expression was subsequently analyzed by a real time PCR kit (Applied Biosystems, Thermo Fisher Scientific).

HLA-A gene expression did not show a significant change in expression in HEK293T cells 72 hr post-transfection with the indicated FOXJ3 gRNAs across three biological replicates. All of the gRNAs target the anchor sequence of the FOXJ3 anchor sequence-mediated conjunction, and do not show non-specific effects on HLA-A mRNA levels.

Enzymatic effectors that modify DNA at or near the CTCF anchor sequence associated with the FOXJ3 gene demonstrated site-specific disruption of the FOXJ3 gene anchor-mediated conjunction and decrease FOXJ3 mRNA levels as compared to the non-targeting controls.

Thus, the present Example demonstrates modulation at a target gene without affecting a non-target gene.

B) Epigenetic Perturbation

This example demonstrates disruption of the FOXJ3 gene Type 1 anchor sequence-mediated conjunction by heterochromatin formation at and near the anchor sequence. dCas9-KRAB is a transcriptional repressor fusion protein with enzymatic activity that is specific to the genomic regions at and in proximity to the anchor sequence, e.g., gRNA binding sites.

TABLE 7

Sequences of gRNAs targeting putative CTCF sites associated with the FOXJ3 gene Type 1 anchor sequence-mediated conjunction.

| ID | Guide RNA Sequence (5'-3') |
|---|---|
| SACR-00064 | GACCCTTTGAAGACTCAACT (SEQ ID NO: 30) |
| SACR-00065 | GCTCTGGTAAGGCAAGATTC (SEQ ID NO: 31) |
| SACR-00067 | AGGTAGCAAATGCCAGCCCA (SEQ ID NO: 32) |
| SACR-00069 | ATCTCTGGATTTCTCATGAG (SEQ ID NO: 33) |
| SACR-00071 | GCAGTGCTGGGGACAAGATG (SEQ ID NO: 34) |
| SACR-00072 | CTAGGTTAGGTATTGTGCTA (SEQ ID NO: 35) |
| SACR-00073 | AAGATAAAAGCAGTAGCTAG (SEQ ID NO: 36) |
| SACR-00074 | ATAATAGCAATTAAGAGTAA (SEQ ID NO: 37) |
| SACR-00077 | TGGAGGCTGCAGGGAGGCGG (SEQ ID NO: 38) |
| SACR-00078 | AATGTGGGCTCCCTCGTCTG (SEQ ID NO: 39) |

HEK293T cells were serially transfected using transfection reagent (Promega), according to the manufacturer's instructions, first with plasmid encoding dCas9-KRAB, a transcriptional repressor fusion protein, then 8 hr later with mixtures of five chemically synthesized gRNAs, listed in Table 7, located proximally around the anchor sequences upstream or downstream of FOXJ3 or a non-targeting gRNA ("Non-targeting," where the guide RNA sequence has no homology to the human genome). At 72 hr post-transfection, cells were harvested for RNA extraction and cDNA was synthesized (Thermo Fisher Scientific) according to the manufacturer's protocols. cDNA was used as a template for quantitative real-time PCR.

FOXJ3-specific quantitative PCR probes/primers (Assay ID: Hs00961536, Thermo Fisher Scientific) were multiplexed with internal control PPIB quantitative PCR probes/primers (Assay ID: Hs00168719, Thermo Fisher Scientific) using the FAM-MGB and VIC-MGB dyes, respectively, and gene expression was analyzed using a real time PCR kit (Applied Biosystems, Thermo Fisher Scientific).

The average change of FOXJ3 gene expression in HEK293T cells 72 hr post-transfection with the indicated anchor-proximal gRNAs or non-targeting control gRNA is shown in FIG. 8C. Empty boxes denote the value of each biological replicate. Guide RNAs targeting the anchor sequence and flanking sequence regions showed reduction in FOXJ3 mRNA levels ** p<0.01, * p<0.05.

Effectors that target epigenetic modifications at or near the CTCF anchor sequence associated with the FOXJ3 gene demonstrate disruption of the FOXJ3 gene anchor-mediated conjunction and decrease FOXJ3 mRNA levels as compared to the non-targeting controls.

C) Physical Perturbation

This example demonstrates disruption of the FOXJ3 gene Type 1 anchor sequence-mediated conjunction by physically preventing CTCF binding at the anchor sequences.

TABLE 8

Sequences of Synthetic Nucleic Acids (SNAs) targeting putative CTCF anchor sequences associated with the FOXJ3 gene Type 1 anchor sequence-mediated conjunction.

| ID | SNA Sequence (5'-3') (* = phosphothiolate linkage) |
|---|---|
| 5084 | C*C*T*A*G*TGGCCACAGG*C*A*C*T*C (SEQ ID NO: 40) |
| 5085 | G*C*C*C*C*CTAGTGGCCACAGG*C*A*C*T*C (SEQ ID NO: 41) |
| 5086 | G*A*G*T*G*CCTGTGGCCA*C*T*A*G*G (SEQ ID NO: 86) |
| 5087 | G*A*G*T*G*CCTGTGGCCACTAG*G*G*G*G*C (SEQ ID NO: 42) |
| 5088 | G*T*G*A*G*TGCCTGTGGCCACTAGGGGCGGGGCTGCCGGC*T*G*T*G*C (SEQ ID NO: 43) |
| 5089 | G*T*G*A*G*TGCCT*G*TGGCCACTAG*G*G*G*GCGG*GGC*T*GCCGGC*T*G*T*G*C (SEQ ID NO: 87) |
| 5091 | A*G*G*G*C*TCCCCGCCAG*C*A*T*G*G (SEQ ID NO: 44) |
| 5092 | C*C*A*G*C*ATGGTGGCTC*A*C*G*T*C (SEQ ID NO: 45) |
| 5093 | C*C*A*T*G*CTGGCGGGA*G*C*C*C*T (SEQ ID NO: 46) |
| 5094 | G*A*C*G*T*GAGCCACCAT*G*C*T*G*G (SEQ ID NO: 47) |

HEK293T cells were transfected using a lipid based transfection reagent (Invitrogen), according to the manufacturer's instructions, with SNAs located proximally around the anchor sequences upstream or downstream of the FOXJ3 gene, listed in Table 8, or a non-targeting SNA. At 72 hr post-transfection, cells were harvested for RNA extraction and cDNA was synthesized (Thermo Fisher Scientific) according to the manufacturer's protocols. cDNA was used as template for quantitative real-time PCR.

FOXJ3-specific quantitative PCR probes/primers (Assay ID: Hs00961536, Thermo Fisher Scientific) were multiplexed with internal control PPIB quantitative PCR probes/primers (Assay ID: Hs00168719, Thermo Fisher Scientific) using the FAM-MGB and VIC-MGB dyes, respectively, and gene expression was analyzed by a real time PCR kit (Applied Biosystems, Thermo Fisher Scientific).

The average change of FOXJ3 gene expression in HEK293T cells 72 hr post-transfection with the indicated SNAs is shown in FIG. 8D. Each biological replicate is depicted by empty box symbols. SNAs proximal to the anchor sequence showed reduction in FOXJ3 mRNA levels compared to non-targeting controls ("Non-targeting," where the SNA sequence has no homology to the human genome). This decrease in gene expression is sequence specific, as not all target-specific SNAs can modulate FOXJ3 mRNA expression. * p<0.05,  p<0.005, * p<0.0005. The dose-response curve using a non-targeting SNA, and 3 FOXJ3-targeted SNAs with various doses for 72 hr post transfection shows a decrease in FOXJ3 mRNA (FIG. 8E).

Effectors that physically disrupt CTCF binding at CTCF anchor sequences associated with the FOXJ3 gene demonstrate disruption of the FOXJ3 gene anchor-mediated conjunction to decrease FOXJ3 mRNA levels as compared to the non-targeting controls.

The present Example demonstrates modulation at a target gene using physical disruptors. The lack of observed effect on FOXJ3 expression using non-targeting controls, and the dose-response curve obtained using SNAs specific for FOXJ3, support a conclusion that disruption was achieved in a site-specific manner. Moreover, the observed dose-response effect confirms that it is possible to tune the extent of decreased gene expression using agents and methods of the present disclosure.

Example 4: Disruption of CTCF Anchor Sequence-Mediated Conjunctions by Genetic Modification, Epigenetic Modification and Physical Perturbation to Increase Expression of the TUSC5 Gene The present Example demonstrates various strategies to increase expression of a gene (in this case, TUSC5) within a Type 2 anchor sequence-mediated conjunction. Among other things, the present Example demonstrates the successful modulation of gene expression by disruption of the anchor sequence-mediated conjunction via, e.g., modification of and/or perturbation at a CTCF anchor sequence.

Tumor suppressor candidate 5 (TUSC5) is a putative transmembrane protein. TUSC5 is frequently deleted in lung cancers, and is therefore classified as a tumor suppressor. Upregulation of TUSC5 might inhibit cancer growth. Thus, upregulation of TUSC5, as demonstrated herein, provided a potential therapeutic strategy. TUSC5 is also highly expressed in brown adipose tissue, and potentially involved in differentiation of brown fat cells.

TUSC5 is located within a CTCF anchor sequence-mediated conjunction. In HEK293T cells, TUSC5 is not expressed, and there are multiple active enhancers outside this conjunction, both upstream and downstream. This conjunction is an example of a Type 2 loop. Disruption of the CTCF anchor sequence at either end of the conjunction is expected to cause the enhancers outside the conjunction to activate expression of TUSC5.

Production of agents: All plasmids and guide RNAs have been chemically synthesized from commercially available vendors. All agents were reconstituted in sterile water. All sequences are provided in the Materials and Methods section.

A) Genetic Modification

This example demonstrates disruption of the TUSC5 gene-associated CTCF anchor sequence-mediated conjunction by genetic modifications.

TABLE 9

Sequences of gRNAs targeting putative CTCF sites associated with the TUSC5 gene Type 2 anchor sequence-mediated conjunctions

| ID | Guide RNA Sequence (5'-3') |
|---|---|
| SACR-00214 | CAGCGGATTTGGGCTCCCGG (SEQ ID NO: 48) |
| SACR-00216 | CCTCATCACTACCTGCCACG (SEQ ID NO: 49) |
| SACR-00217 | CATCACTACCTGCCACGAGG (SEQ ID NO: 50) |
| SACR-00218 | TGAGACTCCAGCATCCCACA (SEQ ID NO: 51) |
| SACR-00219 | CCAGAGTAGTCCCTGGCACG (SEQ ID NO: 52) |

HEK293T cells were serially transfected with plasmid encoding Cas9 and either a non-targeting gRNA ("Non-targeting," where the guide RNA sequence has no homology to the human genome) or a gRNA, as listed in Table 9, targeted at or near the putative CTCF anchor sequence of the conjunction enclosing the TUSC5 gene. HEK293T cells were transfected first with plasmid encoding Cas9, and then transfected 8 hr later with either a chemically synthesized gRNAs targeting the anchor sequence or a non-targeting gRNA ("Non-targeting," where the guide RNA sequence has no homology to the human genome).

At 72 hr post-transfection, cells were harvested for RNA extraction and cDNA synthesis using commercially available reagents and protocols (Qiagen; Thermo Fisher Scientific) and genomic DNA was extracted (Qiagen). The resulting cDNA was used for quantitative real-time PCR (Thermo Fisher Scientific).

TUSC5-specific quantitative PCR probes/primers (Assay ID Hs00542659_m1, Thermo Fisher Scientific) were multiplexed with internal control quantitative PCR probes/primers for PPIB (Assay ID Hs00168719_m1, Thermo Fisher Scientific) using the FAM-MGB and VIC-MGB dyes, respectively, and gene expression was subsequently analyzed by a real time PCR kit (Applied Biosystems, Thermo Fisher Scientific).

Figure 9:
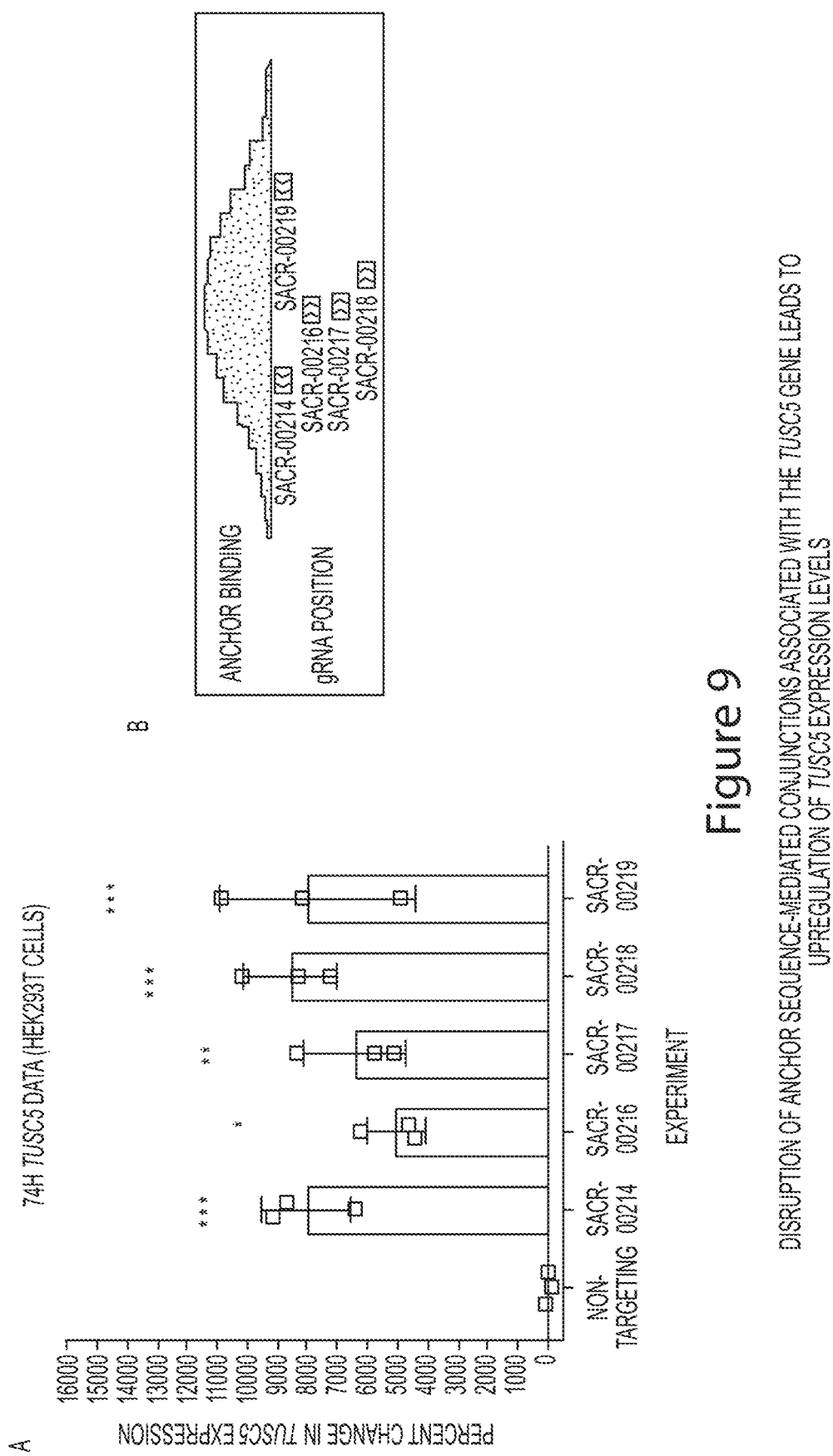
FIG. 9 illustrates disruption of anchor sequence-mediated conjunctions associated with the TUSC5 gene, leading to upregulation of TUSC5 expression levels. As further described in Example 4, panel A depicts upregulation of TUSC5 expression levels, and panel B depicts a map of gRNA sequences.

The average percentage change of TUSC5 gene expression in HEK293T cells 72 hr post-transfection with the indicated gRNAs is shown in FIG. 9A. The gRNAs located most proximally to the nucleating agent-binding region showed efficacy in upregulating TUSC5 gene expression. Guide RNAs SACR00214 through SACR-00219 showed greater than 5000% increases in TUSC5 mRNA at 72 hr relative to the "Non-targeting" control. Each biological replicate is represented by empty box symbol. * $p<0.05$,  $p<0.01$, * $p<0.001$.

The locations of potential CTCF binding (black) upstream of the TUSC5 gene alongside the locations of the gRNAs are shown in FIG. 9B.

Enzymatic effectors that modify DNA at or near the CTCF anchor sequence associated with the TUSC5 gene demonstrated disruption of the TUSC5 gene anchor-mediated conjunction and increased TUSC5 mRNA levels as compared to the non-targeting controls.

To the present inventors' knowledge, the present Example provides the first demonstration that an increase of gene expression of this magnitude (greater than 5000% increase) can be achieved by disrupting an anchor sequence-mediated conjunction with which the gene is associated.

B) Epigenetic Modification

This example demonstrates disruption of the TUSC5 gene associated CTCF anchor sequence-mediated conjunction by epigenetic modifications.

HEK293T cells are serially transfected, first with plasmid encoding either dCas9-DNMT3A-3L (a fusion protein including the active domains from a DNA methyltransferase) or dCas9-KRAB (a transcriptional repressor fusion protein), then 8 hr later with one of the gRNAs tiled around the anchor sequence (listed in Table 9) or a mixture of gRNAs tiled around the anchor sequence.

At 72 hr post-transfection, cells are harvested for RNA extraction and cDNA synthesis using commercially available reagents and protocols (Qiagen; Thermo Fisher Scientific) and genomic DNA is extracted (Qiagen). The resulting cDNA is used for quantitative real-time PCR (Thermo Fisher Scientific).

TUSC5-specific quantitative PCR probes/primers are multiplexed with internal control quantitative PCR probes/primers as described herein and gene expression is subsequently analyzed by a real time PCR kit (Applied Biosystems, Thermo Fisher Scientific). Cells transfected with guide RNAs proximal to the CTCF anchor sequence are expected to show increases in TUSC5 expression at 72 hr after modification by either dCas9-DNMT3A-3L or dCas9-KRAB.

Effectors that target epigenetic modifications at or near the CTCF anchor sequence associated with the TUSC5 gene demonstrate disruption of the TUSC5 gene anchor-mediated conjunction and increase TUSC5 mRNA levels as compared to the non-targeting controls.

C) Physical Perturbation

This example demonstrates disruption of TUSC5 gene associated CTCF anchor sequence-mediated conjunction by physically preventing CTCF binding at the anchor sequence using bulky effector molecules (in this case, fusion proteins).

HEK293T cells are serially transfected, first with plasmid encoding two different dCas9 fusion proteins, then 8 hr later with one of the gRNAs tiled around the anchor sequence (listed in Table 9) or a mixture of guide RNAs tiled around the anchor sequence.

At 72 hr post-transfection, cells are harvested for RNA extraction and cDNA synthesis using commercially available reagents and protocols (Qiagen; Thermo Fisher Scientific; Thermo Fisher Scientific) and genomic DNA is extracted (Qiagen). The resulting cDNA is used for quantitative real-time PCR (Thermo Fisher Scientific).

TUSC5-specific quantitative PCR probes/primers are multiplexed with internal control quantitative PCR probes/primers as described in the previous examples and gene expression is subsequently analyzed by a real time PCR kit (Applied Biosystems, Thermo Fisher Scientific). Cells transfected with guide RNAs proximal to the CTCF anchor sequence are expected to show increases in TUSC5 expression at 72 hr after modification by either dCas9-DNMT3A-3L or dCas9-KRAB.

To determine differential CTCF binding at anchor sequences by targeted gRNAs and protein fusions versus non-targeting control gRNAs and protein fusions, a CTCF chromatin immunoprecipitation-quantitative PCR assay (ChIP-qPCR) is performed. The CTCF ChIP protocol is performed as described in previous examples. Phenol:chloroform purified DNA serves as template for SYBR Green (Thermo Scientific) qPCR using sequence-specific primers (IDT) flanking the CTCF-binding sequence region. Diminished input-normalized amplification indicates reduced CTCF binding due to the targeted physical disruptions.

Bulky effectors that physically disrupt CTCF binding at CTCF anchor sequences associated with the TUSC5 gene demonstrate disruption of the TUSC5 gene anchor-mediated conjunction and increase TUSC5 mRNA levels as compared to the non-targeting controls.

Example 5: Disruption of a CTCF Anchor Sequence-Mediated Conjunction by Genetic Modification, Epigenetic Modification and Physical Perturbation to Increase Expression of the DAND5 Gene The present Example demonstrates various strategies to increase expression of a gene (in this case, DAND5) within a Type 2 anchor sequence-mediated conjunction. Among other things, the present Example demonstrates the successful modulation of gene expression by disruption of the anchor sequence-mediated conjunction via, e.g., modification of and/or perturbation at a CTCF anchor sequence.

DAN Domain BMP Antagonist Family Member 5 (DAND5) is a BMP antagonist. DAND5 mutations have been associated with congenital heart defects.

DAND5 is located within a CTCF anchor sequence-mediated conjunction. In HEK293T cells, DAND5 is expressed at very low levels, and there are active enhancers outside this conjunction upstream of the DAND5 gene. This conjunction is an example of a Type 2 loop. Disruption of the CTCF anchor sequence at the end of the conjunction upstream of DAND5 is expected to cause the enhancers outside the conjunction to interact with DAND5 and increase its expression.

Production of agents: All plasmids and guide RNAs have been chemically synthesized from commercially available vendors. All agents were reconstituted in sterile water. All sequences are provided in the Materials and Methods section.

A) Genetic Modification

This example demonstrates disruption of the DAND5 gene-associated CTCF anchor sequence-mediated conjunction by genetic modifications.

TABLE 10

Sequences of gRNAs targeting putative CTCF sites associated with the DAND5 gene Type 2 anchor sequence-mediated conjunction.

| ID | Guide RNA Sequence (5'-3') |
|---|---|
| SACR-00187 | ACAGCAGAAGGGCAGGTTGG (SEQ ID NO: 53) |
| SACR-00188 | CCAGGACACCCGCCTCCCAG (SEQ ID NO: 54) |
| SACR-00189 | GCGGCGTGCTCGCCCTCTGG (SEQ ID NO: 55) |
| SACR-00190 | GCATCGCACTCGCAGCTCCG (SEQ ID NO: 56) |
| SACR-00191 | GGGTGCGAGATAGAGGTGCC (SEQ ID NO: 57) |
| SACR-00192 | GGCACCTCTATCTCGCACCC (SEQ ID NO: 58) |

HEK293T cells were serially transfected with plasmid encoding Cas9 and either a non-targeting gRNA ("Non-targeting," where the gRNA sequence has no homology to the human genome) or a gRNA, as listed in Table 10, targeted at or near the putative CTCF anchor sequences at end of the conjunction upstream of the DAND5 gene. The HEK293T cells were serially transfected first with plasmid encoding Cas9, and then 8 hr later with either a chemically synthesized gRNAs targeting the CTCF anchor sequence or a non-targeting gRNA ("Non-targeting," where the gRNA sequence has no homology to the human genome).

At 72 hr post-transfection, cells were harvested for RNA extraction and cDNA synthesis using commercially available reagents and protocols (Qiagen; Thermo Fisher Scientific) and genomic DNA was extracted (Qiagen). The resulting cDNA was used for quantitative real-time PCR (Thermo Fisher Scientific).

Figure 10:
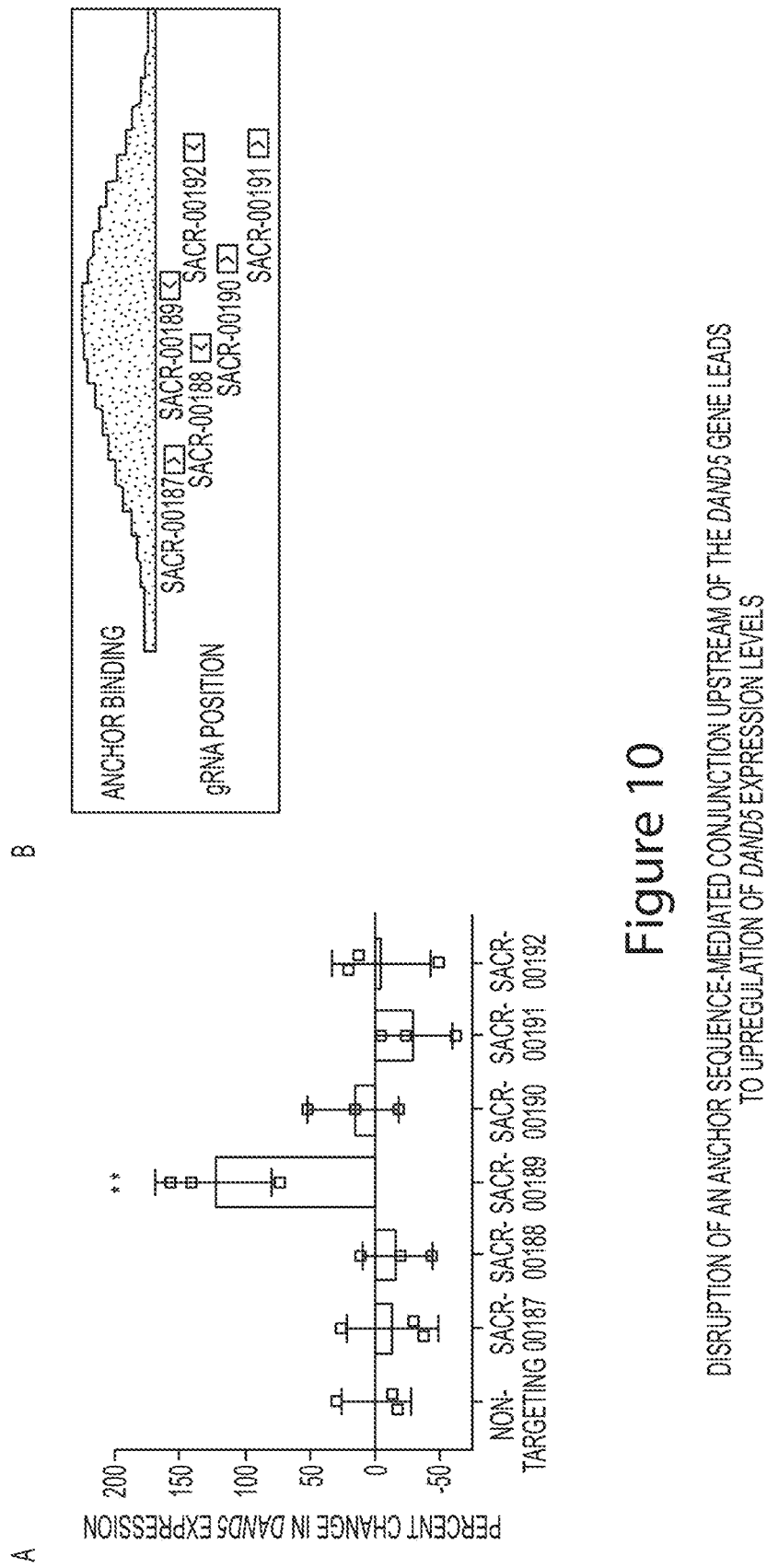
FIG. 10 illustrates disruption of an anchor sequence-mediated conjunction upstream of the DAND5 gene, leading to upregulation of DAND5 expression levels. As further described in Example 5, panel A depicts upregulation of DAND5 expression levels, and panel B depicts a map of gRNA sequences.

DAND5-specific quantitative PCR probes/primers (Assay ID Hs00541488_m1, Thermo Fisher Scientific) were multiplexed with internal control quantitative PCR probes/primers for PPIB (Assay ID Hs00168719_m1, Thermo Fisher Scientific) using the FAM-MGB and VIC-MGB dyes, respectively, and gene expression was subsequently analyzed by a real time PCR kit (Applied Biosystems, Thermo Fisher Scientific). Guide RNA SACR-00189 showed a 124% increase in DAND5 expression relative to the "Non-targeting" control, (FIG. 10). Each biological replicate is represented by empty box symbol.

The average percentage change of DAND5 gene expression in HEK293T cells 72 hr post-transfection with the indicated gRNAs is shown in FIG. 10A. Empty boxes represent each biological replicate. The gRNA closest to the peak of the CTCF-binding region (SACR-00189) showed efficacy in upregulating DAND5 gene expression. ** $p<0.01$.

As shown in FIG. 10A, a robust effect (more than 100% increase) on gene expression was achieved with a single guide RNA targeting the center of CTCF binding site. In contrast with the results described in Example 4A, no significant increases were observed with guide RNAs targeting regions nearby, but not at, the middle of the CTCF binding site.

Without wishing to be bound by any particular theory, the inventors propose that certain factors (e.g., targeting efficiencies of specific guide RNAs, strength and/or types of nearby transcriptional control sequences (e.g., enhancers) etc.) may influence a particular locus's susceptibility to modulation by disruption of anchor sequence-mediated conjunctions.

In FIG. 10B, the locations of potential CTCF-binding (black) upstream of the DAND5 gene are shown alongside the locations of the gRNAs.

Enzymatic effectors that modify DNA at or near the CTCF anchor sequence associated with the DAND5 gene demonstrated disruption of the DAND5 gene anchor-mediated conjunction and increase DAND5 mRNA levels as compared to the non-targeting controls.

B) Epigenetic Modification

This example demonstrates disruption of the DAND5 gene associated CTCF anchor sequence-mediated conjunction by epigenetic modifications.

HEK293T cells are serially transfected, first with plasmid encoding either dCas9-DNMT3A-3L (a fusion protein including the active domains from a DNA methyltransferase) or dCas9-KRAB (a transcriptional repressor fusion protein), then 8 hr later with one of the gRNAs tiled around the anchor sequence (listed in Table 10) or a mixture of gRNAs tiled around the anchor sequence.

At 72 hr post-transfection, cells are harvested for RNA extraction and cDNA synthesis using commercially available reagents and protocols (Qiagen; Thermo Fisher Scientific) and genomic DNA is extracted (Qiagen). The resulting cDNA is used for quantitative real-time PCR (Thermo Fisher Scientific).

DAND5-specific quantitative PCR probes/primers are multiplexed with internal control quantitative PCR probes/primers as described herein and gene expression is subsequently analyzed by a real time PCR kit (Applied Biosystems, Thermo Fisher Scientific). Cells transfected with guide RNAs proximal to the CTCF anchor sequence are expected to show increases in DAND5 expression at 72 hr after modification by either dCas9-DNMT3A-3L or dCas9-KRAB.

Effectors that target epigenetic modifications at or near the CTCF anchor sequence associated with the DAND5 gene demonstrate disruption of the DAND5 gene anchor-mediated conjunction and increase DAND5 mRNA levels as compared to the non-targeting controls.

C) Physical Perturbation

This example demonstrates disruption of DAND5 gene associated CTCF anchor sequence-mediated conjunction by physically preventing CTCF binding at the anchor sequence using bulky effector molecules (in this case, fusion proteins).

HEK293T cells are serially transfected, first with plasmid encoding two different dCas9 fusion proteins, then 8 hr later with one of the gRNAs tiled around the anchor sequence (listed in Table 10) or a mixture of gRNAs tiled around the anchor sequence.

At 72 hr post-transfection, cells are harvested for RNA extraction and cDNA synthesis using commercially available reagents and protocols (Qiagen; Thermo Fisher Scientific; Thermo Fisher Scientific) and genomic DNA is extracted (Qiagen). The resulting cDNA is used for quantitative real-time PCR (Thermo Fisher Scientific).

DAND5-specific quantitative PCR probes/primers are multiplexed with internal control quantitative PCR probes/primers as described in the previous examples and gene expression is subsequently analyzed by a real time PCR kit (Applied Biosystems, Thermo Fisher Scientific). Cells transfected with guide RNAs proximal to the CTCF anchor sequence are expected to show increases in DAND5 expression at 72 hr after modification by either dCas9-DNMT3A-3L or dCas9-KRAB.

To determine differential CTCF binding at anchor sequences by targeted gRNAs and protein fusions versus non-targeting control gRNAs and protein fusions, a CTCF chromatin immunoprecipitation-quantitative PCR assay (ChIP-qPCR) is performed. The CTCF ChIP protocol is performed as described in previous examples. Phenol:chloroform purified DNA serves as template for SYBR Green (Thermo Scientific) qPCR using sequence-specific primers (IDT) flanking the CTCF-binding sequence region. Diminished input-normalized amplification indicates reduced CTCF binding due to the targeted physical disruptions.

Bulky effectors that physically disrupt CTCF binding at CTCF anchor sequences associated with the DAND5 gene demonstrate disruption of the DAND5 gene anchor-mediated conjunction and increase DAND5 mRNA levels as compared to the non-targeting controls.

Example 6: Disruption of a CTCF Anchor Sequence-Mediated Conjunction by Genetic Modification, Epigenetic Modification and Physical Perturbation to Decrease Expression of the SHMT2 Gene The present Example demonstrates various strategies to decrease expression of a gene (in this case, SHMT2) within a Type 3 anchor sequence-mediated conjunction. Among other things, the present Example demonstrates the successful modulation of gene expression by disruption of the anchor sequence-mediated conjunction via, e.g., modification of and/or perturbation at a CTCF anchor sequence.

Serine hydroxymethyltransferase (SHMT2) is a mitochondrial protein that is involved in the glycine synthesis pathway. SHMT2 is highly expressed in cancer cells in glioblastomas and confers these cells with a survival advantage by reducing the requirement for oxygen. SHMT2 might be a potential oncology target.

SHMT2 is located within a CTCF anchor sequence-mediated conjunction. The nucleosomes in the flanking regions of this conjunction are marked with the repressive chromatin mark H3KK27me3. This conjunction is therefore an example of a Type 3 loop. Disruption of the CTCF anchor sequence at either end of the conjunction is expected to cause the spread of the flanking repressive chromatin marks to the SHMT2 gene, thereby causing its downregulation.

Production of agents: All plasmids and guide RNAs have been chemically synthesized from commercially available vendors. All agents were reconstituted in sterile water. All sequences are provided in the Materials and Methods section.

A) Genetic Modification

This example demonstrates disruption of the SHMT2 gene-associated CTCF anchor sequence-mediated conjunction by genetic modifications.

TABLE 11

Sequences of gRNAs targeting putative CTCF sites associated with the SHMT2 gene Type 3 anchor sequence-mediated conjunction

| ID | Guide RNA Sequence (5'-3') |
| --- | --- |
| SACR-00149 | TGGGCTCGGGCGCCCCCTGG (SEQ ID NO: 59) |
| SACR-00151 | AGGGTCGACACTGCCCGACA (SEQ ID NO: 60) |
| SACR-00156 | CGGGGCAGGTCTCCCTCTGG (SEQ ID NO: 61) |
| SACR-00165 | CCAGGCGTACAGACACCACC (SEQ ID NO: 62) |

HEK293T cells were serially transfected with plasmid encoding Cas9 and either a non-targeting gRNA ("Non-targeting," where the gRNA sequence has no homology to the human genome) or a gRNA, as listed in Table 11, targeted at or near the putative CTCF anchor sequences at either end of the conjunction enclosing the SHMT2 gene. HEK293T cells were serially transfected first with plasmid encoding Cas9, and then 8 hr later with either a chemically synthesized gRNAs targeting the anchor sequence or a non-targeting gRNA ("Non-targeting," where the gRNA sequence has no homology to the human genome).

At 72 hr post-transfection, cells were harvested for RNA extraction and cDNA synthesis using commercially available reagents and protocols (Qiagen; Thermo Fisher Scientific) and genomic DNA was extracted (Qiagen). The resulting cDNA was used for quantitative real-time PCR (Thermo Fisher Scientific).

Figure 11:
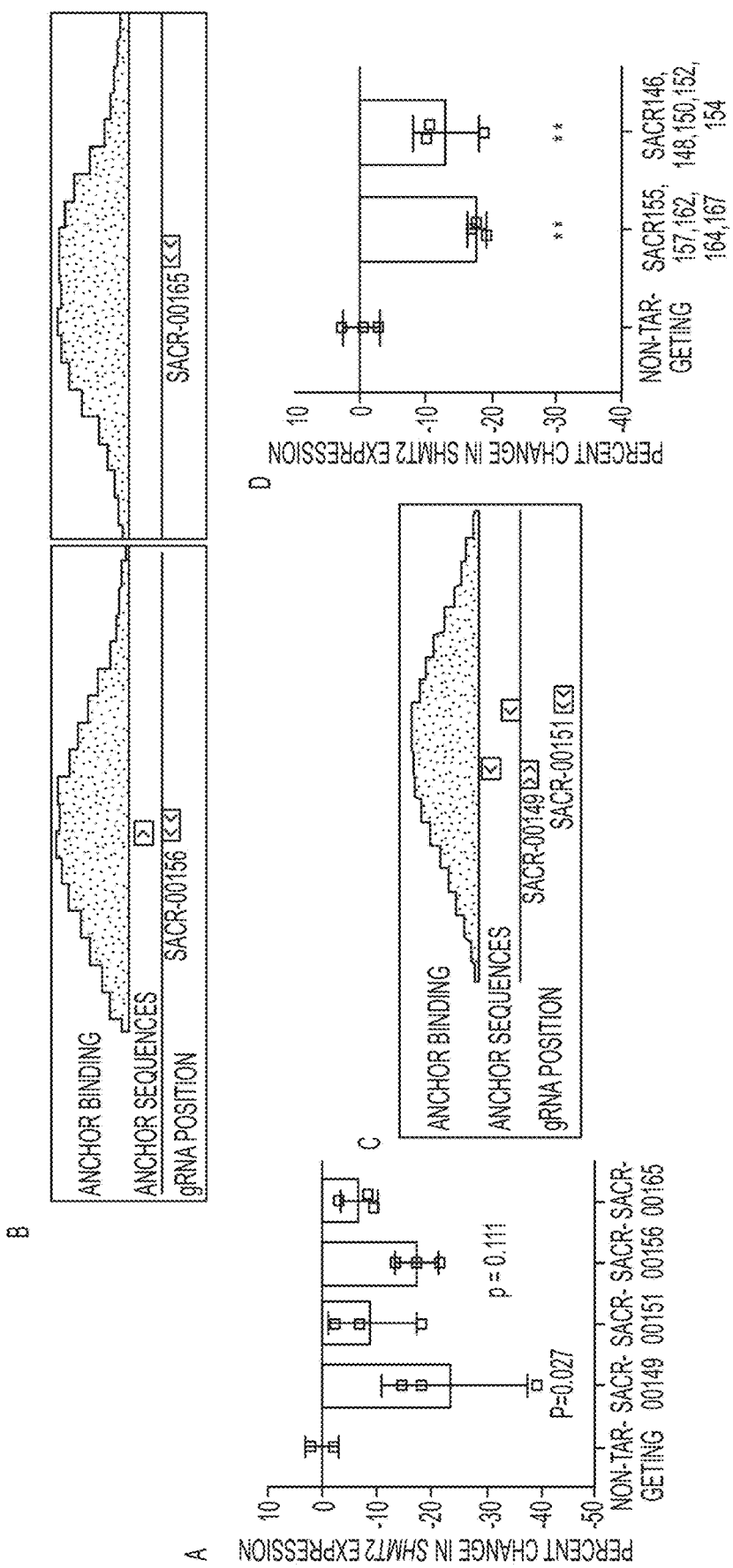
FIG. 11 illustrated disruption of anchor sequence-mediated conjunctions upstream or downstream of the SHMT2 gene, leading to downregulation of SHMT2 expression levels. As further described in Example 6, panels B and C depict maps of gRNA sequences, and panels A and D depict downregulation of SHMT2 expression levels.

SHMT2-specific quantitative PCR probes/primers (Assay ID Hs01059263_g1, Thermo Fisher Scientific) were multiplexed with internal control quantitative PCR probes/primers for PPIB (Assay ID Hs00168719_m1, Thermo Fisher Scientific) using the FAM-MGB and VIC-MGB dyes, respectively, and gene expression was subsequently analyzed by a real time PCR kit (Applied Biosystems, Thermo Fisher Scientific). Cells transfected with guide RNAs SACR-00149 and SACR-00156 showed a 24% and 17% reduction in SHMT2 expression respectively at 72 hr relative to the "Non-targeting" control, while cells transfected with SACR-00151 and SACR-00165 did not (FIG. 11A). Each biological replicate is represented by empty box symbol.

The average percentage change of SHMT2 gene expression in HEK293T cells 72 h post-transfection with the indicated gRNAs is shown in FIG. 11A. Empty boxes denote the value of each biological replicate. Guide RNAs overlapping strong CTCF anchor sequences showed effectiveness in downregulating SHMT2 gene expression.

The locations of potential CTCF-binding (black) upstream (FIG. 11B) and downstream (FIG. 11C) of the SHMT2 gene are shown, alongside the locations of the gRNAs.

Enzymatic effectors that modify DNA at or near the CTCF anchor sequence associated with the SHMT2 gene demonstrated disruption of the DAND5 gene anchor-mediated conjunction to decrease SHMT2 mRNA levels as compared to the non-targeting controls.

Thus, the present Example demonstrates that modulation of gene expression can be achieved by disrupting anchor sequences at either end of an anchor sequence-mediated conjunction.

B) Epigenetic Modification

This example demonstrates disruption of the SHMT2 gene associated CTCF anchor sequence-mediated conjunction by epigenetic modification.

TABLE 12

Sequences of gRNAs targeting putative CTCF anchor sequences associated with the SHMT2 gene Type 3 anchor sequence-mediated conjunction

| ID | Set | Guide RNA Sequence (5'-3') |
|---|---|---|
| SACR-00146 | Set 1 | GCTTGGAGTCCAGTCCCAGC (SEQ ID NO: 63) |
| SACR-00148 | Set 1 | TCAAAGGCAGCGGGACTCAG (SEQ ID NO: 64) |
| SACR-00150 | Set 1 | AAGCTCGGGGAAGAGGCCTT (SEQ ID NO: 65) |
| SACR-00152 | Set 1 | CACTCCAGGCACCAACTTAG (SEQ ID NO: 66) |
| SACR-00154 | Set 1 | ACTCCCGCCTCCAAGACAGT (SEQ ID NO: 67) |
| SACR-00155 | Set 2 | AAAGAAAGAAAAAAAGCCGC (SEQ ID NO: 68) |
| SACR-00157 | Set 2 | GGGCACAGTAAGATGGAGAG (SEQ ID NO: 69) |
| SACR-00162 | Set 2 | GCAGGGGAGGATCTCAGAGT (SEQ ID NO: 70) |
| SACR-00164 | Set 2 | TGGGACACAGACCTCCTACT (SEQ ID NO: 71) |
| SACR-00167 | Set 2 | CAGGTGCATAATGAGTGCTG (SEQ ID NO: 72) |

HEK293T cells were serially transfected, first with plasmid encoding dCas9-KRAB (a transcriptional repressor fusion protein), then 8 hr later with two different mixtures (Set 1, Set 2) of five gRNAs (listed in Table 12) tiled around the CTCF anchor sequence (FIGS. 11B and 11C).

At 72 hr post-transfection, cells were harvested for RNA extraction and cDNA synthesis using commercially available reagents and protocols (Qiagen; Thermo Fisher Scientific) and genomic DNA was extracted (Qiagen). The resulting cDNA was used for quantitative real-time PCR (Thermo Fisher Scientific).

SHMT2-specific quantitative PCR probes/primers were multiplexed with internal control quantitative PCR probes/primers as described in the previous examples and gene expression was subsequently analyzed by a real time PCR kit (Applied Biosystems, Thermo Fisher Scientific). Cells transfected with either of two sets of 5 gRNAs showed reduction in SHMT2 expression (Set 1: 18%, Set 2: 13%) at 72 hr after repression with dCas9-KRAB (FIG. 11D). Empty boxes denote the value of each biological replicate.

The average percentage change of SHMT2 gene expression in HEK293T cells 72 hr post-transfection with the indicated gRNAs is shown in FIG. 11D. Cells transfected with guide RNAs proximal to the strong CTCF anchor sequence showed decreases in SHMT2 expression at 72 hr after treatment with dCas9-KRAB. Empty boxes denote the value of each biological replicate. ** p<0.01

Effectors that target epigenetic modifications at or near the CTCF anchor sequence associated with the SHMT2 gene demonstrate disruption of the SHMT2 gene anchor-mediated conjunction to decrease SHMT2 mRNA levels as compared to the non-targeting controls.

C) Physical Perturbation

This example demonstrates disruption of SHMT2 gene associated CTCF anchor sequence-mediated conjunction by physically preventing CTCF binding at the anchor sequence.

HEK293T cells are serially transfected, first with plasmid encoding two different dCas9 fusion proteins, then 8 hr later with one of the gRNAs tiled around the anchor sequence (listed in Table 12) or a mixture of gRNAs tiled around the anchor sequence.

At 72 hr post-transfection, cells are harvested for RNA extraction and cDNA synthesis using commercially available reagents and protocols (Qiagen; Thermo Fisher Scientific; Thermo Fisher Scientific) and genomic DNA is extracted (Qiagen). The resulting cDNA is used for quantitative real-time PCR (Thermo Fisher Scientific).

SHMT2-specific quantitative PCR probes/primers are multiplexed with internal control quantitative PCR probes/primers as described in the previous examples and gene expression is subsequently analyzed by a real time PCR kit (Applied Biosystems, Thermo Fisher Scientific). Cells transfected with guide RNAs proximal to the CTCF anchor sequence are expected to show decreases in SHMT2 expression at 72 hr after treatment with dCas9-KRAB.

To determine differential CTCF binding at anchor sequences by targeted gRNAs and protein fusions versus non-targeting control gRNAs and protein fusions, a CTCF chromatin immunoprecipitation-quantitative PCR assay (ChIP-qPCR) is performed. The CTCF ChIP protocol is performed as described in previous examples. Phenol:chloroform purified DNA serves as template for SYBR Green (Thermo Scientific) qPCR using sequence-specific primers (IDT) flanking the CTCF-binding sequence region. Diminished input-normalized amplification indicates reduced CTCF binding due to the targeted physical disruptions.

Bulky effectors that physically disrupt CTCF binding at CTCF anchor sequences associated with the SHMT2 gene demonstrate disruption of the SHMT2 gene anchor-mediated conjunction and decrease SHMT2 mRNA levels as compared to the non-targeting controls.

Example 7: Disruption of a CTCF Anchor Sequence-Mediated Conjunction by Genetic Modification to Increase Expression of the TTC21B Gene The present Example demonstrates various strategies to increase expression of a gene (in this case, TTC21B) just outside a Type 2 anchor sequence-mediated conjunction (which contains an enhancer). Among other things, the present Example demonstrates the successful modulation of gene expression by disruption of the anchor sequence-mediated conjunction via, e.g., modification of and/or perturbation at a CTCF anchor sequence.

Tetratricopeptide repeat domain-containing protein 21B (TTC21B) is an axonemal protein involved in ciliary function. Hypomorphic alleles of TTC21B have been associated with human ciliopathies such as nephronophthisis and upregulation of this gene might attenuate the severity of the disease.

TTC21B is located just outside a CTCF anchor sequence-mediated conjunction. In HEK293T cells, TTC21B is not expressed, and there is an active enhancer within the neighboring conjunction. This configuration is an example of a Type 2 loop. Disruption of the CTCF anchor sequence-mediated conjunction is expected to cause the enhancer inside the conjunction to activate the expression of TTC21B.

Production of agents: All plasmids and guide RNAs have been chemically synthesized from commercially available vendors. All agents were reconstituted in sterile water. All sequences are provided in the Materials and Methods section.

A) Genetic Modification

This example demonstrates disruption of a CTCF anchor sequence-mediated conjunction by genetic modifications to increase TTC21B gene expression.

TABLE 13

Sequences of gRNAs targeting putative CTCF anchor sequences associated with the TTC21B gene Type 2 anchor sequence-mediated conjunction.

| ID | Guide RNA Sequence (5'-3') |
| --- | --- |
| SACR-00023 | GTTGTTTTACGGCCACAAGG (SEQ ID NO: 73) |
| SACR-00024 | TTTTTTTCTGCGCCACCTTG (SEQ ID NO: 74) |

HEK293T cells were transfected with plasmid encoding Cas9 and either co- or serially transfected with a non-targeting gRNA ("Non-targeting," where the guide RNA sequence has no homology to the human genome) or a gRNA, as listed in Table 13, targeted at or near the putative CTCF anchor sequences at either end of the conjunction enclosing the TTC21B gene. HEK293T cells were serially transfected first with plasmid encoding Cas9, and then 8 hr later with either a chemically synthesized gRNAs targeting the anchor sequence or a non-targeting gRNA ("Non-targeting," where the gRNA sequence has no homology to the human genome).

At 72 hr and 14 days post-transfection, cells were harvested for RNA extraction and cDNA synthesis using commercially available reagents and protocols (Qiagen; Thermo Fisher Scientific) and genomic DNA was extracted (Qiagen). The resulting cDNA was used for quantitative real-time PCR (Thermo Fisher Scientific).

Figure 12:
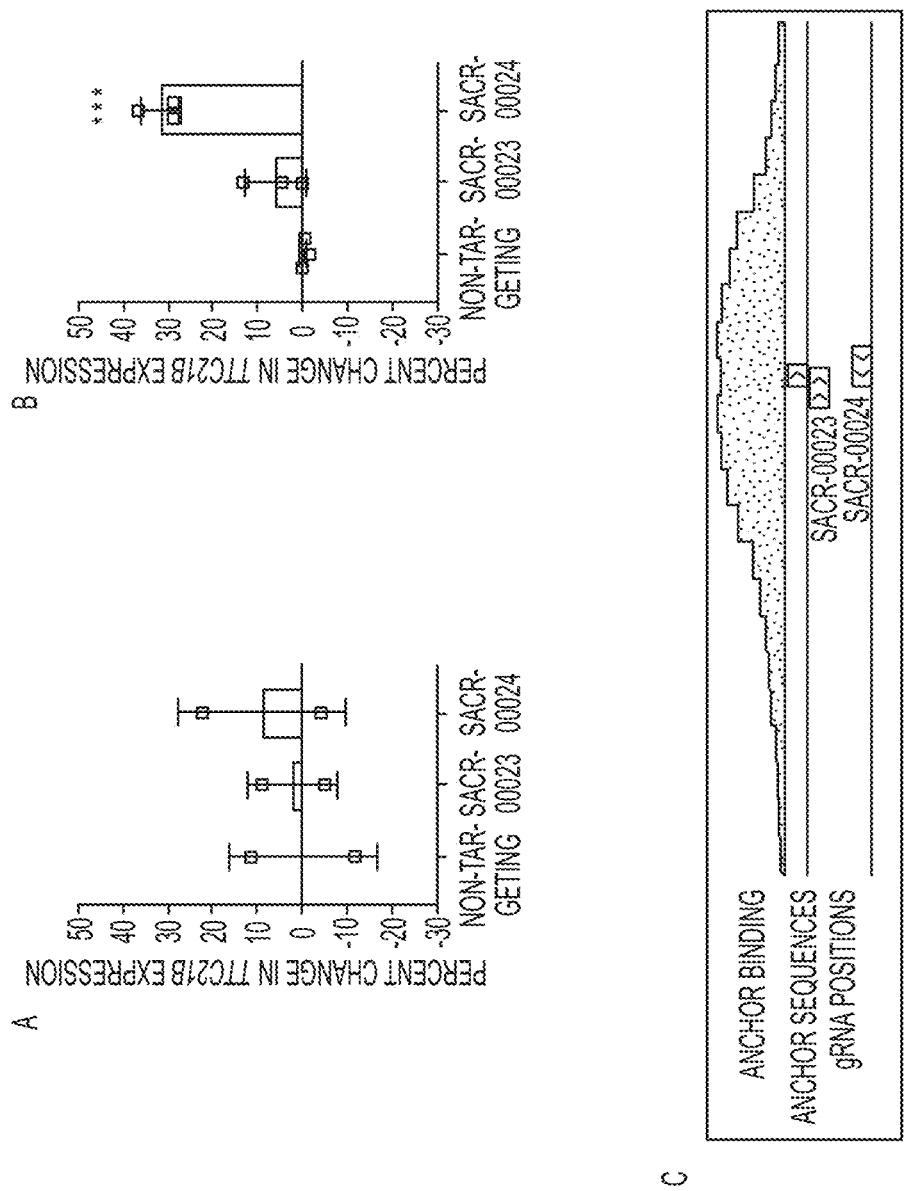
FIG. 12 illustrates disruption of an anchor sequence-mediated conjunction upstream of the TTC21B gene, leading to upregulation of TTC21B expression levels. As further described in Example 7, panels A and B depict upregulation of TTC21B expression levels, and panel C depicts a map of gRNA sequences.

TTC21B-specific quantitative PCR probes/primers (Assay ID Hs01095195_m1, Thermo Fisher Scientific) were multiplexed with internal control quantitative PCR probes/primers for PPIB (Assay ID Hs00168719_m1, Thermo Fisher Scientific) using the FAM-MGB and VIC-MGB dyes, respectively, and gene expression was subsequently analyzed by a real time PCR kit (Applied Biosystems, Thermo Fisher Scientific). Cells transfected with gRNA SACR-00024 showed a trend of upregulating TTC21B expression after 72 hours (FIG. 12A). After 14 days, cells transfected with gRNA SACR-00024 showed a 29% increase in TTC21B expression relative to the "Non-targeting" control, (FIG. 12B). Empty boxes denote the value of each biological replicate.

Enzymatic effectors that modify DNA at or near the CTCF anchor sequence demonstrated disruption of the anchor-mediated conjunction and increased TTC21B mRNA levels as compared to the non-targeting controls.

B) Epigenetic Modification

This example demonstrates disruption of the CTCF anchor sequence-mediated conjunction by epigenetic modifications to increase TTC21B gene expression.

HEK293T cells are serially transfected, first with plasmid encoding either dCas9-DNMT3A-3L (a fusion protein including the active domains from a DNA methyltransferase) or dCas9-KRAB (a transcriptional repressor fusion protein), then 8 hr later with one of the gRNAs tiled around the anchor sequence (listed in Table 13) or a mixture of both gRNAs.

At 14 days post-transfection, cells are harvested for RNA extraction and cDNA synthesis using commercially available reagents and protocols (Qiagen; Thermo Fisher Scientific) and genomic DNA is extracted (Qiagen). The resulting cDNA is used for quantitative real-time PCR (Thermo Fisher Scientific).

TTC21B-specific quantitative PCR probes/primers are multiplexed with internal control quantitative PCR probes/primers as described herein and gene expression is subsequently analyzed by a real time PCR kit (Applied Biosystems, Thermo Fisher Scientific). Cells transfected with guide RNAs proximal to the CTCF anchor sequence are expected to show increases in TTC21B expression at 14 days after modification by either dCas9-DNMT3A-3L or dCas9-KRAB.

Effectors that target epigenetic modifications at or near the CTCF anchor sequence adjacent to the TTC21B gene demonstrate disruption of the gene anchor-mediated conjunction and increase TTC21B mRNA levels as compared to the non-targeting controls.

C) Physical Perturbation

This example demonstrates disruption of the CTCF anchor sequence-mediated conjunction by physically preventing CTCF binding at the anchor sequence.

HEK293T cells are serially transfected, first with plasmid encoding two different dCas9 fusion proteins, then 8 hr later with one of the guide RNAs tiled around the anchor sequence (listed in Table 13) or a mixture of both guide RNAs.

At 14 days post-transfection, cells are harvested for RNA extraction and cDNA synthesis using commercially available reagents and protocols (Qiagen; Thermo Fisher Scientific; Thermo Fisher Scientific) and genomic DNA is extracted (Qiagen). The resulting cDNA is used for quantitative real-time PCR (Thermo Fisher Scientific).

TTC21B-specific quantitative PCR probes/primers are multiplexed with internal control quantitative PCR probes/primers as described in the previous examples and gene expression is subsequently analyzed by a real time PCR kit (Applied Biosystems, Thermo Fisher Scientific). Cells transfected with guide RNAs proximal to the CTCF anchor sequence are expected to show increases in TTC21B expression at 14 days after modification by either dCas9-DNMT3A-3L or dCas9-KRAB.

To determine differential CTCF binding at anchor sequences by targeted gRNAs and protein fusions versus non-targeting control gRNAs and protein fusions, a CTCF chromatin immunoprecipitation-quantitative PCR assay (ChIP-qPCR) is performed. The CTCF ChIP protocol is performed as described in previous examples. Phenol:chloroform purified DNA serves as template for SYBR Green (Thermo Scientific) qPCR using sequence-specific primers (IDT) flanking the CTCF-binding sequence region. Diminished input-normalized amplification indicates reduced CTCF binding due to the targeted physical disruptions.

Bulky effectors that physically disrupt CTCF binding at CTCF anchor sequences adjacent to the TTC21B gene demonstrate disruption of the anchor-mediated conjunction and increase TTC21B mRNA levels as compared to the non-targeting controls.

Example 8: Disruption of a CTCF Anchor Sequence-Mediated Conjunction by Genetic Modification to Decrease Expression of the CDK6 Gene The present Example demonstrates various strategies to decrease expression of a gene (in this case, CDK6) within a Type 1 anchor sequence-mediated conjunction. Among other things, the present Example demonstrates the successful modulation of gene expression by disruption of the anchor sequence-mediated conjunction via, e.g., modification of and/or perturbation at a CTCF anchor sequence.

Cyclin Dependent Kinase 6 (CDK6) is a member of the cyclin-dependent kinase (CDK) family. Cyclins are important regulators of cell cycle progression. CDK6 is involved in regulation of cell proliferation by controlling a point of restriction in cell cycle. Dysregulation in CDK6 has been found in 80-90% of tumors suggesting that modulation of CDK6 activity might be relevant for cancer therapy. So far, development of CDK6-specific small molecular inhibitors has been unsuccessful.

CDK6 is found within a CTCF anchor sequence-mediated conjunction. This conjunction also includes an associated transcriptional control sequence, i.e. an enhancer, and is an example of Type 1 loop. Disruption of the CTCF anchor sequence of the conjunction is expected to result in down-regulation of CDK6.

Production of agents: All plasmids and guide RNAs (gRNA) have been chemically synthesized from commercially available vendors. All agents were reconstituted in sterile water. All sequences are provided in the Materials and Methods section.

A) Genetic Perturbation

This example demonstrates disruption of the CDK6 gene Type 1 anchor sequence-mediated conjunction through genetic mutation of the putative CTCF sites using CRISPR Cas9 technology.

TABLE 14

Sequences of gRNAs targeting putative CTCF anchor sequences associated with the CDK6 gene Type 1 anchor sequence-mediated conjunction.

| ID | Guide RNA Sequence (5'-3') |
| --- | --- |
| SACR-00046 | CACATTAAAAATGTTACTAT (SEQ ID NO: 75) |
| SACR-00047 | TGTTTGAGTCAAACCTAAAA (SEQ ID NO: 76) |
| SACR-00048 | ACGGTGGGTTCACGACTCAA (SEQ ID NO: 77) |
| SACR-00049 | AAAGTAACACTGCCATCTAA (SEQ ID NO: 78) |
| SACR-00050 | AACACATAGAATCCATTAGA (SEQ ID NO: 79) |
| SACR-00051 | TGTGTTACTGCCATTGTCTG (SEQ ID NO: 80) |
| SACR-00052 | TTAAATGTTGCCTCAGACAA (SEQ ID NO: 81) |
| SACR-00053 | AAAAACACAAAATAAGGTGG (SEQ ID NO: 82) |
| SACR-00054 | AAATCAATCCAACAGATTAT (SEQ ID NO: 83) |

HEK293T cells were serially transfected with plasmid encoding Cas9 and either a non-targeting gRNA ("Non-targeting," where the guide RNA sequence has no homology to the human genome) or a gRNA, as listed in Table 14, targeted at or near the putative CTCF anchor sequences associated with the CDK6 gene. HEK293T cells were transfected first with plasmid encoding Cas9, and then 8 hr later with either a chemically synthesized gRNAs targeting the anchor sequence or a non-targeting gRNA ("Non-targeting," where the guide RNA sequence has no homology to the human genome).

At 72 hr post-transfection, cells were harvested for RNA extraction and cDNA synthesis using commercially available reagents and protocols (Qiagen; Thermo Fisher Scientific) and genomic DNA was extracted (Qiagen). The resulting cDNA was used for quantitative real-time PCR (Thermo Fisher Scientific).

Figure 13:
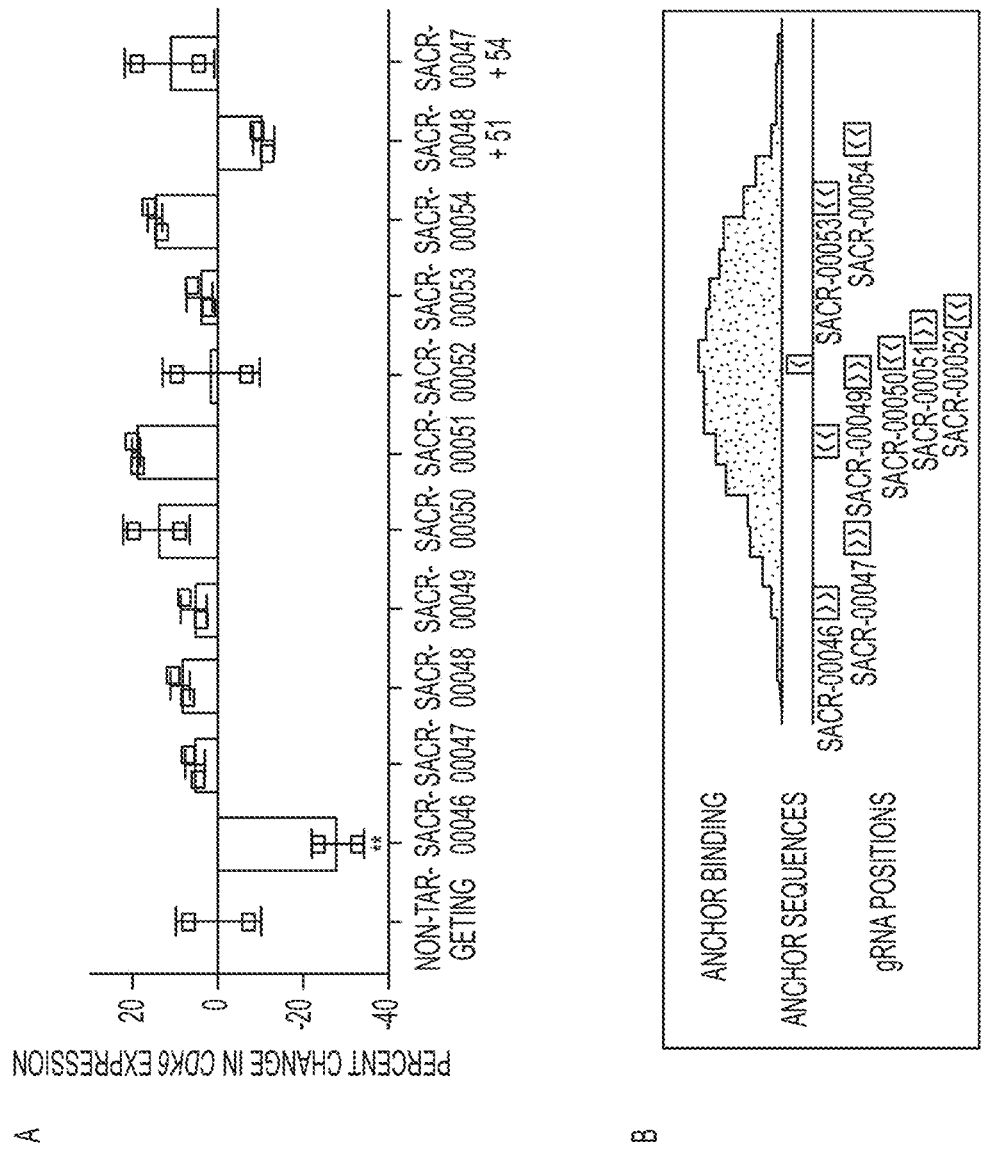
FIG. 13 illustrates disruption of an anchor sequence-mediated conjunction downstream of the CDK6 Gene, leading to downregulation of CDK6 expression levels. As further described in Example 13, panel A depicts downregulation of CDK6 expression levels, and panel B depicts a map of gRNA sequences.

CDK6-specific quantitative PCR probes/primers (Assay ID Hs01026371_m1, Thermo Fisher Scientific) were multiplexed with internal control quantitative PCR probes/primers for PPIB (Assay ID Hs00168719_m1, Thermo Fisher Scientific) using the FAM-MGB and VIC-MGB dyes, respectively, and gene expression was subsequently analyzed by a real time PCR kit (Applied Biosystems, Thermo Fisher Scientific). Cells transfected with guide RNA SACR-00046 showed about 30% decrease in CDK6 mRNA levels at 72 hr relative to the "Non-targeting" control, (FIG. 13). Each biological replicate is represented by empty box symbol.

Enzymatic effectors that modify DNA at or near the CTCF anchor sequence associated with the CDK6 gene demonstrated disruption of the CDK6 gene anchor-mediated conjunction and decrease CDK6 mRNA levels as compared to the non-targeting controls B) Epigenetic Modification This example demonstrates disruption of the CDK6 gene associated CTCF anchor sequence-mediated conjunction by epigenetic modifications.

HEK293T cells are serially transfected, first with plasmid encoding either dCas9-DNMT3A-3L (a fusion protein including the active domains from a DNA methyltransferase) or dCas9-KRAB (a transcriptional repressor fusion protein), then 8 hr later with one of the gRNAs tiled around the anchor sequence (listed in Table 14) or a mixture of gRNAs tiled around the anchor sequence.

At 72 hr post-transfection, cells are harvested for RNA extraction and cDNA synthesis using commercially available reagents and protocols (Qiagen; Thermo Fisher Scientific) and genomic DNA is extracted (Qiagen). The resulting cDNA is used for quantitative real-time PCR (Thermo Fisher Scientific).

CDK6-specific quantitative PCR probes/primers are multiplexed with internal control quantitative PCR probes/primers as described herein and gene expression is subsequently analyzed by a real time PCR kit (Applied Biosystems, Thermo Fisher Scientific). Cells transfected with guide RNAs proximal to the CTCF anchor sequence are expected to show decreases in CDK6 expression at 72 hr after modification by either dCas9-DNMT3A-3L or dCas9-KRAB.

Effectors that target epigenetic modifications at or near the CTCF anchor sequence associated with the CDK6 gene demonstrate disruption of the CDK6 gene anchor-mediated conjunction to decrease CDK6 mRNA levels as compared to the non-targeting controls.

C) Physical Perturbation

This example demonstrates disruption of CDK6 gene associated CTCF anchor sequence-mediated conjunction by physically preventing CTCF binding at the anchor sequence.

HEK293T cells are serially transfected, first with plasmid encoding two different dCas9 fusion proteins, then 8 hr later with one of the gRNAs tiled around the anchor sequence (listed in Table 14) or a mixture of gRNAs tiled around the anchor sequence.

At 72 hr post-transfection, cells are harvested for RNA extraction and cDNA synthesis using commercially available reagents and protocols (Qiagen; Thermo Fisher Scientific; Thermo Fisher Scientific) and genomic DNA is extracted (Qiagen). The resulting cDNA is used for quantitative real-time PCR (Thermo Fisher Scientific).

CDK6-specific quantitative PCR probes/primers are multiplexed with internal control quantitative PCR probes/primers as described in the previous examples and gene expression is subsequently analyzed by a real time PCR kit (Applied Biosystems, Thermo Fisher Scientific). Cells transfected with guide RNAs proximal to the CTCF anchor sequence are expected to show decreases in CDK6 expression at 72 hr after modification by either dCas9-DNMT3A-3L or dCas9-KRAB.

To determine differential CTCF binding at anchor sequences by targeted gRNAs and protein fusions versus non-targeting control gRNAs and protein fusions, a CTCF chromatin immunoprecipitation-quantitative PCR assay (ChIP-qPCR) is performed. The CTCF ChIP protocol is performed as described in previous examples. Phenol:chloroform purified DNA serves as template for SYBR Green (Thermo Scientific) qPCR using sequence-specific primers (IDT) flanking the CTCF-binding sequence region. Diminished input-normalized amplification indicates reduced CTCF binding due to the targeted physical disruptions.

Bulky effectors that physically disrupt CTCF binding at CTCF anchor sequences associated with the CDK6 gene demonstrate disruption of the CDK6 gene anchor-mediated conjunction to decrease CDK6 mRNA levels as compared to the non-targeting controls.

Example 9: Epigenetic Disruption of CTCF Binding in Anchor Sequence-Mediated Conjunctions The present Example demonstrates various therapeutic strategies that incorporate disclosed methods and agents to epigenetically disrupt CTCF binding in anchor sequence-mediated conjunctions.

A) Demethylation of a Specific CTCF Binding Motif for the Treatment Muscular Dystrophy Type 1 myotonic dystrophy (DM1), also known as Steinert disease, has a severe congenital form and a milder childhood-onset form as well as an adult-onset form. The gene implicated in DM1 is dmpk, whose gene product is a Ser/Thr protein kinase homologous to the MRCK p21-activated kinases and the Rho family of kinases. The 3' untranslated region of this gene contains 5-37 copies of a CTG trinucleotide repeat. Expansion of this unstable motif to 50-5,000 copies causes myotonic dystrophy type I, which increases in severity with increasing repeat element copy number. Repeat expansion is associated with condensation of local chromatin structure that disrupts the expression of genes in this region. Healthy human cells are enriched in CTCF bound to the CTCF sites flanking the dmpk repeat regions, whereas cells from DM1 patients lack CTCF binding (Cho et al., Antisense Transcription and Short Article Heterochromatin at the DM1 CTG Repeats Are Constrained by CTCF. Molecular Cell, Vol. 20, 483-489 (2005).

In this example, a dCas9-TET1 fusion construct (using a *Staphylococcus aureus* dCas9) is designed with a sgRNA to target to the specific CTCF sites flanking the repeats at the DM1 locus. The construct is packaged in an adeno-associated virus (AAV) system, and is administered systemically (IV) to a subject having Steinert disease. A week subsequent to administration, site specific DNA methylation levels are measured in the subject: a sample of genomic DNA is taken from the subject and analyzed by bisulphite analysis (Patterson et al., DNA Methylation: Bisulphite Modification and Analysis. J Vis Exp. 2011; (56): 3170). In addition, the sample is analyzed for transcription of antisense and sense transcripts from the locus.

B) Restoration of Sodium Currents in a Cell Line Modeling Severe Myoclonic Epilepsy in Infancy by Disruption of CTCF Interactions to Modulate a Type 2 Anchor Sequence-Mediated Conjunction Voltage-gated Na+ channels in the brain are complexes of a 260-kDa α-subunit in association with auxiliary β-subunits (b1-b4) of 33 to 36 kDa. The α-subunit includes the voltage sensors and the ion-conducting pore in four internally repeated domains (I-IV), each of which has six α-helical transmembrane segments (S1-S6) and a pore loop that connects S5 and S6. The association of β-subunits modifies the kinetics and voltage dependence of gating, and these subunits are cell adhesion molecules that interact with the extracellular matrix, other cell adhesion molecules and the cytoskeleton. The type I sodium channel, NaV1.1, is the prototype of the voltage-gated sodium channel family in mammals. NaV1.1 is specifically localized in the neuronal cell body; NaV1.3 is abundant in the cell bodies of neurons during fetal and neonatal development but declines in adult rodents as the level of NaV1.1 channels increases rapidly in the second postnatal week.

Voltage-gated sodium channels have crucial roles in the initiation and propagation of action potentials and are crucial regulators of neuronal excitability. Mutations in the NaV1.1 channel gene, SCN1A, cause genetically distinct epilepsy syndromes. Severe myoclonic epilepsy in infancy (SMEI) is linked to de novo loss-of-function mutations in the SCN1A gene, which lead to haploinsufficiency of NaV1.1 channels. This rare convulsive disorder begins during the first year of life, with seizures often associated with fever, and progresses to prolonged, clustered or continuous seizures and to status epilepticus. After the second year of life, patients develop psychomotor delay, ataxia and cognitive impairment. They have an unfavorable long-term outcome because of the ineffectiveness of antiepileptic drug therapy.

The SCN1A gene is located on Chromosome 2 within a CTCF bound loop, whereas the upstream anchor is within 166,800,000-166,850, 000 (GRCh37/hg19 assembly, see below), which separates it from an upstream enhancing sequences. Disruption of the interaction between CTCF and its anchor site on coordinates 166,800,000-166,850,000 enable the upstream enhancing sequences to interact with SCN1A and upregulate its transcription.

To disrupt the interaction between CTCF and its anchor site on coordinates 166,800,000-166,850, 000, the anchor site is methylated by targeting dCas9-DNMT3a. The CTCF upstream of the SCN1a gene in chromosome 2, which in MCF7 cells and K562 is located within coordinates 166810549-166810939, and the downstream CTCF site is located within coordinates 166981175-166990179.

PCR amplified Dnmt3a from pcDNA3-hDNMT3A (Addgene plasmid: 35521) is cloned in modified pdCas9 plasmid (Addgene plasmid: 44246) with BamHI and EcoRI sites. dCas9-NLS-Dnmt3a is PCR amplified and cloned into FUW vector (Addgene plasmid: 14882) with AscI and EcoRI to package lentiviruses. The gRNA expression plasmids are cloned by inserting annealed oligos into modified pgRNA plasmid (Addgene plasmid: 44248) with AarI site. All constructs are sequenced before transfection. Lentiviruses expressing dCas9-Dnmt3a, and gRNAs are produced by transfecting HEK293T cells with FUW constructs or pgRNA constructs together with standard packaging vectors (pCMV-dR8.74 and pCMV-VSVG) followed by ultra-centrifugation-based concentration. Virus titer (T) are calculated based on the infection efficiency for 293T cells, where $T=(P*N)/(V)$, T=titer (TU/ul), p=% of infection positive cells according to the fluorescence marker, N=number of cells at the time of transduction, V=total volume of virus used. SCN1a cell lines are used for this experiment.

Briefly, cells are cultured for viral infection. Cells are analyzed 3 days post-infection in this study.

Sodium currents are measured by electrophysiological recordings. Whole-cell patch-clamp recordings are carried out at room temperature using an Axopatch 200B amplifier (Axon Instruments) with PCLAMP 6 software (Axon Instruments) in voltage- or current-clamp configuration. For voltage-clamp experiments, cell capacitance (Cm) is calculated from $Cm = Q/V$, where Q is the charge measured by integrating the capacitative current evoked by a hyperpolarizing 10-mV voltage step (V) from a holding potential of −70 mV. For other recordings, capacitative currents are minimized using the amplifier circuitry. 70% prediction and 90% series resistance compensation are routinely used. The remaining linear capacity and leakage currents are eliminated by P/4 subtraction.

The intracellular solution contains 177 mM N-methyl-D-glucamine, 40 mM HEPES, 4 mM MgCl2, 10 mM EGTA, 1 mM NaCl, 25 mM phosphocreatine-Tris, 2 mM ATP-Tris, 0.2 mM Na2GTP and 0.1 mM leupeptin, adjusted to pH 7.2 with H2SO4.

The extracellular solution for the recording of peak Na+ currents contains 20 mM NaCl, 116 mM glucose, 10 mM HEPES, 1 mM BaCl2, 2 mM MgCl2, 55 mM CsCl2, 1 mM CdCl2, 1 mM CaCl2 and 20 mM tetraethylammonium chloride, adjusted to pH 7.35 with NaOH.

Conductance-voltage (g-V) relationships (activation curves) are calculated according to $g = INa/(V−ENa)$, where INa is the peak Na+ current measured at potential V, and ENa is the calculated equilibrium potential. Normalized activation and inactivation curves are fit to Boltzmann relationships of the form $y = 1/(1+\exp[(V-V\frac{1}{2})/k])+A$, where y is normalized gNa or INa, A is the baseline conductance or current, V is the membrane potential, V½ is the voltage of half-maximal activation (Va) or inactivation (Vh) and k is a slope factor. In fitting the activation curves, A is fixed at 0. Analyses are carried out using Origin (Microcal) and pClamp (Axon Instruments).

For current-clamp experiments, cells are held at −80 mV, and their firing patterns are recorded in response to sustained depolarizations or hyperpolarizations (duration, 800 ms; increments, ±10 pA). The input-output relationship; action potential threshold, half-width, width and peak, minimum voltage; and input resistance of cells are measured. The input-output relationship is defined as the dependence of the number of action potentials generated upon the amplitude of current injection. The threshold is measured for the first action potential during the depolarization protocol as the voltage corresponding to the peak of the third differential of the action potential waveform. Action potential half-width and width are measured at half-height and threshold, respectively. Input resistance is determined as the slope of the linear regression of the I-V plot for a series of hyperpolarizing pulses, where I is current amplitude and V is steady-state voltage.

A successful intervention increases sodium current upon hyperpolarization.

Example 10: Physical Interference Between CTCF and its DNA Anchor Sequence

The present Example demonstrates various therapeutic strategies that incorporate disclosed methods and agents to disrupt CTCF binding in anchor sequence-mediated conjunctions.

A) Disruption of miR290 Anchor Sequence-Mediated Conjunction by Physical Interference Polypeptide beta: PFDILYQ-GG-RGQGDC (SEQ ID NO: 3), and dCas9-TET1 fusion as described in Xu, et al., Cell Discovery, 2015, 2):16009; doi:10.1038/celldisc.2016.9.

Experimental Design:

Peptides are synthesized using Fmoc solid-phase synthesis chemistry on a Symphony Peptide Synthesizer (Protein Technologies, Tucson, Ariz.). The Fmoc group (N-(9-fluorenyl)methoxycarbonyl) is removed by 20% piperidine, and Fmoc-amino acids are coupled using 0.1 M HBTU in DMF containing 0.4 M 4-methyl morpholine for 60 min. The resin-bound peptide is deprotected and cleaved from the resin using trifluoroacetic acid (TFA). Ethyl ether is added to precipitate the peptide from the TFA solution. The precipitated peptide is then lyophilized.

The crude peptide is purified on a reversed-phase Vydac 218TP1010 C18 column (Hesperia, Calif.) using a BioCad Sprint (Applied Biosystems, Foster City, Calif.). A flow rate of 10 mL/min with solvent A (0.1% TFA in deionized water) and solvent B (0.1% TFA in acetonitrile) is used. The column is equilibrated with 5% solvent B. After sample loading, the column is eluted with a linear gradient from 5% solvent B to 100% solvent B in 60 min. The pure peptide fraction is identified by matrix-assisted laser desorption/ ionization time-of-flight mass spectrometry (MALDI-TOF MS). The mass peaks are observed that correlate with the correct amino acid sequence.

The polypeptide beta is joined to dCas9-TET1 (Xu, et al., Cell Discovery, 2015, 2):16009; doi:10.1038/cell-disc.2016.9) through click chemistry.

To prepare for the click reaction, polypeptides are labeled with DBCO (Glen Research, Sterling, Va.). DBCO-sulfo-NHS ester is dissolved at a concentration of 5.2 mg per 60 µL in water or anhydrous DMSO. This stock solution is used to conjugate the amino-modified polypeptides in sodium carbonate/bicarbonate conjugation buffer, pH=–9.

For a 0.2 µmol synthesis of polypeptide, polypeptide is dissolved in 500 µL of conjugation buffer. Approx. a 6 fold excess (6 µL) of DBCO-sulfo-NHS ester solution is added to the dissolved polypeptide. The mixture is vortexed and incubated at room temperature for 2-4 hours up to about overnight. The conjugated polypeptide is desalted on a desalting column (Glen Research, Sterling, Va.) to remove salts and organics.

dCas9-TET1 fusion is resuspended in 500 µL of conjugation buffer. Approx. a 6 fold excess (6 µL) of azide solution is added to dCas9-TET1 fusion. The mixture is vortexed and incubated at room temperature for 2-4 hours up to about overnight. The conjugated fusion is desalted on a desalting column (Glen Research, Sterling, Va.) to remove salts and organics.

For the click reaction, 1 mg of azide fusion is dissolved in 150 µL of DMSO. The azide-fusion is added to 10 OD of DBCO conjugated polypeptide in 100 µL of water. The mixture is incubated at room temperature overnight. The ligated fusion and polypeptides are desalted on a desalting column (Glen Research, Sterling, Va.) to remove salts and organics.

This example demonstrates physical interference of gene expression with polypeptides that target CpG dinucleotides of a gene.

Gene regulatory elements and their target genes generally occur within anchor sequence-mediated conjunctions, chromosomal loop structures formed by the interaction of two DNA sites bound by the CTCF protein and occupied by the cohesin complex. Anchor sequence-mediated conjunctions for specific enhancing sequence-gene interactions are essential for both normal gene activation and repression, and form a chromosome scaffold that is largely preserved throughout development. Anchor sequence-mediated conjunctions are perturbed genetically and epigenetically in order to alter gene transcription in a targeted manner. This is achieved by methylation (loop disruption) and de-methylation (promotes loop formation) of CpG dinucleotides on a CTCF binding motif (CCGCGNGGNGGCAG, SEQ ID NO: 4), and by genome editing of the aforementioned sequence. Alternatively, a loop is disrupted by physical interference with the CTCF-anchor sequence interaction.

Figure 14:
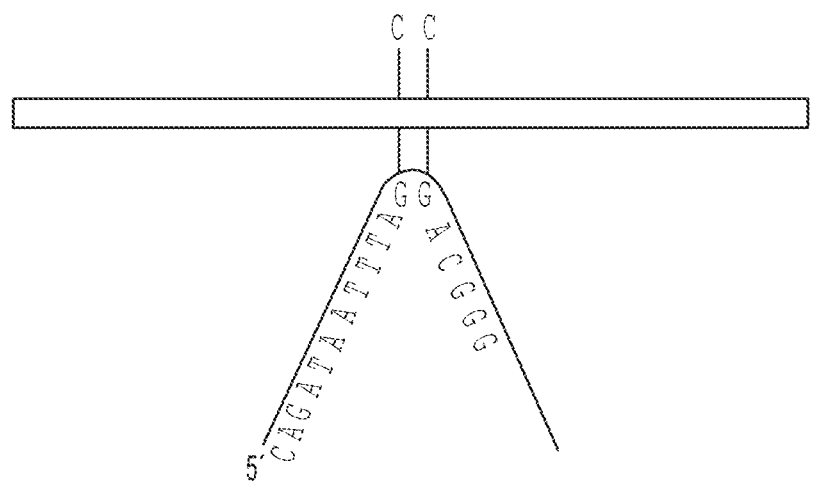
FIG. 14 is an illustration of a polypeptide beta hybridized to a CTCF site in the miR290 loop to physically interfere (mediated by the polypeptide backbone and the polynucleotide sequence) with the looping function of CTCF.

Therapeutic Design:

This approach is tested experimentally by targeting the CTCF anchor sequences of the miR290 loop, a loop with activating polarity, that harbors a super-enhancing sequence in mouse embryonic stem cells (mESCs). The polypeptide beta fusion with dCas9-TET1 includes sequence specific polynucleotides that bind the two CTCF sites to physically interfere (mediated by the polypeptide backbone and the polynucleotide sequence) with the looping function of CTCF, see FIG. 14.

Experimental Design:

In this experimental system, mouse embryonic stem cells are cultured on irradiated mouse embryonic fibroblasts (MEFs) with standard ESCs medium: (500 ml) DMEM supplemented with 10% FBS (Hyclone), 10 ug recombinant leukemia inhibitory factor (LIF), 0.1 mM b-mer-captoethanol (Sigma-Aldrich), penicillin/streptomycin, 1 mM L-glutamine, and 1% nonessential amino acids (all from Invitrogen), and exposed to the polypeptides in their growth medium. After 2, 4, 6 h of exposure, mRNA is extracted from cells and analyzed for transcript number by RT-PCR: Cells are harvested using Trizol followed by Direct-zol (Zymo Research), according to manufacturer's instructions. RNA is converted to cDNA using first-strand cDNA synthesis (Invitrogen SuperScript III). Quantitative PCR reactions are prepared with SYBR Green (Invitrogen), and performed in 7900HT Fast ABI instrument.

Successful interference causes an elevation of Nlrp12 gene, which is outside of this super-enhancing sequence-containing anchor sequence-mediated conjunction and next to the targeted CTCF site, without affecting the expression of genes that are located inside the miR290 loop or of genes in other neighboring loops including AU018091 and Myadm.

B) Nuclear Suppression of ELANE Transcription by Physical Interference

This example demonstrates ligating multiple polypeptide betas through click chemistry.

Click chemistry involves the rapid generation of compounds by joining small units together via heteroatom links (C—X—C). The main objective of click chemistry is to develop a set of powerful, selective, and modular blocks that are useful for small- and large-scale applications. These click reactions are bio-orthogonal, i.e. they can occur within organisms without interfering with native biochemical processes. The reaction of a dibenzylcyclooctyne (DBCO) linker with an azide linker to form a stable triazole. This click reaction is very fast at room temperature, does not require a cytotoxic Cu(I) catalyst and creates stable triazoles. This unique covalent bond is created when DBCO, incorporated into one type of biomolecule, reacts with an azide linker, incorporated into a second biomolecule. The DBCO strain-promoted or Cu(I)-free [2+3] cycloaddition strategy relies on the use of strained dibenzylcyclooctynes. Their use decreases the activation energy for the cycloaddition click reaction, enabling it to be carried out without the need for catalysis at low temperatures with an efficiency greater than that of the Cu(I)-catalyzed ligation.

Polypeptide beta is modified with dibenzylcyclooctyne (DBCO) modification and another polypeptide beta with an azide modification.

Experimental Design:

In the click reaction, succinimidyl esters, (5/6-carboxyfluorescein succinimidyl ester and succinimidyl-2-(biotinamido)ethyl-1,3-dithiopropionate, Thermo Fisher Scientific, Waltham, USA) are dissolved in dry DMSO (Acros, Geel, Belgium). Primary amine labeling is carried out at 4° C. for 1 hour in 20 mM Na Phosphate buffer pH 7.2 containing 0.05% dodecyl maltoside.

Maleimides, dibenzylcyclooctyne-PEG4-maleimide and azido-PEG3-maleimide (Jena Bioscience), are dissolved in dry DMSO. Sulfhydryl labeling is performed at 25° C. for 2 hours in 20 mM Na Phosphate buffer pH 7.2 containing 0.05% dodecyl maltoside. Copper-free coupling by click chemistry is performed in the same buffer for 10 hours at 4° C.

After the reaction with 5/6-carboxyfluoresceine succinimidyl ester and the maleimides, the labeled protein is separated from unreacted label using spin columns (Micro Biospin TM6 columns, Bio-Rad, Hercules, USA), according to the manufacturer's instructions.

Reaction products after coupling are analyzed by HPLC. 20-40 µl samples are injected and separated on a chromatography system equipped with an analytical column (300 mm×4.60 mm) eluted with 20 mM Na Phosphate buffer pH 7.2 containing 0.05% dodecyl maltoside at a flow rate of 0.5 ml/min and followed by absorption at 280 nm. Absorption spectra of peaks are obtained from the integrated spectral detector (Agilent technologies G1315D diode array detector).

This example demonstrates inhibition of gene expression with polypeptides that target an anchor sequence associated with the ELANE gene.

ELANE-related neutropenia includes severe congenital neutropenia (SCN) and cyclic neutropenia, both of which are primary hematologic disorders characterized by recurrent fever, skin and oropharyngeal inflammation (i.e., mouth ulcers, gingivitis, sinusitis, and pharyngitis), and cervical adenopathy. Infectious complications are generally more severe in congenital neutropenia than in cyclic neutropenia and can lead to death if untreated. Most cases of SCN respond to treatment with granulocyte colony-stimulating factor, which increases the neutrophil count and decreases the severity and frequency of infections. However, after 15 years with granulocyte colony stimulating factor treatment, the risk of developing myelodysplasia (MDS) or acute myelogenous leukemia AML is approximately 15%-25%.

Figure 15:
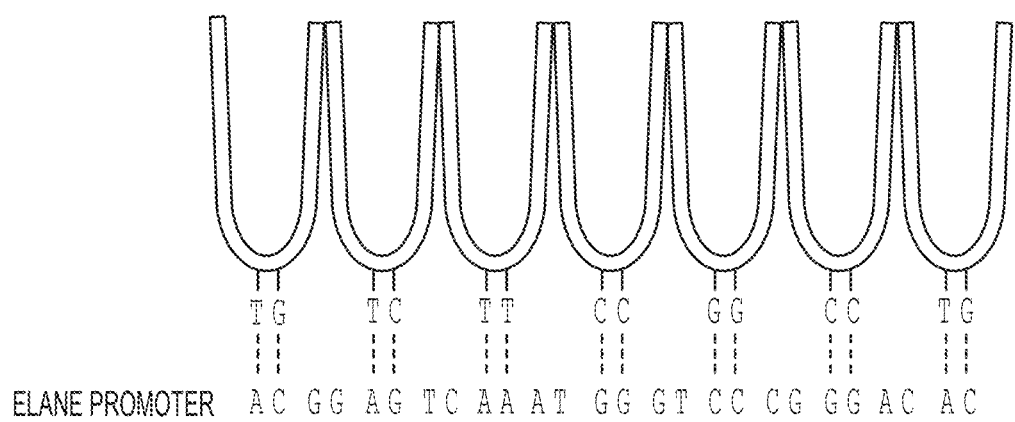
FIG. 15 is an illustration of multimerized polypeptide beta hybridized to the promoter of the ELANE gene.

Mutations in the neutrophil elastase gene, ELANE, are the most common cause of severe congenital neutropenia as well as of cyclic neutropenia. ELANE maps to 19p13.31 and mutations in the ELANE gene are identified in approximately 35-84% of individuals with SCN. SCN and cyclic neutropenia secondary to mutations in ELANE are inherited as autosomal dominant conditions. ELANE consists of five exons and encodes a 218 amino acid protein known as neutrophil elastase (NE). NE belongs to the class of serine proteases and is expressed exclusively in mature myelomonocytic cells and their committed immature precursors (promyelocytes and promonocytes). Stored as an active protease in azurophilic granules, NE is released upon exposure of the neutrophil to inflammatory stimuli. In the extracellular environment, NE cleaves extracellular matrix proteins, while serine protease inhibitors antagonize the proteinase activity Therapeutic Design:

In this example, the phenotype is reversed by silencing the transcription of the ELANE gene in neutrophil precursors. In order to achieve that, the multimerized polypeptide betas are hybridized to a nucleic acid sequence complimentary to an anchor sequence associated with the ELANE gene (e.g. caacggccgggccaaggctgtcgcaagaac, SEQ ID NO: 5), see FIG. 15, and delivered to myelomonocytes, promyelocytes and promonocytes. The polypeptide-oligonucleotide passes through the cell membrane and the nuclear membrane to hybridize to its target the anchor sequence, thereby disrupting the anchor sequence-mediated conjunction that harbors the ELANE gene, and the polypeptide-oligonucleotide hybrid physically interferes with the anchor sequence-mediated conjunction, and therefore decreases the expression of ELANE.

Experimental Design:

This approach is tested in iPSC derived from SCN patients. To determine if gene correction of ELANE mutations restores granulopoietic differentiation, the SCN iPSCs are exposed to polypeptides containing a nucleic acid sequence that complements the ELANE ORF, or a scrambled sequence, and selected for incorporation of the polypeptide. iPSCs are differentiated into CD45+CD34+ hematopoietic progenitors by 10 days of culture in myeloid expansion medium (IMDM+Ham's F12 at 3:1 ratio) containing 0.5% N2 supplement, 1% B27 supplement without vitamin A, 0.5% human serum albumin, 100 µM monothioglycerol, 50 µg/ml ascorbic acid, 100 ng/ml recombinant SCF, 10 ng/ml IL-3, and 10 ng/ml GM-CSF. The cultures are further differentiated using granulopoietic culture conditions (IMDM+Ham's F12 at 3:1 ratio) containing 0.5% N2 supplement, 1% B27 supplement without vitamin A, 0.5% human serum albumin, 100 µM monothioglycerol, 50 µg/ml ascorbic acid, and 50 ng/ml G-CSF (Neupogen filgrastim) for 5 days. At the granulopoietic differentiation stage, cells are cultured at low (50 ng/ml) or high (1,000 ng/ml) G-CSF doses. During myeloid expansion and granulopoietic differentiation, cells are cultured in presence or absence of Sivelestat (Sigma-Aldrich) at a concentration of 230 nM (~5 times the IC50 for NE). At the end of granulopoietic differentiation, cells are cytospun onto a Superfrost Plus Microscope slide (Fisher Scientific). The cells are Wright-Giemsa stained and then scored for myeloid cell types (promyelocytes, myelocytes, metamyelocytes, bands, neutrophils, and monocytes) using an upright microscope (Motic BA310). For sorting the promyelocytes, cells at the end of myeloid expansion are stained for CD45-Pacific Blue, CD34-PECy7, CD33-APC, CD11b-APCCy7 (catalog 557754, clone ICRF44, BD Biosciences), and CD15-FITC (catalog 562370, clone W6D3, BD Biosciences). The promyelocytes/myelocyte population (defined as $CD45^+/CD34^-/CD33^+/CD11b^-/CD15^{dim}$) is selected by FACS.

Expression of ELANE is quantitatively measured by PCR and determined to be greater than untreated cells.

Example 11: Generation of Novel Anchor Sequence-Mediated Conjunctions

A) Generation of Novel Anchor Sequence-Mediated Conjunctions by Hybridization of Methylated DNA with Exogenous Unmethylated Polynucleotide-Polypeptide Effectors This example demonstrates modulation of gene expression to create allele-specific anchor sequence-mediated conjunctions.

Gene regulatory elements and their target genes generally occur within anchor sequence-mediated conjunctions, chromosomal loop structures formed by the interaction of two DNA sites bound by the CTCF protein and occupied by the cohesin complex. Anchor sequence-mediated conjunctions provide for specific enhancing sequence-gene interactions, are essential for both normal gene activation and repression, and form a chromosome scaffold that is largely preserved throughout development. Anchor sequence-mediated conjunctions are perturbed genetically and epigenetically in order to alter gene transcription in a targeted manner. This is achieved by methylation (loop disruption) and de-methylation (promotes loop formation) of CpG dinucleotides on the CTCF binding motif (CCGCGNGGNGGCAG, SEQ ID NO: 4), and by genome editing of the aforementioned sequence. Alternatively, a loop is generated by the targeted, exogenous delivery of a specific DNA strand and serves as an anchor sequence for CTCF.

The H19-IGF2 locus shows parent-of-origin specific loop conformations: An anchor sequence-mediated conjunction on the maternal allele allows an enhancing sequence-promoter interaction that activates the H19 gene, but not the IGF2 gene, which is excluded from the anchor sequence-mediated conjunction. A larger anchor sequence-mediated conjunction is formed on the paternal allele to allow an enhancing sequence-promoter interaction that activates the IGF2 gene. Paternal allele-specific DNA methylation of a CTCF site in the H19 promoter region abrogates CTCF binding, thus causing differential CTCF-CTCF loop formation that decreases H19 expression. Individuals who lose these allele-specific anchor sequence-mediated conjunctions develop Beckwith-Wiedemann syndrome (when both alleles have the paternal type of anchor sequence-mediated conjunction) or Silver-Russell syndrome (when both alleles have the maternal type of anchor sequence-mediated conjunction).

Figure 16:
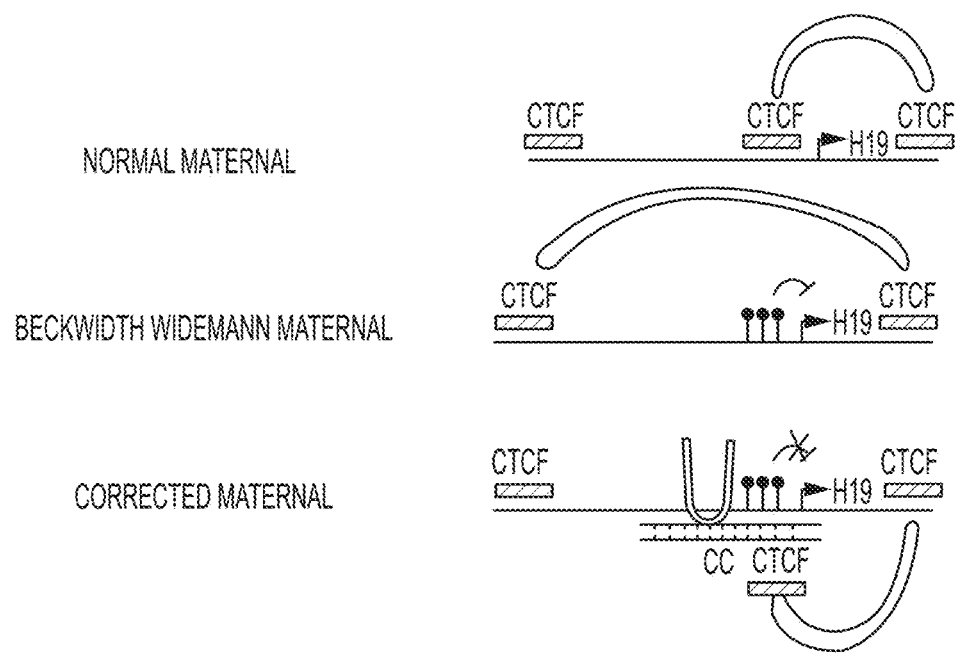
FIG. 16 is an illustration of a polypeptide beta linked to a double stranded, unmethylated CTCF anchor sequence with specificity for the H19-IGF2 locus to mimic an unmethylated CTCF binding motif on one of the paternal alleles to form a maternal type of loop.

Therapeutic Design:

One polypeptide beta is designed to contain a double stranded, unmethylated CTCF anchor sequence with specificity to target the CTCF anchor sequences in the H19-IGF2 locus. See FIG. 16. The polypeptide described herein mimics an unmethylated CTCF binding motif on one of the paternal alleles to form a maternal type of loop in cells from patients with Beckwith-Wiedemann syndrome caused by uniparental disomy.

Experimental Design:

In this experiment, skin fibroblasts derived from Beckwith-Widemann patients are plated in standard primary fibroblast medium: (500 ml) DMEM supplemented with 15% FBS (Hyclone), 0.1 mM b-mer-captoethanol (Sigma-Aldrich), penicillin/streptomycin, 1 mM L-glutamine, and 1% nonessential amino acids (all from Invitrogen), and exposed to the polypeptides in their growth medium. After 2, 4, 6 h of exposure, mRNA is extracted from cells and analyzed for transcript number by RT-PCR: Cells are harvested using Trizol followed by Direct-zol (Zymo Research), according to manufacturer's instructions. RNA is converted to cDNA using First-strand cDNA synthesis (Invitrogen SuperScript III). Quantitative PCR reactions are prepared with SYBR Green (Invitrogen), and performed in 7900HT Fast ABI instrument.

A successful manipulation causes an elevation of H19 gene expression, usually silent in the paternal allele.

B) Treatment of Fragile X Syndrome by Creating a Novel Anchor Sequence-Mediated Conjunction Fragile X is the leading cause of inherited intellectual disability. It is caused by the amplification of a CGG repeat in the FMR1gene on the X chromosome. The amplification causes DNA methylation of the CpG dinucleotides within the repeat as well as in the neighboring sequence, and subsequent decrease in expression of the gene. It is believed that transcriptional silencing of the FMR1 gene is responsible for the pathology characteristic of the disease.

In this example, the FMR1 gene is activated by moving it into an anchor sequence-mediated conjunction that includes an enhancing sequence. To identify such anchor sequence-mediated conjunction, a ChIA-PET analysis is first carried out, where CTCF bound DNA elements are mapped on the genome. This data is then overlayed with genome wide analysis of enhancing sequences, as defined by Acetlyation of H3K27 and DNAseI hypersensitivity analysis (Kundaje et al 2015). The location of CTCF binding motifs in the proximity of FMR1 is then analyzed to identify the ones that need to be removed in order to bring the nearest and strongest enhancing sequences in close proximity to the FMR1 gene. Once the target CTCF is identified, one of three approaches is applied:

Abolition of the CTCF2 anchor sequence by DNA methylation: a dCas9-DNMT3a fusion is designed, with a guide or antisense DNA oligonucleotide that targets the CTCF site to be methylated. *Staphylococcus Aureus* Cas9 will be used, and the construct will be introduced by electroporation to cells derived from Fragile X patients or to a Fragile X patient. Targeted methylation of the relevant CTCF anchor sequences by DNMT3a would lead to the looping of FMR1 together with enhancing sequences and subsequent activation. 48 h after electroporation, chromatin, genomic DNA and total mRNA will be prepared from the electroporated cells. ChIA-PET analysis will be carried out to determine if a loop was formed, encompassing the FMR gene and the enhancing sequences. Bisulphite analysis will be then used to determine methylation levels at the target CTCF as well as within the FMR1 gene. Transcriptional activity of FMR1 will be assessed by RT-PCR from total RNA derived from the cells.

Genome editing and deletion of a CTCF2 anchor sequence: Alternatively, genome editing is used to mutate CTCF2 and in this way bring FMR1 to the activating anchor sequence-mediated conjunction. In this case, a Sa CRISPR-Cas9 targeting the relevant CTCF is designed, and incorporated into cells or to a Fragile X patient by electroporation. 48 h after the manipulation, genomic DNA is extracted and sequenced to determine whether the target CTCF was modified. FMR1 transcription is determined by RT-PCR analysis of total mRNA.

Use of a Dominant negative form of CTCF and competitive inhibition of binding: To block the CTCF binding motif by means of a dominant negative effector, a protein is designed, with the ability to recognize and bind the CTCF anchor sequence, but with a mutated dimerization domain. With this purpose, a Zinc Finger array can be designed with target CTCF specificity, fused to a dominant negative CTCF protein lacking the dimerization domain, and having a Flag peptide. DNA encoding for the fusion protein will be introduced to cells or to a Fragile X patient by electroporation. ChIP analysis is carried out 48 h after the electroporation with a Flag antibody, to determine binding of the dominant negative effector to the target CTCF. Further analysis is carried out as described above, to determine FMR1 transcription levels.

All three approaches may lead to the effective abolition of CTCF2 and subsequent co-looping of the nearest enhancing sequences with the FMR1 gene.

Example 12: Exemplary Anchor Sequences

Those of skill in the art reading the specification will understand anchor sequences can, in some embodiments, vary to some degree from known anchor sequences and/or those anchor sequences disclosed in the present specification. For example, although the present specification discloses CTCF binding sequences as, in some embodiments, having or comprising a portion having the sequence of SEQ ID NO: 1 or SEQ ID NO: 2, in some embodiments, an anchor sequence to which CTCF binds is a variant of SEQ I D NO: 1 or SEQ ID NOL 2. For example, the below table shows the probabilities of each of the four bases at a given position in SEQ ID NO: 1 for a CTCF binding domain.

TABLE 15

Probabilities of bases appearing in a CTCF binding domain

| Position | A | C | G | T |
|---|---|---|---|---|
| 5 | 0.061 | 0.876 | 0.023 | 0.039 |
| 6 | 0.009 | 0.989 | 0.000 | 0.002 |
| 7 | 0.815 | 0.014 | 0.071 | 0.100 |
| 8 | 0.044 | 0.578 | 0.366 | 0.012 |
| 9 | 0.117 | 0.475 | 0.053 | 0.355 |
| 10 | 0.933 | 0.012 | 0.035 | 0.020 |

TABLE 15-continued

Probabilities of bases appearing in a CTCF binding domain

| Position | A | C | G | T |
|---|---|---|---|---|
| 11 | 0.005 | 0.000 | 0.991 | 0.003 |
| 12 | 0.366 | 0.003 | 0.621 | 0.010 |
| 13 | 0.059 | 0.013 | 0.553 | 0.374 |
| 14 | 0.013 | 0.000 | 0.978 | 0.009 |
| 15 | 0.062 | 0.009 | 0.852 | 0.078 |
| 16 | 0.114 | 0.806 | 0.006 | 0.074 |
| 17 | 0.409 | 0.014 | 0.558 | 0.019 |

What is claimed is:

1. A method of decreasing expression of a gene within a cell, the gene being within an anchor sequence-mediated conjunction that comprises a first anchor sequence, a second anchor sequence, and an enhancer, the method comprising a step of:
  contacting the cell with a composition comprising a targeting element or a nucleic acid encoding the targeting element, wherein the targeting element comprises a Cas protein and gRNA which bind specifically to the first anchor sequence, the second anchor sequence, or both of the first anchor sequence and the second anchor sequence, relative to non-target anchor sequences within the cell with sufficient affinity that it competes with binding of CTCF within the cell, wherein the first and second anchor sequences each comprise a CTCF binding site wherein the CTCF binding site has the sequence of SEQ ID NO: 1 or SEQ ID NO: 2.

2. The method of claim 1, wherein neither the first nor second anchor sequences are located within an enhancer or a promoter.

3. The method of claim 1, wherein the gene is FOXJ3.

4. The method of claim 1, wherein the gRNA comprises a sequence of any of SEQ ID NOs: 40-47, 86, or 87.

5. The method of claim 1, wherein the cell is a human cell.

6. The method of claim 1, wherein the Cas protein comprises Cas9.

7. The method of claim 1, wherein contacting comprises transfecting the cell with the composition.

8. The method of claim 1, wherein the method further comprises substituting, adding or deleting one or more nucleotides within an anchor sequence of the anchor sequence-mediated conjunction.

9. The method of claim 8, wherein the substitution, addition, or deletion of one or more nucleotides is in a CTCF binding site.

10. The method of claim 1, wherein the gRNA has a length from about 10 to about 100 nucleotides.

11. The method of claim 1, wherein the gRNA is or comprises a sequence at least 90% complementary to the first and/or second anchor sequence.

12. The method of claim 1, wherein the composition physically interferes with formation and/or maintenance of the anchor sequence-mediated conjunction.

13. The method of claim 1, wherein the gene is an oncogene, a tumor suppressor, or a gene associated with a nucleotide repeat.

* * * * *

UNITED STATES PATENT AND TRADEMARK OFFICE
CERTIFICATE OF CORRECTION

| | | |
|---|---|---|
| PATENT NO. | : 11,312,955 B2 | Page 1 of 1 |
| APPLICATION NO. | : 15/821632 | |
| DATED | : April 26, 2022 | |
| INVENTOR(S) | : Berry et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 460 days.

Signed and Sealed this
Seventh Day of January, 2025

Derrick Brent
*Acting Director of the United States Patent and Trademark Office*

SEQUENCE LISTING

```
<160> NUMBER OF SEQ ID NOS: 87

<210> SEQ ID NO 1
<211> LENGTH: 20
<212> TYPE: DNA
<213> ORGANISM: Unknown
<220> FEATURE:
<223> OTHER INFORMATION: Description of Unknown: CTCF-binding motif
<220> FEATURE:
<221> NAME/KEY: variation
<222> LOCATION: (1)..(1)
<223> OTHER INFORMATION: a, c, t, or g
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: variation
<222> LOCATION: (3)..(3)
<223> OTHER INFORMATION: a, c, t, or g
<220> FEATURE:
<221> NAME/KEY: misc_feature
<222> LOCATION: (3)..(3)
<223> OTHER INFORMATION: n is a, c, g, or t

<400> SEQUENCE: 1
nbndccdsha grkgghrshv                                               20

<210> SEQ ID NO 2
<211> LENGTH: 20
<212> TYPE: DNA
<213> ORGANISM: Unknown
<220> FEATURE:
<223> OTHER INFORMATION: Description of Unknown: CTCF-binding motif
<220> FEATURE:
<221> NAME/KEY: variation
<222> LOCATION: (18)..(18)
<223> OTHER INFORMATION: a, c, t, or g
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: variation
<222> LOCATION: (20)..(20)
<223> OTHER INFORMATION: a, c, t, or g
<220> FEATURE:
<221> NAME/KEY: misc_feature
<222> LOCATION: (20)..(20)
<223> OTHER INFORMATION: n is a, c, g, or t

<400> SEQUENCE: 2
vhsrhggkrg ahsdccdnbn                                               20

<210> SEQ ID NO 3
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 3

Pro Phe Asp Ile Leu Tyr Gln Gly Gly Arg Gly Gln Gly Asp Cys
1               5                   10                  15

<210> SEQ ID NO 4
<211> LENGTH: 14
<212> TYPE: DNA
<213> ORGANISM: Unknown
<220> FEATURE:
<223> OTHER INFORMATION: Description of Unknown: CTCF binding motif
<220> FEATURE:
<221> NAME/KEY: variation
<222> LOCATION: (6)..(6)
<223> OTHER INFORMATION: a, c, t, or g
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: variation
<222> LOCATION: (9)..(9)
<223> OTHER INFORMATION: a, c, t, or g
<220> FEATURE:
<221> NAME/KEY: misc_feature
<222> LOCATION: (9)..(9)
<223> OTHER INFORMATION: n is a, c, g, or t

<400> SEQUENCE: 4
ccgcgnggng gcag                                                      14

<210> SEQ ID NO 5
<211> LENGTH: 30
<212> TYPE: DNA
<213> ORGANISM: Unknown
<220> FEATURE:
<223> OTHER INFORMATION: Description of Unknown: Complimentary anchor
      sequence associated with ELANE gene

<400> SEQUENCE: 5
caacggccgg gccaaggctg tcgcaagaac                                     30

<210> SEQ ID NO 6
<211> LENGTH: 7
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6 tatawaw                                                               7

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
aaagtaagtg tgccctctac                                                20

<210> SEQ ID NO 8
<211> LENGTH: 19
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 8
gctggaaacc ttgcacctc                                                 19

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
cgttcaggtt tgcgaaagta                                                20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
ctattcaacc gcataagaga                                                20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
cgctgagctg caaactcaac                                                20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
gcctggatgt caacgagggc                                                20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
gcgggtgctg cccagagagg                                                20

<210> SEQ ID NO 14
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 14
gcaaaatcca gcatagcgat                                                     20

<210> SEQ ID NO 15
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(6)
<223> OTHER INFORMATION: Phosphothiolate linkages between nucleotides
<220> FEATURE:
<221> NAME/KEY: misc_feature
<222> LOCATION: (53)..(58)
<223> OTHER INFORMATION: Phosphothiolate linkages between nucleotides

<400> SEQUENCE: 15
tccaggcgcg atgatctctg ctgccagtag agggcacact tactttactt tcgcaaac         58

<210> SEQ ID NO 16
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(6)
<223> OTHER INFORMATION: Phosphothiolate linkages between nucleotides
<220> FEATURE:
<221> NAME/KEY: misc_feature
<222> LOCATION: (35)..(40)
<223> OTHER INFORMATION: Phosphothiolate linkages between nucleotides

<400> SEQUENCE: 16
aggcgcgatg atctctgctg ccagtagagg gcacacttac                               40

<210> SEQ ID NO 17
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(6)
<223> OTHER INFORMATION: Phosphothiolate linkages between nucleotides
<220> FEATURE:
<221> NAME/KEY: misc_feature
<222> LOCATION: (27)..(32)
<223> OTHER INFORMATION: Phosphothiolate linkages between nucleotides

<400> SEQUENCE: 17
tgatctctgc tgccagtaga gggcacactt ac                                       32

<210> SEQ ID NO 18
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<221> NAME/KEY: misc_feature
<222> LOCATION: (1)..(6)
<223> OTHER INFORMATION: Phosphothiolate linkages between nucleotides
<220> FEATURE:
<221> NAME/KEY: misc_feature
<222> LOCATION: (53)..(58)
<223> OTHER INFORMATION: Phosphothiolate linkages between nucleotides

<400> SEQUENCE: 18
gtttgcgaaa gtaaagtaag tgtgccctct actggcagca gagatcatcg cgcctgga      58

<210> SEQ ID NO 19
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(6)
<223> OTHER INFORMATION: Phosphothiolate linkages between nucleotides
<220> FEATURE:
<221> NAME/KEY: misc_feature
<222> LOCATION: (27)..(32)
<223> OTHER INFORMATION: Phosphothiolate linkages between nucleotides

<400> SEQUENCE: 19
gtaagtgtgc cctctactgg cagcagagat ca                                   32

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
tgcagaaggt ccgaagaaag                                                 20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
aagaataaca aggaggtggc                                                 20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
agattctaaa ggctggctag                                                 20

<210> SEQ ID NO 23
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 23
gggagcacag ccctaagtaa                                                20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
gaaaccctcc aaaagaggaa                                                20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
gagtgcctgt ggccactagg                                                20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
gcctaattgc aaagtagctt                                                20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
agcgaccagg cggagaatga                                                20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
gggcctgaaa cagcacaatg                                                20

<210> SEQ ID NO 29
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 29
acattggagc tgaatggcct                                                   20

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
gaccctttga agactcaact                                                   20

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
gctctggtaa ggcaagattc                                                   20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
aggtagcaaa tgccagccca                                                   20

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
atctctggat ttctcatgag                                                   20

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
gcagtgctgg ggacaagatg                                                   20

<210> SEQ ID NO 35
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 35
ctaggttagg tattgtgcta                                                    20

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
aagataaaag cagtagctag                                                    20

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
ataatagcaa ttaagagtaa                                                    20

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
tggaggctgc agggaggcgg                                                    20

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
aatgtgggct ccctcgtctg                                                    20

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(6)
<223> OTHER INFORMATION: Phosphothiolate linkages between nucleotides
<220> FEATURE:
<221> NAME/KEY: misc_feature
<222> LOCATION: (15)..(20)
<223> OTHER INFORMATION: Phosphothiolate linkages between nucleotides
```

```
<400> SEQUENCE: 40
cctagtggcc acaggcactc                                                     20

<210> SEQ ID NO 41
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(6)
<223> OTHER INFORMATION: Phosphothiolate linkages between nucleotides
<220> FEATURE:
<221> NAME/KEY: misc_feature
<222> LOCATION: (19)..(24)
<223> OTHER INFORMATION: Phosphothiolate linkages between nucleotides

<400> SEQUENCE: 41
gccccctagt ggccacaggc actc                                                24

<210> SEQ ID NO 42
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(6)
<223> OTHER INFORMATION: Phosphothiolate linkages between nucleotides
<220> FEATURE:
<221> NAME/KEY: misc_feature
<222> LOCATION: (19)..(24)
<223> OTHER INFORMATION: Phosphothiolate linkages between nucleotides

<400> SEQUENCE: 42
gagtgcctgt ggccactagg gggc                                                24

<210> SEQ ID NO 43
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(6)
<223> OTHER INFORMATION: Phosphothiolate linkages between nucleotides
<220> FEATURE:
<221> NAME/KEY: misc_feature
<222> LOCATION: (38)..(43)
<223> OTHER INFORMATION: Phosphothiolate linkages between nucleotides

<400> SEQUENCE: 43
gtgagtgcct gtggccacta gggggcgggg ctgccggctg tgc                           43

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(6)
<223> OTHER INFORMATION: Phosphothiolate linkages between nucleotides
```

```
<220> FEATURE:
<221> NAME/KEY: misc_feature
<222> LOCATION: (15)..(20)
<223> OTHER INFORMATION: Phosphothiolate linkages between nucleotides

<400> SEQUENCE: 44
agggctcccc gccagcatgg                                                    20

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(6)
<223> OTHER INFORMATION: Phosphothiolate linkages between nucleotides
<220> FEATURE:
<221> NAME/KEY: misc_feature
<222> LOCATION: (15)..(20)
<223> OTHER INFORMATION: Phosphothiolate linkages between nucleotides

<400> SEQUENCE: 45
ccagcatggt ggctcacgtc                                                    20

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(6)
<223> OTHER INFORMATION: Phosphothiolate linkages between nucleotides
<220> FEATURE:
<221> NAME/KEY: misc_feature
<222> LOCATION: (15)..(20)
<223> OTHER INFORMATION: Phosphothiolate linkages between nucleotides

<400> SEQUENCE: 46
ccatgctggc ggggagccct                                                    20

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(6)
<223> OTHER INFORMATION: Phosphothiolate linkages between nucleotides
<220> FEATURE:
<221> NAME/KEY: misc_feature
<222> LOCATION: (15)..(20)
<223> OTHER INFORMATION: Phosphothiolate linkages between nucleotides

<400> SEQUENCE: 47
gacgtgagcc accatgctgg                                                    20

<210> SEQ ID NO 48
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 48
cagcggattt gggctcccgg                                              20

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
cctcatcact acctgccacg                                              20

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
catcactacc tgccacgagg                                              20

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
tgagactcca gcatcccaca                                              20

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
ccagagtagt ccctggcacg                                              20

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
acagcagaag ggcaggttgg                                              20

<210> SEQ ID NO 54
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 54
ccaggacacc cgcctcccag                                              20

<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
gcggcgtgct cgccctctgg                                              20

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
gcatcgcact cgcagctccg                                              20

<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
gggtgcgaga tagaggtgcc                                              20

<210> SEQ ID NO 58
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
ggcacctcta tctcgcaccc                                              20

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
tgggctcggg cgccccctgg                                              20

<210> SEQ ID NO 60
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 60
agggtcgaca ctgcccgaca                                                    20

<210> SEQ ID NO 61
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
cggggcaggt ctccctctgg                                                    20

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
ccaggcgtac agacaccacc                                                    20

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
gcttggagtc cagtcccagc                                                    20

<210> SEQ ID NO 64
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
tcaaaggcag cgggactcag                                                    20

<210> SEQ ID NO 65
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
aagctcgggg aagaggcctt                                                    20

<210> SEQ ID NO 66
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 66
cactccaggc accaacttag                                                   20

<210> SEQ ID NO 67
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
actcccgcct ccaagacagt                                                   20

<210> SEQ ID NO 68
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
aaagaaagaa aaaaagccgc                                                   20

<210> SEQ ID NO 69
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
gggcacagta agatggagag                                                   20

<210> SEQ ID NO 70
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
gcaggggagg atctcagagt                                                   20

<210> SEQ ID NO 71
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
tgggacacag acctcctact                                                   20

<210> SEQ ID NO 72
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 72
caggtgcata atgagtgctg                                                    20

<210> SEQ ID NO 73
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
gttgttttac ggccacaagg                                                    20

<210> SEQ ID NO 74
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
tttttttctg cgccaccttg                                                    20

<210> SEQ ID NO 75
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
cacattaaaa atgttactat                                                    20

<210> SEQ ID NO 76
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
tgtttgagtc aaacctaaaa                                                    20

<210> SEQ ID NO 77
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
acggtgggtt cacgactcaa                                                    20

<210> SEQ ID NO 78
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 78
aaagtaacac tgccatctaa                                               20

<210> SEQ ID NO 79
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
aacacataga atccattaga                                               20

<210> SEQ ID NO 80
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
tgtgttactg ccattgtctg                                               20

<210> SEQ ID NO 81
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
ttaaatgttg cctcagacaa                                               20

<210> SEQ ID NO 82
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
aaaaacacaa aataaggtgg                                               20

<210> SEQ ID NO 83
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
aaatcaatcc aacagattat                                               20

<210> SEQ ID NO 84
<211> LENGTH: 18
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 84
cagataattt aggacggg                                                    18

<210> SEQ ID NO 85
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
acggagtcaa atgggtcccg ggacac                                           26

<210> SEQ ID NO 86
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(6)
<223> OTHER INFORMATION: Phosphothiolate linkages between nucleotides
<220> FEATURE:
<221> NAME/KEY: misc_feature
<222> LOCATION: (15)..(20)
<223> OTHER INFORMATION: Phosphothiolate linkages between nucleotides

<400> SEQUENCE: 86
gagtgcctgt ggccactagg                                                  20

<210> SEQ ID NO 87
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(6)
<223> OTHER INFORMATION: Phosphothiolate linkages between nucleotides
<220> FEATURE:
<221> NAME/KEY: misc_feature
<222> LOCATION: (10)..(12)
<223> OTHER INFORMATION: Phosphothiolate linkages between nucleotides
<220> FEATURE:
<221> NAME/KEY: misc_feature
<222> LOCATION: (21)..(25)
<223> OTHER INFORMATION: Phosphothiolate linkages between nucleotides
<220> FEATURE:
<221> NAME/KEY: misc_feature
<222> LOCATION: (28)..(29)
<223> OTHER INFORMATION: Phosphothiolate linkages between nucleotides
<220> FEATURE:
<221> NAME/KEY: misc_feature
<222> LOCATION: (31)..(33)
<223> OTHER INFORMATION: Phosphothiolate linkages between nucleotides
<220> FEATURE:
<221> NAME/KEY: misc_feature
<222> LOCATION: (38)..(43)
<223> OTHER INFORMATION: Phosphothiolate linkages between nucleotides

<400> SEQUENCE: 87
gtgagtgcct gtggccacta gggggcgggg ctgccggctg tgc                        43
```